(12) United States Patent
Li et al.

(10) Patent No.: US 8,999,967 B2
(45) Date of Patent: Apr. 7, 2015

(54) TRICYCLIC FUSED RING INHIBITORS OF HEPATITIS C

(75) Inventors: Leping Li, Burlingame, CA (US); Min Zhong, Palo Alto, CA (US)

(73) Assignee: Presidio Pharmaceuticals, Inc., San Francisco, CA (US)

( * ) Notice: Subject to any disclaimer, the term of this patent is extended or adjusted under 35 U.S.C. 154(b) by 0 days.

(21) Appl. No.: 13/877,151

(22) PCT Filed: Sep. 28, 2011

(86) PCT No.: PCT/US2011/053759
§ 371 (c)(1),
(2), (4) Date: Jun. 27, 2013

(87) PCT Pub. No.: WO2012/050918
PCT Pub. Date: Apr. 19, 2012

(65) Prior Publication Data
US 2013/0296304 A1 Nov. 7, 2013

Related U.S. Application Data

(60) Provisional application No. 61/387,974, filed on Sep. 29, 2010.

(51) Int. Cl.
*C07D 405/14* (2006.01)
*C07D 413/14* (2006.01)
*C07D 401/14* (2006.01)
*C07D 403/14* (2006.01)
*C07D 409/14* (2006.01)
*C07D 417/14* (2006.01)

(52) U.S. Cl.
CPC ............ *C07D 413/14* (2013.01); *C07D 401/14* (2013.01); *C07D 403/14* (2013.01); *C07D 405/14* (2013.01); *C07D 409/14* (2013.01); *C07D 417/14* (2013.01)

(58) Field of Classification Search
CPC .. C07D 405/14; C07D 413/14; C07D 401/14; C07D 403/14; C07D 409/14; C07D 417/14
See application file for complete search history.

(56) References Cited

U.S. PATENT DOCUMENTS

| | | | |
|---|---|---|---|
| 3,453,315 A | 7/1969 | Rigaudy | |
| 4,371,690 A | 2/1983 | Anderson et al. | |
| 5,288,914 A | 2/1994 | Kirchhoff | |
| 5,527,808 A | 6/1996 | Lowe, III et al. | |
| 6,242,602 B1 | 6/2001 | Giri et al. | |
| 6,255,483 B1 | 7/2001 | Fletcher et al. | |
| 8,088,368 B2 | 1/2012 | Guo et al. | |
| 8,101,643 B2 | 1/2012 | Qiu et al. | |
| 8,314,135 B2 | 11/2012 | Qiu et al. | |
| 2004/0082635 A1 | 4/2004 | Hashimoto et al. | |
| 2007/0299050 A1 | 12/2007 | Lal et al. | |
| 2008/0044380 A1 | 2/2008 | Bachand et al. | |
| 2010/0226882 A1 | 9/2010 | Or et al. | |
| 2011/0064695 A1 | 3/2011 | Qiu et al. | |

FOREIGN PATENT DOCUMENTS

| | | |
|---|---|---|
| WO | WO 2004/099241 A1 | 11/2004 |
| WO | WO 2006/039356 A2 | 4/2006 |
| WO | WO 2006/120010 A2 | 11/2006 |
| WO | WO 2007/019937 A1 | 2/2007 |
| WO | WO 2008/021927 A2 | 2/2008 |
| WO | WO 2008/021928 A2 | 2/2008 |
| WO | WO 2008/021936 A2 | 2/2008 |
| WO | WO 2008/144380 A1 | 11/2008 |
| WO | WO 2010/065668 A1 | 6/2010 |
| WO | WO 2010/065674 A1 | 6/2010 |
| WO | WO 2010/065681 A1 | 6/2010 |
| WO | WO 2010/096462 A1 | 8/2010 |
| WO | WO 2010/111534 A1 | 9/2010 |

OTHER PUBLICATIONS

PCT International Search Report and Written Opinion, PCT/US2011/053759, Apr. 27, 2012, 13 Pages.
Albert, A. et al., "275. Benzylamine Analogues of Chemotherapeutic Diamidines," Journal of the Chemical Society, 1947, pp. 1452-1455.
Koyama, K. et al., "Free Radical Reactions in Organic Electrode Processes—III," Tetrahedron, 1967, pp. 2665-2674, vol. 23.
PCT International Search Report and Written Opinion, PCT Application No. PCT/US2010/028730, Jun. 17, 2010, 11 pages.
Shelton, J.R. et al., "Reactions of Free Radicals with Olefins. Dehydro Dimer Structures of 4-Vinylcyclohexene," The Journal of Organic Chemistry, 1966, pp. 2028-2030, vol. 31.
Sindelar, K. et al., "Potential Antidepressants. Synthesis of 6,11 Dihydrodibenzo[b,e]thiepin-11-yl 4-(Dimethylaminomethyl)phenyl Ketone and of Some Related Compounds," Journal of Heterocyclic Chemistry, Sep.-Oct. 1989, pp. 1325-1330, vol. 26.
Xing, B. et al., "Multivalent Antibiotics Via Metal Complexes: Potent Divalent Vancomycins Against Vancomycin-Resistant Enterococci," Journal of Medicinal Chemistry, 2003, pp. 4904-4909, vol. 46.
Ziyaev, A.A. et al., "Dimerization of N-Methylanabasine in the Presence of Raney Nickel," Chemistry of Heterocyclic Compounds, Sep. 1978, pp. 988-989, vol. 14, No. 9.

*Primary Examiner* — Anna Pagonakis
(74) *Attorney, Agent, or Firm* — Morrison & Foerster LLP

(57) ABSTRACT

Provided herein are compounds, pharmaceutical compositions and combination therapies for treatment of hepatitis C.

4 Claims, No Drawings

TRICYCLIC FUSED RING INHIBITORS OF HEPATITIS C

This application is the 35 USC §371 national stage entry of PCT/US2011/053759, filed Sep. 28, 2011 which claims the benefit of U.S. Provisional Application 61/387,974 filed Sep. 29, 2010, both of which are hereby incorporated herein in their entirety for all purposes.

FIELD OF THE INVENTION

The invention relates to compounds useful for inhibiting hepatitis C virus ("HCV") replication, particularly functions of the non-structural 5A ("NS5A") protein of HCV.

BACKGROUND OF THE INVENTION

HCV is a single-stranded RNA virus that is a member of the Flaviviridae family. The virus shows extensive genetic heterogeneity as there are currently seven identified genotypes and more than 50 identified subtypes. In HCV infected cells, viral RNA is translated into a polyprotein that is cleaved into ten individual proteins. At the amino terminus are structural proteins: the core (C) protein and the envelope glycoproteins, E1 and E2, and p7, an integral membrane protein that follows E1 and E2. Additionally, there are six non-structural proteins, NS2, NS3, NS4A, NS4B, NS5A and NS5B, which play a functional role in the HCV lifecycle. (see, for example, Lindenbach, B. D. and Rice, C. M. *Nature*. 436:933-938, 2005).

Infection by HCV is a serious health issue. It is estimated that 170 million people worldwide are chronically infected with HCV. HCV infection can lead to chronic hepatitis, cirrhosis, liver failure and hepatocellular carcinoma. Chronic HCV infection is thus a major worldwide cause of liver-related premature mortality.

The present standard of care treatment regimen for HCV infection involves interferon-alpha, alone or in combination with ribavirin. The treatment is cumbersome and sometimes has debilitating and severe side effects and many patients do not durably respond to treatment. New and effective methods of treating HCV infection are urgently needed.

SUMMARY OF THE INVENTION

Essential features of the NS5A protein of HCV make it an ideal target for inhibitors. The present invention describes a class of compounds targeting the NS5A protein and methods of their use to treat HCV infection in humans.

In a first aspect, compounds of formula I are provided:

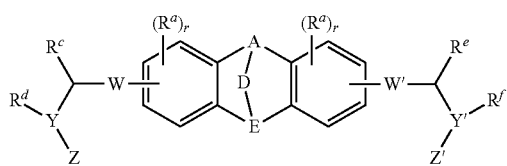

I wherein:
D is either present or absent and if present selected from the group consisting of —$CR_2CR_2$—, —$CR_2$—, —$NR^N$—, —O— and S wherein:
  $R^N$ is H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and, each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

A and E are:
  each independently —$CR_2$—, —CR=, —$CR_2$—$CR_2$—, —CR=CR—, —N=CR—, —$(CR_2)_a$—N($R^N$)—$(CR_2)_a$—, —$(CR_2)_a$—C(O)—N($R^N$)—$(CR_2)_a$—, —$(CR_2)_a$—N($R^N$)—C(O)—$(CR_2)_a$— or $(CR_2)_b$—O—$(CR_2)_b$—, wherein:
    $R^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;
    each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:
      two R's either both on a single C or on adjoining C's, together with the C or C's to which they are attached, optionally form a cycle, and
      where two R's are possible on a C, the C may optionally be linked to a single R with a double bond;
    each a and b are independently 0, 1, 2, or 3 with the proviso that if D is present both b's are not 0; and
    $R^N$ and R may be replaced by a bond to D if D is present,
  if D is absent, A and E can additionally each independently be a bond, —O—, —S—, —$S(O_2)$—, —S(O)—, —C(O)— or —N=, and
  with the proviso that if W and W' are both 5-membered rings, A and E are either both a bond or both other than a bond;

each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

W and W' are each independently selected from the group consisting of

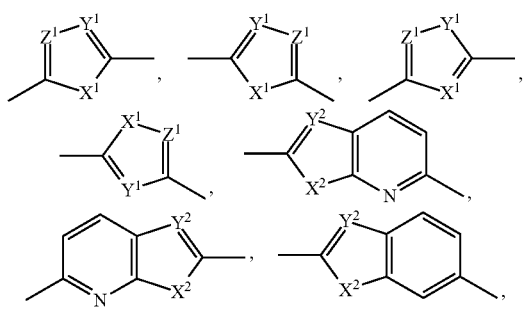

-continued

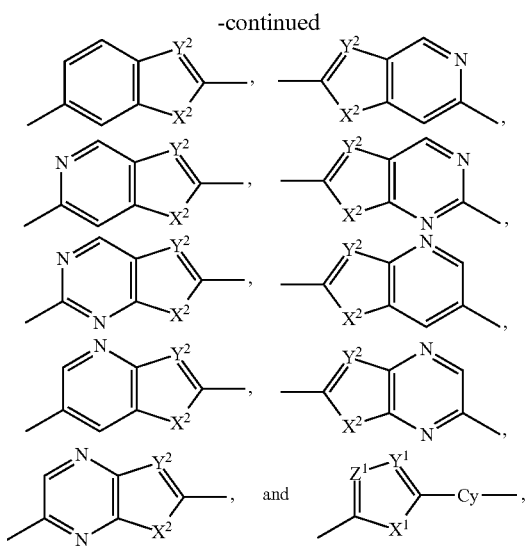

wherein:
X¹ is CH$_2$, NH, O or S,
Y¹, Y² and Z¹ are each independently CH or N,
X² is NH, O or S,
W and W' are each independently optionally substituted with one or more substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
Cy is a monocyclic, bicyclic or tricyclic 5- to 12-membered cycloalkyl, heterocycle, aryl group or heteroaryl group wherein up to three heteroatoms are independently N, S or O and which is optionally substituted with one or more substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each R$^c$, R$^d$, R$^e$ and R$^f$ is independently selected from the group consisting of: hydrogen, C$_1$ to C$_8$ alkyl, C$_1$ to C$_8$ heteroalkyl, aralkyl and a 4- to 8-membered ring which may be cycloalkyl, heterocycle, heteroaryl or aryl, wherein,
each hetero atom, if present, is independently N, O or S,
each of R$^c$, R$^d$, R$^e$ and R$^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S,
R$^c$ and R$^d$ are optionally joined to form a 4- to 8-membered heterocycle which is optionally fused to another 3- to 5-membered heterocycle or heteroaryl ring, and
R$^e$ and R$^f$ are optionally joined to form a 4- to 8-membered heterocycle which is optionally fused to another 3- to 5-membered heterocycle or heteroaryl ring;
Y and Y' are each independently carbon or nitrogen; and
Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein,
U is selected from the group consisting of —C(O)—, —C(S)— and —S(O)$_2$—,
each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl,
R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl,
optionally, R$^7$ and R$^8$ together form a 4-7 membered ring,
each t is independently 0, 1, 2, 3, or 4, and
u is 0, 1, or 2.

In a first embodiment of the first aspect, one or both of W and W' are selected from the group consisting of

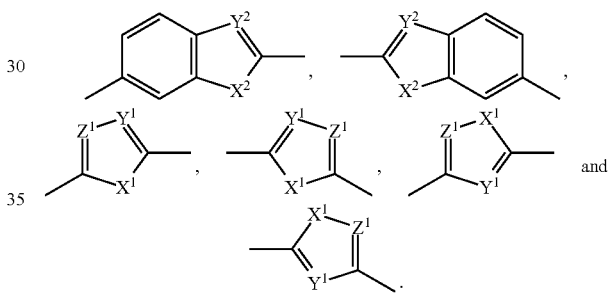

In a second embodiment of the first aspect, one or both of W and W' are selected from the group consisting of

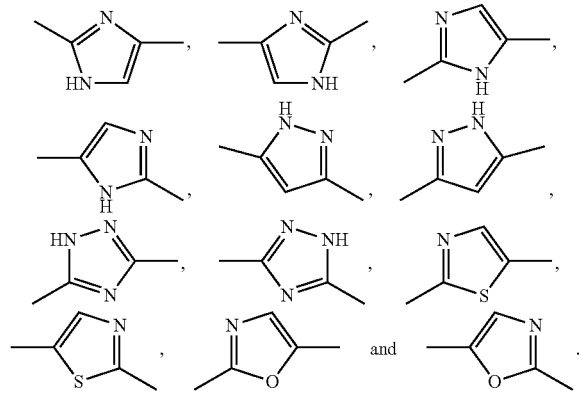

In a third embodiment of the first aspect, R$^c$, R$^d$, R$^e$ and R$^f$ are each independently selected from the group consisting of: hydrogen, C$_1$ to C$_8$ alkyl and C$_1$ to C$_8$ heteroalkyl, wherein,
each hetero atom, if present, is independently N, O or S,
R$^c$ and R$^d$ are optionally joined to form a 4- to 8-membered heterocycle which is optionally fused to another 3- to 6-membered heterocycle, and $R^e$ and $R^f$ are optionally joined to form a 4- to 8-membered heterocycle which is optionally fused to another 3- to 6-membered heterocycle.

In a fourth embodiment of the first aspect, one or both of $R^c$ and $R^d$ or $R^e$ and $R^f$ are optionally joined to form a 4- to 8-membered heterocycle which is optionally fused to another 3- to 6-membered heterocycle.

In a fifth embodiment of the first aspect, $R^c$ and $R^d$ are joined and form a heterocyclic fused ring system selected from the group consisting of:

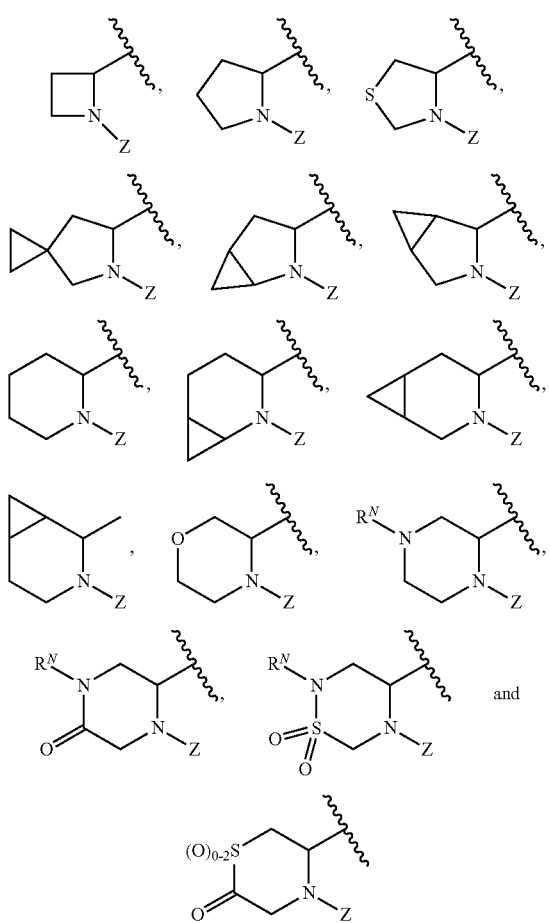

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a sixth embodiment of the first aspect, $R^e$ and $R^f$ are joined and form a heterocyclic fused ring system selected from the group consisting of:

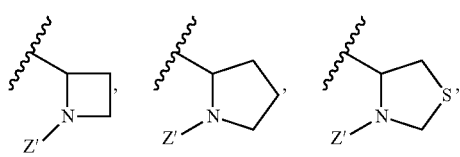

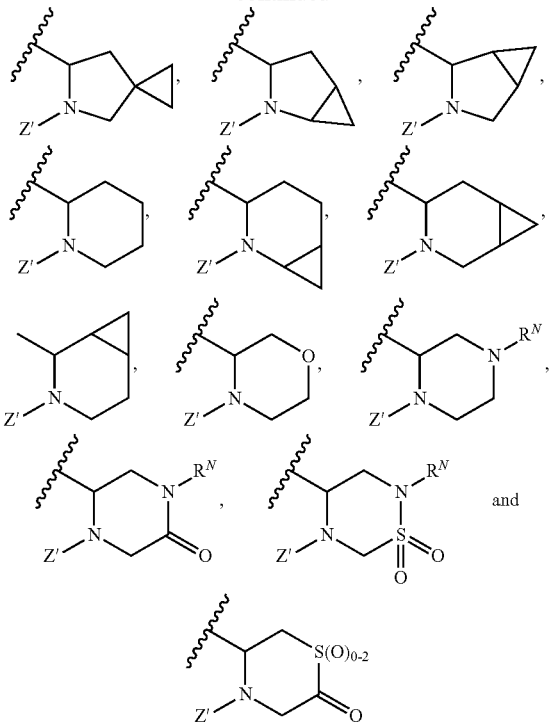

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a second aspect of the invention, compounds have formula II:

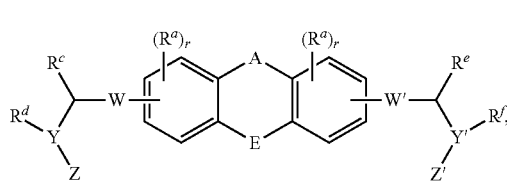

wherein:
A and E are:
each independently a bond, —O—, —S—, —S(O$_2$)—, —S(O)—, —C(O)—, —N=, —CR$_2$—, —CR=, —CR$_2$—CR$_2$—, —CR=CR—, —N=CR—, —(CR$_2$)$_a$—N(R$^N$)—(CR$_2$)$_a$—, —(CR$_2$)$_a$—C(O)—N(R$^N$)—(CR$_2$)$_a$—, —(CR$_2$)$_a$—N(R$^N$)—C(O)—(CR$_2$)$_a$— or —(CR$_2$)$_b$—O—(CR$_2$)$_b$—, wherein:
R$^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;
each R is independently selected from the group consisting of hydrogen, —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:

two R's either both on a single C or on adjoining C's, together with the C or C's to which they are attached, optionally form a cycle, and
where two R's are possible on a C, the C may optionally be linked to a single R with a double bond; and
each a and b are independently 0, 1, 2, or 3; and
with the proviso that if W and W' are both 5-membered rings, A and E are either both a bond or both other than a bond;
each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each r is independently 0, 1, 2 or 3;
W and W' are each independently selected from the group consisting of

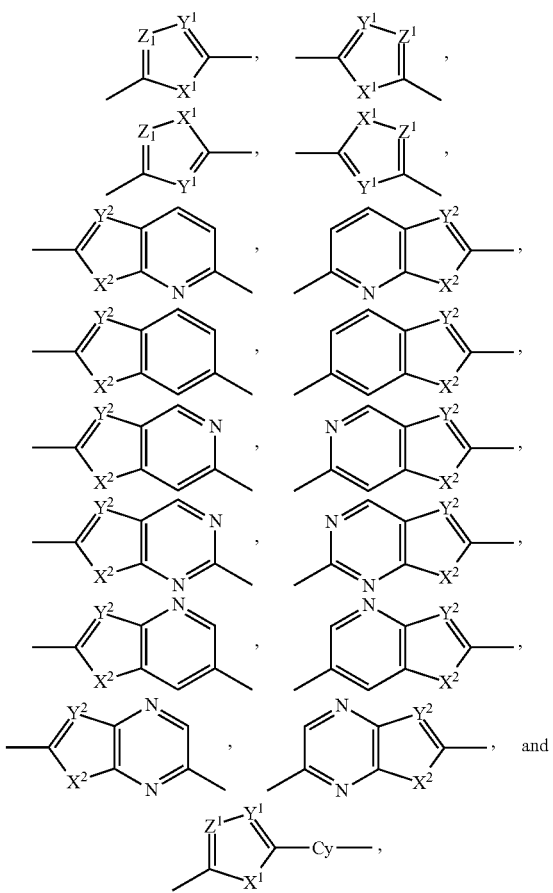

wherein:
$X^1$ is CH$_2$, NH, O or S,
$Y^1$, $Y^2$ and $Z^1$ are each independently CH or N,
$X^2$ is NH, O or S,
W and W' are each independently optionally substituted with one or more substituents selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and Cy is a monocyclic, bicyclic or tricyclic 5- to 12-membered cycloalkyl, heterocycle, aryl group or heteroaryl group wherein up to three heteroatoms are independently N, S or O and which is optionally substituted with one or more substituents selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids,
—[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the second aspect, compounds of formula IIa are provided:

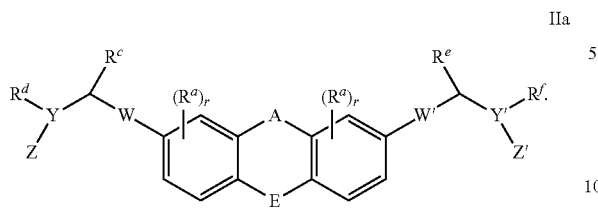

IIa

In a second embodiment of the second aspect, compounds of formula IIb are provided:

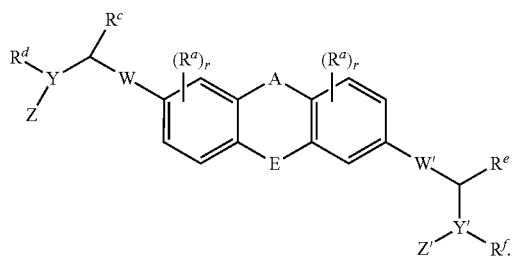

IIb

In a third embodiment of the second aspect, both A and E are —O—.

In a fourth embodiment of the second aspect, A is —O— and E is —CH$_2$—, —C(CH$_3$)$_2$—, —C(CH$_2$CH$_2$)— or —C(O)—.

In a fifth embodiment of the second aspect, W in formula IIa or IIb is

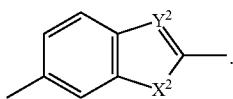

In a sixth embodiment of the second aspect, W' in formula IIa or IIb is

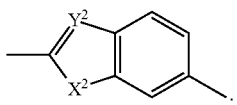

In a seventh embodiment of the second aspect, in compounds of IIa or IIb, W is

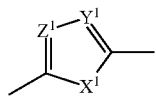

and W' is

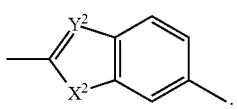

In an eighth embodiment of the second aspect, in compounds of IIa or IIb, W is

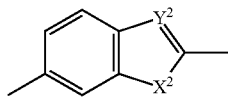

and W'

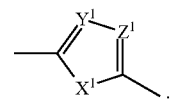

In a ninth embodiment of the second aspect, X$^1$ is —NH— and Y$^1$ or Z$^1$ is —N—.

In a tenth embodiment of the second aspect, X$^2$ is —NH— and Y$^2$ is —N—.

In an eleventh embodiment of the second aspect, R$^e$ and R$^f$ are joined and form

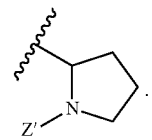

In a twelfth embodiment of the second aspect, R$^c$ and R$^d$ are joined and form

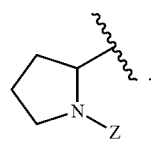

In a thirteenth embodiment of the second aspect, R$^e$ and R$^f$ are joined and form

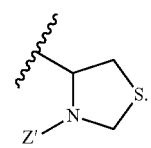

In a fourteenth embodiment of the second aspect, R$^c$ and R$^d$ are joined and form

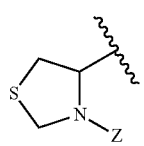

In a fifteenth embodiment of the second aspect, $R^e$ and $R^f$ are joined and form

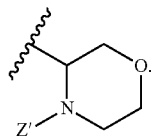

In a sixteenth embodiment of the second aspect, $R^c$ and $R^d$ are joined and form

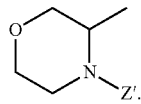

In a third aspect of the invention, compounds of formula III are provided:

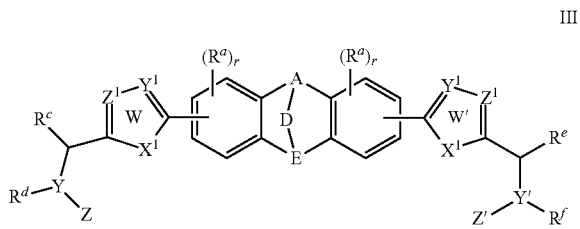

wherein:
D is either present or absent and if present selected from the group consisting of —$CR_2CR_2$—, —$CR_2$—, —$NR^N$—, —O— and —S— wherein $R^N$ is H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide and each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

A and E are:
each independently —$CR_2$—, —CR=, —$CR_2$—$CR_2$—, —CR=CR—, —N=CR—, —$(CR_2)_a$—N$(R^N)$—$(CR_2)_a$—, —$(CR_2)_a$—C(O)—N$(R^N)$—$(CR_2)_a$—, —$(CR_2)_a$—N$(R^N)$—C(O)—$(CR_2)_a$— or —$(CR_2)_b$—O—$(CR_2)_b$—, wherein:
$R^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;
each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
wherein:
two R's either both on a single C or on adjoining C's, together with the C or C's to which they are attached, optionally form a cycle, and
where two R's are possible on a C, the C may optionally be linked to a single R with a double bond;
each a and b are independently 0, 1, 2, or 3 with the proviso that if D is present both b's are not 0; and $R^N$ and R may be replaced by a bond to D if D is present,
if D is absent, A and E can additionally each independently be a bond, —O—, —S—, —$S(O_2)$—, —S(O)—, —C(O)— or —N=, and
with the proviso that if W and W' are both 5-membered rings, A and E are either both a bond or both other than a bond;
each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each r is independently 0, 1, 2 or 3;
$X^1$ is $CH_2$, NH, O or S,
$Y^1$ and $Z^1$ are each independently CH or N,
W and W' are each independently optionally substituted with one or more substituents selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein,
each hetero atom, if present, is independently N, O or S,
each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
$R^c$ and $R^d$ are optionally joined to form a 4- to 8-membered heterocycle which is optionally fused to another 3- to 5-membered heterocycle or heteroaryl ring, and
$R^e$ and $R^f$ are optionally joined to form a 4- to 8-membered heterocycle which is optionally fused to another 3- to 5-membered heterocycle or heteroaryl ring;
Y and Y' are each independently carbon or nitrogen; and
Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids,
—[U—$(CR^4_2)_t$—$NR^5$—$C(R^4_2)_t]_u$—U—$(CR^4_2)_t$—$NR^7$—$(CR^4_2)_t$—$R^8$, —U—$(CR^4_2)_t$—$R^8$, and —[U—$(CR^4_2)_t$—$NR^5$—$(CR^4_2)_t]_u$—U—$(CR^4_2)_t$—O—$(CR^4_2)_t$—$R^8$, wherein,
U is selected from the group consisting of —C(O)—, —C(S)— and —$S(O)_2$—,
each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl,
$R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N—$R^{81}_2$, —$S(O)_2$—$R^{81}$ and —$S(O)_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the third aspect, compounds of formula IIIa are provided:

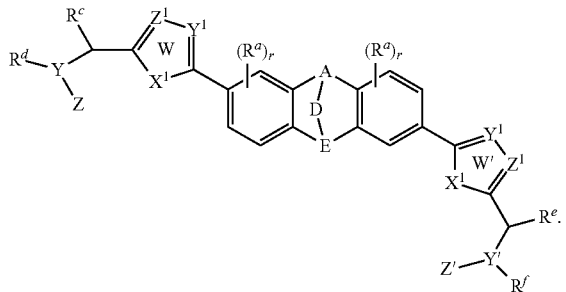

IIIa

In a second embodiment of the third aspect, compounds of formula IIIb are provided:

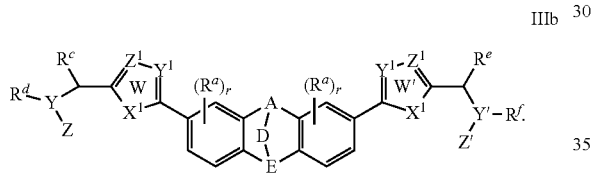

IIIb

In a third embodiment of the third aspect, both A and E are —O— and D is absent.

In a fourth embodiment of the third aspect, A is —O—, D is absent and E is —$CH_2$—, —$C(CH_3)_2$—, —$C(CH_2CH_2)$— or —C(O)—.

In a fifth embodiment of the third aspect, one or both of $X^1$ are —S—.

In a sixth embodiment of the third aspect, one or both of $X^1$ are —O—.

In a seventh embodiment of the third aspect, one or both of $X^1$ are —NH—.

In an eighth embodiment of the third aspect, one or both of $Y^1$ is —N—.

In a ninth embodiment of the third aspect, one or both of $Z^1$ is —N—.

In a fourth aspect of the invention, compounds of formula IV are provided:

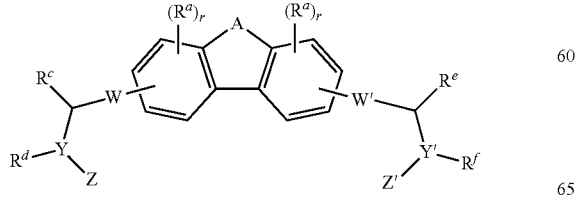

IV wherein:

A is a bond, —$CR_2$—, —CR=, —$CR_2$—$CR_2$—, —CR=CR—, —N=CR—, —$(CR_2)_a$—$N(R^N)$—$(CR_2)_a$—, —O—, —S—, —$S(O_2)$—, —S(O)—, —C(O)—, —N=, —$(CR_2)_a$—C(O)—$N(R^N)$—$(CR_2)_a$—, —$(CR_2)_a$—$N(R^N)$—C(O)—$(CR_2)_a$— or —$(CR_2)_b$—O—$(CR_2)_b$—, wherein:

$R^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:

two R's either both on a single C or on adjoining C's, together with the C or C's to which they are attached, optionally form a cycle, and where two R's are possible on a C, the C may optionally be linked to a single R with a double bond;

each a and b are independently 0, 1, 2, or 3; and with the proviso that if W and W' are both 5-membered rings, A is a bond;

each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

W and W' are each independently selected from the group consisting of

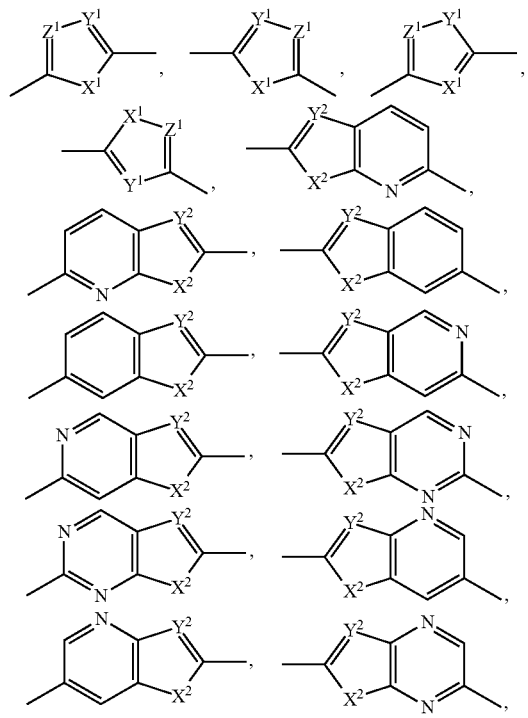

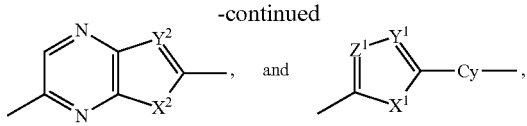

-continued

, and wherein:
X$^1$ is CH$_2$, NH, O or S,
Y$^1$, Y$^2$ and Z$^1$ are each independently CH or N,
X$^2$ is NH, O or S,
W and W' are each independently optionally substituted with one or more substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
Cy is a monocyclic, bicyclic or tricyclic 5- to 12-membered cycloalkyl, heterocycle, aryl group or heteroaryl group wherein up to three heteroatoms are independently N, S or O and which is optionally substituted with one or more substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each R$^c$, R$^d$, R$^e$ and R$^f$ is independently selected from the group consisting of: hydrogen, C$_1$ to C$_8$ alkyl, C$_1$ to C$_8$ heteroalkyl, aralkyl and a 4- to 8-membered ring which may be cycloalkyl, heterocycle, heteroaryl or aryl, wherein,
each hetero atom, if present, is independently N, O or S,
each of R$^c$, R$^d$, R$^e$ and R$^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S,
R$^c$ and R$^d$ are optionally joined to form a 4- to 8-membered heterocycle which is optionally fused to another 3- to 5-membered heterocycle or heteroaryl ring, and
R$^e$ and R$^f$ are optionally joined to form a 4- to 8-membered heterocycle which is optionally fused to another 3- to 5-membered heterocycle or heteroaryl ring;
Y and Y' are each independently carbon or nitrogen; and
Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids,
[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—CR$^4_2$)$_t$—R$^8$, wherein,
U is selected from the group consisting of —C(O)—, —C(S)— and —S(O)$_2$—,
each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl,
R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl,
optionally, R$^7$ and R$^8$ together form a 4-7 membered ring,
each t is independently 0, 1, 2, 3, or 4, and
u is 0, 1, or 2.

In a first embodiment of the fourth aspect, compounds of formula IVa are provided:

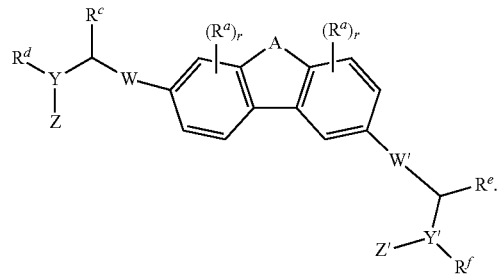

IVa

In a second embodiment of the fourth aspect, compounds of formula IVb are provided:

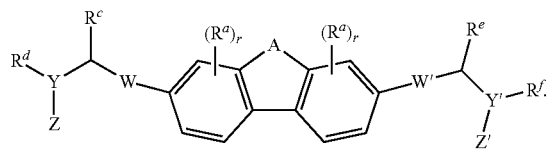

IVb

In a third embodiment of the fourth aspect, A is —S—.
In a fourth embodiment of the fourth aspect, A is —S(O)$_2$—.
In a fifth embodiment of the fourth aspect, A is —O—.
In a sixth embodiment of the fourth aspect, A is —CH$_2$—.
In a seventh embodiment of the fourth aspect, A is —CH$_2$CH$_2$—.
In a fifth aspect of the embodiment, compounds of formula V are provided:

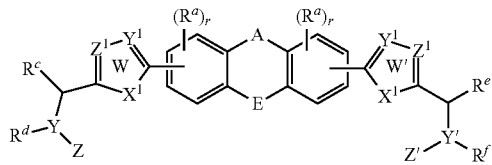

V wherein:
A and E are:
each independently a bond, —CR$_2$—, —CR=, —CR$_2$—CR$_2$—, —CR=CR—, —N=CR—, —(CR$_2$)$_a$—C(O)—N(R$^N$)—(CR$_2$)$_a$—, —(CR$_2$)$_a$—N(R$^N$)—C(O)—(CR$_2$)$_a$—(CR$_2$)$_a$—N(R$^N$) —(CR$_2$)$_a$—, —(CR$_2$)$_b$—O—(CR$_2$)$_b$—, —O—, —S—, —S(O)$_2$—, —S(O)—, —C(O)— or —N=,
wherein:
R$^N$ is selected from the group consisting of H, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:

two R's either both on a single C or on adjoining C's, together with the C or C's to which they are attached, optionally form a cycle, and where two R's are possible on a C, the C may optionally be linked to a single R with a double bond;

each a and b are independently 0, 1, 2, or 3; and with the proviso that A and E are either both a bond or both other than a bond;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

X$^1$ is CH$_2$, NH, O or S,

Y$^1$, and Z$^1$ are each independently CH or N,

W and W' are each independently optionally substituted with one or more substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and each R$^c$, R$^d$, R$^e$ and R$^f$ is independently selected from the group consisting of: hydrogen, C$_1$ to C$_8$ alkyl, C$_1$ to C$_8$ heteroalkyl, aralkyl and a 4- to 8-membered ring which may be cycloalkyl, heterocycle, heteroaryl or aryl, wherein, each hetero atom, if present, is independently N, O or S, each of R$^c$, R$^d$, R$^e$ and R$^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S, R$^c$ and R$^d$ are optionally joined to form a 4- to 8-membered heterocycle which is optionally fused to another 3- to 5-membered heterocycle or heteroaryl ring, and R$^e$ and R$^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl, R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, optionally, R$^7$ and R$^8$ together form a 4-7 membered ring, each t is independently 0, 1, 2, 3, or 4, and u is 0, 1, or 2.

In a first embodiment of the fifth aspect, compounds of formula Va are provided:

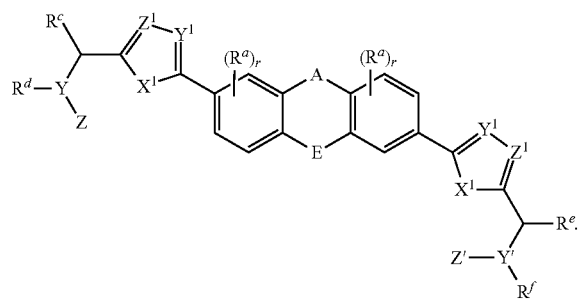

Va

In a second embodiment of the fifth aspect, compounds of formula Vb are provided:

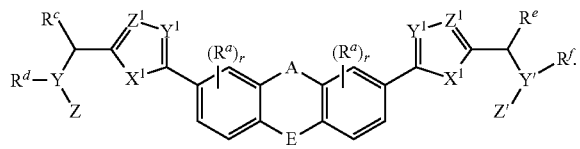

Vb

In a third embodiment of the fifth aspect, both A and E are —O—.

In a fourth embodiment of the fifth aspect, A is —O— and E is —CH$_2$—, —C(CH$_3$)$_2$—, —C(CH$_2$CH$_2$)— or —C(O)—.

In a fifth embodiment of the fifth aspect, one or both of X$^1$ are —S—.

In a sixth embodiment of the fifth aspect, one or both of X$^1$ are —O—.

In a seventh embodiment of the fifth aspect, one or both of X$^1$ are —NH—.

In an eighth embodiment of the fifth aspect, one or both of Y$^1$ are —N—.

In a ninth embodiment of the fifth aspect, one or both of Z$^1$ is —N—.

In tenth embodiment of the fifth aspect, R$^e$ and R$^f$ are joined and form

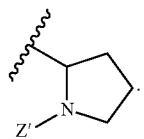

In an eleventh embodiment of the fifth aspect, $R^c$ and $R^d$ are joined and form

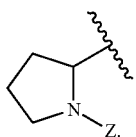

In a twelfth embodiment of the fifth aspect, $R^e$ and $R^f$ are joined and form

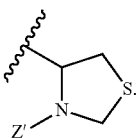

In a thirteenth embodiment of the fifth aspect, $R^c$ and $R^d$ are joined and form

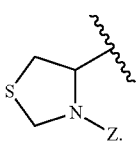

In a fourteenth embodiment of the fifth aspect, $R^e$ and $R^f$ are joined and form

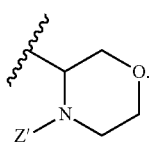

In a fifteenth embodiment of the fifth aspect, $R^c$ and $R^d$ are joined and form

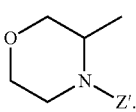

In a sixth aspect, compounds of formula VI are provided:

VI wherein:
A and E are:
  each independently —$CR_2$—, —$CR_2$—$CR_2$—, —CR=CR—, —N=CR—, —$(CR_2)_a$—$N(R^N)$—$(CR_2)_a$—, —$(CR_2)_a$—C(O)—$N(R^N)$—$(CR_2)_a$—, —$(CR_2)_a$—$N(R^N)$—C(O)—$(CR_2)_a$— or —$(CR_2)_b$—O—$(CR_2)_b$—, wherein:
    $R^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide,
    each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:
      two R's either both on a single C or on adjoining C's, together with the C or C's to which they are attached, optionally form a cycle, and
      where two R's are possible on a C, the C may optionally be linked to a single R with a double bond, and
    each a and b are independently 0, 1, 2, or 3 with the proviso that both b's are not 0; and
  each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
  each r is independently 0, 1, 2 or 3;
  $X^1$ is $CH_2$, NH, O or S,
  $Y^1$ and $Z^1$ are each independently CH or N,
  W and W' are each independently optionally substituted with one or more substituents selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
  each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein,
    each hetero atom, if present, is independently N, O or S,
    each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
    $R^c$ and $R^d$ are optionally joined to form a 4- to 8-membered heterocycle which is optionally fused to another 3- to 5-membered heterocycle or heteroaryl ring, and
    $R^e$ and $R^f$ are optionally joined to form a 4- to 8-membered heterocycle which is optionally fused to another 3- to 5-membered heterocycle or heteroaryl ring;
  Y and Y' are each independently carbon or nitrogen; and
  Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids,
    —[U—$(CR^4_2)_t$—$NR^5$—C$(R^4_2)_t]_u$—U—$(CR^4_2)_t$—$NR^7$—$(CR^4_2)_t$—$R^8$, —U—$(CR^4_2)_t$—$R^8$, and —[U—$(CR^4_2)_t$—$NR^5$—$(CR^4_2)_t]_u$—U—$(CR^4_2)_t$—O—$(CR^4_2)_t$—$R^8$, wherein, U is selected from the group consisting of —C(O)—, —C(S)— and —S(O)$_2$—, each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl, R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}$$_2$, —S(O)$_2$—R$^{81}$ and —S(O)$_2$—N—R$^{81}$$_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, optionally, R$^7$ and R$^8$ together form a 4-7 membered ring, each t is independently 0, 1, 2, 3, or 4, and u is 0, 1, or 2.

In a first embodiment of the sixth aspect, compounds of formula VIa are provided:

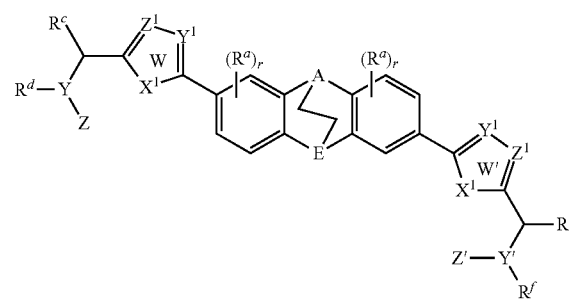

VIa

In a second embodiment of the sixth aspect, compounds of formula VIb are provided:

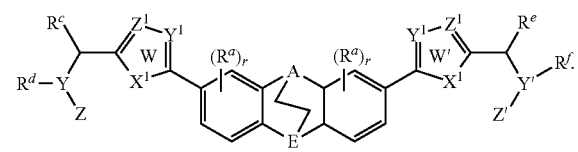

VIb

In a third embodiment of the sixth aspect, compounds of formula VII are provided:

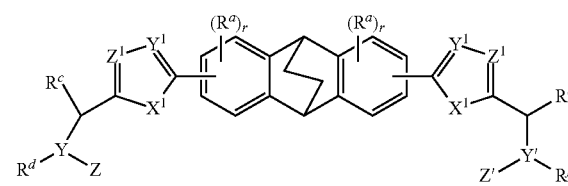

VII

In a fourth embodiment of the sixth aspect, compounds of formula VIIa are provided:

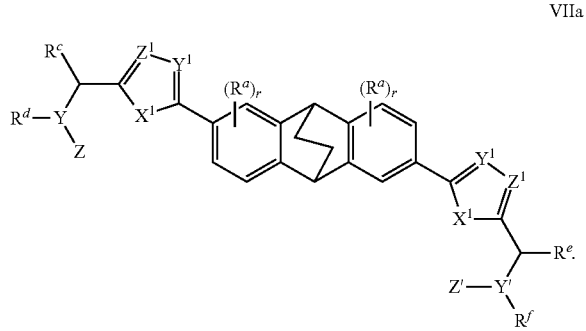

VIIa

In a fifth embodiment of the sixth aspect, compounds of formula VIIb are provided:

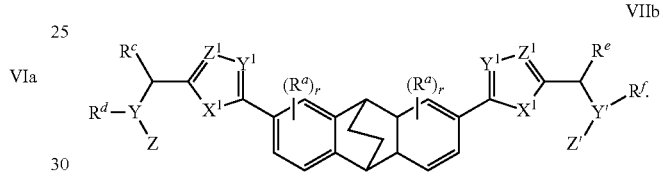

VIIb

In a sixth embodiment of the sixth aspect, compounds of formula VIII are provided:

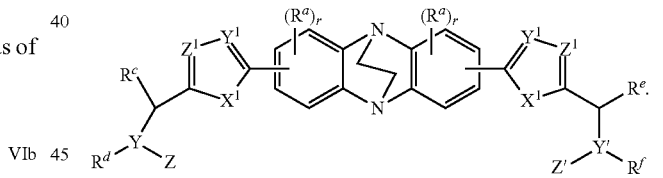

VIII

In a seventh embodiment of the sixth aspect, compounds of formula VIIIa are provided:

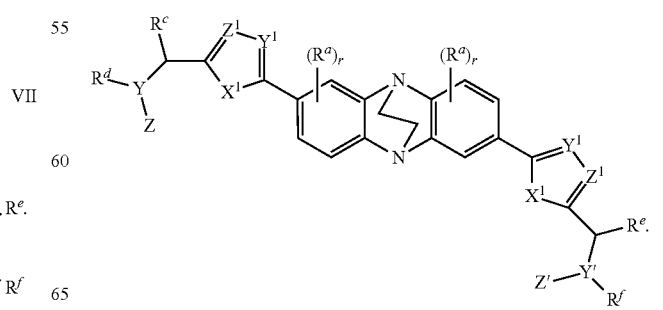

VIIIa

In an eighth embodiment of the sixth aspect, compounds of formula VIIIb are provided:

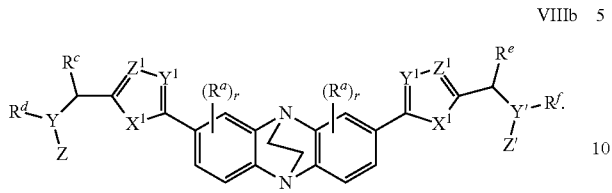

VIIIb

In a ninth embodiment of the sixth aspect, one or both of $X^1$ are —O—.

In a tenth embodiment of the sixth aspect, one or both of $X^1$ are —NH—.

In an eleventh embodiment of the sixth aspect, one or both of $X^1$ are —S—.

In a twelfth embodiment of the sixth aspect, one or both of $Z^1$ is —N—.

In a thirteenth embodiment of the sixth aspect, one or both of $Y^1$ is —N—.

In a seventh aspect of the invention, compounds of formula IX are provided:

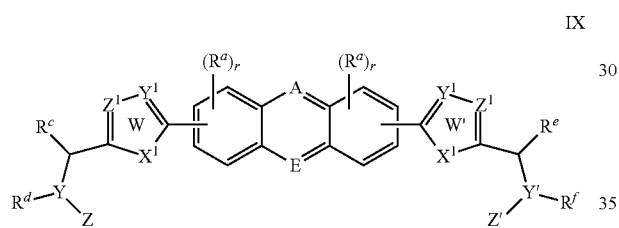

IX wherein:
  A and E are each independently —CR═ or —N═ wherein R is selected from the group consisting of hydrogen, —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
  each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
  each r is independently 0, 1, 2 or 3;
  $X^1$ is CH$_2$, NH, O or S,
  $Y^1$ and $Z^1$ are each independently CH or N,
  W and W' are each independently optionally substituted with one or more substituents selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
  each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S,
  each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
  $R^c$ and $R^d$ are optionally joined to form a 4- to 8-membered heterocycle which is optionally fused to another 3- to 5-membered heterocycle or heteroaryl ring, and
  $R^e$ and $R^f$ are optionally joined to form a 4- to 8-membered heterocycle which is optionally fused to another 3- to 5-membered heterocycle or heteroaryl ring;
Y and Y' are each independently carbon or nitrogen; and
Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids,
  —[U—(CR$^4_2$)$_t$—NR$^5$—C(R$^4_2$)$_t$]$_u$—U—(CR$^4_2$)$_t$—NR$^7$—(CR$^4_2$)$_t$—R$^8$,   —U—(CR$^4_2$)$_t$—R$^8$,   and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein,
  U is selected from the group consisting of —C(O)—, —C(S)— and —S(O)$_2$—,
  each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl,
  $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl,
  optionally, $R^7$ and $R^8$ together form a 4-7 membered ring,
  each t is independently 0, 1, 2, 3, or 4, and
  u is 0, 1, or 2.

In a first embodiment of the seventh aspect compounds of formula IXa are provided:

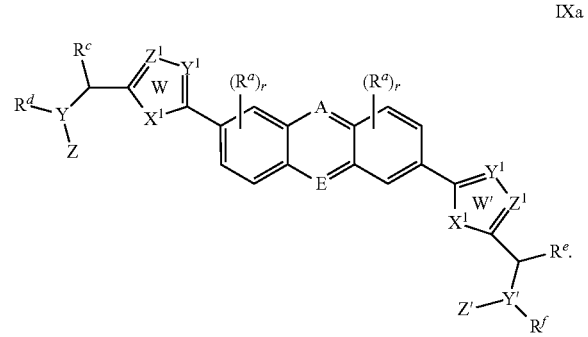

IXa

In a second embodiment of the seventh aspect compounds of formula IXb are provided:

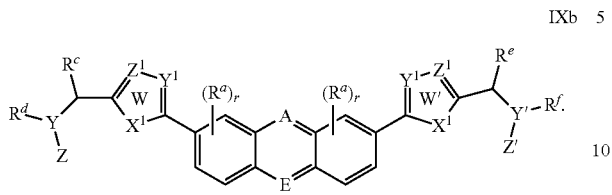

In a third embodiment of the seventh aspect A and E are —N=.

In a fourth embodiment of the seventh aspect, one or both of $X^1$ are —S—.

In a fifth embodiment of the seventh aspect, one or both of $X^1$ are —O—.

In a sixth embodiment of the seventh aspect, one or both of $X^1$ are —NH—.

In a seventh embodiment of the seventh aspect, one or both of $Y^1$ are —N—.

In an eighth embodiment of the seventh aspect, one or both of $Z^1$ is —N—.

In an eighth aspect of the invention, compounds of formula X are provided:

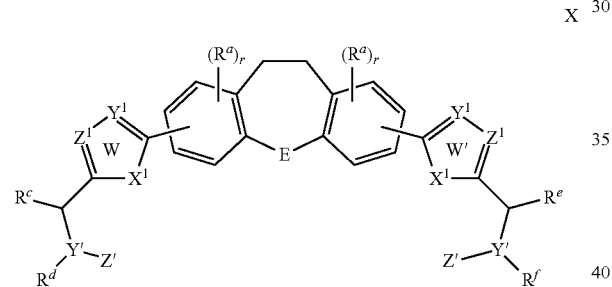

wherein:
E is —$CR_2$—, —CR=, —$CR_2$—$CR_2$—, —CR=CR—, —N=CR—, —$(CR_2)_a$—$N(R^N)$—$(CR_2)_a$—$(CR_2)_a$—C(O)—$N(R^N)$—$(CR_2)_a$—, —$(CR_2)_a$—$N(R^N)$—C(O)—$(CR_2)_a$—, or —$(CR_2)_b$—O—$(CR_2)_b$—, wherein:
  $R^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide,
  each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:
    two R's either both on a single C or on adjoining C's, together with the C or C's to which they are attached, optionally form a cycle, and
    where two R's are possible on a C, the C may optionally be linked to a single R with a double bond;
  each a and b are independently 0, 1, 2, or 3;
  each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
  each r is independently 0, 1, 2 or 3;
  $X^1$ is $CH_2$, NH, O or S,
  $Y^1$ and $Z^1$ are each independently CH or N,
  W and W' are each independently optionally substituted with one or more substituents selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
  each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein,
    each hetero atom, if present, is independently N, O or S,
    each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
    $R^c$ and $R^d$ are optionally joined to form a 4- to 8-membered heterocycle which is optionally fused to another 3- to 5-membered heterocycle or heteroaryl ring, and
    $R^e$ and $R^f$ are optionally joined to form a 4- to 8-membered heterocycle which is optionally fused to another 3- to 5-membered heterocycle or heteroaryl ring;
  Y and Y' are each independently carbon or nitrogen; and
  Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids,
    —$[U—(CR^4_2)_t—NR^5—C(R^4_2)_t]_u—U—(CR^4_2)_t—NR^7—(CR^4_2)_t—R^8$, —$U—(CR^4_2)_t—R^8$, and —$[U—(CR^4_2)_t—NR^5—(CR^4_2)_t]_u—U—(CR^4_2)_t—O—(CR^4_2)_t—R^8$, wherein,
    U is selected from the group consisting of —C(O)—, —C(S)— and —$S(O)_2$—,
    each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl,
    $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N—$R^{81}_2$, —$S(O)_2$—$R^{81}$ and —$S(O)_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl,
    optionally, $R^7$ and $R^8$ together form a 4-7 membered ring,
    each t is independently 0, 1, 2, 3, or 4, and
    u is 0, 1, or 2.

In a first embodiment of the eighth aspect, compounds of formula Xa are provided:

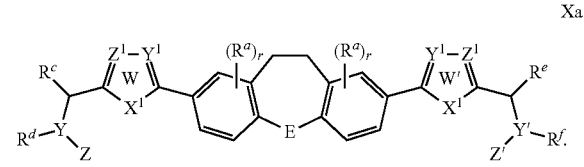

In a second embodiment of the eighth aspect, compounds of formula Xb are provided:

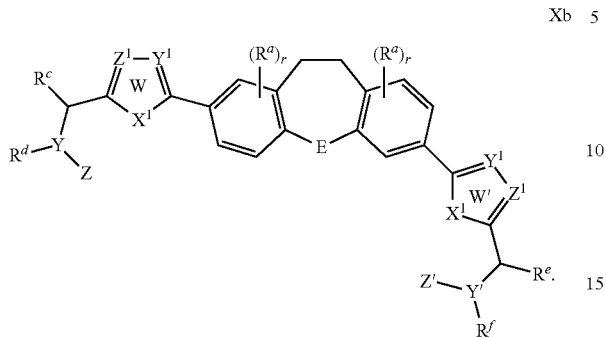

In a third embodiment of the eighth aspect, one or both of $X^1$ are —S—.

In a fourth embodiment of the eighth aspect, one or both of $X^1$ are —O—.

In a fifth embodiment of the eighth aspect, one or both of $X^1$ are —NH—.

In a sixth embodiment of the eighth aspect, one or both of $Y^1$ are —N—.

In a seventh embodiment of the eighth aspect, one or both of $Z^1$ is —N—.

In a ninth aspect of the invention, compounds of formula XI are provided:

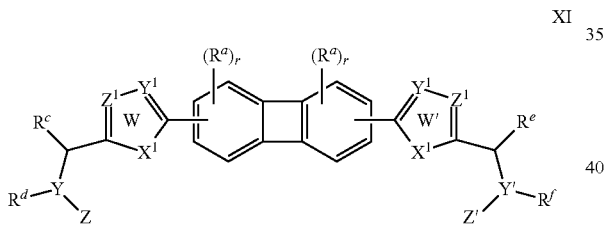

wherein:

each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

$X^1$ is CH$_2$, NH, O or S, $Y^1$ and $Z^1$ are each independently CH or N,

W and W' are each independently optionally substituted with one or more substituents selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—(CR$^4_2$)$_t$—NR$^5$—C(R$^4_2$)$_t$]$_u$—U—(CR$^4_2$)$_t$—NR$^5$—(CR$^4_2$)$_t$—R$^8$,    —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the ninth aspect, compounds of formula XIa are provided:

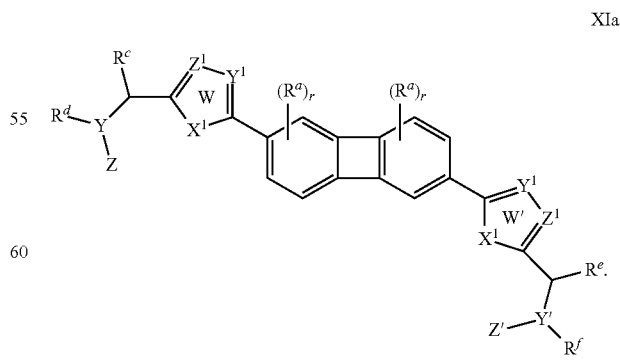

In a second embodiment of the ninth aspect, compounds of formula XIb are provided:

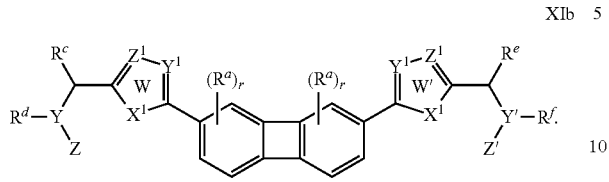

XIb

In a third embodiment of the ninth aspect, one or both of $X^1$ are —S—.

In a fourth embodiment of the ninth aspect, one or both of $X^1$ are —O—.

In a fifth embodiment of the ninth aspect, one or both of $X^1$ are —NH—.

In a sixth embodiment of the ninth aspect, one or both of $Y^1$ are —N—.

In a seventh embodiment of the ninth aspect, one or both of $Z^1$ is —N—.

In a tenth aspect of the invention, compounds of formula XII are provided:

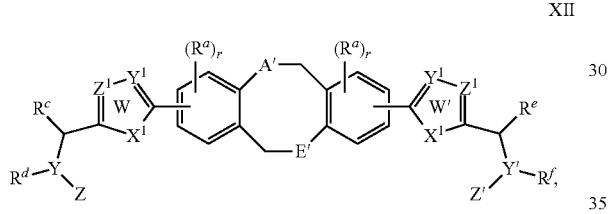

XII wherein:
A' and E' are each independently —CR$_2$—, —CR=, —N(R$^N$)—, —O—, —S—, —S(O$_2$)—, —S(O)—, or —N=, wherein:
  R$^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and
  R is selected from the group consisting of hydrogen, —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each r is independently 0, 1, 2 or 3;
$X^1$ is CH$_2$, NH, O or S,
$Y^1$ and $Z^1$ are each independently CH or N,
W and W' are each independently optionally substituted with one or more substituents selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein,
  each hetero atom, if present, is independently N, O or S,
  each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
  $R^c$ and $R^d$ are optionally joined to form a 4- to 8-membered heterocycle which is optionally fused to another 3- to 5-membered heterocycle or heteroaryl ring, and
  $R^e$ and $R^f$ are optionally joined to form a 4- to 8-membered heterocycle which is optionally fused to another 3- to 5-membered heterocycle or heteroaryl ring;
Y and Y' are each independently carbon or nitrogen; and
Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids,
—[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein,
  U is selected from the group consisting of —C(O)—, —C(S)— and —S(O)$_2$—,
  each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl,
  $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl,
  optionally, $R^7$ and $R^8$ together form a 4-7 membered ring,
  each t is independently 0, 1, 2, 3, or 4, and
  u is 0, 1, or 2.

In a first embodiment of the tenth aspect, compounds of formula XIIa are provided:

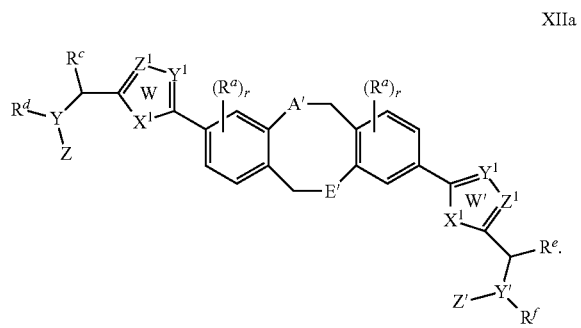

XIIa

In a second embodiment of the tenth aspect, compounds of formula XIIb are provided:

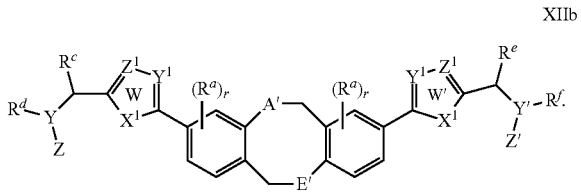

XIIb

In a third embodiment of the tenth aspect, one or both of $X^1$ are —S—.

In a fourth embodiment of the tenth aspect, one or both of $X^1$ are —O—.

In a fifth embodiment of the tenth aspect, one or both of $X^1$ are —NH—.

In a sixth embodiment of the tenth aspect, one or both of $Y^1$ are —N—.

In a seventh embodiment of the tenth aspect, one or both of $Z^1$ is —N—.

In an eleventh aspect of the invention Z and Z' in any of the previous aspects are each 1-3 amino acids.

In a first embodiment of the eleventh aspect, the amino acids are all in the D or all in the L configuration.

In a second embodiment of the eleventh aspect, Z and Z' are each independently selected from the group consisting of $[U-(CR^4{}_2)_t-NR^5-(CR^4{}_2)_t]_u-U-(CR^4{}_2)_t-NR^7-(CR^4{}_2)_t-R^8$,
—$U-(CR^4{}_2)_t-R^8$ and —$[U-(CR^4{}_2)_t-NR^5-(CR^4{}_2)_t]_u-U-(CR^4{}_2)_t-O-(CR^4{}_2)_t-R^8$.

In a third embodiment of the eleventh aspect, one or both of Z and Z' are —$[U-(CR^4{}_2)_t-NR^5-(CR^4{}_2)_t]_u-U-(CR^4{}_2)_t-NR^7-(CR^4{}_2)_t-R^8$.

In a fourth embodiment of the eleventh aspect, one or both of Z and Z' are —$U-(CR^4{}_2)_t-NR^5-(CR^4{}_2)_t-U-(CR^4{}_2)_t-NR^7-(CR^4{}_2)_t-R^8$.

In a fifth embodiment of the eleventh aspect, one or both of Z and Z' are —$U-(CR^4{}_2)_t-NR^7-(CR^4{}_2)_t-R^8$.

In a sixth embodiment of the eleventh aspect, one or both of Z and Z' are —$[C(O)-(CR^4{}_2)_t-NR^5-(CR^4{}_2)_t]_u-U-(CR^4{}_2)_t-NR^7-(CR^4{}_2)_t-R^8$.

In a seventh embodiment of the eleventh aspect, one or both of Z and Z' are —$C(O)-(CR^4{}_2)_t-NR^5-(CR^4{}_2)_t-U-(CR^4{}_2)_t-NR^7-(CR^4{}_2)_t-R^8$.

In an eighth embodiment of the eleventh aspect, one or both of Z and Z' are —$[C(O)-(CR^4{}_2)_t-NR^5-(CR^4{}_2)_t]_u-C(O)-(CR^4{}_2)_t-NR^7-(CR^4{}_2)_t-R^8$.

In a ninth embodiment of the eleventh aspect, one or both of Z and Z' are —$C(O)-(CR^4{}_2)_t-NR^5-(CR^4{}_2)_t-C(O)-(CR^4{}_2)_t-NR^7-(CR^4{}_2)_t-R^8$.

In a tenth embodiment of the eleventh aspect, one or both of Z and Z' are —$C(O)-(CR^4{}_2)_t-NR^7-(CR^4{}_2)_t-R^8$.

In an eleventh embodiment of the eleventh aspect, one or both of Z and Z' are —$C(O)-(CR^4{}_2)_n-NR^7-(CR^4{}_2)_n-C(O)-R^{81}$.

In a twelfth embodiment of the eleventh aspect, one or both of Z and Z' are —$C(O)-(CR^4{}_2)_n-NR^7-C(O)-R^{81}$.

In a thirteenth embodiment of the eleventh aspect, one or both of Z and Z' are —$C(O)-(CR^4{}_2)_n-NR^7-(CR^4{}_2)_n-C(O)-O-R^{81}$.

In a fourteenth embodiment of the eleventh aspect, one or both of Z and Z' are —$C(O)-(CR^4{}_2)_n-NR^7-C(O)-O-R^{81}$.

In a fifteenth embodiment of the eleventh aspect, one or both of Z and Z' are —$U-(CR^4{}_2)_t-R^8$.

In a sixteenth embodiment of the eleventh aspect, one or both of Z and Z' are —$C(O)-(CR^4{}_2)_t-R^8$.

In a seventeenth embodiment of the eleventh aspect, one or both of Z and Z' are —$[U-(CR^4{}_2)_t-NR^5-(CR^4{}_2)_t]_u-U-(CR^4{}_2)_t-O-(CR^4{}_2)_t-R^8$.

In an eighteenth embodiment of the eleventh aspect, one or both of Z and Z' are —$U-(CR^4{}_2)_t-NR^5-(CR^4{}_2)_t-U-(CR^4{}_2)_t-O-(CR^4{}_2)_t-R^8$.

In a nineteenth embodiment of the eleventh aspect, one or both of Z and Z' are —$C(O)-(CR^4{}_2)_t-NR^5-(CR^4{}_2)_t-C(O)-(CR^4{}_2)_t-O-(CR^4{}_2)_t-R^8$.

In a twentieth embodiment of the eleventh aspect, one or both of Z and Z' are —$U-(CR^4{}_2)_t-O-(CR^4{}_2)_t-R^8$.

In a twenty-first embodiment of the eleventh aspect, one or both of Z and Z' are —$C(O)-(CR^4{}_2)_t-O-(CR^4{}_2)_t-R^8$.

In a twenty-second embodiment of the eleventh aspect, one or both of Z and Z' are —$C(O)-(CR^4{}_2)_n-NR^7-R^8$ wherein $R^7$ and $R^8$ together form a 4-7 membered ring.

A twelfth aspect of the invention provides a pharmaceutical composition comprising the compounds of the invention.

A thirteenth aspect of the invention provides use of the compounds of the invention in the manufacture of a medicament.

In a first embodiment of the thirteenth aspect the medicament is for the treatment of hepatitis C.

A fourteenth aspect of the invention provides a method of treating hepatitis C comprising administering to a subject in need thereof, a therapeutically effective amount of a compound of the invention.

DETAILED DESCRIPTION

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) "Advanced Organic Chemistry 5$^{th}$ Ed." Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology.

The term "alkanoyl" as used herein contemplates a carbonyl group with a lower alkyl group as a substituent.

The term "alkenyl" as used herein contemplates substituted or unsubstituted, straight and branched chain alkene radicals, including both the E- and Z-forms, containing from two to eight carbon atoms. The alkenyl group may be optionally substituted with one or more substituents selected from the group consisting of halogen, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —S(O)R, —SO$_2$R, —SO$_3$R, —S(O)$_2$N(R$^N$)$_2$, phosphate, phosphonate, cycloalkyl, cycloalkenyl, aryl and heteroaryl.

The term "alkoxy" as used herein contemplates an oxygen with a lower alkyl group as a substituent and includes methoxy, ethoxy, butoxy, trifluoromethoxy and the like. It also includes divalent substituents linked to two separated oxygen atoms such as, without limitation, —O—(CH$_2$)$_{1-4}$—O—, —O—CF$_2$—O—, —O—(CH$_2$)$_{1-4}$—O—(CH$_2$CH$_2$—O)$_{1-4}$— and —(O—CH$_2$CH$_2$—O)$_{1-4}$—.

The term "alkoxycarbonyl" as used herein contemplates a carbonyl group with an alkoxy group as a substituent.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl and the like. The alkyl group may be optionally substituted with one or more substituents selected from halogen, —CN, —NO$_2$, —C(O)$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "alkylene," "alkenylene" and "alkynylene" as used herein refers to the groups "alkyl," "alkenyl" and "alkynyl" respectively, when they are divalent, ie, attached to two atoms.

The term "alkylsulfonyl" as used herein contemplates a sulfonyl group which has a lower alkyl group as a substituent.

The term "alkynyl" as used herein contemplates substituted or unsubstituted, straight and branched carbon chain containing from two to eight carbon atoms and having at least one carbon-carbon triple bond. The term alkynyl includes, for example ethynyl, 1-propynyl, 2-propynyl, 1-butynyl, 3-methyl-1-butynyl and the like. The alkynyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "amino" as used herein contemplates a group of the structure —NR$^N{}_2$.

The term "amino acid" as used herein contemplates a group of the structure

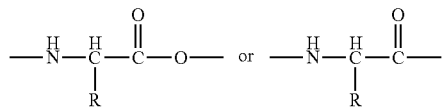

in either the D or the L configuration and includes but is not limited to the twenty "standard" amino acids: isoleucine, leucine, lysine, methionine, phenylalanine, threonine, tryptophan, valine, alanine, asparagine, aspartate, cysteine, glutamate, glutamine, glycine, proline, serine, tyrosine, arginine and histidine. The present invention also includes, without limitation, D-configuration amino acids, beta-amino acids, amino acids having side chains as well as all non-natural amino acids known to one skilled in the art.

The term "aralkyl" as used herein contemplates a lower alkyl group which has as a substituent an aromatic group, which aromatic group may be substituted or unsubstituted. The aralkyl group may be optionally substituted with one or more substituents selected from halogen, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The terms "aryl," "aromatic group" or "aromatic ring" as used herein contemplates substituted or unsubstituted single-ring and multiple aromatic groups (for example, phenyl, pyridyl and pyrazole, etc.) and polycyclic ring systems (naphthyl and quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halogen, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The term "arylsulfonyl" as used herein contemplates a sulfonyl group which has as a substituent an aryl group. The term is meant to include, without limitation, monovalent as well as multiply valent aryls (eg, divalent aryls).

The term "carbamoyl" as used herein contemplates a group of the structure

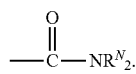

The term "carbonyl" as used herein contemplates a group of the structure

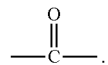

The term "carboxyl" as used herein contemplates a group of the structure

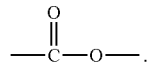

The term "cycloalkyl" as used herein contemplates substituted or unsubstituted cyclic alkyl radicals containing from three to twelve carbon atoms and includes cyclopropyl, cyclopentyl, cyclohexyl and the like. The term "cycloalkyl" also includes polycyclic systems having two rings in which two or more atoms are common to two adjoining rings (the rings are "fused"). The cycloalkyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —S(O)$_2$N(R$^N$)$_2$, phosphate, phosphonate, alkyl, cycloalkenyl, aryl and heteroaryl.

The term "cycloalkenyl" as used herein contemplates substituted or unsubstituted cyclic alkenyl radicals containing from four to twelve carbon atoms in which there is at least one double bond between two of the ring carbons and includes cyclopentenyl, cyclohexenyl and the like. The term "cycloalkenyl" also includes polycyclic systems having two rings in which two or more atoms are common to two adjoining rings (the rings are "fused"). The cycloalkenyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —S(O)$_2$N(R$^N$)$_2$, phosphate, phosphonate, alkyl, cycloalkenyl, aryl and heteroaryl.

The term "halo" or "halogen" as used herein includes fluorine, chlorine, bromine and iodine.

The term "heteroalkyl" as used herein contemplates an alkyl with one or more heteroatoms.

The term "heteroatom", particularly within a ring system, refers to N, O and S.

The term "heterocyclic group," "heterocycle" or "heterocyclic ring" as used herein contemplates substituted or unsubstituted aromatic and non-aromatic cyclic radicals having at least one heteroatom as a ring member. Preferred heterocyclic groups are those containing five or six ring atoms which includes at least one hetero atom and includes cyclic amines such as morpholino, piperidino, pyrrolidino and the like and cyclic ethers, such as tetrahydrofuran, tetrahydropyran and the like. Aromatic heterocyclic groups, also termed "heteroaryl" groups, contemplates single-ring hetero-aromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic hetero-aromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting of halo, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The term "oxo" as used herein contemplates an oxygen atom attached with a double bond.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

The terms "phosphate" and "phosphonate" as used herein refer to the moieties having the following structures, respectively:

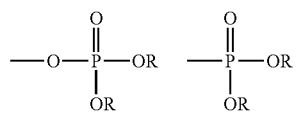

The terms "salts" and "hydrates" refers to the hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity, flowability and manufacturability of the resulting bulk drug.

The term sulfonamide as used herein contemplates a group having the structure

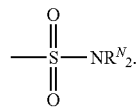

The term "sulfonate" as used herein contemplates a group having the structure

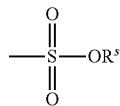

wherein R$^s$ is selected from the group consisting of hydrogen, C$_1$-C$_{10}$ alkyl, C$_2$-C$_{10}$ alkenyl, C$_2$-C$_{10}$ alkynyl, C$_1$-C$_{10}$ alkanoyl or C$_1$-C$_{10}$ alkoxycarbonyl.

The term "sulfonyl" as used herein contemplates a group having the structure

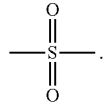

"Substituted sulfonyl" as used herein contemplates a group having the structure

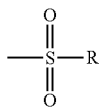

including, but not limited to alkylsulfonyl and arylsulfonyl.

The term "thiocarbonyl," as used herein, means a carbonyl wherein an oxygen atom has been replaced with a sulfur.

Each R is independently selected from hydrogen, —OH, —CN, —NO$_2$, halogen, C$_1$ to C$_{12}$ alkyl, C$_1$ to C$_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate, sulfonamide, amino and oxo.

Each R$^N$ is independently selected from the group consisting of hydrogen, —OH, C$_1$ to C$_{12}$ alkyl, C$_1$ to C$_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate and sulfonamide. Two R$^N$ may be taken together with C, O, N or S to which they are attached to form a five to seven membered ring which may optionally contain a further heteroatom.

The compounds of the present invention may be used to inhibit or reduce the activity of HCV, particularly HCV's NS5A protein. In these contexts, inhibition and reduction of activity of the NS5A protein refers to a lower level of the measured activity relative to a control experiment in which the cells or the subjects are not treated with the test compound. In particular aspects, the inhibition or reduction in the measured activity is at least a 10% reduction or inhibition. One of skill in the art will appreciate that reduction or inhibition of the measured activity of at least 20%, 50%, 75%, 90% or 100% or any number in between, may be preferred for particular applications.

In a first aspect, compounds of formula I are provided:

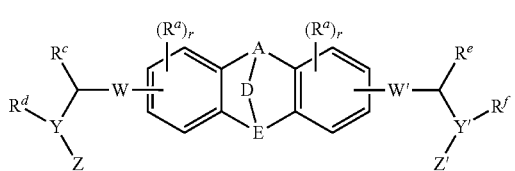

I wherein:
  D is either present or absent and if present selected from the group consisting of —CR$_2$CR$_2$—, —CR$_2$—, —NR$^N$—, —O— and —S— wherein:
    R$^N$ is H, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and,
    each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
  A and E are:
    each independently —CR$_2$—, —CR═, —CR$_2$—CR$_2$—, —CR═CR—, —N═CR—, —(CR$_2$)$_a$—N(R$^N$)—(CR$_2$)$_a$—, —(CR$_2$)$_a$—, —(CR$_2$)$_a$—C(O)—N(R$^N$)—(CR$_2$)$_a$—, —(CR$_2$)$_a$—N(R$^N$)—C(O)—(CR$_2$)$_a$— or —(CR$_2$)$_b$—O—(CR$_2$)$_b$—, wherein:
      R$^N$ is selected from the group consisting of H, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;
      each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:
        two R's either both on a single C or on adjoining C's, together with the C or C's to which they are attached, optionally form a cycle, and
        where two R's are possible on a C, the C may optionally be linked to a single R with a double bond;
      each a and b are independently 0, 1, 2, or 3 with the proviso that if D is present both b's are not 0; and
      R$^N$ and R may be replaced by a bond to D if D is present,
    if D is absent, A and E can additionally each independently be a bond, —O—, —S—, —S(O$_2$)—, —S(O)—, —C(O)— or —N═, and
    with the proviso that if W and W' are both 5-membered rings, A and E are either both a bond or both other than a bond;
  each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
  each r is independently 0, 1, 2 or 3;
  W and W' are each independently selected from the group consisting of

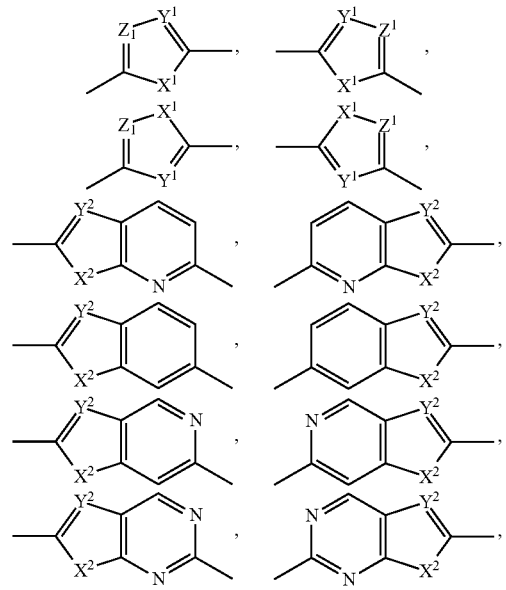

-continued

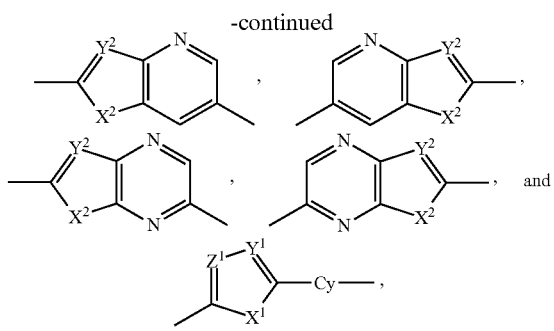

wherein:
$X^1$ is $CH_2$, NH, O or S,
$Y^1$, $Y^2$ and $Z^1$ are each independently CH or N,
$X^2$ is NH, O or S,
W and W' are each independently optionally substituted with one or more substituents selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
Cy is a monocyclic, bicyclic or tricyclic 5- to 12-membered cycloalkyl, heterocycle, aryl group or heteroaryl group wherein up to three heteroatoms are independently N, S or O and which is optionally substituted with one or more substituents selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein,
each hetero atom, if present, is independently N, O or S,
each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
$R^c$ and $R^d$ are optionally joined to form a 4- to 8-membered heterocycle which is optionally fused to another 3- to 5-membered heterocycle or heteroaryl ring, and
$R^e$ and $R^f$ are optionally joined to form a 4- to 8-membered heterocycle which is optionally fused to another 3- to 5-membered heterocycle or heteroaryl ring;
Y and Y' are each independently carbon or nitrogen; and
Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids,
—[U—$(CR^4_2)_t$—$NR^5$—$C(R^4_2)_t]_u$—U—$(CR^4_2)_t$— $NR^7$—$(CR^4_2)_t$—$R^8$, —U—$(CR^4_2)_t$—$R^8$, and —[U—$(CR^4_2)_t$—$NR^5$—$(CR^4_2)_t]_u$—U—$(CR^4_2)_t$— O—$(CR^4_2)_t$—$R^8$, wherein,
U is selected from the group consisting of —C(O)—, —C(S)— and —$S(O)_2$—,
each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N— $R^{81}_2$, —$S(O)_2$—$R^{81}$ and —$S(O)_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl,
optionally, $R^7$ and $R^8$ together form a 4-7 membered ring,
each t is independently 0, 1, 2, 3, or 4, and
u is 0, 1, or 2.
In a first embodiment of the first aspect, one or both of W and W' are selected from the group consisting of

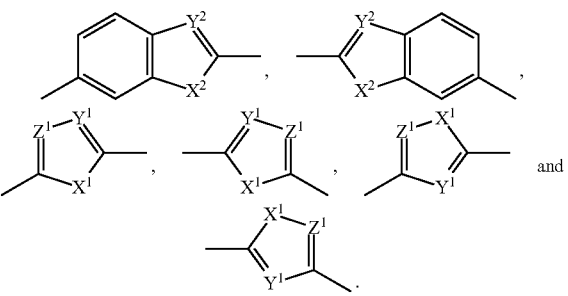

In a second embodiment of the first aspect, one or both of W and W' are selected from the group consisting of

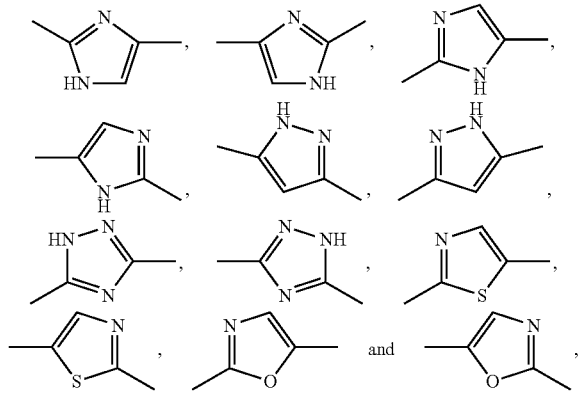

In a third embodiment of the first aspect, $R^c$, $R^d$, $R^e$ and $R^f$ are each independently selected from the group consisting of: hydrogen, $C_1$ to $C_8$ alkyl and $C_1$ to $C_8$ heteroalkyl, wherein,
each hetero atom, if present, is independently N, O or S,
$R^c$ and $R^d$ are optionally joined to form a 4- to 8-membered heterocycle which is optionally fused to another 3- to 6-membered heterocycle, and
$R^e$ and $R^f$ are optionally joined to form a 4- to 8-membered heterocycle which is optionally fused to another 3- to 6-membered heterocycle.
In a fourth embodiment of the first aspect, one or both of $R^c$ and $R^d$ or $R^e$ and $R^f$ are optionally joined to form a 4- to 8-membered heterocycle which is optionally fused to another 3- to 6-membered heterocycle.
In a fifth embodiment of the first aspect, $R^c$ and $R^d$ are joined and form a heterocyclic fused ring system selected from the group consisting of:

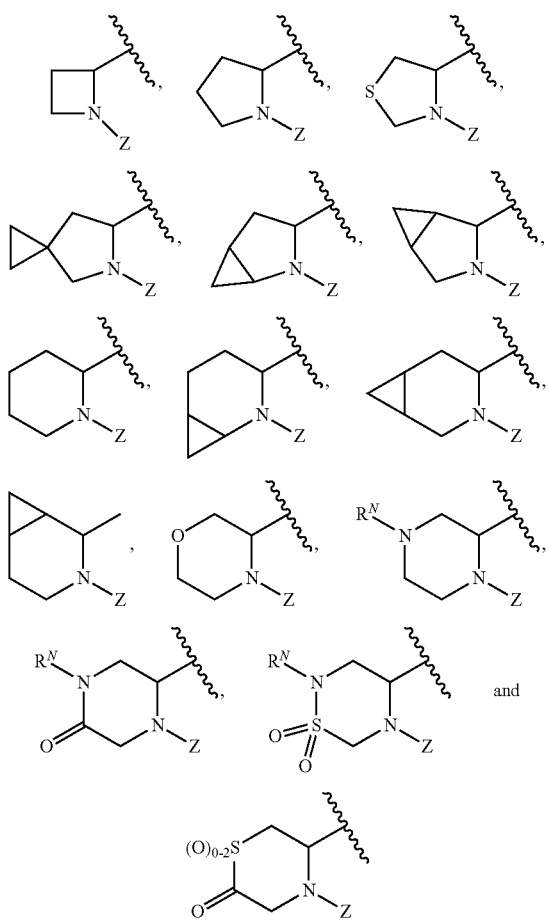

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a sixth embodiment of the first aspect, $R^e$ and $R^f$ are joined and form a heterocyclic fused ring system selected from the group consisting of:

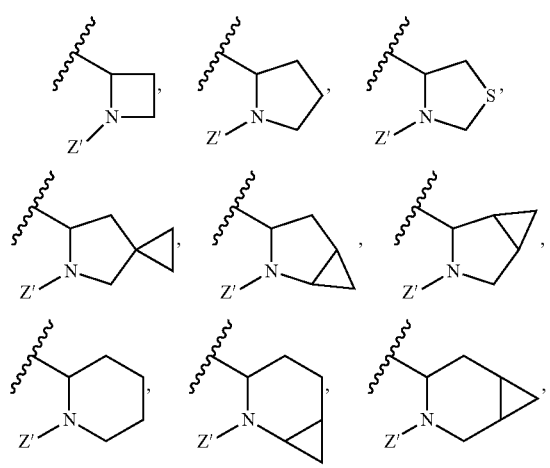

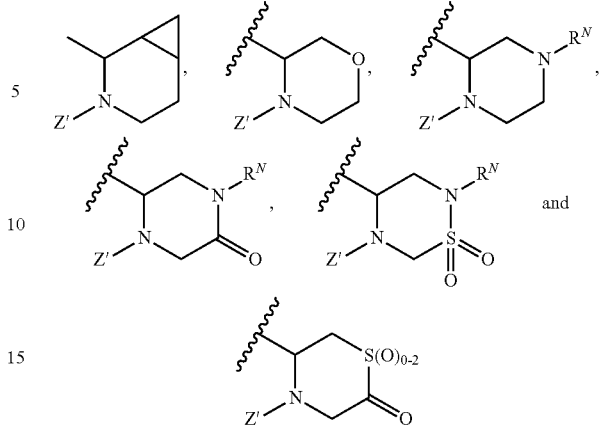

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a second aspect of the invention, compounds have formula II:

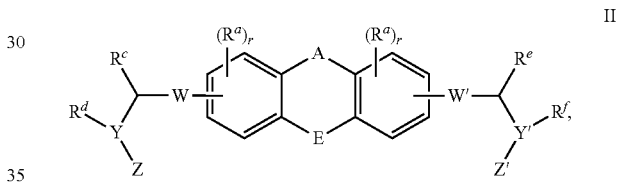

wherein:
  A and E are:
    each independently a bond, —O—, —S—, —S(O$_2$)—, —S(O)—, —C(O)—, —N═, —CR$_2$—, —CR═, —CR$_2$—CR$_2$—, —CR═CR—, —N═CR—, —(CR$_2$)$_a$—N(R$^N$)—(CR$_2$)$_a$—, —(CR$_2$)$_a$—C(O)—N(R$^N$)—(CR$_2$)$_a$—, —(CR$_2$)$_a$—N(R$^N$)—C(O)—(CR$_2$)$_a$— or —(CR$_2$)$_b$—O—(CR$_2$)$_b$—, wherein:
      $R^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;
    each R is independently selected from the group consisting of hydrogen, —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:
      two R's either both on a single C or on adjoining C's, together with the C or C's to which they are attached, optionally form a cycle, and
      where two R's are possible on a C, the C may optionally be linked to a single R with a double bond; and
    each a and b are independently 0, 1, 2, or 3; and
    with the proviso that if W and W' are both 5-membered rings, A and E are either both a bond or both other than a bond;

each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

W and W' are each independently selected from the group consisting of

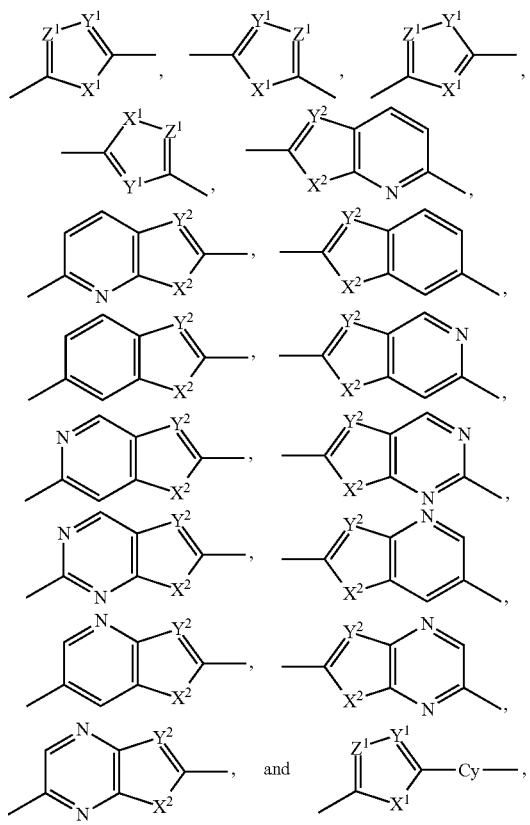

wherein:

X$^1$ is CH$_2$, NH, O or S,

Y$^1$, Y$^2$ and Z$^1$ are each independently CH or N,

X$^2$ is NH, O or S,

W and W' are each independently optionally substituted with one or more substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and Cy is a monocyclic, bicyclic or tricyclic 5- to 12-membered cycloalkyl, heterocycle, aryl group or heteroaryl group wherein up to three heteroatoms are independently N, S or O and which is optionally substituted with one or more substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each R$^c$, R$^d$, R$^e$ and R$^f$ is independently selected from the group consisting of: hydrogen, C$_1$ to C$_8$ heteroalkyl, aralkyl and a 4- to 8-membered ring which may be cycloalkyl, heterocycle, heteroaryl or aryl, wherein, each hetero atom, if present, is independently N, O or S, each of R$^c$, R$^d$, R$^e$ and R$^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S, R$^c$ and R$^d$ are optionally joined to form a 4- to 8-membered heterocycle which is optionally fused to another 3- to 5-membered heterocycle or heteroaryl ring, and R$^e$ and R$^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl, R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, optionally, R$^7$ and R$^8$ together form a 4-7 membered ring, each t is independently 0, 1, 2, 3, or 4, and u is 0, 1, or 2.

In a first embodiment of the second aspect, compounds of formula IIa are provided:

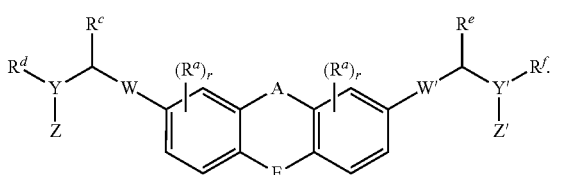

IIa

In a second embodiment of the second aspect, compounds of formula IIb are provided:

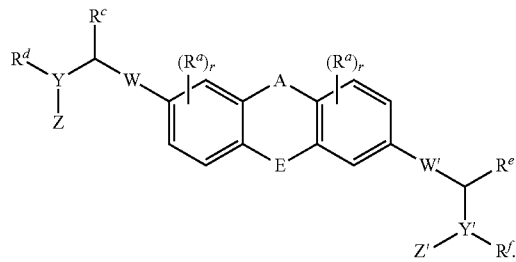

IIb

In a third embodiment of the second aspect, both A and E are —O—.

In a fourth embodiment of the second aspect, A is —O— and E is —CH$_2$—, —C(CH$_3$)$_2$—, —C(CH$_2$CH$_2$)— or —C(O)—.

In a fifth embodiment of the second aspect, W in formula IIa or IIb is

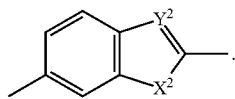

In a sixth embodiment of the second aspect, W' in formula IIa or IIb is

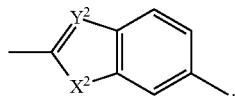

In a seventh embodiment of the second aspect, in compounds of IIa or IIb, W is

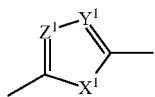

and W' is

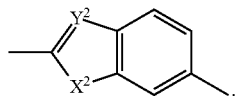

In an eighth embodiment of the second aspect, in compounds of IIa or IIb, W is

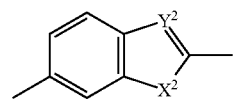

and W'

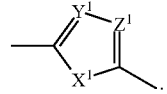

In a ninth embodiment of the second aspect, X$^1$ is —NH— and Y$^1$ or Z$^1$ is —N—.

In a tenth embodiment of the second aspect, X$^2$ is —NH— and Y$^2$ is —N—.

In an eleventh embodiment of the second aspect, R$^e$ and R$^f$ are joined and form

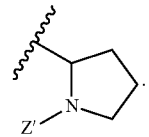

In a twelfth embodiment of the second aspect, R$^c$ and R$^d$ are joined and form

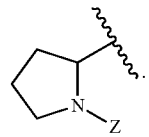

In a thirteenth embodiment of the second aspect, R$^e$ and R$^f$ are joined and form

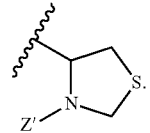

In a fourteenth embodiment of the second aspect, R$^c$ and R$^d$ are joined and form

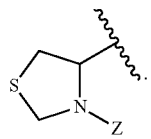

In a fifteenth embodiment of the second aspect, R$^e$ and R$^f$ are joined and form

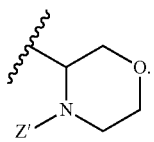

In a sixteenth embodiment of the second aspect, $R^c$ and $R^d$ are joined and form

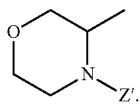

In a third aspect of the invention, compounds of formula III are provided:

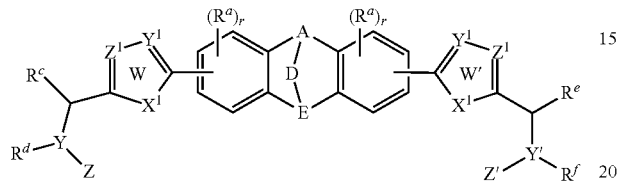

wherein:
D is either present or absent and if present selected from the group consisting of —$CR_2CR_2$—, —$CR_2$—, —$NR^N$—, —O— and —S— wherein $R^N$ is H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide and each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

A and E are:
each independently —$CR_2$—, —CR=, —$CR_2$—$CR_2$—, —CR=CR—, —N=CR—, —$(CR_2)_a$—N($R^N$)—$(CR_2)_a$—, —$(CR_2)_a$—C(O)—N($R^N$)—$(CR_2)_a$—, —$(CR_2)_a$—N($R^N$)—C(O)—$(CR_2)_a$— or —$(CR_2)_b$—O—$(CR_2)_b$—, wherein:
$R^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;
each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:
two R's either both on a single C or on adjoining C's, together with the C or C's to which they are attached, optionally form a cycle, and
where two R's are possible on a C, the C may optionally be linked to a single R with a double bond;
each a and b are independently 0, 1, 2, or 3 with the proviso that if D is present both b's are not 0; and
$R^N$ and R may be replaced by a bond to D if D is present,
if D is absent, A and E can additionally each independently be a bond, —O—, —S—, —$S(O_2)$—, —S(O)—, —C(O)— or —N=, and with the proviso that if W and W' are both 5-membered rings, A and E are either both a bond or both other than a bond;
each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each r is independently 0, 1, 2 or 3;
$X^1$ is $CH_2$, NH, O or S,
$Y^1$, and $Z^1$ are each independently CH or N,
W and W' are each independently optionally substituted with one or more substituents selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein,
each hetero atom, if present, is independently N, O or S,
each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
$R^c$ and $R^d$ are optionally joined to form a 4- to 8-membered heterocycle which is optionally fused to another 3- to 5-membered heterocycle or heteroaryl ring, and
$R^e$ and $R^f$ are optionally joined to form a 4- to 8-membered heterocycle which is optionally fused to another 3- to 5-membered heterocycle or heteroaryl ring;
Y and Y' are each independently carbon or nitrogen; and
Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids,
[U—$(CR^4_2)_t$—$NR^5$—$C(R^4_2)_t]_u$—U—$(CR^4_2)_t$—$NR^7$—$(CR^4_2)_t$—$R^8$, —U—$(CR^4_2)_t$—$R^8$, and —[U—$(CR^4_2)_t$—$NR^5$—$(CR^4_2)_t]_u$—U—$(CR^4_2)_t$—O—$CR^4_2)_t$—$R^8$, wherein,
U is selected from the group consisting of —C(O)—, —C(S)— and —$S(O)_2$—,
each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl,
$R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N—$R^{81}_2$, —$S(O)_2$—$R^{81}$ and —$S(O)_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl,
optionally, $R^7$ and $R^8$ together form a 4-7 membered ring,
each t is independently 0, 1, 2, 3, or 4, and
u is 0, 1, or 2.

In a first embodiment of the third aspect, compounds of formula IIIa are provided:

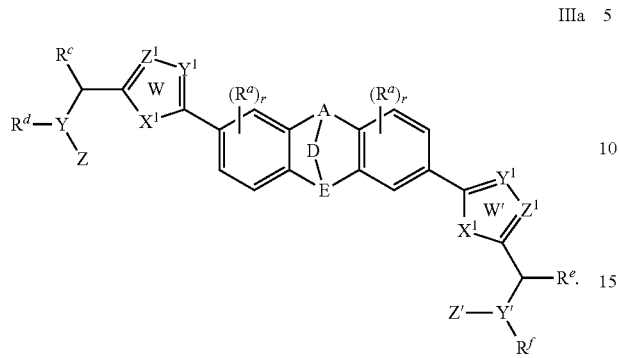

In a second embodiment of the third aspect, compounds of formula IIIb are provided:

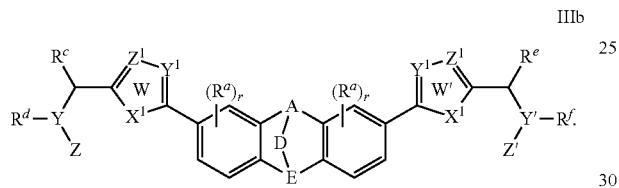

In a third embodiment of the third aspect, both A and E are —O— and D is absent.

In a fourth embodiment of the third aspect, A is —O—, D is absent and E is —CH$_2$—, —C(CH$_3$)$_2$—, —C(CH$_2$CH$_2$)— or —C(O)—.

In a fifth embodiment of the third aspect, one or both of $X^1$ are —S—.

In a sixth embodiment of the third aspect, one or both of $X^1$ are —O—.

In a seventh embodiment of the third aspect, one or both of $X^1$ are —NH—.

In an eighth embodiment of the third aspect, one or both of $Y^1$ are —N—.

In a ninth embodiment of the third aspect, one or both of $Z^1$ is —N—.

In a fourth aspect of the invention, compounds of formula IV are provided:

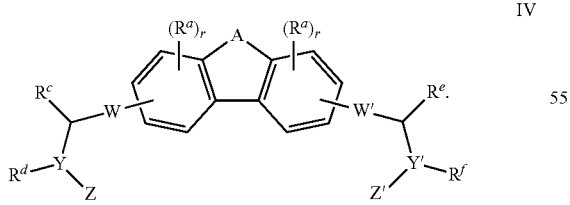

wherein:
A is a bond, —CR$_2$—, —CR═, —CR$_2$—CR$_2$—, —CR═CR—, —N═CR—, —(CR$_2$)$_a$—N(R$^N$)—(CR$_2$)$_a$—, —O—, —S—, —S(O$_2$)—, —S(O)—, —C(O)—, —N═, —(CR$_2$)$_a$—C(O)—N(R$^N$)—(CR$_2$)$_a$—, —(CR$_2$)$_a$—N(R$^N$)—C(O)—(CR$_2$)$_a$— or —(CR$_2$)$_b$—O—(CR$_2$)$_b$—, wherein:

R$^N$ is selected from the group consisting of H, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:
two R's either both on a single C or on adjoining C's, together with the C or C's to which they are attached, optionally form a cycle, and
where two R's are possible on a C, the C may optionally be linked to a single R with a double bond;

each a and b are independently 0, 1, 2, or 3; and
with the proviso that if W and W' are both 5-membered rings, A is a bond;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

W and W' are each independently selected from the group consisting of

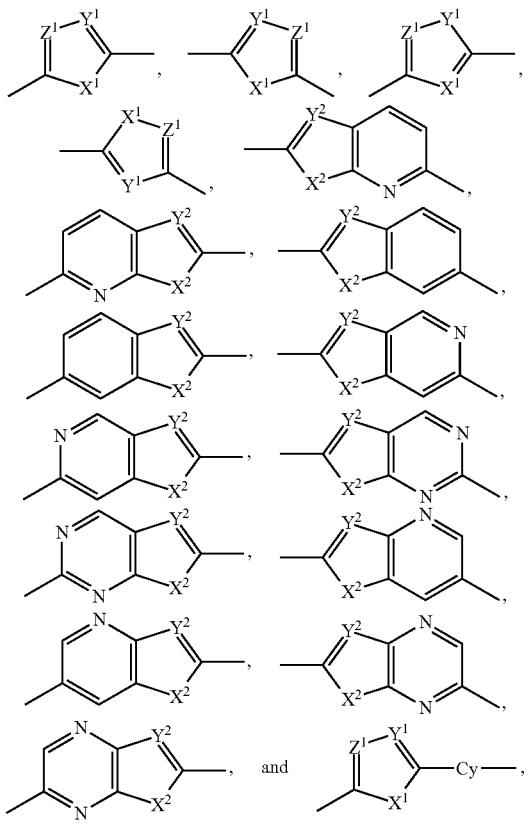

wherein:
$X^1$ is CH$_2$, NH, O or S,
$Y^1$, $Y^2$ and $Z^1$ are each independently CH or N,
$X^2$ is NH, O or S, W and W' are each independently optionally substituted with one or more substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and Cy is a monocyclic, bicyclic or tricyclic 5- to 12-membered cycloalkyl, heterocycle, aryl group or heteroaryl group wherein up to three heteroatoms are independently N, S or O and which is optionally substituted with one or more substituents selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each R$^c$, R$^d$, R$^e$ and R$^f$ is independently selected from the group consisting of: hydrogen, C$_1$ to C$_8$ alkyl, C$_1$ to C$_8$ heteroalkyl, aralkyl and a 4- to 8-membered ring which may be cycloalkyl, heterocycle, heteroaryl or aryl, wherein, each hetero atom, if present, is independently N, O or S, each of R$^c$, R$^d$, R$^e$ and R$^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S, R$^c$ and R$^d$ are optionally joined to form a 4- to 8-membered heterocycle which is optionally fused to another 3- to 5-membered heterocycle or heteroaryl ring, and R$^e$ and R$^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl, R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl, optionally, R$^7$ and R$^8$ together form a 4-7 membered ring, each t is independently 0, 1, 2, 3, or 4, and u is 0, 1, or 2.

In a first embodiment of the fourth aspect, compounds of formula IVa are provided:

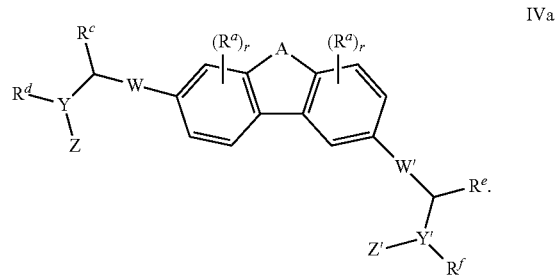

IVa

In a second embodiment of the fourth aspect, compounds of formula IVb are provided:

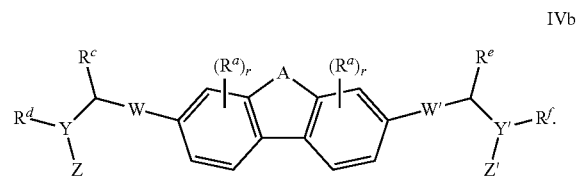

IVb

In a third embodiment of the fourth aspect, A is —S—.
In a fourth embodiment of the fourth aspect, A is —S(O)$_2$—.
In a fifth embodiment of the fourth aspect, A is —O—.
In a sixth embodiment of the fourth aspect, A is —CH$_2$—.
In a seventh embodiment of the fourth aspect, A is —CH$_2$—CH$_2$—.

In a fifth aspect of the embodiment, compounds of formula V are provided:

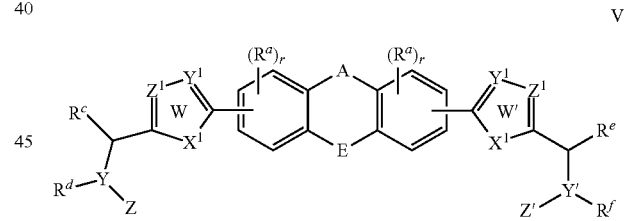

V wherein:
A and E are:
each independently a bond, —CR$_2$—, —CR=, —CR$_2$—CR$_2$—, —CR=CR—, —N=CR—, —(CR$_2$)$_a$—C(O)—N(R$^N$)—(CR$_2$)$_a$—, —(CR$_2$)$_a$—N(R$^N$)—C(O)—(CR$_2$)$_a$—(CR$_2$)$_a$—N(R$^N$)—(CR$_2$)$_a$—, —(CR$_2$)$_b$—O—(CR$_2$)$_b$—, —O—, —S—, —S(O$_2$)—, —S(O)—, —C(O)— or —N=,
wherein:
R$^N$ is selected from the group consisting of H, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;
each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:
- two R's either both on a single C or on adjoining C's, together with the C or C's to which they are attached, optionally form a cycle, and
- where two R's are possible on a C, the C may optionally be linked to a single R with a double bond;

each a and b are independently 0, 1, 2, or 3; and
with the proviso that A and E are either both a bond or both other than a bond;

each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

$X^1$ is CH$_2$, NH, O or S, $Y^1$ and $Z^1$ are each independently CH or N,

W and W' are each independently optionally substituted with one or more substituents selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein,
- each hetero atom, if present, is independently N, O or S,
- each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
- $R^c$ and $R^d$ are optionally joined to form a 4- to 8-membered heterocycle which is optionally fused to another 3- to 5-membered heterocycle or heteroaryl ring, and
- $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids,
—[U—(CR$^4_2$)$_t$—NR$^5$—C(R$^4_2$)$_t$]$_u$—U—(CR$^4_2$)$_t$—NR$^7$—(CR$^4_2$)$_t$—R$^8$,    —U—(CR$^4_2$)$_t$—R$^8$,    and
—[U—(CR$^4_2$)$_t$—NR$^5$—(CR$^4_2$)$_t$]$_u$—U—(CR$^4_2$)$_t$—O—CR$^4_2$)$_t$—R$^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the fifth aspect, compounds of formula Va are provided:

In a second embodiment of the fifth aspect, compounds of formula Vb are provided:

In a third embodiment of the fifth aspect, both A and E are —O—.

In a fourth embodiment of the fifth aspect, A is —O— and E is —CH$_2$—, —C(CH$_3$)$_2$—, —C(CH$_2$CH$_2$)— or —C(O)—.

In a fifth embodiment of the fifth aspect, one or both of $X^1$ are —S—.

In a sixth embodiment of the fifth aspect, one or both of $X^1$ are —O—.

In a seventh embodiment of the fifth aspect, one or both of $X^1$ are —NH—.

In an eighth embodiment of the fifth aspect, one or both of $Y^1$ are —N—.

In a ninth embodiment of the fifth aspect, one or both of $Z^1$ is —N—.

In tenth embodiment of the fifth aspect, $R^e$ and $R^f$ are joined and form

In an eleventh embodiment of the fifth aspect, $R^c$ and $R^d$ are joined and form

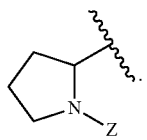

In a twelfth embodiment of the fifth aspect, $R^e$ and $R^f$ are joined and form

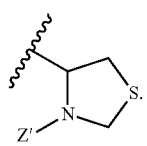

In a thirteenth embodiment of the fifth aspect, $R^c$ and $R^d$ are joined and form

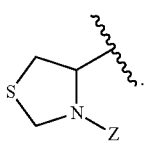

In a fourteenth embodiment of the fifth aspect, $R^e$ and $R^f$ are joined and form

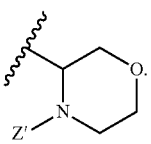

In a fifteenth embodiment of the fifth aspect, $R^c$ and $R^d$ are joined and form

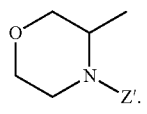

In a sixth aspect, compounds of formula VI are provided:

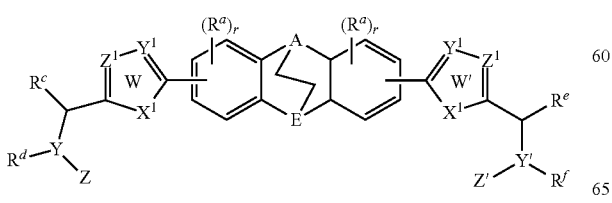

VI wherein:
A and E are:
  each independently —$CR_2$—, —$CR_2$—$CR_2$—, —CR=CR—, —N=CR—, —$(CR_2)_a$—$N(R^N)$—$(CR_2)_a$—, —$(CR_2)_a$—C(O)—$N(R^N)$—$(CR_2)_a$—, —$(CR_2)_a$—$N(R^N)$—C(O)—$(CR_2)_a$— or —$(CR_2)_b$—O—$(CR_2)_b$—, wherein:
    $R^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide,
    each R is independently selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:
      two R's either both on a single C or on adjoining C's, together with the C or C's to which they are attached, optionally form a cycle, and
      where two R's are possible on a C, the C may optionally be linked to a single R with a double bond, and
    each a and b are independently 0, 1, 2, or 3 with the proviso that both b's are not 0; and
  each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
  each r is independently 0, 1, 2 or 3;
  $X^1$ is $CH_2$, NH, O or S,
  $Y^1$ and $Z^1$ are each independently CH or N,
  W and W' are each independently optionally substituted with one or more substituents selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
  each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein,
    each hetero atom, if present, is independently N, O or S,
    each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S,
    $R^c$ and $R^d$ are optionally joined to form a 4- to 8-membered heterocycle which is optionally fused to another 3- to 5-membered heterocycle or heteroaryl ring, and
    $R^e$ and $R^f$ are optionally joined to form a 4- to 8-membered heterocycle which is optionally fused to another 3- to 5-membered heterocycle or heteroaryl ring;
  Y and Y' are each independently carbon or nitrogen; and
  Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids,
    —[U—$(CR^4_2)_t$—$NR^5$—$C(R^4_2)_t]_u$—U—$(CR^4_2)_t$—$NR^7$—$(CR^4_2)_t$—$R^8$, —U—$(CR^4_2)_t$—$R^8$, and —[U—$(CR^4_2)_t$—$NR^5$—$(CR^4_2)_t]_u$—U—$(CR^4_2)_t$—O—$(CR^4_2)_t$—$R^8$, wherein,
    U is selected from the group consisting of —C(O)—, —C(S)— and —$S(O)_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N—$R^{81}_2$, —S(O)$_2$—$R^{81}$ and —S(O)$_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the sixth aspect, compounds of formula VIa are provided:

VIa

In a second embodiment of the sixth aspect, compounds of formula VIb are provided:

VIb

In a third embodiment of the sixth aspect, compounds of formula VII are provided:

VII

In a fourth embodiment of the sixth aspect, compounds of formula VIIa are provided:

VIIa

In a fifth embodiment of the sixth aspect, compounds of formula VIIb are provided:

VIIb

In a sixth embodiment of the sixth aspect, compounds of formula VIII are provided:

VIII

In a seventh embodiment of the sixth aspect, compounds of formula VIIIa are provided:

VIIIa

In an eighth embodiment of the sixth aspect, compounds of formula VIIIb are provided:

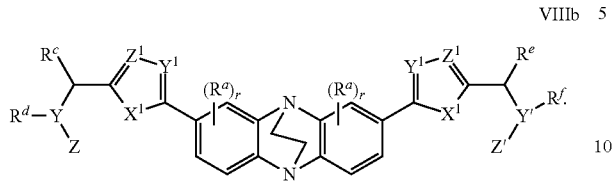

In a ninth embodiment of the sixth aspect, one or both of $X^1$ are —O—.

In a tenth embodiment of the sixth aspect, one or both of $X^1$ are —NH—.

In an eleventh embodiment of the sixth aspect, one or both of $X^1$ are —S—.

In a twelfth embodiment of the sixth aspect, one or both of $Z^1$ is —N—.

In a thirteenth embodiment of the sixth aspect, one or both of $Y^1$ is —N—.

In a seventh aspect of the invention, compounds of formula IX are provided:

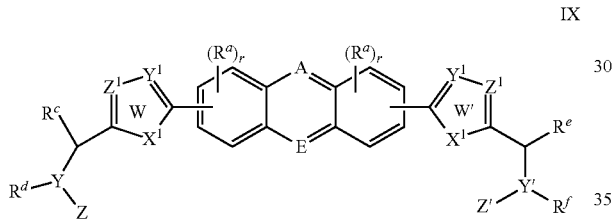

wherein:

A and E are each independently —CR= or —N= wherein R is selected from the group consisting of hydrogen, —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

$X^1$ is CH$_2$, NH, O or S, $Y^1$ and $Z^1$ are each independently CH or N,

W and W' are each independently optionally substituted with one or more substituents selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the seventh aspect compounds of formula IXa are provided:

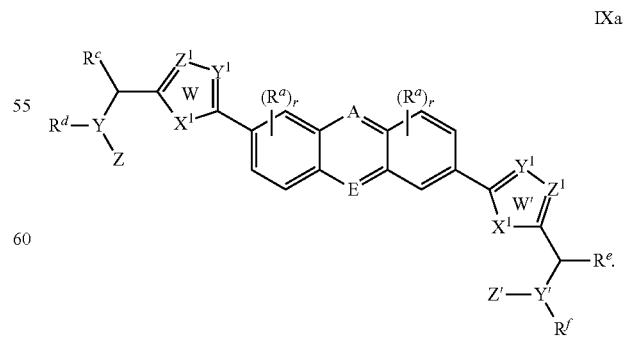

In a second embodiment of the seventh aspect compounds of formula IXb are provided:

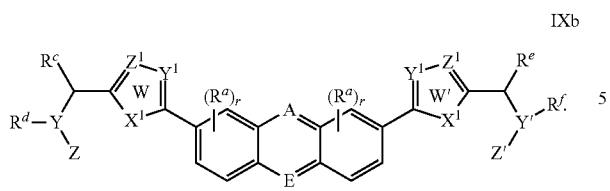

IXb

In a third embodiment of the seventh aspect A and E are —N=.

In a fourth embodiment of the seventh aspect, one or both of $X^1$ are —S—.

In a fifth embodiment of the seventh aspect, one or both of $X^1$ are —O—.

In a sixth embodiment of the seventh aspect, one or both of $X^1$ are —NH—.

In a seventh embodiment of the seventh aspect, one or both of $Y^1$ are —N—.

In an eighth embodiment of the seventh aspect, one or both of $Z^1$ is —N—.

In an eighth aspect of the invention, compounds of formula X are provided:

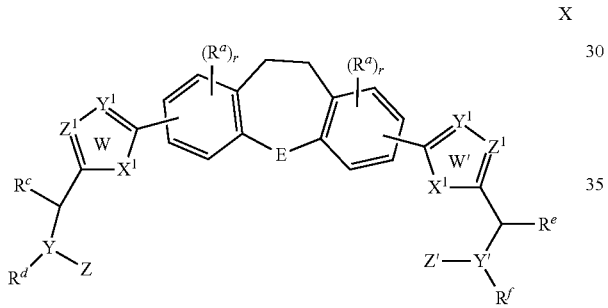

X wherein:
E is —CR$_2$—, —CR=, —CR$_2$—CR$_2$—, —CR=CR—, —N=CR—, —(CR$_2$)$_a$—N(R$^N$)—(CR$_2$)$_a$—(CR$_2$)$_a$—C(O)—N(R$^N$)—(CR$_2$)$_a$—, —(CR$_2$)$_a$—N(R$^N$)—C(O)—(CR$_2$)$_a$—, or —(CR$_2$)$_b$—O—(CR$_2$)$_b$—, wherein:

$R^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, each R is independently selected from the group consisting of hydrogen, —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, wherein:

two R's either both on a single C or on adjoining C's, together with the C or C's to which they are attached, optionally form a cycle, and where two R's are possible on a C, the C may optionally be linked to a single R with a double bond;

each a and b are independently 0, 1, 2, or 3;

each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

$X^1$ is CH$_2$, NH, O or S, $Y^1$ and $Z^1$ are each independently CH or N,

W and W' are each independently optionally substituted with one or more substituents selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the eighth aspect, compounds of formula Xa are provided:

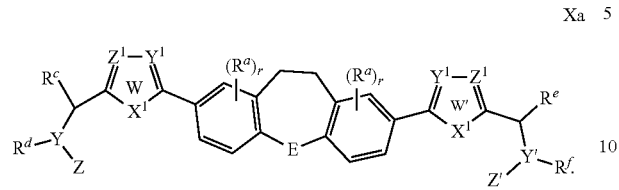

Xa

In a second embodiment of the eighth aspect, compounds of formula Xb are provided:

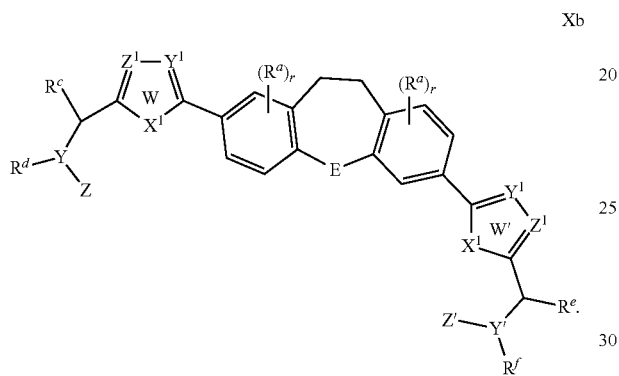

Xb

In a third embodiment of the eighth aspect, one or both of $X^1$ are —S—.

In a fourth embodiment of the eighth aspect, one or both of $X^1$ are —O—.

In a fifth embodiment of the eighth aspect, one or both of $X^1$ are —NH—.

In a sixth embodiment of the eighth aspect, one or both of $Y^1$ are —N—.

In a seventh embodiment of the eighth aspect, one or both of $Z^1$ is —N—.

In a ninth aspect of the invention, compounds of formula XI are provided:

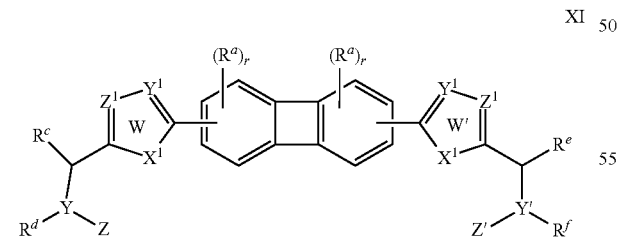

XI wherein:
each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

$X^1$ is CH$_2$, NH, O or S, $Y^1$ and $Z^1$ are each independently CH or N,

W and W' are each independently optionally substituted with one or more substituents selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—(CR$^4_2$)$_t$—NR$^5$—C(R$^4_2$)$_t$]$_u$—U—(CR$^4_2$)$_t$—NR$^7$—(CR$^4_2$)$_t$—R$^8$, —U—(CR$^4_2$)$_t$—R$^8$, and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the ninth aspect, compounds of formula XIa are provided:

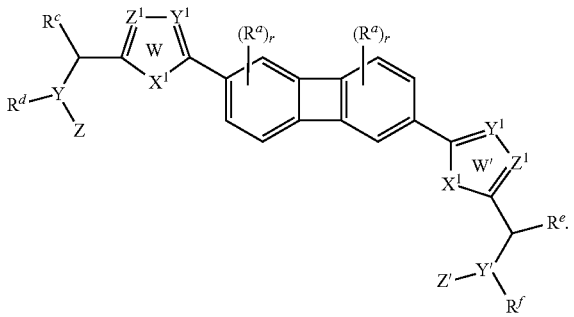

In a second embodiment of the ninth aspect, compounds of formula XIb are provided:

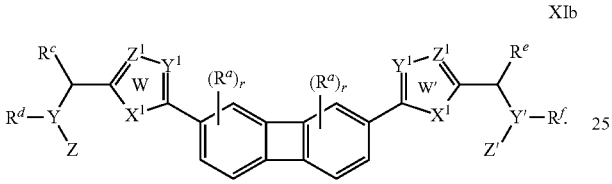

In a third embodiment of the ninth aspect, one or both of $X^1$ are —S—.

In a fourth embodiment of the ninth aspect, one or both of $X^1$ are —O—.

In a fifth embodiment of the ninth aspect, one or both of $X^1$ are —NH—.

In a sixth embodiment of the ninth aspect, one or both of $Y^1$ are —N—.

In a seventh embodiment of the ninth aspect, one or both of $Z^1$ is —N—.

In a tenth aspect of the invention, compounds of formula XII are provided:

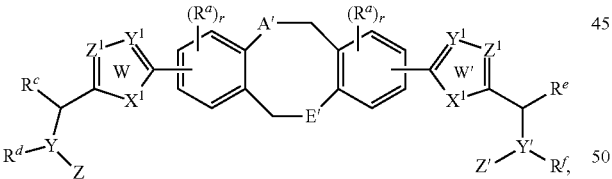

wherein:
- A' and E' are each independently —$CR_2$—, —CR=, —N($R^N$)—, —O—, —S—, —S($O_2$)—, —S(O)—, or —N=, wherein:
  - $R^N$ is selected from the group consisting of H, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and
  - R is selected from the group consisting of hydrogen, —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each $R^a$ is independently selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

$X^1$ is $CH_2$, NH, O or S, $Y^1$ and $Z^1$ are each independently CH or N,

W and W' are each independently optionally substituted with one or more substituents selected from the group consisting of —OH, —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—$(CR^4_2)_t$—$NR^5$—$C(R^4_2)_t]_u$—U—$(CR^4_2)_t$—$NR^7$—$(CR^4_2)_t$—$R^8$, —U—$(CR^4_2)_t$—$R^8$, and —[U—$(CR^4_2)_t$—$NR^5$—$(CR^4_2)_t]_u$—U—$(CR^4_2)_t$—O—$(CR^4_2)_t$—$R^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N—$R^{81}_2$, —S(O)$_2$—$R^{81}$ and —S(O)$_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the tenth aspect, compounds of formula XIIa are provided:

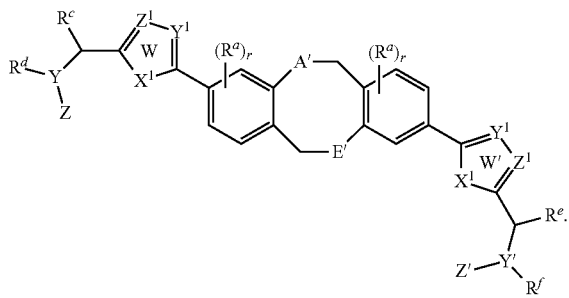

XIIa

In a second embodiment of the tenth aspect, compounds of formula XIIb are provided:

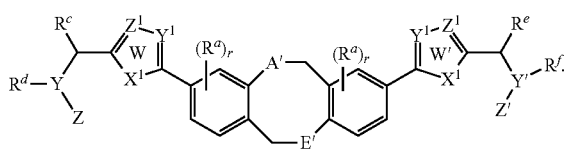

XIIb

In a third embodiment of the tenth aspect, one or both of $X^1$ are —S—.

In a fourth embodiment of the tenth aspect, one or both of $X^1$ are —O—.

In a fifth embodiment of the tenth aspect, one or both of $X^1$ are —NH—.

In a sixth embodiment of the tenth aspect, one or both of $Y^1$ are —N—.

In a seventh embodiment of the tenth aspect, one or both of $Z^1$ is —N—.

In an eleventh aspect of the invention Z and Z' in any of the previous aspects are each 1-3 amino acids.

In a first embodiment of the eleventh aspect, the amino acids are all in the D or all in the L configuration.

In a second embodiment of the eleventh aspect, Z and Z' are each independently selected from the group consisting of —[U—$(CR^4_2)_t$—$NR^5$—$(CR^4_2)_t]_u$—U—$(CR^4_2)_t$—$NR^7$—$(CR^4_2)_t$—$R^8$, —U—$(CR^4_2)_t$—$R^8$ and —[U—$(CR^4_2)_t$—$NR^5$—$(CR^4_2)_t]_u$—U—$(CR^4_2)_t$—O—$(CR^4_2)_t$—$R^8$.

In a third embodiment of the eleventh aspect, one or both of Z and Z' are —[U—$(CR^4_2)_t$—$NR^5$—$(CR^4_2)_t]_u$—U—$(CR^4_2)_t$—$NR^7$—$(CR^4_2)_t$—$R^8$.

In a fourth embodiment of the eleventh aspect, one or both of Z and Z' are —U—$(CR^4_2)_t$—$NR^5$—$(CR^4_2)_t$—U—$(CR^4_2)_t$—$NR^7$—$(CR^4_2)_t$—$R^8$.

In a fifth embodiment of the eleventh aspect, one or both of Z and Z' are —U—$(CR^4_2)_t$—$NR^7$—$(CR^4_2)_t$—$R^8$.

In a sixth embodiment of the eleventh aspect, one or both of Z and Z' are —[C(O)—$(CR^4_2)_t$—$NR^5$—$(CR^4_2)_t]_u$—U—$(CR^4_2)_t$—$NR^7$—$(CR^4_2)_t$—$R^8$.

In a seventh embodiment of the eleventh aspect, one or both of Z and Z' are —C(O)—$(CR^4_2)_t$—$NR^5$—$(CR^4_2)_t$—U—$(CR^4_2)_t$—$NR^7$—$(CR^4_2)_t$—$R^8$.

In an eighth embodiment of the eleventh aspect, one or both of Z and Z' are —[C(O)—$(CR^4_2)_t$—$NR^5$—$(CR^4_2)_t]_u$—C(O)—$(CR^4_2)_t$—$NR^7$—$(CR^4_2)_t$—$R^8$.

In a ninth embodiment of the eleventh aspect, one or both of Z and Z' are —C(O)—$(CR^4_2)_t$—$NR^5$—$(CR^4_2)_t$—C(O)—$(CR^4_2)_t$—$NR^7$—$(CR^4_2)_t$—$R^8$.

In a tenth embodiment of the eleventh aspect, one or both of Z and Z' are —C(O)—$(CR^4_2)_t$—$NR^7$—$(CR^4_2)_t$—$R^8$.

In an eleventh embodiment of the eleventh aspect, one or both of Z and Z' are —C(O)—$(CR^4_2)_n$—$NR^7$—$(CR^4_2)_n$—C(O)—$R^{81}$.

In a twelfth embodiment of the eleventh aspect, one or both of Z and Z' are —C(O)—$(CR^4_2)_n$—$NR^7$—C(O)—$R^{81}$.

In a thirteenth embodiment of the eleventh aspect, one or both of Z and Z' are —C(O)—$(CR^4_2)_n$—$NR^7$—$(CR^4_2)_n$—C(O)—O—$R^{81}$.

In a fourteenth embodiment of the eleventh aspect, one or both of Z and Z' are —C(O)—$(CR^4_2)_n$—$NR^7$—C(O)—O—$R^{81}$.

In a fifteenth embodiment of the eleventh aspect, one or both of Z and Z' are —U—$(CR^4_2)_t$—$R^8$.

In a sixteenth embodiment of the eleventh aspect, one or both of Z and Z' are —C(O)—$(CR^4_2)_t$—$R^8$.

In a seventeenth embodiment of the eleventh aspect, one or both of Z and Z' are —[U—$(CR^4_2)_t$—$NR^5$—$(CR^4_2)_t]_u$—U—$(CR^4_2)_t$—O—$(CR^4_2)_t$—$R^8$.

In an eighteenth embodiment of the eleventh aspect, one or both of Z and Z' are —U—$(CR^4_2)_t$—$NR^5$—$(CR^4_2)_t$—U—$(CR^4_2)_t$—O—$(CR^4_2)_t$—$R^8$.

In a nineteenth embodiment of the eleventh aspect, one or both of Z and Z' are —C(O)—$(CR^4_2)_t$—$NR^5$—$(CR^4_2)_t$—C(O)—$(CR^4_2)_t$—O—$(CR^4_2)_t$—$R^8$.

In a twentieth embodiment of the eleventh aspect, one or both of Z and Z' are —U—$(CR^4_2)_t$—O—$(CR^4_2)_t$—$R^8$.

In a twenty-first embodiment of the eleventh aspect, one or both of Z and Z' are —C(O)—$(CR^4_2)_t$—O—$(CR^4_2)_t$—$R^8$.

In a twenty-second embodiment of the eleventh aspect, one or both of Z and Z' are —C(O)—$(CR^4_2)_n$—$NR^7$—$R^8$ wherein $R^7$ and $R^8$ together form a 4-7 membered ring.

A twelfth aspect of the invention provides a pharmaceutical composition comprising the compounds of the invention.

A thirteenth aspect of the invention provides use of the compounds of the invention in the manufacture of a medicament.

In a first embodiment of the thirteenth aspect the medicament is for the treatment of hepatitis C.

A fourteenth aspect of the invention provides a method of treating hepatitis C comprising administering to a subject in need thereof, a therapeutically effective amount of a compound of the invention.

General Synthesis

The following abbreviations are used throughout this application:

ACN Acetonitrile
AcOH Acetic acid
aq Aqueous
Bn Benzyl
BnOH Benzyl alcohol
Boc t-Butoxycarbonyl
Cbz Benzoxylcarbonoyl
DCE Dichloroethane
DCM Dichloromethane
DEAD Diethyl azodicarboxylate
DEPBT 3-(Diethoxy-phosphoryloxy)-3H-benzo[d][1,2,3]triazin-4-one
DIEA (DIPEA) Diisopropylethylamine
DIBAL Diisobutylaluminium hydride
DMA N,N-Dimethylacetamide
DME 1,2-Dimethoxyethane
DMF N,N-Dimethylformamide
DMSO Dimethylsulfoxide
DMTMM 4-(4,6-Dimethoxy-1,3,5-triazin-2-yl)-4-methyl-morpholinium chloride DPPA Diphenylphosphoryl azide
dppp 1,3-Bis(diphenylphosphino)propane
DTT Dithiothreitol
EDCI 1-Ethyl-3-[3-(dimethylamino) propyl]carbodiimide hydrochloride
EDTA Ethylene diamine tetraacetic acid
$EC_{50}$ Effective concentration to produce 50% of the maximal effect
ESI Electrospray Ionization
$Et_3N$, TEA Triethylamine
EtOAc, EtAc Ethyl acetate
EtOH Ethanol
g Gram(s)
h or hr(s) Hour(s)
HATU 2-(7-Aza-1H-benzotriazole-1-yl)-1,1,3,3-tetramethyluronium hexafluorophosphate
HBTU O-Benzotriazol-1-yl-N,N,N',N'-tetramethyluronium hexafluorophosphate
HOBt 1-Hydroxybenzotriazole
$IC_{50}$ The concentration of an inhibitor that causes a 50% reduction in a measured activity
LAH Lithium aluminum hydride
LDA Lithium diisopropylamide
LC-MS Liquid Chramatography Mass Spectrometry
mCPBA m-Chloroperoxybenzoic acid
MeI Methyl Iodide
MeOH Methanol
min Minute(s)
mmol Millimole(s)
Moc Methoxylcarbonyl
NMM 4-Methylmorpholine
NMP N-methylpyrrolidinone
PG Protective Group
PTT Phenyl trimethyl tribromide
Py, Pyr Pyridine
rt Room temperature
TEA Triethylamine
Tf Trifluoromethanesulfonate
TFA Trifluoroacetic acid
TFAA Trifluoroacetic anhydride
THF Tetrahydrofuran
TLC Thin Layer Chromatography
TMSOTf Trimethylsilyl trifluoronnethanesulfonate Reagents and solvents used below can be obtained from commercial sources such as Aldrich Chemical Co. (Milwaukee, Wis., USA). $^1$HNMR spectra were recorded on a Bruker 400 MHz or 500 MHz NMR spectrometer. Significant peaks are tabulated in the order: chemical shift, multiplicity (s, singlet; d, doublet; t, triplet; q, quartet; m, multiplet; br s, broad singlet), coupling constant(s) in Hertz (Hz) and number of protons.

The following examples are provided by way of illustration only and not by way of limitation. Those skilled in the art will readily recognize a variety of noncritical parameters that could be changed or modified to yield essentially similar results. Efforts have been made to ensure accuracy with respect to numbers used (e.g., amounts, temperatures, etc.), but some experimental errors and deviations should, of course, be allowed for.

Liquid chromatography mass spectra (LC-MS) were obtained using an electrospray ionization (ESI) source in either the positive or negative mode.

The compounds were named using ChemDraw program from Cambridge Soft Inc.

The compounds of formula I in this invention can be prepared following the synthetic strategies outlined in Scheme A. The synthesis generally starts with the tricyclic central core A-1, which is either available from commercial sources, prepared following literature reports or prepared as disclosed here. The cyclic core can be prepared bearing the suitable substituents. The flanking W and W' moieties, along with the groups attached to them, may be constructed through a stepwise functional group transformations of G and G' in parallel (route A) or one side at a time (route B and then route C or vice versa). The W and W' and respective moieties attached to them can be introduced through a cross coupling step. Once the central core scaffold is in place, further elaboration of the two ends yields additional compounds.

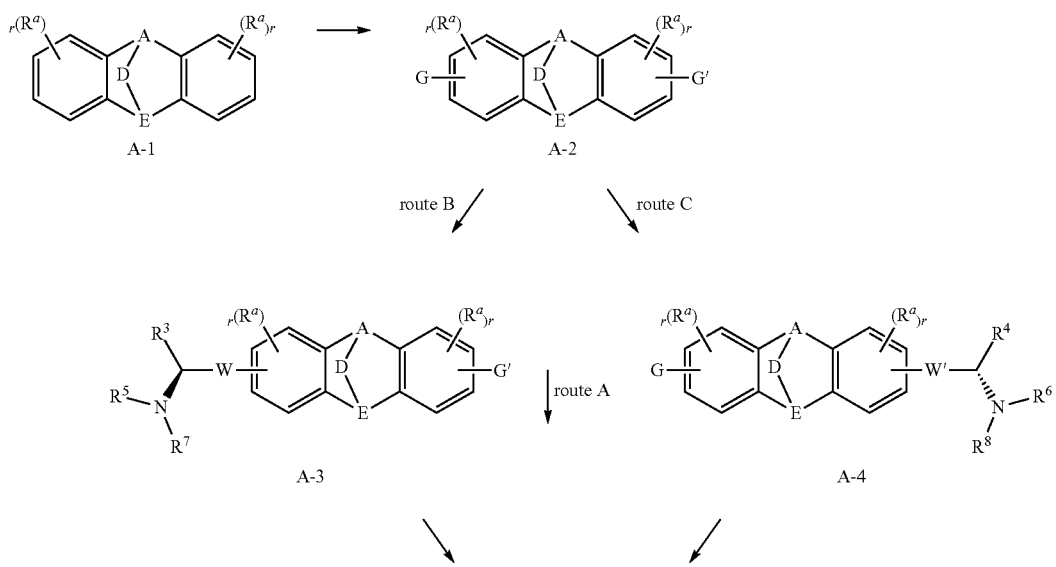

Scheme A

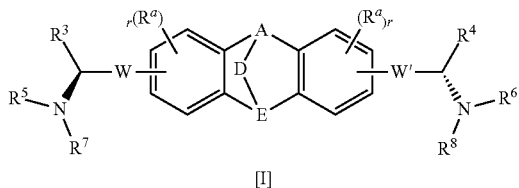

[I]

The preparations of the various claimed chemical series are further illustrated in the schemes outlined below and in greater details in the Example section. These reactions are often carried out using known procedures, methods or analogous methods thereof. Examples of such known methods include these described in a general reference text such as Comprehensive Organic Transformations; Volumes 1-10, 1974-2002, Wiley Interscience; Comprehensive Organic Synthesis Volumes 1-9, Ed. B. M. Trost, I. Fleming, 1991, Pergamon. Using 9,10-dihydro-9,10-ethanoanthracene, 5,10-dimethyl-5,10-dihydrophenazine, phenoxathiine and dibenzo[1,5]dioxocine systems as examples, we show some of the ways how W and W' groups are installed.

Scheme B

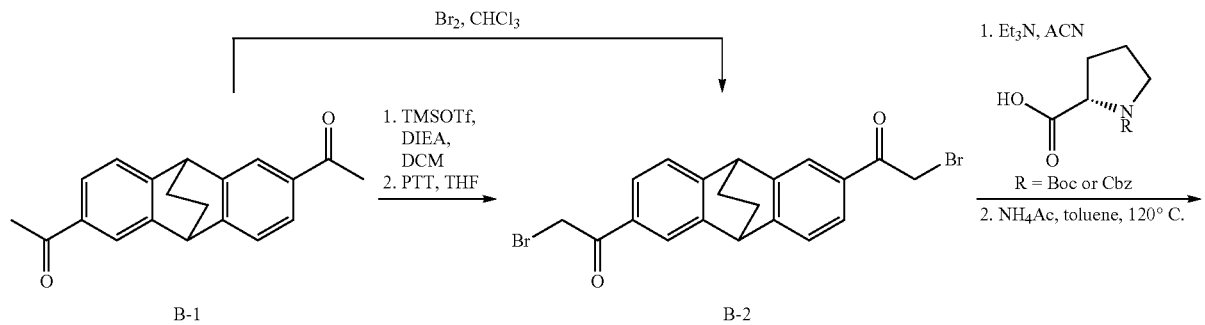

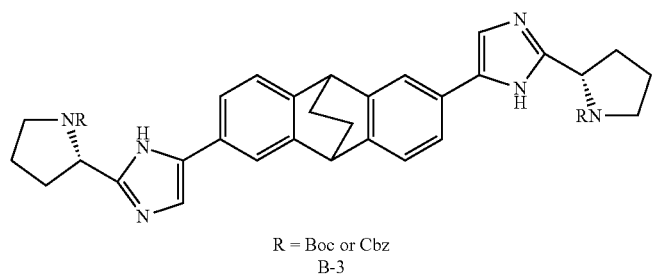

As shown in Scheme B, compound B-1 is converted to the corresponding α-bromoketone B-2, followed by reacting with N-substituted-L-Pro-OH and ring formation, to give bis-imidazole derivative B-3 which can be further transformed to give various analogs bearing different R groups through a sequence of typical de-protection and amide formation steps. Moreover, N-substituted L-Pro-OH can be replaced with other N-substituted D- or L-amino acids to generate bis-imidazole analogs of B-3.

Scheme C

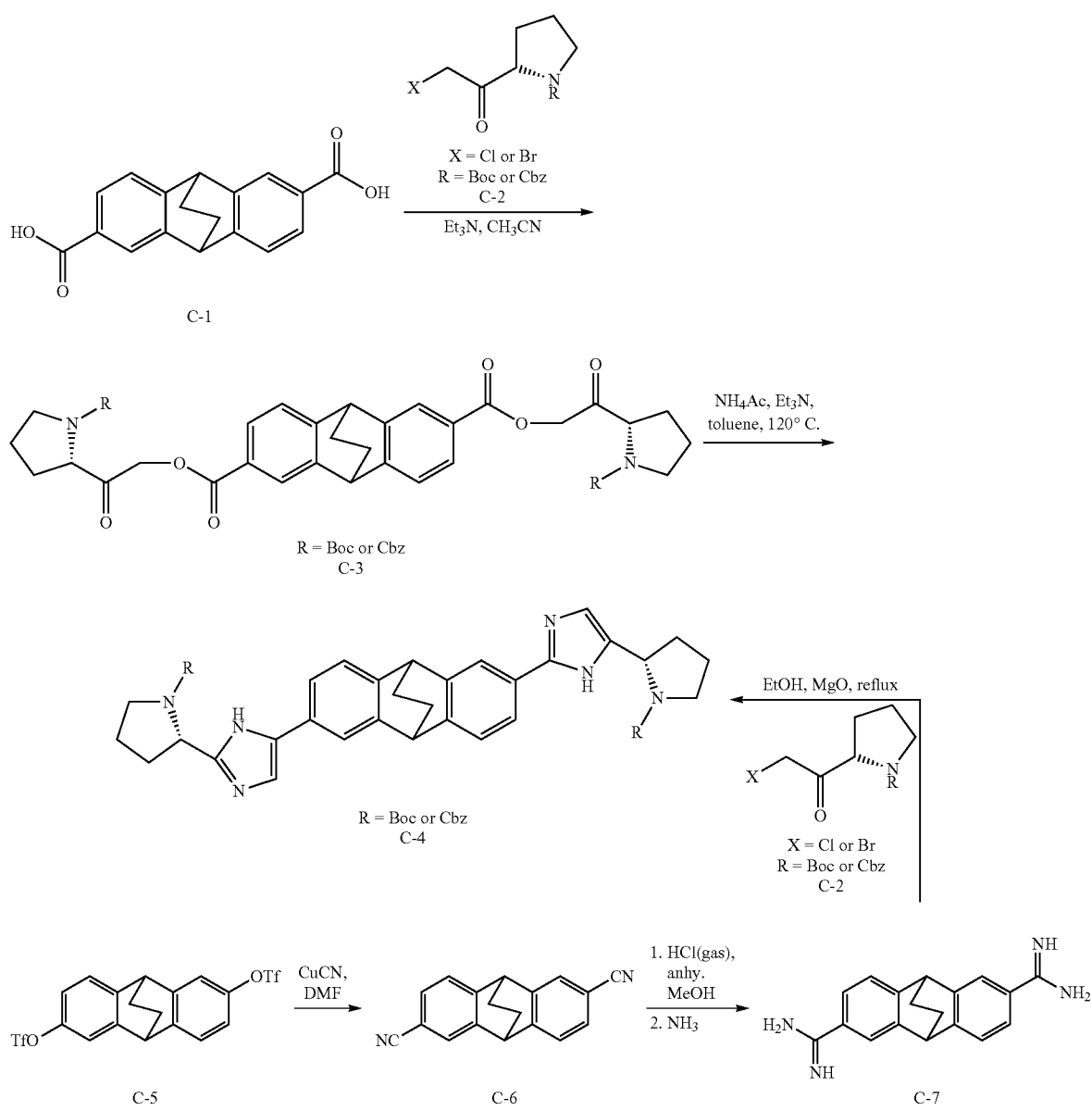

As described in Scheme C, the regioisomer of B-3 with respect to the substitution pattern on the imidazole moiety is synthesized. Coupling of C1 and (S)-2-halo-1-(pyrrolidin-2-yl)ethanone C-2, followed by ring formation, gives bis-imidazole C-4, which can be further transformed to give various analogs bearing different R groups through a sequence of typical de-protection and amide formation steps. Alternatively, C-4 can be obtained by condensing C-2 and bis-imidamide C-7. Moreover, (S)-2-halo-1-(pyrrolidin-2-yl)ethanone C-2 can be replaced with other α-halo ketones derived from N-substituted D- or L-amino acids to generate bis-imidazole analogs of C-4.

Scheme D

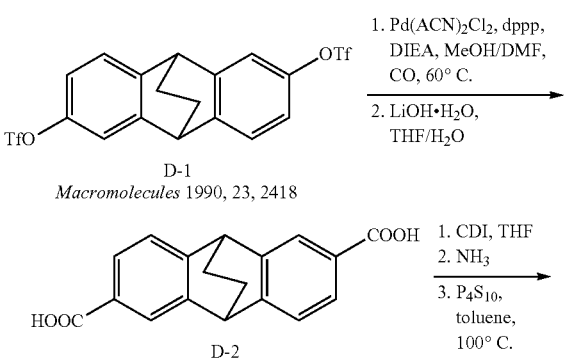

-continued

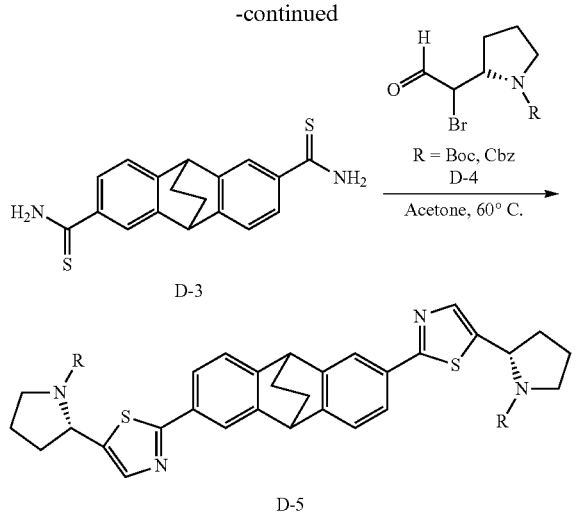

As illustrated in Scheme D, bis-triflate D-1 is readily converted to the corresponding carboxylic acid D-2 via a palladium-mediated carbonylation, followed by saponification. Subsequently, the carboxylic acid residues are converted to thio-amides D-3, followed by treatment with N-substituted 2-bromo-2-((S)-pyrrolidin-2-yl)acetaldehyde D-4 to give bis-thiazole analog D-5, which can be further transformed to give various analogs bearing different R groups through a sequence of typical de-protection and amide formation steps. Moreover, 2-bromo-2-((S)-pyrrolidin-2-yl)acetaldehyde D-4 can be replaced with other 2-bromo-2-substitutedacetaldehydes, derived from N-substituted D- or L-amino acids to generate bis-thiazole analogs of D-5.

Scheme E

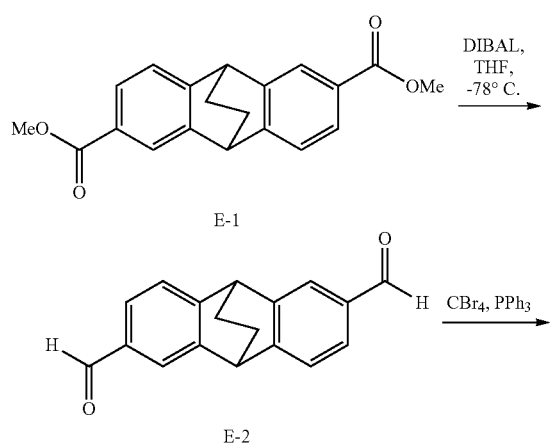

-continued

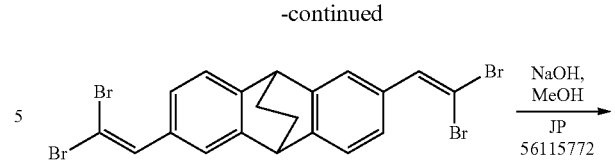

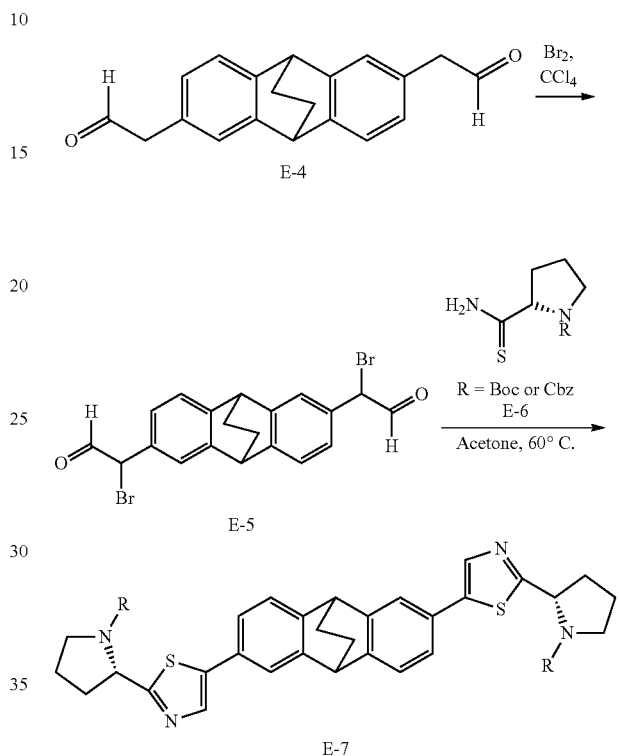

As depicted in Scheme E, the regio-isomer of bis-thioazole D-5 with respect to the substitution pattern on the thiazole moiety is prepared. Reduction of E-1, followed by condensation and hydrolysis, gives bis-substituted acetaldehyde E-4. Bromination of E-4, followed by cyclization with N-substituted (S)-pyrrolidine-2-carbothioamide E-6, affords bis-thiazole E-7, which can be further transformed to give various analogs bearing different R groups through a sequence of typical de-protection and amide formation steps. Moreover, N-substituted (S)-pyrrolidine-2-carbothioamide E-6 can be replaced with other thio-amides derived from N-substituted D- or L-amino acids to give bis-thiazole analogs of E-7.

Scheme F

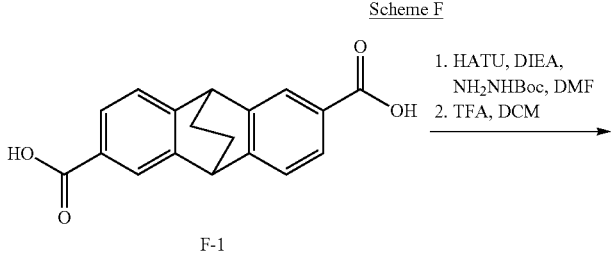

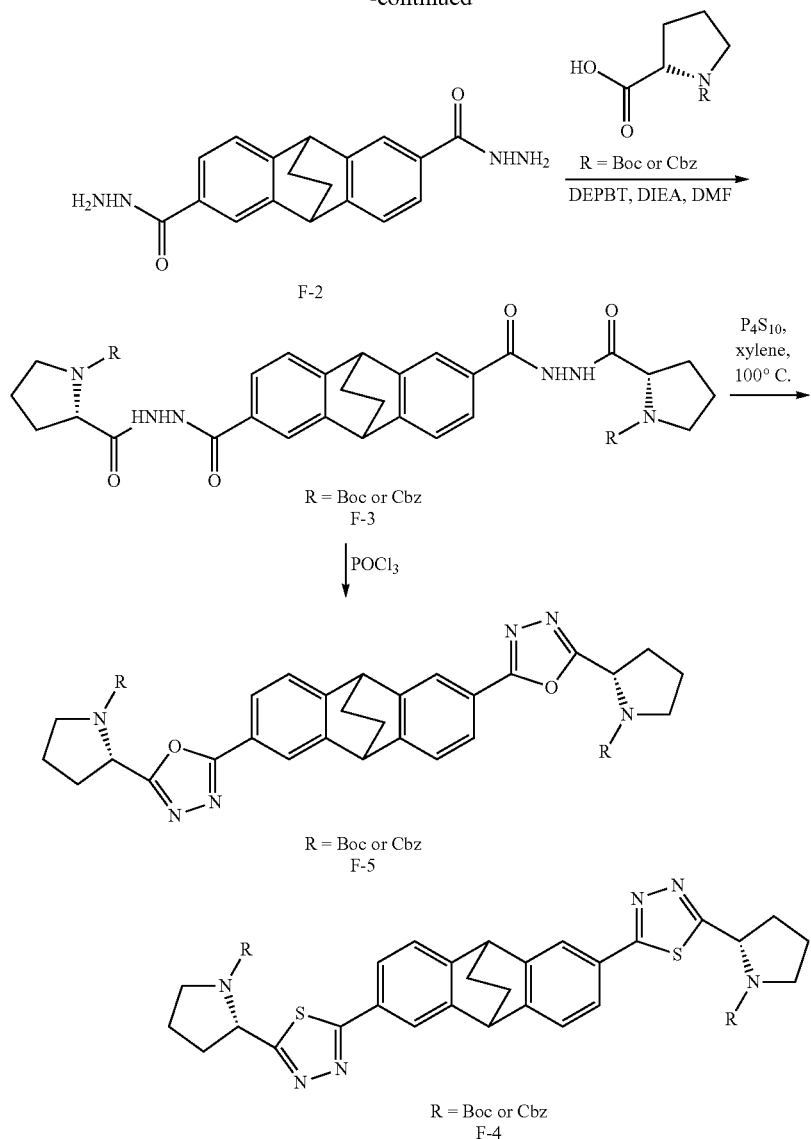

As outlined in Scheme F, bis-carboxylic acid F-1 is converted to N,N'-diacylhydrazide F-3 through a three step sequence of amide formation, de-protection and amide formation. Ring cyclization of F-3 gives either bis-thiodiazole F-4 or bis-oxadiazole F-5 when the proper de-hydration reagents are used. Both F-4 and F-5 can be further transformed to give various analogs bearing different R groups through a sequence of typical de-protection and amide formation steps. Moreover, N-substituted L-Pro-OH can be replaced with other N-substituted D- or L-amino acids to generate analogs of F-4 and F-5, respectively.

Scheme G

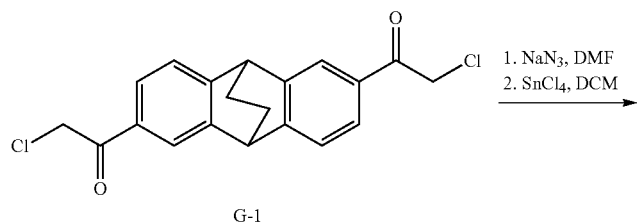

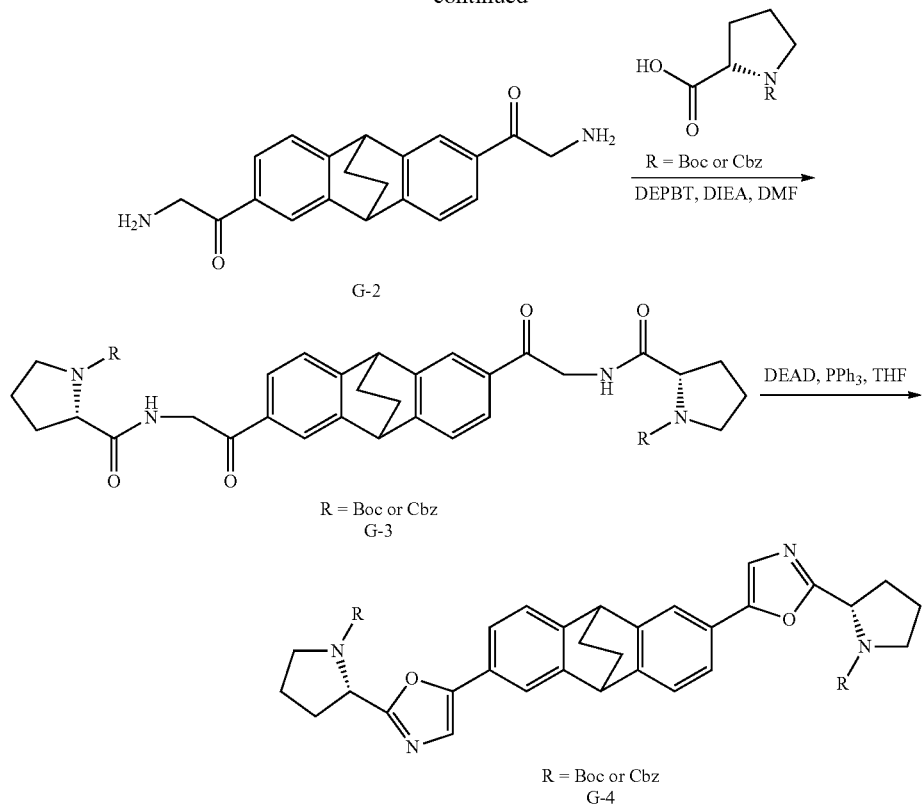

As shown in Scheme G, α-chloro ketone G-1 is converted to the corresponding α-amino ketone G-2. Amide formation of G-2 with N-substituted L-Pro-OH, followed by dehydration, affords bis-oxazole G-4, which can be further transformed to give various analogs bearing different R groups through a sequence of typical de-protection and amide formation steps. Moreover, N-substituted L-Pro-OH can be replaced with other N-substituted D- or L-amino acids to generate bis-oxazole analogs of G-4.

Scheme H

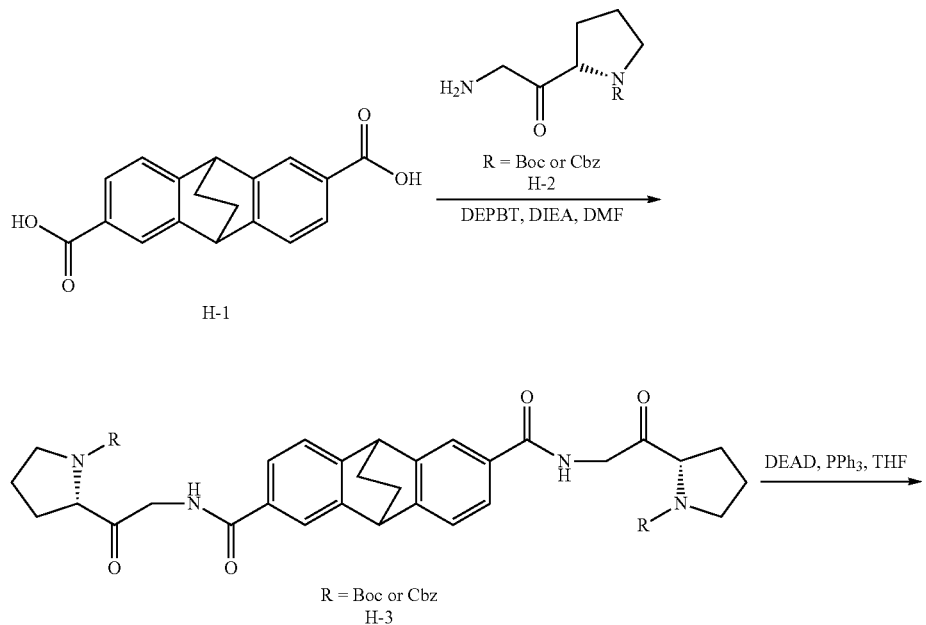

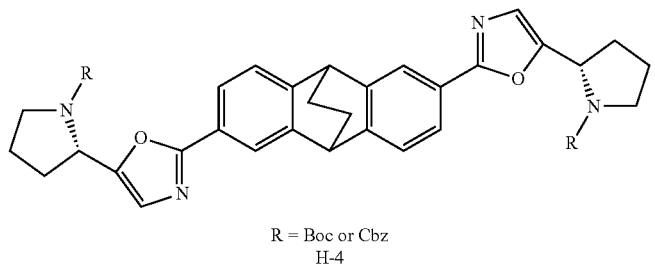

R = Boc or Cbz
H-4

As outlined in Scheme H, the regioisomer of G-4 with respect to the substitution pattern on the oxazole moiety is prepared. Amide formation of bis-carboxylic acid H-1 with (S)-2-amino-1-(pyrrolidin-2-yl)ethanone H-2, followed by dehydration, gives bis-oxazole H-4, which can be further transformed to give various analogs bearing different R groups through a sequence of typical de-protection and amide formation steps. Moreover, (S)-2-amino-1-(pyrrolidin-2-yl) ethanone H-2 can be replaced with other α-amino ketones derived from N-substituted D- or L-amino acids to generate bis-oxazole analogs of H-4.

Scheme I

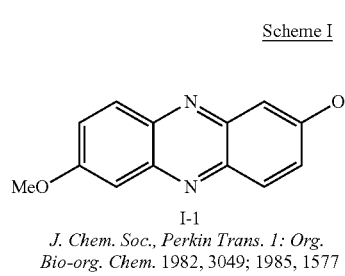

I-1
*J. Chem. Soc., Perkin Trans. 1: Org. Bio-org. Chem.* 1982, 3049; 1985, 1577

1. Na₂(S₂O₄)₂, H₂O, EtOH
2. n-BuLi, DME; MeI

*J. Heterocyclic Chem.* 1989, 26, 435

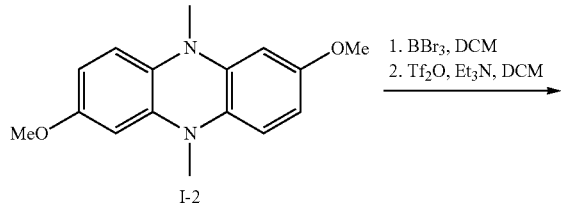

I-2

1. BBr₃, DCM
2. Tf₂O, Et₃N, DCM

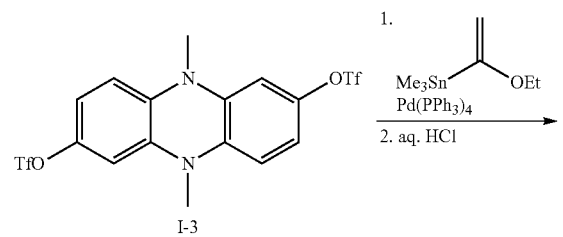

I-3

1. Me₃Sn﹨OEt, Pd(PPh₃)₄
2. aq. HCl

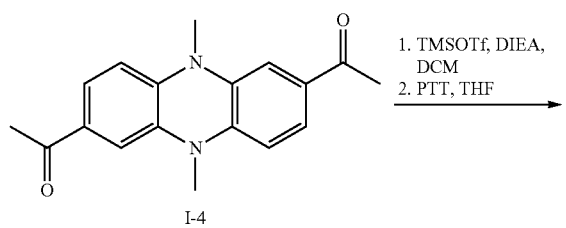

I-4

1. TMSOTf, DIEA, DCM
2. PTT, THF

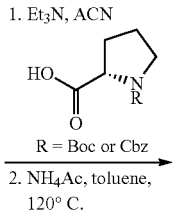

I-5

1. Et₃N, ACN

HO—⟨pro⟩—N-R
R = Boc or Cbz

2. NH₄Ac, toluene, 120° C.

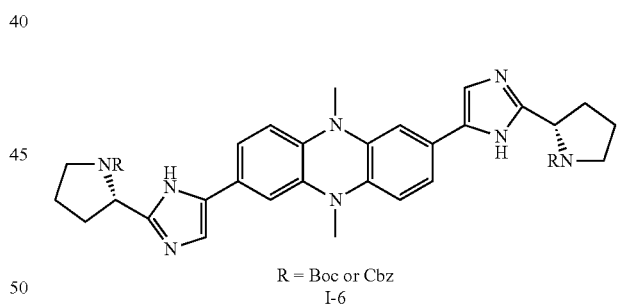

R = Boc or Cbz
I-6

As shown in Scheme I, reduction of I-1 and the subsequent N-alkylation give I-2, which is readily converted to the corresponding bis-triflate I-3. Stille coupling of I-3, followed by α-bromination, O-alkylation and ring formation affords bis-imidazole I-6, which can be further transformed to give various analogs bearing different R groups through a sequence of typical de-protection and amide formation steps. Moreover, N-substituted L-Pro-OH can be replaced with other N-substituted D- or L-amino acids to generate bis-imidazole analogs of I-6.

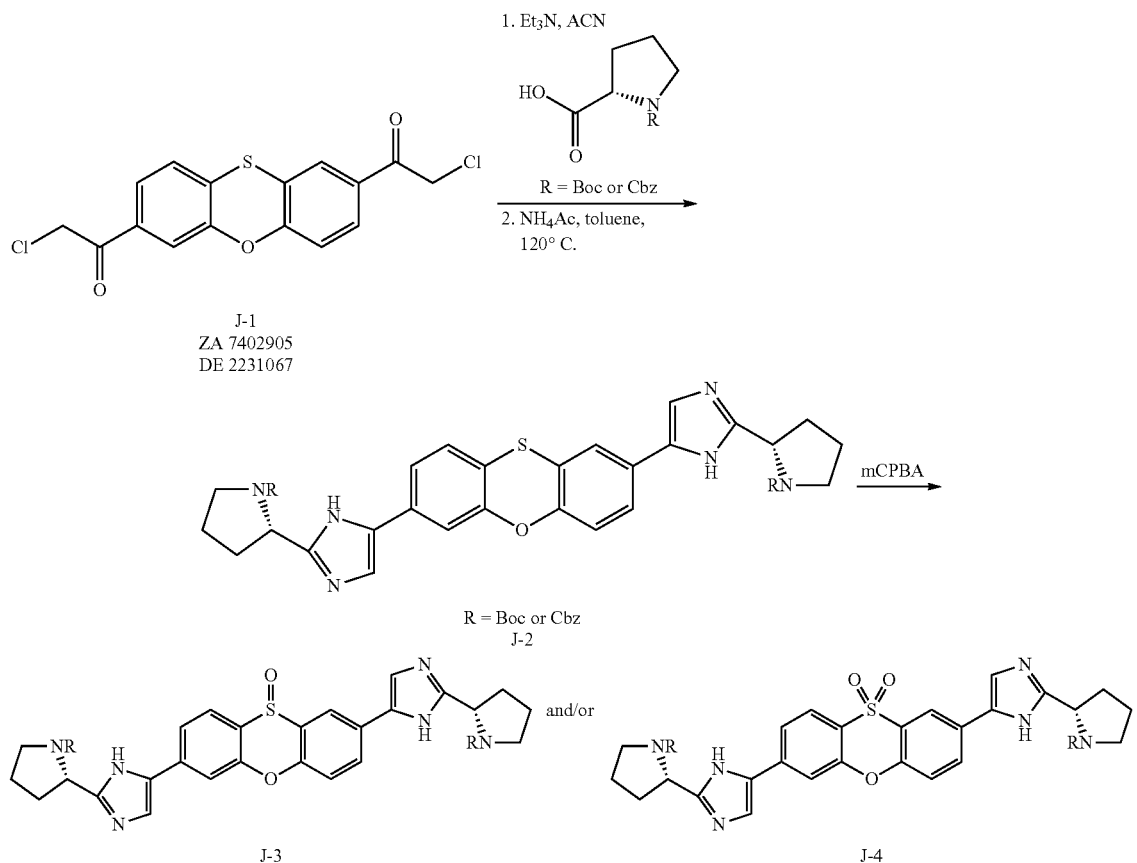

Scheme J

As described in Scheme J, O-alkylation of J-1, followed by ring cyclization, gives bis-imidazole J-2, which can be selectively oxidized to yield the corresponding sulfoxide J-3 and sulphone J-4. J-2, J-3 and J-4 can be further transformed to give various analogs bearing different R groups through a sequence of typical de-protection and amide formation steps. Moreover, N-substituted L-Pro-OH can be replaced with other N-substituted D- or L-amino acids to generate analogs of J-2, J-3 and J-4, respectively.

Scheme K

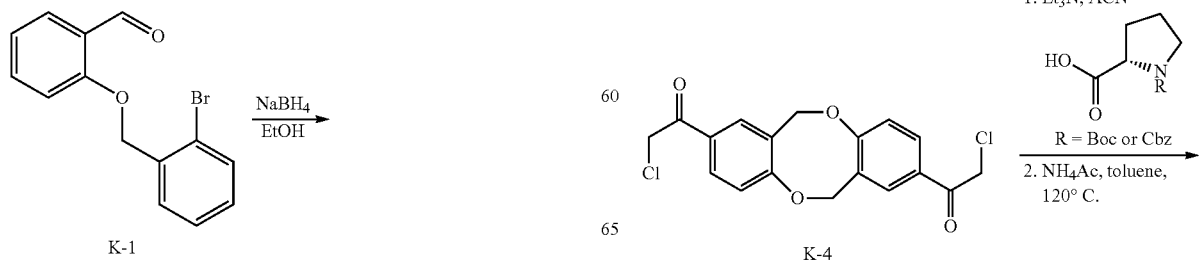

-continued

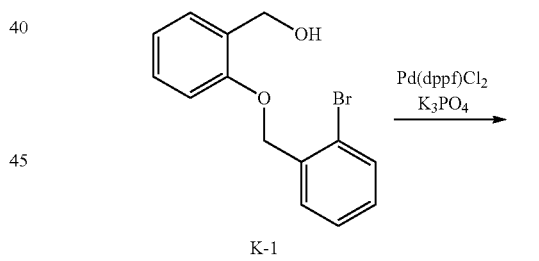

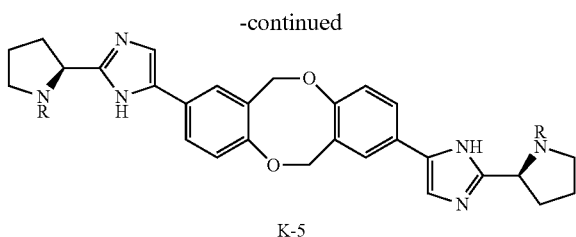

K-5

Analogs built on a dibenzo[1,5]dioxocine scaffold are prepared by using the synthetic route outlined in Scheme K or a variation of it. A properly substituted aryl ether K-2, prepared from the reduction of K-1, is cyclized to give dioxocine compound K-3 under the catalysis of a palladium catalyst such as Pd(dppf)Cl$_2$. Treatment of K-3 with chloroacetyl chloride under the standard Friedal-Craft reaction condition yields bischloromethylketone K-4. Similarly to what has been described above, bis-immidazole compound K-5 is obtained by reacting K-4 with an N-substituted-L-Pro-OH in two steps. The N-substituted L-Pro-OH used in this Scheme K can be substituted with other N-substituted D- or L-amino acids to generate bis-imidazole analogs bearing corresponding 2-substituents off the 2-position of the imidazole.

The following schemes exemplify some of the synthetic routes that are used for the preparation of compounds and their analogs included in this invention. Those skilled in the art will understand that alternative routes may also be used to reach the same and similarly functionalized intermediates and target molecules. Alternative reagents for a given transformation are also possible.

Scheme 1

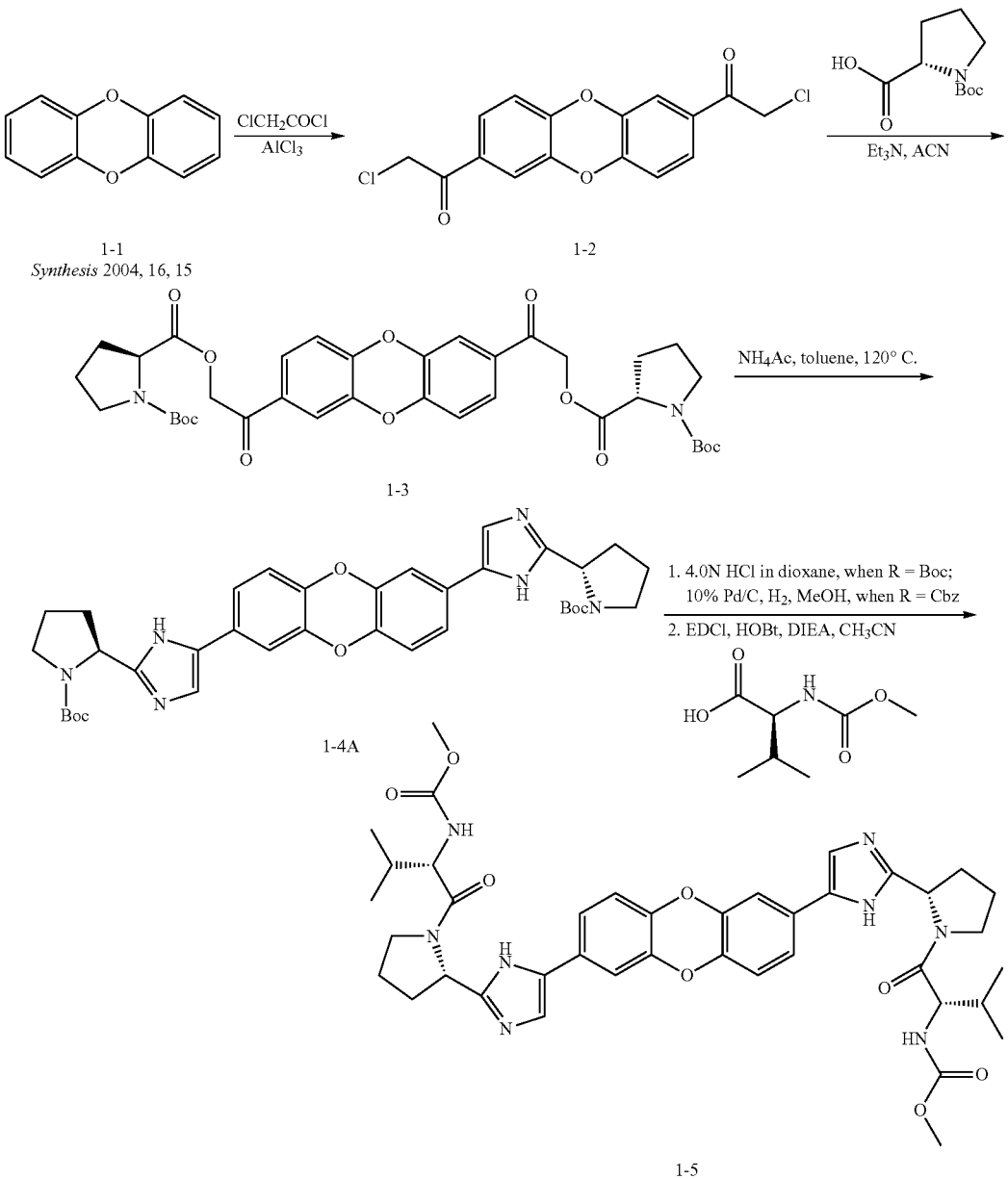

Example 1

Preparation of 1-5, dimethyl (2S,2'S)-1,1'-((2S,2'S)-2,2'-(5,5'-(dibenzo[b,e][1,4]dioxine-2,7-diyl)bis(1H-imidazole-5,2-diyl))bis(pyrrolidine-2,1-diyl))bis(3-methyl-1-oxobutane-2,1-diyl)dicarbamate Step 1.

A solution of dibenzo-p-dioxine (1-1) (5.0 g, 27.14 mmol) and chloroacetyl chloride (4.5 mL, 57 mmol) in dichloromethane (50 mL) was added over 20 min to a stirred suspension of aluminum chloride (14.5 g, 108.6 mmol) in dichloromethane (300 mL) at −78° C. and the reaction mixture was stirred at −78° C. for 15 min and allowed to warm up to room temperature over 30 min. The reaction mixture was then heated at 50° C. for 3 hrs and stirring continued at rt overnight. The reaction was cooled to 0° C. and quenched carefully with ice-cold water (250 mL). The volatiles were removed in vacuo and the precipitate formed was collected by vacuum filtration and washed with ethyl ether and dried at 50° C. in vacuo to afford crude product 1-2 (8.85 g, 97% yield), which was used in the next step without further purification. $^1$H NMR (CDCl$_3$, 300 MHz): δ 7.82-7.50 (m, 4H), 7.20 (m, 2H), 5.18 (s, 4H) ppm.

Step 2. General Procedure A—Synthesis of an Imidazole from an α-Bromoketone (or α-Chloroketone) and a Carboxylic Acid.

a. Diisopropylethylamine (6.85 mL, 39.58 mmol) was added to a stirred suspension of chloromethyl ketone 1-2 (5.54 g, 16.49 mmol), N-Boc-L-proline (7.80 g, 36.28 mmol), and KI (1.09 g, 6.6 mmol) in DMF (30 mL), and the mixture was stirred at 50° C. for 3 hrs. The cooled reaction mixture was poured into water and extracted with ethyl acetate. The combined organic layers were washed with water, brine, dried over MgSO$_4$ and then filtered. The volatiles were removed in vacuo, and the crude product was purified by flash column chromatography (SiO$_2$, EtOAc/hexanes=1/1 (v/v)) to afford ketoester 1-3 (6.85 g, 60% yield) as a light yellow solid.

b. Ketoester 1-3 from above (4.85 g, 6.98 mmol) was taken up in xylene (20 mL) and placed in a 100 mL pressure vessel. Ammonium acetate (5.34 g, 69.8 mmol) and triethylamine (5 mL) were added and the reaction mixture was heated at 140° C. for 2 hrs. The cooled mixture was diluted with ethyl acetate (150 mL) and then washed with saturated NaHCO$_3$ aqueous solution followed by brine. The organic layer was dried over anhydrous MgSO$_4$, filtered and volatiles were removed in vacuo. The crude product was purified by flash column chromatography (SiO$_2$, EtOAc) to afford product 1-4A (3.15 g, 69% yield) as a white solid. $^1$H NMR (CDCl$_3$, 300 MHz): δ 7.40-6.60 (m, 8H), 7.44 (m, 2H), 4.98 (m, 2H), 3.60-1.85 (m, 12H), 1.47 (s, 18H) ppm. LC-MS (ESI): m/z 653 [M−H]$^-$.

Step 3. General Procedure B—Deprotection and Re-Acylation.

To a stirred solution of compound 1-4A (194 mg, 0.296 mmol) in dioxane (3 mL) was added 4.0 N HCl in dioxane (3 mL). After stirring at rt for 4 hrs, the reaction mixture was concentrated and the residue was dried in vacuo to give an HCl salt, which was used for the next step without further purification. LC-MS (ESI) m/z: 455 [M+H]$^+$. The obtained HCl salt was dissolved in DMF (3 mL). To the resulting mixture were sequentially added DIEA (388 mg, 3.0 mmol), N-Moc-L-Val-OH (116 mg, 0.66 mmol) and HATU (251 mg, 0.66 mmol). After stirring at rt for 2 hrs, the reaction mixture was poured into water (50 mL) and the resulting suspension was extracted with DCM several times (20 mL×3). The extracts were combined, washed with brine and dried with anhydrous MgSO$_4$. The solvent was removed and the residue was purified by preparative HPLC and to give compound 1-5. LC-MS (ESI): m/z 769 [M+H]$^+$.

Example 2

Preparation of 1-4B

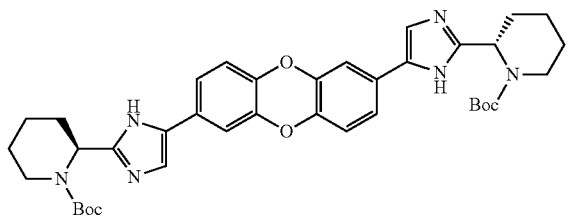 [SMILES: CC(C)(C)OC(=O)N1CCCC[C@H]1c1ncc(-c2ccc3c(c2)Oc2ccc(-c4cnc([C@@H]5CCCCN5C(=O)OC(C)(C)C)[nH]4)cc2O3)[nH]1]

Following General Procedure A described above for the synthesis of 1-4 and substituting N-Boc-L-proline with N-Boc-L-pipecolic acid in Step a, compound 1-4B (0.82 g) was obtained in 60% yield. LC-MS (ESI): m/z 681 [M−H]$^-$.

Example 3

Preparation of 1-5B

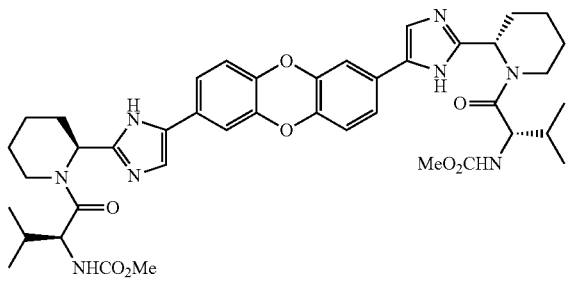

Following General Procedure B and substituting compound 1-4B for 1-4A, compound 1-5B—was obtained. LC-MS (ESI): m/z 797 [M+H]$^+$.

Example 4

Preparation of 1-4C

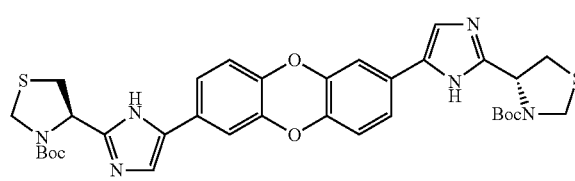

Following General Procedure A described above for synthesis of 1-4A and replacing N-Boc-L-proline with N-Boc-L-thiaproline, the corresponding ketoester 1-3C was obtained in 37% yield. ¹H NMR (CDCl₃, 300 MHz): δ 7.56 (d, 2H), 7.56 (d, 2H), 7.44 (s, 2H), 5.53-5.16 (m, 4H), 4.98 (m, 1H), 4.88 (m, 1H), 4.73-4.48 (m, 4H), 3.44 (m, 4H), 1.48 (s, 18H) ppm. LC-MS (ESI): m/z 729 [M−H]⁻.

Treatment of 1-3C with NH₄OAc under conditions as described in General Procedure A resulted in 1-4C (0.27 g) in 35% yield. ¹H NMR (CDCl₃, 300 MHz): δ 7.18 (m, 6H), 6.81 (s, 2H), 5.48 (m, 2H), 4.68 (m, 4H), 4.44 (br s, 2H), 3.43 (m, 4H), 1.48 (s, 18H) ppm. LC-MS (ESI): m/z 689 [M−H]⁻.

Example 5

Preparation of 1-5C

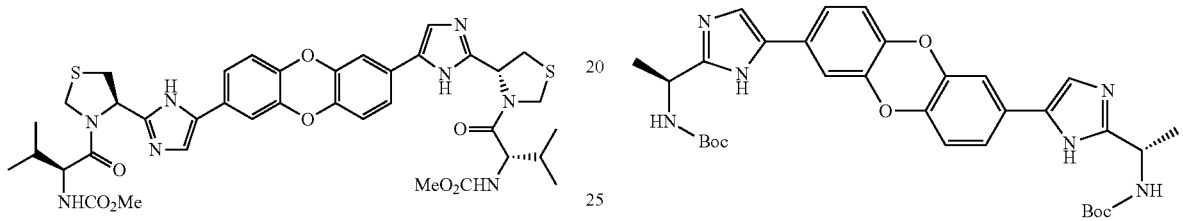

Following procedure B and substituting compound 1-4C for 1-4A, the title compound was obtained. LC-MS (ESI): m/z 805 [M+H]⁺.

Example 6

Preparation of 1-4D

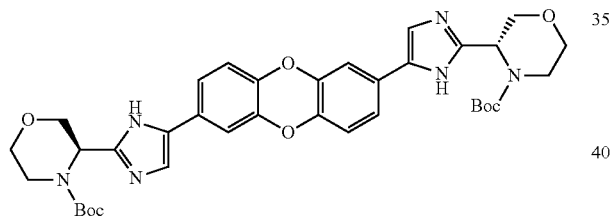

Following General Procedure A described above for synthesis of 1-4A, and replacing N-Boc-L-proline with 4-N-Boc-3(S)-morphorline carboxylic acid, compound 1-4D was obtained in 70% yield. LC-MS (ESI): m/z 686 [M−H]⁺.

Example 7

Preparation of 1-5D

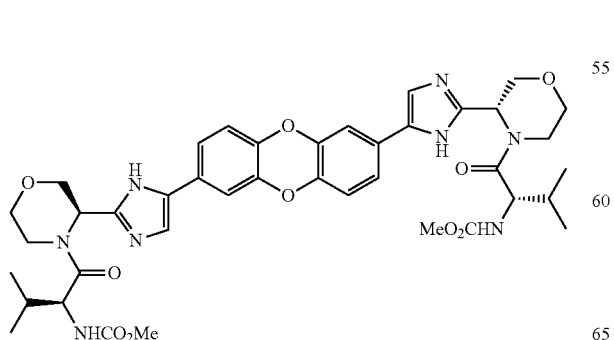

Following procedure B and substituting compound 1-4D for 1-4A, compound 1-5D was obtained. LC-MS (ESI): m/z 801 [M+H]⁺.

Example 8

Preparation of 1-4E

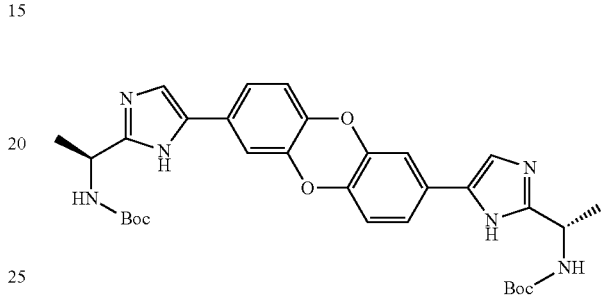

Following General Procedure A described above for synthesis of 1-4A, and replacing N-Boc-L-proline with N-Boc-L-alanine, compound 1-4E was obtained in 72% yield in two steps. LC-MS (ESI): m/z 601 [M−H]⁻.

Example 9

Preparation of 1-5E

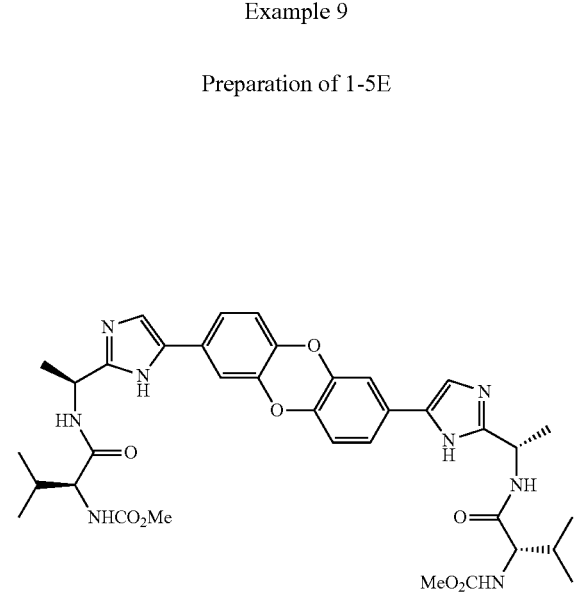

Following General Procedure B and substituting compound 1-4E for 1-4A, the title compound was obtained. LC-MS (ESI): m/z 717 [M+H]⁺.

Scheme 2
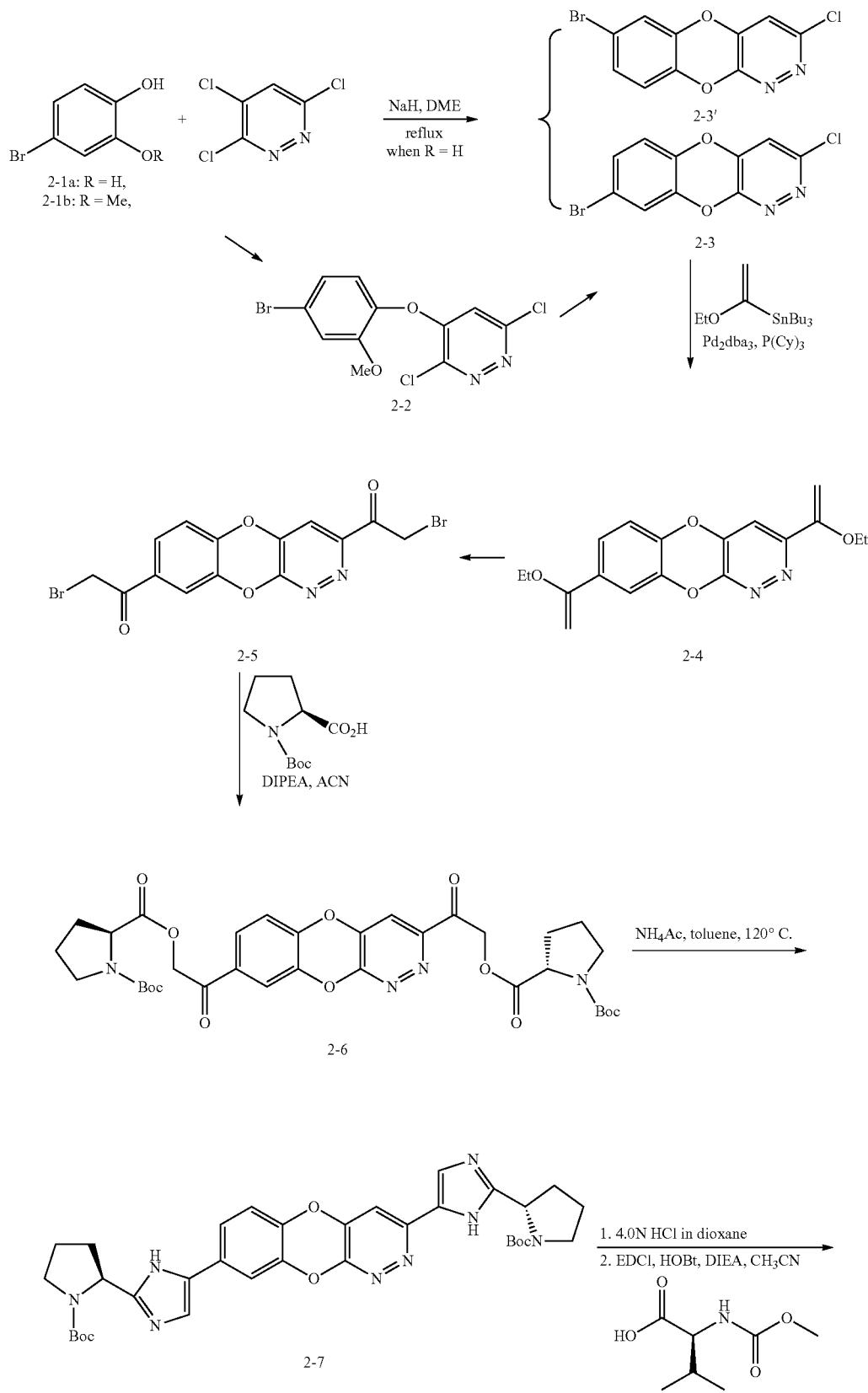

-continued

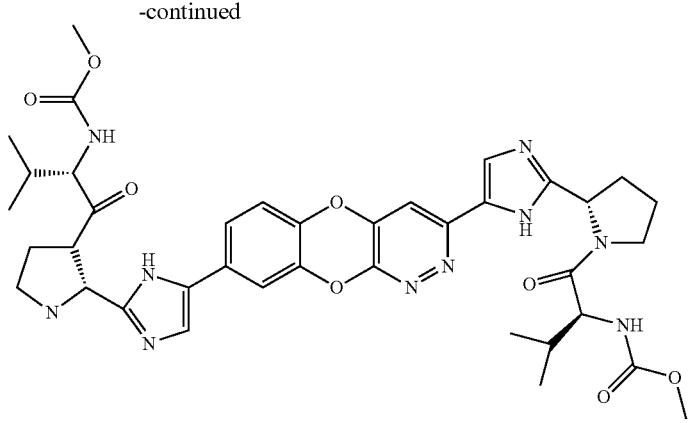

2-8

Step 1.

Referring to Scheme 2, to a solution of 4-bromobenzene-1,2-diol (2-1a) (1.0 g, 5.29 mmol) in anhydrous DME (10 mL), sodium hydride (50% dispersion, 0.51 g, 10.6 mmol) was added. The reaction suspension was stirred at rt for 30 min protected by an atmosphere of $N_2$. 3,4,6-Trichloropyridazine (2-2) (0.97 g, 5.30 mmol) was added and the reaction mixture was warmed up to 85° C. for two hrs. After cooled to rt and concentrated to remove all solvents, the residue was diluted with ice-water (30 mL) and collected by filtration. The filter cake was rinsed with 1M sodium hydroxide, water and dried under vacuum. Regio-isomers 2-3 and 2-3' (1.7 g) were obtained as a mixture which were used without further purification. LC-MS (ESI): m/z 298.95/300.9 [M+H]$^+$.

An alternative, and regiospecific, route to compound 2-3 was achieved by using the procedures described below.

Step 1-a.

To a solution of 4-bromo-2-methoxyphenol (2-1b R=Me) (or 2-1c R=Bn) (2.0 g, 9.85 mmol) in anhydrous DME (40 mL), sodium hydride (50% dispersion, 0.473 g, 9.85 mmol) was added. The reaction suspension was stirred at rt for 30 min under $N_2$. 3,4,6-Trichloropyridazine (2-2) (1.80 g, 9.85 mmol) was added, and the reaction mixture was stirred for 3 days at rt. After removal of all solvents, the residue was diluted with ice-water, product precipitated out and was collected by filtration. The filter cake was washed with 1M sodium hydroxide, water and dried under vacuum. The crude mixture was purified by flash column chromatography (hexanes/ethyl acetate=6/1 (v/v)) to afford compound 2-2b (2.8 g). LC-MS (ESI): m/z 350.9 [M+H]$^+$.

Step 1-b.

Pyridine (0.5 mL) was added to concentrated HCl (0.5 mL) at room temperature. The mixture was heated to 220° C. in a microwave oven for 5 min. After the solution was cooled to rt, compound 2-2b was added in. The entire mixture was heated to 220° C. in a microwave oven for another 15 min. Compound 2-3 was formed as the major isomer. LC-MS (ESI): m/z 299.0/301.0 [M+H]$^+$.

Step 2.

A seal tube was charged with $Pd_2(dba)_3$ (45 mg, 0.049 mmol), tricyclohexylphosphine (27.5 mg, 0.098 mmol) and dioxane (10 mL). The resulting solution was bubbled with $N_2$ for 5 min and stirred for 30 min at rt. Compound 2-3 (500 mg, 1.67 mmol), tri-n-butyl(1-ethoxyvinyl)stannane (1.24 mL, 3.66 mmol) were added under the protection of an atmosphere of $N_2$. After sealed and stirred for 18 hrs at 100° C., the reaction mixture was diluted with dichloromethane, washed with saturated sodium bicarbonate, brine, water. The organic phase was dried over anhydrous $Na_2SO_4$, filtered and concentrated to give the crude product, which was purified by flash column chromatography (hexane/ethyl acetate/28% $NH_4OH$=4/1/0.05 (v/v/v)) to afford compound 2-4 (470 mg).

Step 3.

To a solution of the compound 2-4 (460 mg, 1.41 mmol) in dioxane (15 mL) and water (4 mL), NBS (502 mg, 2.82 mmol) was added in portions over 15 min at 0° C. After 30 min, the reaction was warmed up to rt and stirred for another 30 min. The reaction mixture was diluted with dichloromethane and washed with 1M sodium bisulfite, brine, water, dried over anhydrous $Na_2SO_4$. After concentration to remove all solvents, compound 2-5 (450 mg) was obtained and used in the next step without further purification.

Step 4.

A solution of 2-5 (450 mg, 1.05 mmol) in $CH_3CN$ (10 mL) was added (S)-Boc-proline (500 mg, 2.32 mmol) and N,N-Diisopropylethylamine (0.403 mL, 2.31 mmol). The mixture was stirred overnight. The volatile components were removed by evaporation, and the residue was partitioned between water and DCM. The aqueous layer was back extracted with DCM. The combined organic phase was washed by brine, saturated sodium carbonate and water, dried over anhydrous $Na_2SO_4$. After concentration, the crude mixture was purified by flash column chromatography (dichloromethane/ethyl acetate=2/1 (v/v)) to afford compound 2-6 (250 mg). LC-MS (ESI): m/z 697.4 [M+H]$^+$.

Step 5.

A sealed tube was charged with 2-6 (120 mg, 0.172 mmol), ammonium acetate (200 mg, 2.60 mmol), triethylamine (0.196 mL, 1.40 mmol) and xylene (40 mL). The resulting mixture was stirred at 140° C. for 2 hrs, at which point LC-MS showed the reaction was completed. The solvent was removed in vacuo, and the residue was partitioned between water and DCM. The aqueous layer was extracted with DCM. The combined organic phase was washed by brine, water, and dried over anhydrous $Na_2SO_4$. After removing the solvents, the crude mixture was purified by prep-TLC (hexane/ethyl acetate=1/3 (v/v)) to afford compound 2-7 (60 mg). LC-MS (ESI): m/z 657.4 [M+H]$^+$.

Step 6.

Following General Procedure B (described in Step 3 of Example 1), compound 2-8 was obtained. -MS (ESI): m/z 771.8 [M+H]$^+$.

Scheme 5

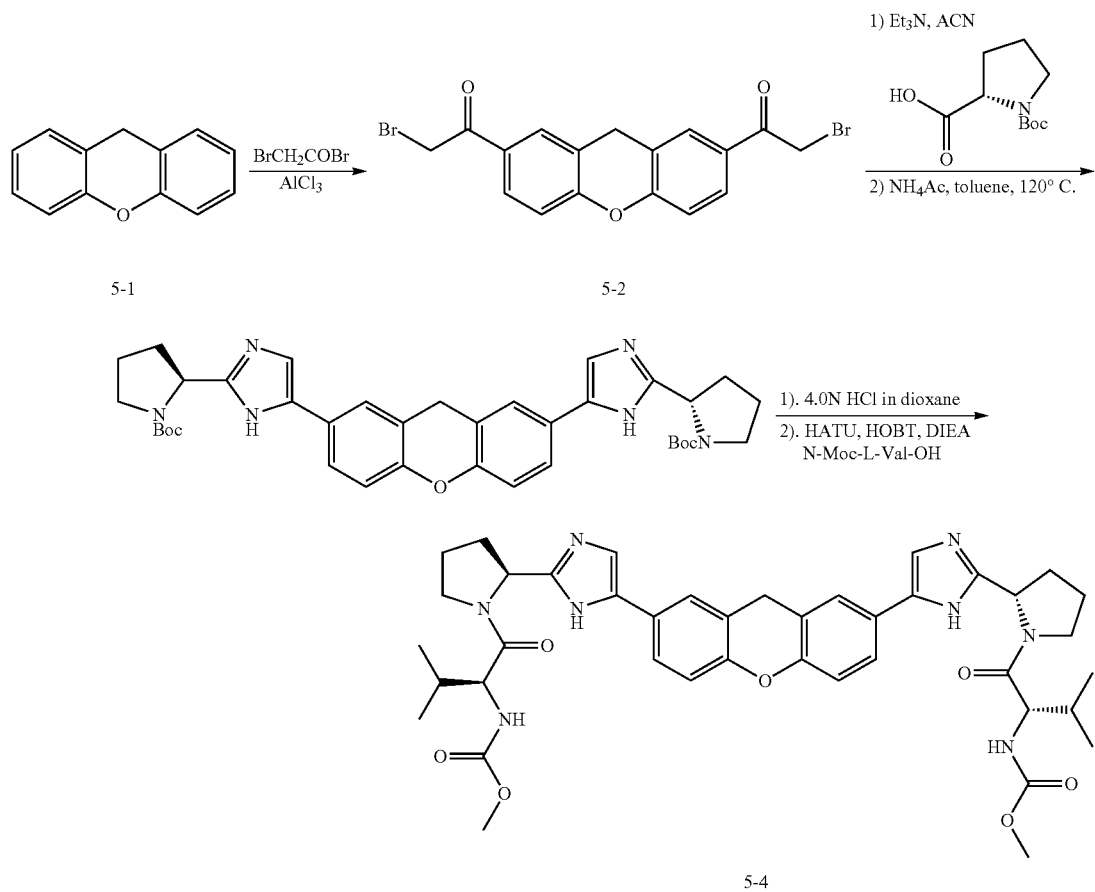

Example 10

(2S,2S')-tert-butyl 2,2'(5,5'-(9H-xanthene-2,7-diyl)bis(1H-imidazole-5,2-diyl))dipyrrolidine-1-carboxylate (5-3)

Step 1.

Referring to Scheme 5, bromoacetyl chloride (4.59 ml, 54.9 mmol) was added dropwise to a solution of 9H-xanthene (5 g, 27.4 mmol) and $AlCl_3$ (8.05 g, 60.4 mmol), DCM (100 mL) at 0° C. The reaction mixture was allowed to warm up to rt and left to stir for 72 hrs. The reaction mixture was poured onto ice (400 mL), extracted with DCM (2×200 mL). The combined organic phase was washed with brine (400 mL), dried over $MgSO_4$, filtered and evaporated to dryness. The crude material was precipitated in EtOAc and filtered to give 1,1'-(9H-xanthene-2,7-diyl)bis(2-bromoethanone) (5-2) as a white solid (4.27 g, 36.7% yield). LC-MS (ESI): m/z 425.9 [M+H]$^+$.

Step 2.

Following General Procedure A as described in the synthesis of 1-4A, and substituting 1,1'-(9H-xanthene-2,7-diyl)bis(2-bromoethanone) (5-2) for 1,1'-(dibenzo[b,e][1,4]dioxine-2,7-diyl)bis(2-chloroethanone) (1-2) in Step 2a of the procedure, compound 5-3 was obtained as a brown solid in 35% yield. LC-MS (ESI): m/z 653.7 [M+H]$^+$; 651.8 [M−H]$^-$.

Example 11

Dimethyl (2S,2'S)-1,1'-((2S,2'S)-2,2'-(5,5'-(9H-xanthene-2,7-diyl)bis(1H-imidazole-5,2-diyl))bis(pyrrolidine-2,1-diyl))bis(3-methyl-1-oxobutane-2,1-diyl) dicarbamate Following General Procedure B, product 5-4 was obtained in 2 steps from 5-3 as a white solid (161 mg, 59% yield) from 5-3. LC-MS (ESI): m/z 767.0 [M+H]$^+$; 765.2 [M−H]$^-$.

Example 12

Dimethyl-(1R,1'R)-2,2'-((2S,2'S)-2,2'-(5,5'-(9H-xanthene-2,7-diyl)bis(1H-imidazole-5,2-diyl))bis(pyrrolidine-2,1-diyl))bis(2-oxo-1-phenylethane-2,1-diyl) dicarbamate (5-5)

Following General Procedure B and using N-Moc-D-phenylglycine as the coupling amino acid, product 5-5 was obtained as a white solid (209 mg, 67% yield). LC-MS (ESI): m/z 835.1 [M+H]$^+$; 833.0 [M−H]$^-$.

Other compounds bearing the same 2,7-disubstituted xanthenes scaffold are prepared similarly and listed in Table 1.

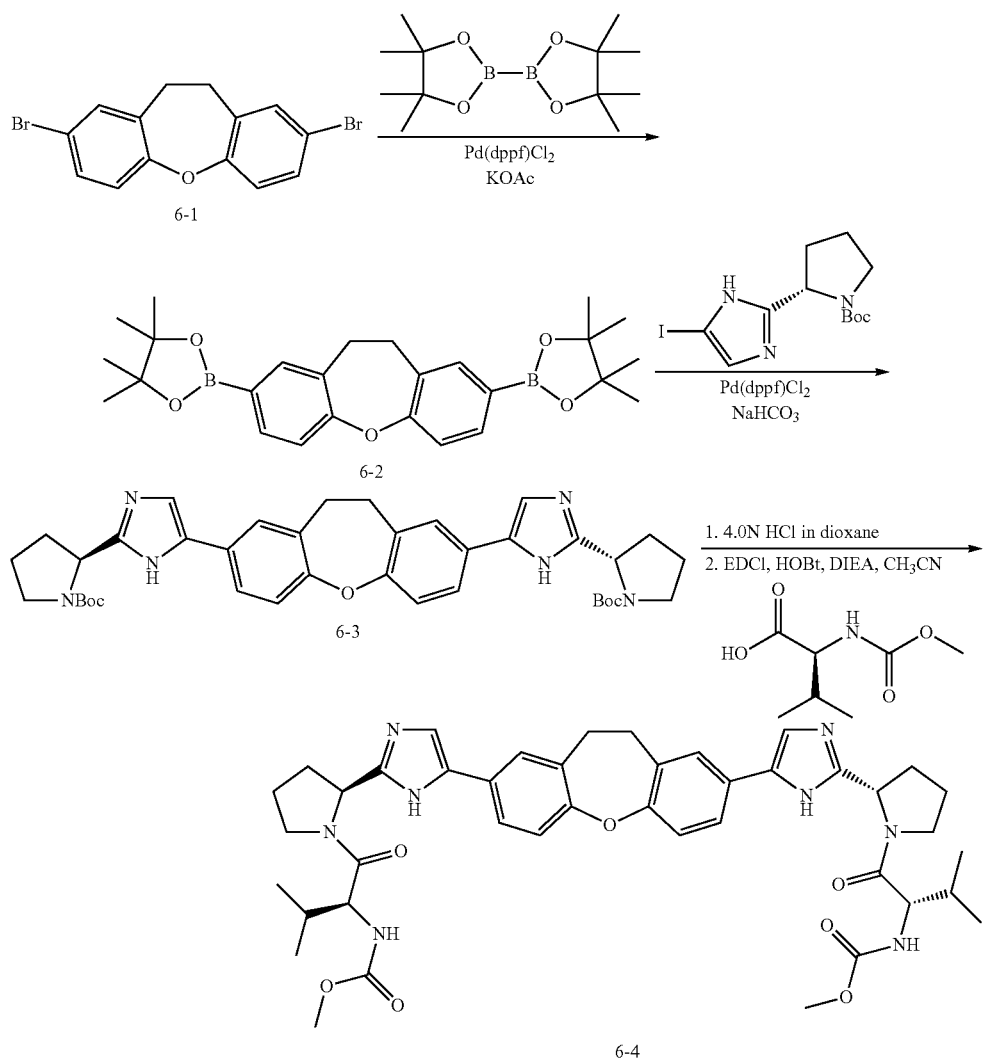

Example 13

Dimethyl(2S,2'S)-1,1'-(2S,2'S)-2,2'-(5,5'-(10,11-dihydrodibenzo[b,f]oxepine-2,8-diyl)bis(1H-imidazole-5,2-diyl))bis(pyrrolidine-2,1-diyl)bis(3-methyl-1-oxobutane-2,1-diyl)dicarbamate (6-4)

Step 1. General Procedure C: Preparation of an Arylborate from an Aryl Bromide, Aryl Iodide or Aryl Trifoliate.

Referring to Scheme 6, a solution of 2,8-dibromo-10,11-dihydrodibenzo[b,f]oxepine (6-1) (prepared according procedures reported in WO2005090337) (435 mg, 1.229 mmol), potassium acetate (627 mg, 6.39 mmol), bis(pinacolato)diboron (1.31 g, 5.16 mmol) and Pd(dppf)Cl$_2$ (90 mg, 0.123 mmol) in dioxane (15 mL) was degassed and heated at 90° C. overnight. Reaction mixture was allowed to cool to room temperature and then filtered through celite, adsorbed on SiO$_2$ and then purified by column chromatography (SiO$_2$, 0-100% (v/v) of DCM/isohexanes) to give 2,8-bis(4,4,5,5-tetramethyl-1,3,2-dioxaborolan-2-yl)-10,11-dihydrodibenzo[b,f]oxepine (6-2) (169 mg, 31% yield) as a white solid. $^1$H NMR (CDCl$_3$): δ 7.63-7.57 (4H, m), 7.17-7.13 (2H, m), 3.13 (4H, s), 1.33 (24H, s) ppm. LC-MS (ESI): m/z 449.0 [M+H]$^+$.

Step 2.

Preparation of (2S,2'S)-tert-butyl-2,2'-(5,5'-(10,11-dihydrodibenzo[b,f]oxepine-2,8-diyl)bis(1H-imidazole-5,2-diyl))dipyrrolidine-1-carboxylate (6-3). General Procedure D: A mixture of 6-2 (300 mg, 0.669 mmol), (S)-tert-butyl 2-(5-iodo-1H-imidazol-2-yl)pyrrolidine-1-carboxylate (486 mg, 1.339 mmol), NaHCO$_3$ (450 mg, 5.36 mmol) and Pd(dppf)Cl$_2$ (98 mg, 0.134 mmol) in DME (4.5 mL), water (1.5 mL) was degassed and then heated at 80° C. for 18 hrs. Water (40 ml) was then added and the mixture extracted with 20% MeOH/CHCl$_3$ (3×50 mL). The combined organics were washed with brine, dried over MgSO$_4$, filtered and evaporated to dryness. The product was purified by silica gel chromatography (Companion, 40 g cartridge, 0-10% MeOH/DCM+1% NH$_3$) to give ~300 mg brown oil. Further purification by silica gel chromatography eluting with 10% MeOH in DCM containing 1% NH$_3$ gave (2S,2'S)-tert-butyl-2,2'-(5,5'-(10,11-dihydrodibenzo[b,f]oxepine-2,8-diyl)bis(1H-imidazole-5,2-diyl))dipyrrolidine-1-carboxylate (6-3) as a clear oil (210 mg, 47% yield). LC-MS (ESI): m/z 667.1 [M+H]$^+$; 666.2 [M−H]$^−$.

Step 3.

Compound 6-4 was prepared as a white solid (69 mg, 38% yield) following General Procedure B. LC-MS (ESI): m/z 782.0 [M+H]$^+$.

Example 14

Dimethyl-(1R,1'R)-2,2'-((2S,2'S)-2,2'-(5,5'-(10,11-dihydrodibenzo[b,f]oxepine-2,8-diyl)bis(1H-imidazole-5,2-diyl))bis(pyrrolidine-2,1-diyl))bis(2-oxo-1-phenylethane-2,1-diyl)dicarbamate (6-5)

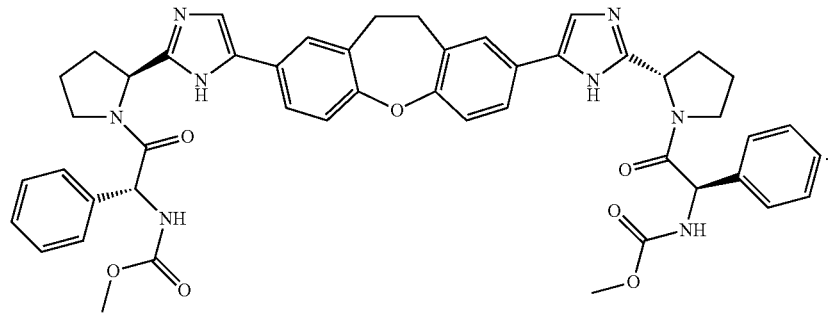 [SMILES: COC(=O)N[C@@H](C(=O)N1CCC[C@H]1c1ncc(-c2ccc3c(c2)CCc2cc(-c4cnc([C@@H]5CCCN5C(=O)[C@H](NC(=O)OC)c5ccccc5)[nH]4)ccc2O3)[nH]1)c1ccccc1]

Following General Procedure B, the title product (6-5) was obtained as a white solid (15 mg, 9% yield). LC-MS (ESI): m/z 849.4 [M+H]$^+$.

Scheme 7

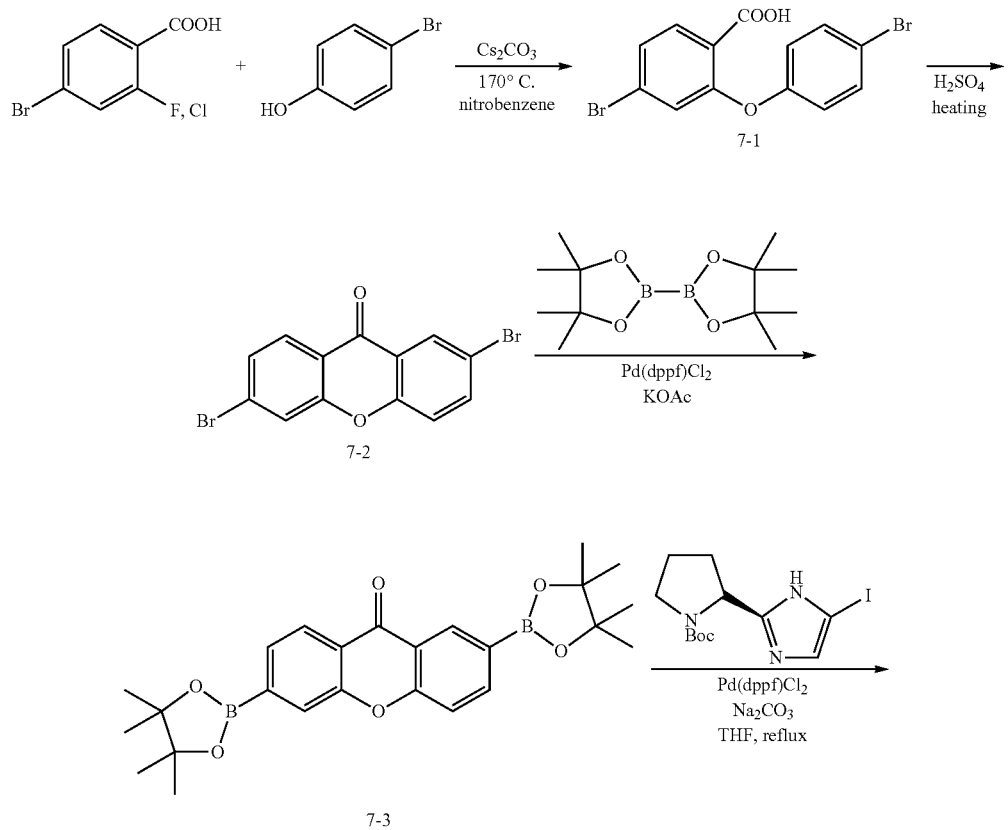

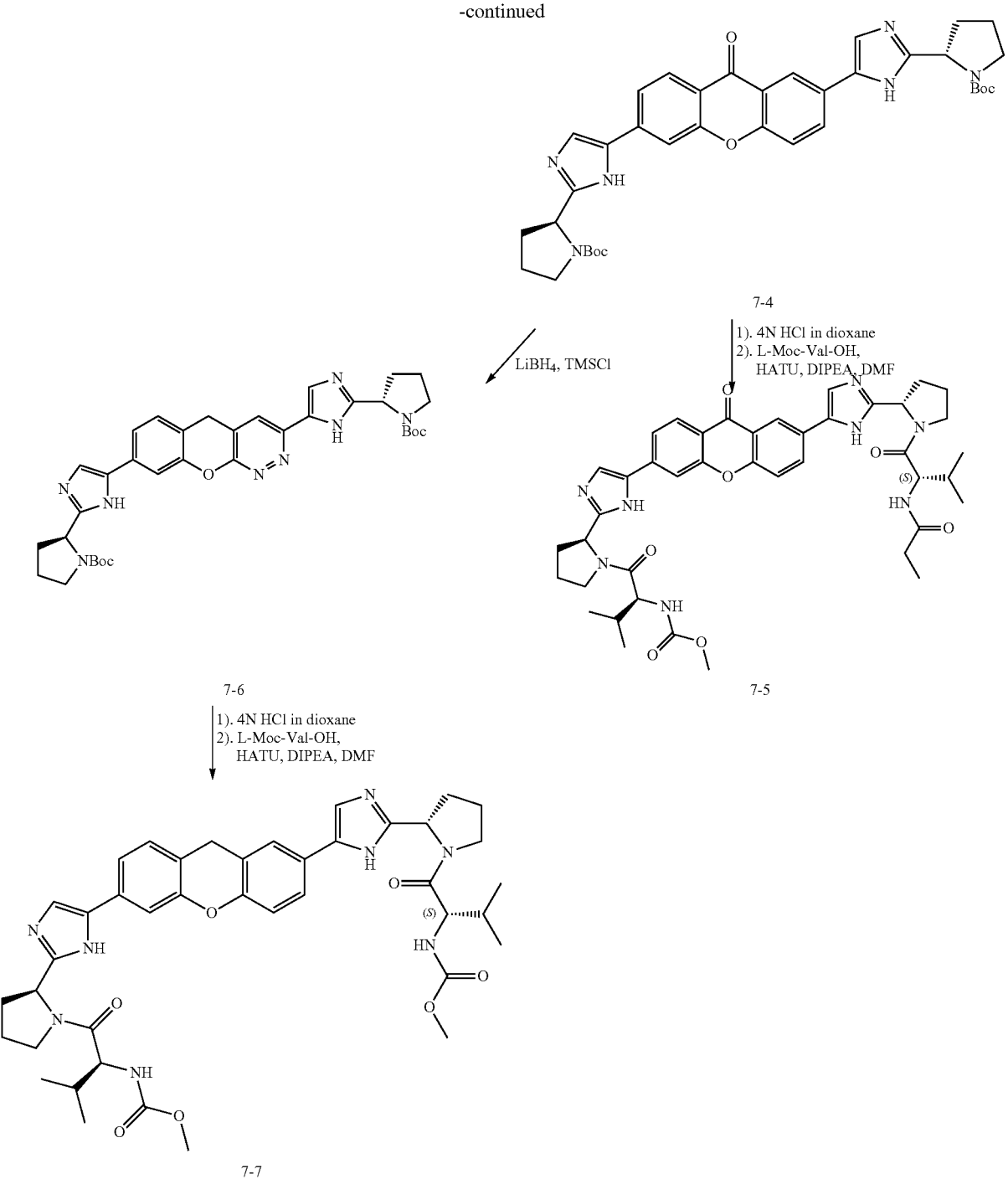

Example 15

Preparation of dimethyl (2S,2'S)-1,1'-((2S,2'S)-2,2'-(5,5'-(9-oxo-9H-xanthene-2,6-diyl)bis(1H-imidazole-5,2-diyl))bis(pyrrolidine-2,1-diyl))bis(3-methyl-1-oxobutane-2,1-diyl)dicarbamate (7-5)

Step 1. General Procedure E—Synthesis of Xanthen-9-one.

Referring to Scheme 7, to a solution of 4-bromo-2-chlorobenzoic acid (18.4 g, 83.9 mmol) and 4-bromophenol (24 g, 109 mmol) in nitrobenzene was added cesium carbonate (82 g, 251.7 mmol). The resulting solution was heated at 170° C. with a condenser for 1 day. The reaction mixture was cooled to 70° C. and filtered at this temperature. The residue was washed with toluene. The organic layer was removed by vacuum distillation till a thick dark residue remained. To the dark residue was added aqueous HCl (1N, 400 mL) and DCM (200 mL). The resulting solution was stirred until dark oil dispersed into DCM solution. The mixture was filtered. The organic layer was dried over anhydrous $Na_2SO_4$ and concentrated to afford the crude product. The residue was purified by column chromatography on silica gel, eluted first with DCM and then with a mixture of DCM and MeOH to give 7-1.

Step 2.

Compound 7-1 (16 g, 5:3 ratio, 44.3 mmol) was treated with concentrated sulfuric acid (95 mL). The solution was heated at 105° C. for 2 hrs. The reaction mixture was cooled and poured into ice water. The product precipitated out and was collected by filtration, washed with $Et_2O$ and $H_2O$. The solid was dried and further purified by silica gel flash column chromatography (eluents: Hexane/AcOEt=9:1 (v/v), pure AcOEt and pure DCM) to afford 7-2 (12 g).

Step 3.

Compound 7-4 was prepared according to conditions described in general procedure C. LC-MS (ESI): m/z 667.3 [M+H]$^+$.

Step 4.

Compound 7-5 was prepared according to conditions described in general procedure B. LC-MS (ESI): m/z 781.3 [M+H]$^+$.

Example 16

Preparation of 7-7

Step 1.

To a solution of compound 7-4 (1.6 g, 2.39 mmol) in anhydrous THF (40 mL) was added lithium borohydride (1.0 g, 45.6 mmol). The resulting solution was warmed up to 60° C. After stirring for 3 hrs, the reaction was cooled to rt and slowly transferred to another bottle that was charged with chlorotrimethylsilane (3.0 mL, 23.6 mmol) in THF (100 mL). The mixture was stirred for an additional 20 mins at rt, and quenched by addition of methanol (10 mL). After removal of all the solvents in vacuo, 7-6 was obtained. LC-MS (ESI): m/z 667.3 [M+H]$^+$.

Step 2.

Treatment of 7-6 under the conditions of general procedure B afforded compound 7-7. LC-MS (ESI): m/z 767 [M+H]$^+$.

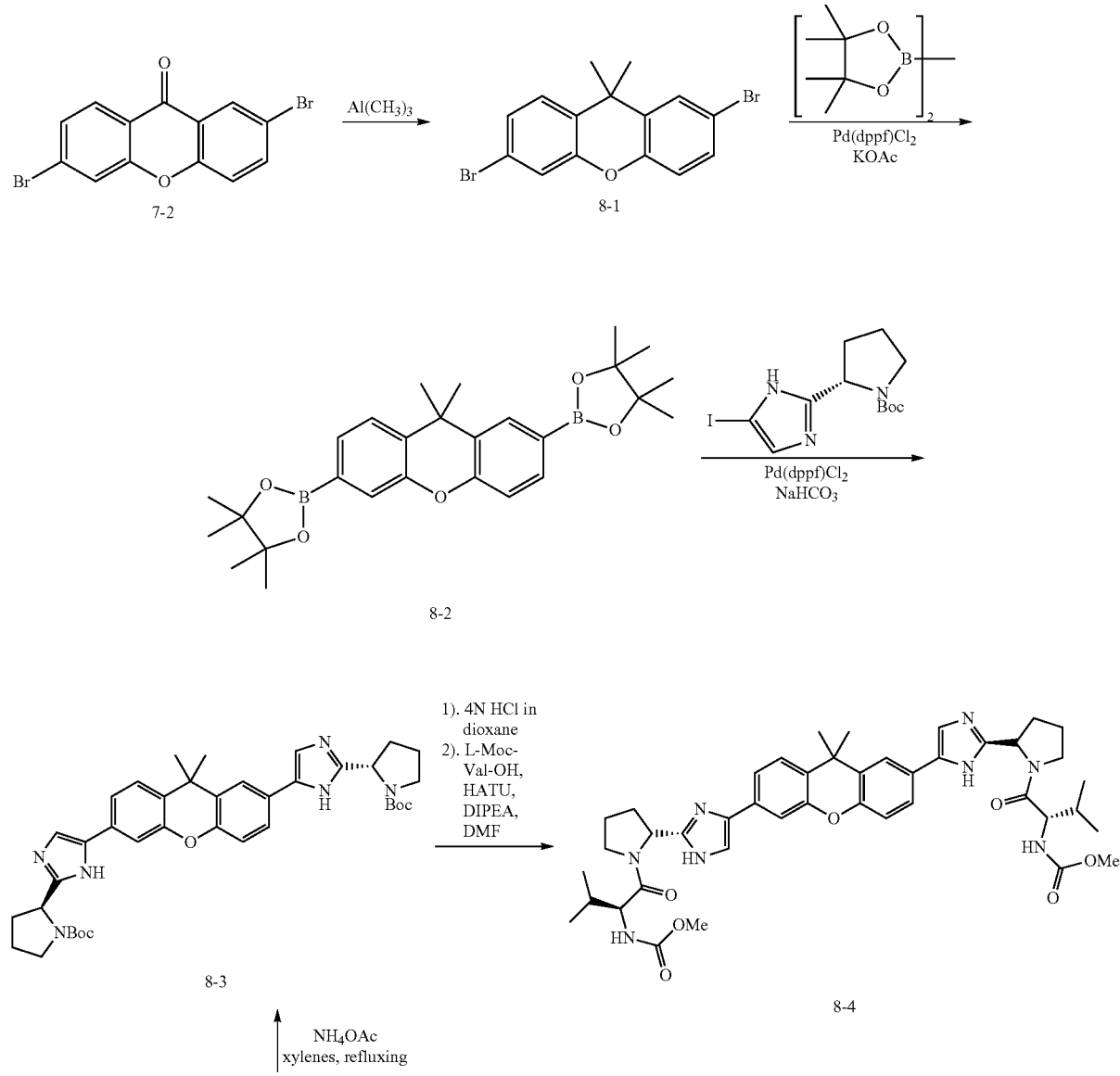

Scheme 8

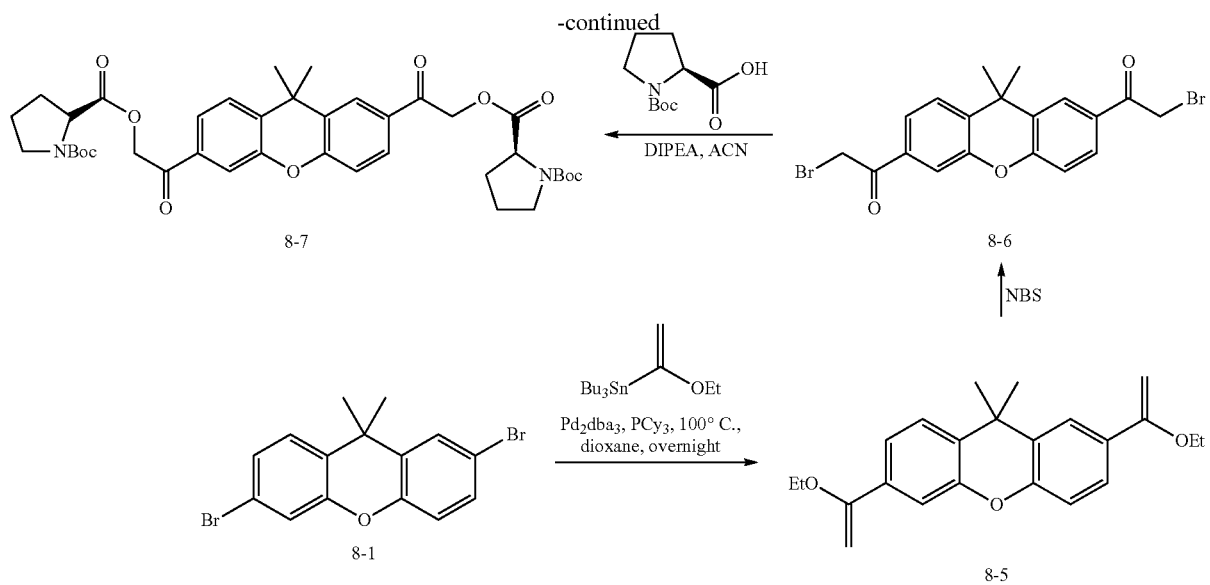

Example 17

Preparation of 8-3

Step 1.

Referring to Scheme 8, trimethylaluminum (2.4 mL, 2 M in hexanes, 4.80 mmol) was added dropwise to a degassed stirred solution of 2,6-dibromo-9H-xanthen-9-one 7-2 (500 mg, 1.412 mmol) in toluene (8 mL) at 0° C. The resulting solution was allowed to warm up to rt and left to stir for 16 h. The crude reaction mixture was poured into ice-cold 1M HCl aq (200 mL), and the aqueous layer was washed with DCM (2×150 mL), dried over $MgSO_4$, filtered and solvents were removed in vacuo to give 2,6-dibromo-9,9-dimethyl-9H-xanthene (8-1) (482 mg, 93% yield) as a white solid. $^1$H NMR ($CDCl_3$): δ 7.77-7.74 (1H, m), 7.55-7.51 (1H, m), 7.44-7.40 (1H, m), 7.33-7.29 (2H, m), 7.06-7.02 (1H, m), 1.58 (6H, s) ppm.

Step 2.

The product 8-2 was prepared using general procedure C and obtained as a white solid (280 mg, 53% yield). $^1$H NMR (DMSO): δ 7.78-7.76 (1H, m), 7.60-7.53 (2H, m), 7.43-7.39 (1H, m), 7.29-7.27 (1H, m), 7.07-7.04 (1H, m), 1.31-1.28 (24H, m) ppm. LC-MS (ESI): m/z 463.2 [M+H]$^+$.

Step 3. (2R,2'S)-tert-butyl-2,2'-(5,5'-(9,9-dimethyl-9H-xanthene-2,6-diyl)bis(1H-imidazole-5,2-diyl))dipyrrolidine-1-carboxylate (8-3)

Compound 8-3 was prepared using general procedure D to give the product as a brown solid (183 mg, 47% yield). LC-MS (ESI): m/z 681.26 [M+H]$^+$.

Example 18

Preparation of 8-4

Compound 8-4 was prepared as a white solid (42 mg, 21% yield) following general procedure C. LC-MS (ESI): m/z 795.54 [M+H]$^+$.

Compound 8-3 of Scheme 8 was also prepared using an alternative route described below.

General Procedure E—conversion of an aryl bromide (or iodide or a triflate) to an α-bromoketone, Steps 1a, and 2a.

Step 1a.

A sealed tube was charged with $Pd_2(dba)_3$ (55 mg, 0.06 mmol), tricyclohexylphosphine (34 mg, 0.12 mmol) and dioxane (20 mL). The resulting solution was bubbled with $N_2$ for 5 mins and stirred for 30 mins at rt. Compound 8-1 (1.0 g, 2.71 mmol), tri-n-butyl(1-ethoxyvinyl)stannane (2.1 mL, 6.20 mmol) and cesium fluoride (1.8 g, 11.9 mmol) were added while being protected under an atmosphere of $N_2$. After stirring 30 hrs at 145° C., the reaction mixture was cooled to rt and filtered through a pad of Celite, which was rinsed with dioxane (20 mL).

Step 2a.

General Procedure E—conversion of an aryl bromide (or iodide or a triflate) to an α-bromoketone. The combined dioxane solution (of 8-5) was diluted with $H_2O$ (10 mL) and cooled to 0° C. NBS (1.00 g, 5.62 mmol) was then added in portions over 15 mins. After about 30 mins stirring, the volatile component was removed in vacuo, and the residue was partitioned between DCM (100 mL) and water. The aqueous layer was extracted with DCM (3×20 mL). The combined organic phases were washed by brine, water, dried over $Na_2SO_4$. After concentration to remove all solvents, the crude residue was triturated by DCM (3×15 mL) to remove most of stannane derivative to afford crude 8-6 (1.1 g). $^1$H NMR (300 MHz, $CDCl_3$): δ 8.14 (d, J=2.2 Hz, 1H), 7.86 (dd, $J_1$=8.5 Hz, $J_2$=2.2 Hz, 1H), 7.75 (dd, $J_1$=8.1 Hz, $J_2$=1.7 Hz, 1H), 7.70 (d, J=1.7 Hz), 7.56 (d, J=8.0 Hz), 7.16 (d, J=8.5 Hz), 4.44 (s, 2H), 4.42 (s, 2H), 1.70 (s, 6H) ppm.

Step 3a.

A solution of 8-6 (1.1 g, 2.43 mmol) in $CH_3CN$ (30 mL) was added (S)-Boc-proline (1.29 g, 6.00 mmol) and N,N-diisopropylethylamine (1.04 mL, 6.00 mmol). The mixture was stirred overnight. The volatile component was removed in vacuo, and the residue was partitioned between water and DCM. The aqueous layer was extracted with DCM. The combined organic phase was washed by brine, saturated sodium carbonate, water, dried over anhydrous $Na_2SO_4$. After concentration, the crude mixture was purified by flash column chromatography (Hexane/Ethyl acetate=3/1 (v/v)) to afford compound 8-7 (1.2 g). $^1$H NMR (300 MHz, $CDCl_3$): δ 8.025 (br. s, 1H), 7.76-7.74 (m, 1H), 7.73-7.61 (m, 1H), 7.57 (br. d, J=4.7 Hz, 1H), 7.52 (br. d, J=8.0 Hz, 1H), 7.10 (dd, $J_1$=8.2 Hz, $J_2=1.4$ Hz, 1H), 5.53 (dd, $J_1=16.3$ Hz, $J_2=3.3$ Hz, 1H), 5.42-5.26 (m, 2H), 5.20 (dd, $J_1=16.3$ Hz, $J_2=5.8$ Hz, 1H), 4.45 (dd, $J_1=8.0$ Hz, $J_2=3.6$ Hz, 1H), 4.36 (dd, $J_1=6.5$ Hz, $J_2=1.0$ Hz, 1H), 3.59-3.31 (m, 4H), 2.32-2.22 (m, 4H), 2.10-2.00 (m, 2H), 1.95-1.80 (m, 2H), 1.64 (s, 6H), 1.43 (s, 18H) ppm.

The combined organic phase was washed by brine, water, and dried over $Na_2SO_4$. After removing the solvents, the crude mixture was purified by flash column chromatography (DCM/MeOH=10/1 (v/v)) to afford compound 8-3 (780 mg). LC-MS (ESI): m/z 341 $[M+2H]^{2+}$.

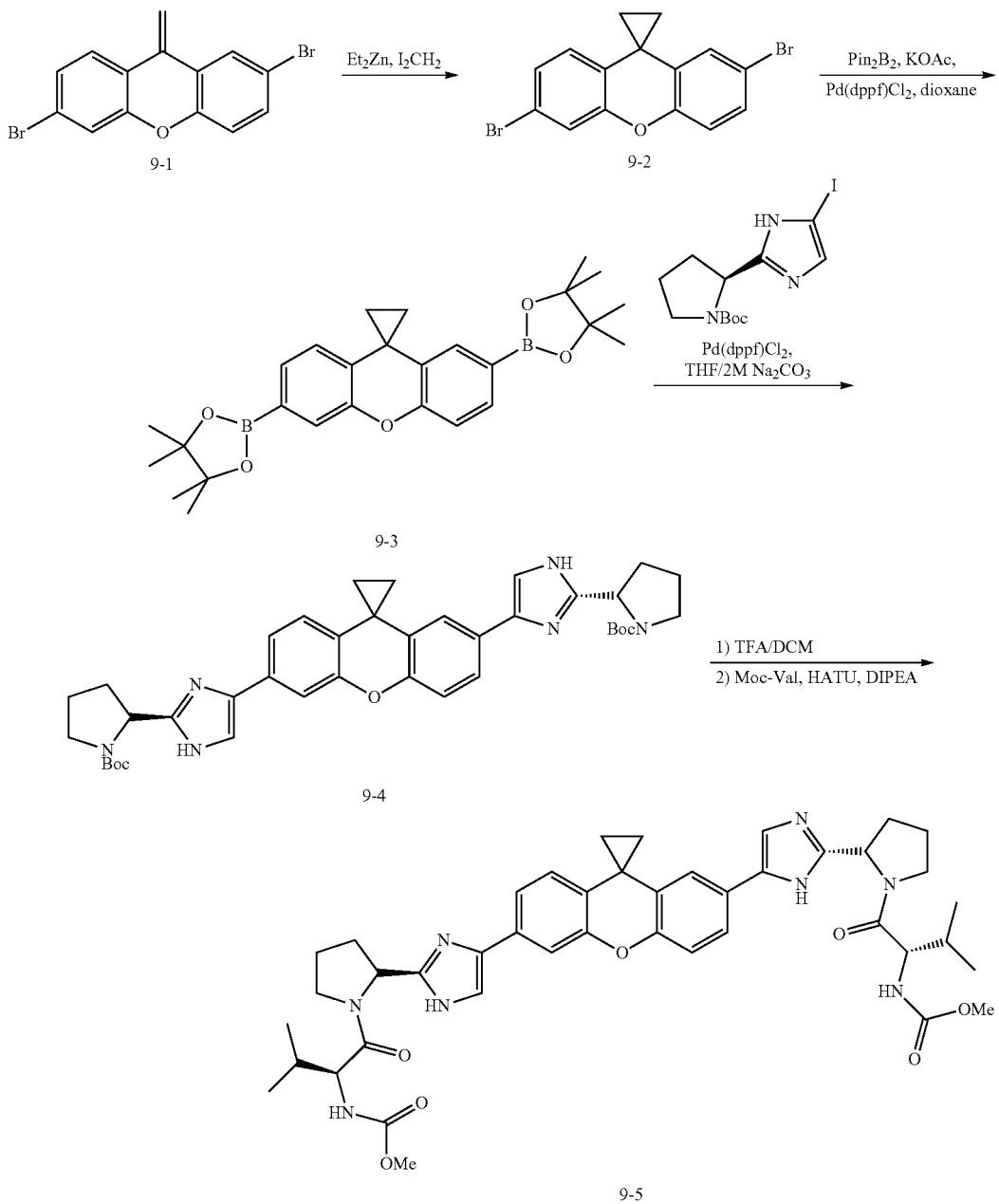

Scheme 9

Step 4a.

In a sealed tube, 8-7 (1.2 g, 1.76 mmol), ammonium acetate (680 mg, 8.83 mmol) and N,N-diisopropylethylamine (1.53 mL, 8.75 mmol) were added in xylene (20 mL). The resulting mixture was stirred at 140° C. for 3 hrs. The solvent was removed in vacuo, and the residue was partitioned between water and DCM. The aqueous layer was extracted with DCM.

Example 19

Preparation of 9-4

Step 1.

To a solution of 9-1 (1.3 g, 3.70 mmol) in anhydrous DCM (40 mL) was added $Et_2Zn$ (1.0 M in heptane, 18.5 mL) at rt. Diiodomethane (2.97 mL, 37 mmol) was then added drop-wisely. The reaction mixture was heated up to reflux. After stirring overnight, the reaction was cooled to rt and diluted with DCM, washed with brine, saturated NH₄Cl and water and dried over sodium sulfate. After removing the solvents, the crude mixture was purified by flash column chromatography (Hexane/Ethyl acetate=30/1 (v/v)) to afford compound 9-2 (0.50 g).

Step 2.

General Procedure D. To a solution of 9-2 (350 mg, 0.959 mmol) in dioxane (20 mL) was added bis(pinacolato)diboron (584 mg, 2.3 mmol), [1,1'-Bis(diphenylphosphino)ferrocene]-dichloropalladium(II) DCM (39 mg, 0.048 mmol) and potassium acetate (565 mg, 5.75 mmol). The resulting solution was bubbled with $N_2$ for 15 minutes, then heated at 85° C. overnight. The solvent was removed in vacuo and the residue was partitioned between water and DCM. The aqueous layer was extracted with DCM. The combined organic extracts were washed with brine and water and dried over anhydrous $Na_2SO_4$. The solvents were removed by vacuum to afford crude 9-3 (450 mg). LC-MS (ESI): m/z 461 [M+H]⁺.

Step 3.

To a solution of the crude 9-3 (0.959 mmol) in THF (10 mL) was added (S)-tert-butyl 2-(5-iodo-1H-imidazol-2-yl) pyrrolidine-1-carboxylate (766 mg, 2.11 mmol), dichloro[1, 1'-bis(diphenylphosphino)ferrocene]palladium(II) (40 mg, 0.049 mmol) and 2 M sodium carbonate (4 mL). The resulting solution was bubbled with $N_2$ for 15 mins, then heated at 85° C. overnight. The solvent was removed in vacuo, and the residue was partitioned between water and DCM. The aqueous layer was extracted with DCM. The combined organic phase was dried over anhydrous $Na_2SO_4$, filtered and concentrated. The crude mixture was purified by flash column chromatography (DCM/Methanol=20/1 (v/v)) to afford compound 9-4 (110 mg). LC-MS (ESI): m/z 340 [M+2H]²⁺.

Example 20

Preparation of 9-5

To a solution of the 9-4 (20 mg, 0.0295 mmol) in DCM (1 mL) was added trifluoroacetic acid (0.3 mL). The reaction was stirred for 3 h at rt. The reaction was concentrated to afford compound de-Boc-9-4 (20 mg). LCMS (ESI): m/z 240 1/2(M+2H)²⁺ To a solution of de-Boc-9-4 (20 mg) in DMF (2 mL), DIPEA (24 μL, 0.138 mmol), N-Moc-L-Val-OH (12 mg, 0.068 mmol) and HATU (26 mg, 0.068 mmol) was added. After one hour stirring, the reaction was diluted with methanol and directly subject to prep-HPLC (Phenomenex, C18-Luna column, H₂O-MeCN, 0.1% HCO₂H) to provide 9-5 (12.0 mg). LC-MS (ESI): m/z 397 [M+2H]²⁺. ¹H NMR (300 MHz, CD₃OD): δ 7.87 (s, 1H), 7.80 (s, 1H), 7.52 (d, J=8.2 Hz, 1H), 7.38 (d, J=8.2 Hz, 1H), 7.36 (s, 1H), 7.22 (s, 1H), 7.08 (d, J=9.2 Hz, 1H), 6.98 (d, J=8.2 Hz, 1H), 5.23-5.20 (m, 2H), 4.23 (d, J=7.1 Hz, 2H), 4.10-4.07 (m, 2H), 3.94-3.88 (m, 2H), 3.65 (s, 6H), 2.60-2.55 (m, 2H), 2.38-2.05 (m, 8H), 1.68-1.50 (m, 4H), 0.98-0.88 (m, 12H) ppm.

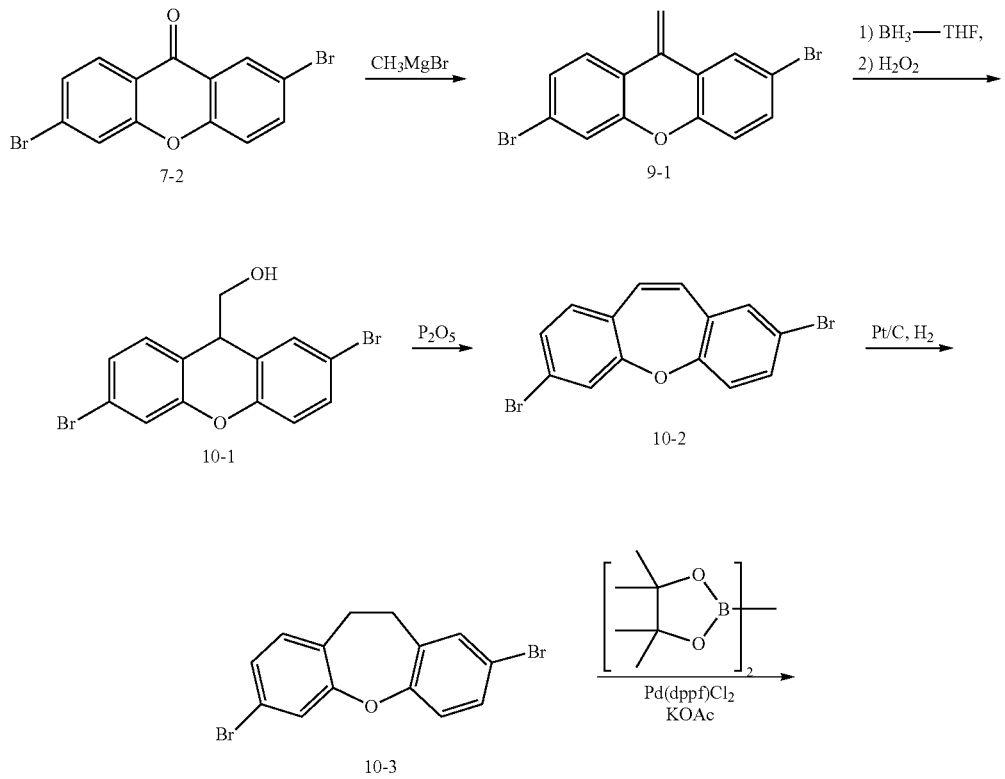

Scheme 10

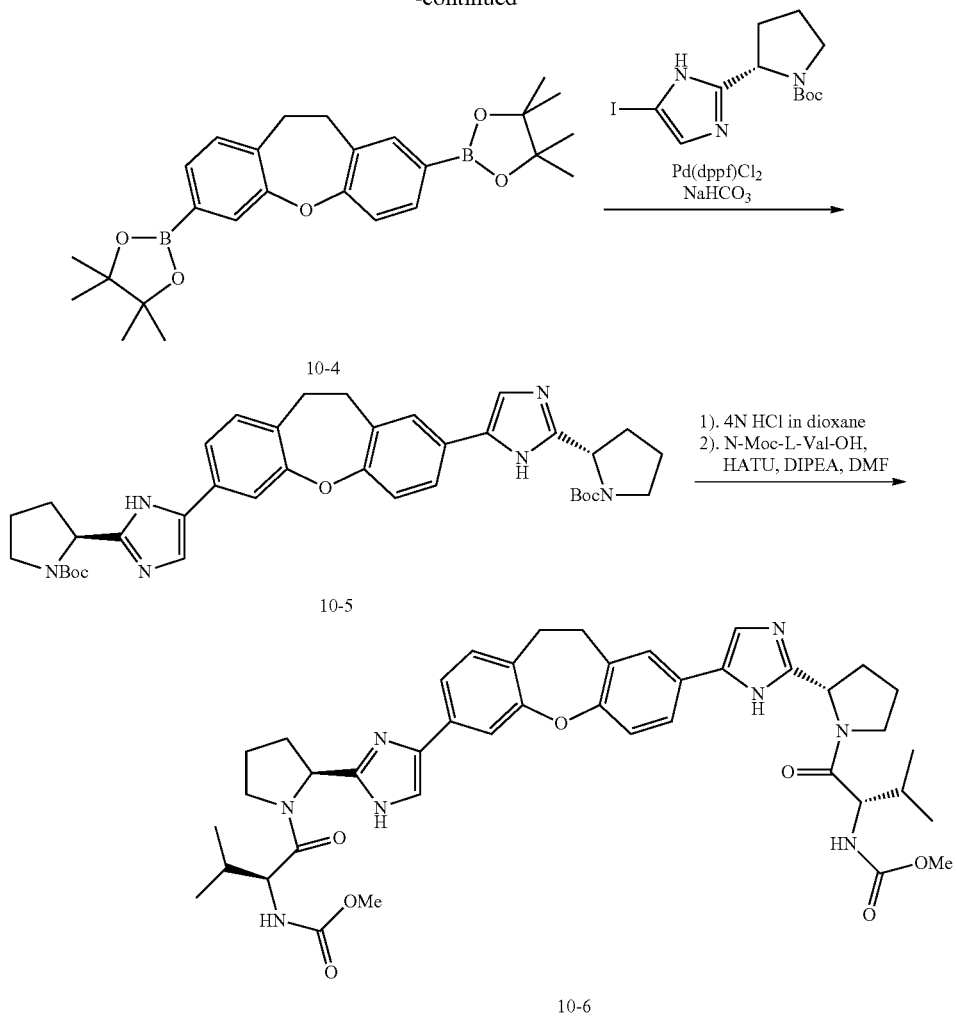

Example 21

Preparation of 10-6

Step 1.

Referring to Scheme 10, methylmagnesium iodide (14.12 mL, 3 M in Et$_2$O, 42.4 mmol) was added to a stirred solution of 2,6-dibromo-9H-xanthen-9-one (7-2) (10 g, 28.2 mmol) in THF (30 mL) at 0° C. The reaction mixture was allowed to warm up to rt and stirred for 2 h. The reaction mixture was cooled to 0° C. and quenched with saturated NH$_4$Cl solution (250 mL) and stirred for 30 min. The volatiles were removed in vacuo. The residue was taken up in CHCl$_3$ (200 mL), and the organic layer was separated and the aqueous phase was extracted with CHCl$_3$ (2×200 mL) and combined organics was dried over MgSO$_4$, filtered and solvents removed in vacuo to crude product (9.46 g). The crude reaction was taken up in EtOAc (200 mL) and AcOH was added (20 mL) and the reaction mixture was stirred at room temperature for 3 hrs, the volatiles removed in vacuo and the residue was precipitated from isohexanes to give 2,6-dibromo-9-methylene-9H-xanthene (9-1) (6.43 g, 64.7% yield).

Step 2.

Borane-THF complex (36.5 mL, 1M THF, 36.5 mmol) was added to a stirred solution of 2,6-dibromo-9H-xanthene (9-1) (6.43 g, 18.27 mmol) in THF (75 mL) at 0° C. The mixture was allowed to warm up to rt and stirred for 1 h. The reaction mixture was cooled to 0° C. and a mixture of hydrogen peroxide (35 wt % in water) (5.76 mL, 65.8 mmol) and NaOH (25.6 mL, 2 M aq, 51.1 mmol) was added cautiously. The mixture was allowed to warm up to rt over 30 min. The reaction mixture was then poured into water (200 mL) and extracted with DCM (3×150 mL). The combined organics were washed with water (2×200 mL), brine (200 mL), dried over anhydrous MgSO$_4$, filtered and volatiles removed in vacuo to give a yellow solid. The crude product was purified by column chromatography (SiO$_2$, 0-100% (v/v) of EtOAc/isohexanes) to afford (2,6-dibromo-9H-xanthen-9-yl)methanol (10-1) (2.5 g, 37.0% yield) as a yellow solid. $^1$H NMR (CDCl$_3$): δ 7.42-7.39 (1H, m), 7.37-7.35 (1H, m), 7.28-7.27 (1H, m), 7.25-7.21 (1H, m), 7.16-7.12 (1H, m), 7.00-6.97 (1H, m), 4.00 (1H, t, J=5.9 Hz), 1.46 (2H, d, J=5.9 Hz) ppm.

Step 3.

Phosphorus pentoxide (5.04 g, 35.5 mmol) was added portion-wisely to a stirred solution of (2,6-dibromo-9H-xanthen-9-yl)methanol (10-1) (1.01 g, 2.73 mmol) in toluene (100 mL) and the suspension was heated under reflux for 20 min. The mixture was allowed to cool to rt and toluene was removed by decantation. The residual solid was washed with toluene (2×100 mL) by further decantation. The combined organics were cooled in an ice bath and brine (400 mL) was added slowly. The layers were separated and the organic washed with water (300 mL), brine (300 mL), dried over anhydrous $MgSO_4$ and evaporated to dryness, to give a yellow oily solid. The product was purified by column chromatography ($SiO_2$, O-10% EtOAc/isohexanes) to give 2,7-dibromodibenzo[b,f]oxepine (10-2) (763 mg, 79% yield) as a clear oil. $^1H$ NMR ($CDCl_3$): δ 7.41-7.36 (1H, m), 7.33-7.31 (1H, m), 7.29-7.24 (2H, m), 7.04-6.99 (2H, m), 6.68-6.57 (2H, m) ppm.

Step 4.

A solution of 2,7-dibromodibenzo[b,f]oxepine (10-2) (663 mg, 1.88 mmol) in EtOAc (40 mL) was degassed under $N_2$. Pt/C 10% by wt (200 mg) was added and the reaction was evacuated and placed under $H_2$ gas. After 2 h reaction mixture was degassed and filtered through Celite®545 (eluant EtOAc) and solvent was removed in vacuo to give a yellow oil. The compound was dissolved in petroleum ether and passed through a short pad of $SiO_2$, eluting with isohexanes 400 mL. Solvent was removed in vacuo, to give 2,7-dibromo-10,11-dihydrodibenzo[b,f]oxepine (10-3) (542 mg, 81% yield) as a colorless oil. $^1H$ NMR ($CDCl_3$): δ 7.33-7.32 (1H, m), 7.29-7.24 (2H, m), 7.18-7.14 (1H, m), 7.04-6.96 (2H, m), 3.08 (4H, s) ppm.

Step 5.

Compound 10-4 was prepared as a white solid (360 mg, 53% yield) following General Procedure C. LC-MS (ESI): m/z 449.51 [M+H]$^+$.

Step 6.

Preparation of (2S,2'R)-tert-butyl 2,2'-(5,5'-(10,11-dihydrodibenzo[b,f]oxepine-2,7-diyl)bis(1H-imidazole-5,2-diyl))dipyrrolidine-1-carboxylate (10-5). Compound 10-5 was prepared as brown oil (59 mg, 11% yield) following general procedure D. LC-MS (ESI): m/z 667.34 [M+H]$^+$.

Step 7.

Product 10-6 was prepared as a white solid (6 mg, 11% yield) following general procedure C. LC-MS (ESI): m/z 781.69 [M+H]$^+$.

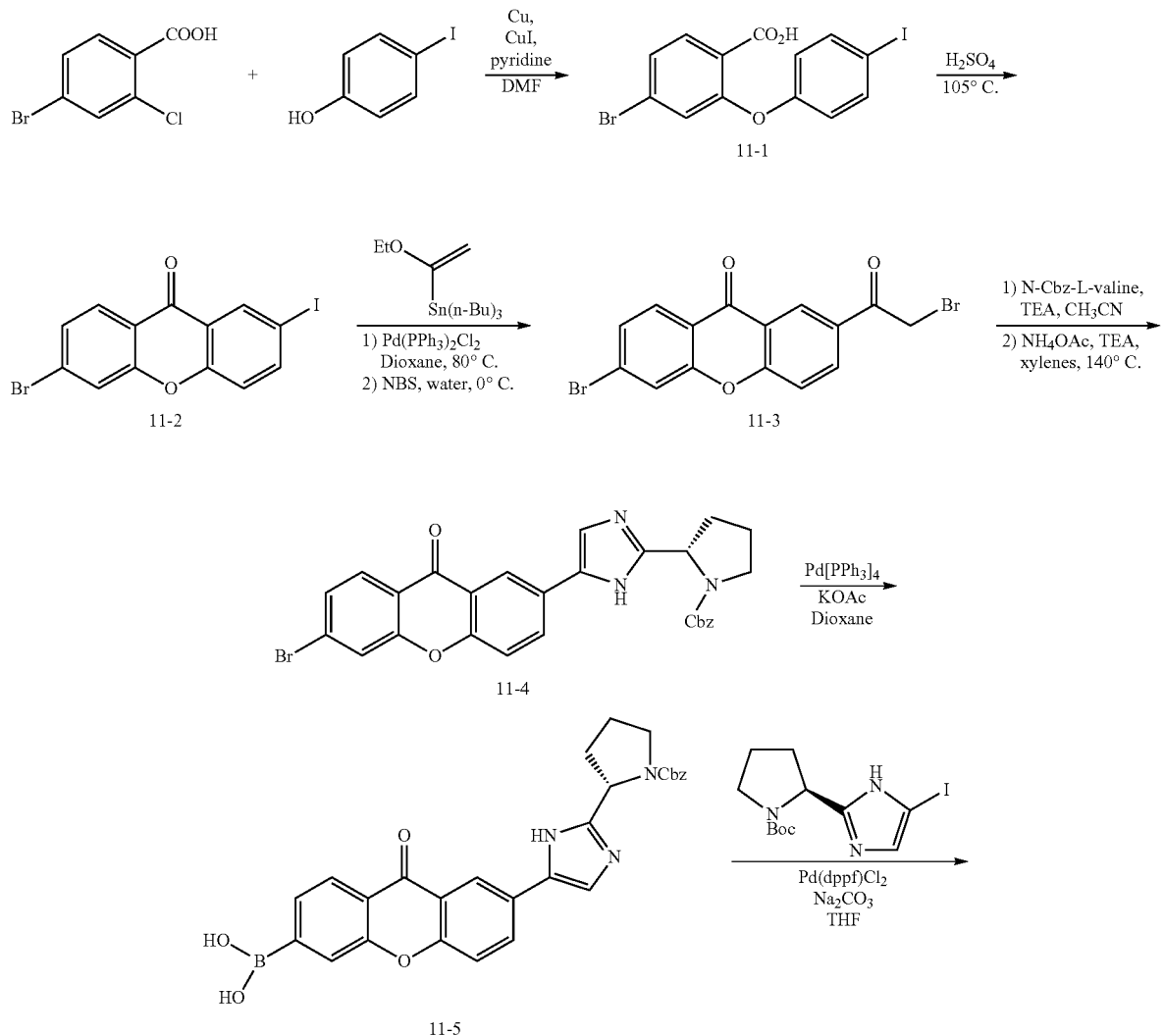

-continued
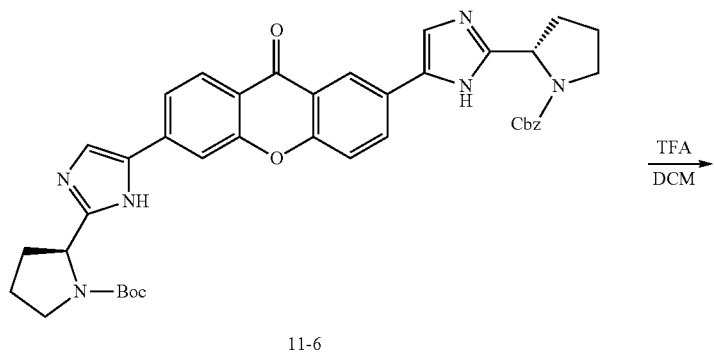
11-6
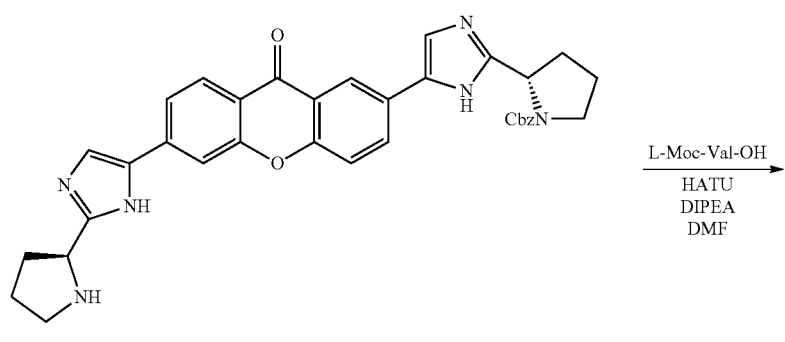
11-7
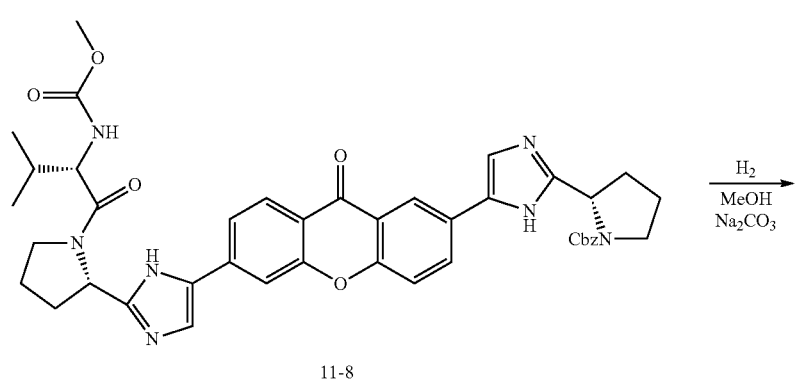
11-8
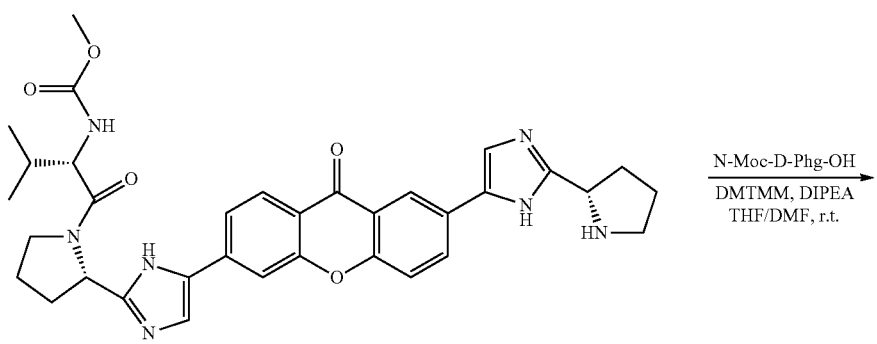
11-9

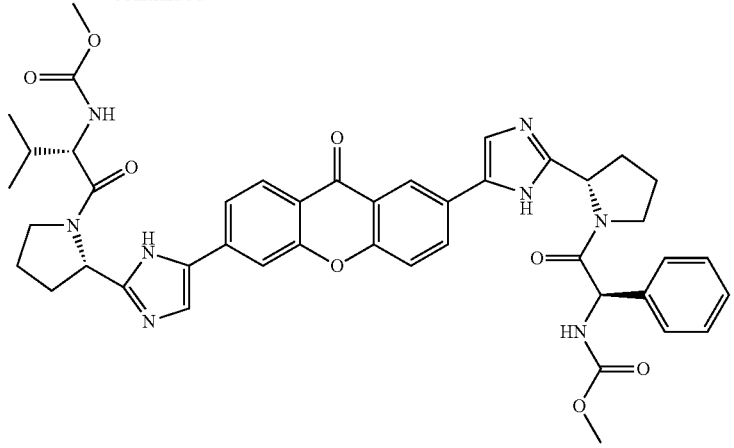

11-10

Example 22

Preparation of 11-8

Step 1.

Referring to Scheme 11, to a solution of 4-bromo-2-chlorobenzoic acid (18.4 g, 83.9 mmol) and 4-bromophenol (24 g, 109 mmol) in nitrobenzene was added cesium carbonate (82 g, 251.7 mmol). The resulting solution was heated at 170° C. with condenser for 1 day. The reaction mixture was cooled to 70° C. and filtrated at this temperature. The residue was washed with toluene. The organic layer was removed by vacuum distillation till a thick dark residue remained. The dark residue was added to aqueous HCl (1N, 400 mL) and DCM (200 mL). The resulting solution was stirred until the dark oil dispersed into DCM solution. The mixture was filtered. The organic layer was dried ($Na_2SO_4$) and concentrated to afford the crude product. The residue was purified by column chromatography on silica gel, eluted first with DCM and then with a mixture of DCM and MeOH in a 10/1 (v/v) ratio to give 11-1 along with the corresponding des-iodo compound 11-1' (16 g, a 5/3 ratio). LC-MS (ESI): m/z 419 [M+H]+ for 11-1, m/z 293 [M+H]+ for 11-1'. The mixture was used in the next step.

Step 2.

The mixture of 11-1 and 11-1' (16 g, 5:3 ratio, 44.3 mmol) was treated with concentrated sulfuric acid (95 mL). The solution was heated at 105° C. for 2 h. The reaction mixture was cooled down and poured into ice water. The product was precipitated out and was collected by filtration, washed with $Et_2O$ and $H_2O$. The solid was dried and further purified by flash column chromatography on silica gel (eluents: Hexanes/AcOEt=9/1(v/v), AcOEt, and DCM) to afford 11-2 (7 g) and 11-2' (5 g). LC-MS (ESI): m/z 401 [M+H]+ for 11-2, m/z 275 [M+H]+ for 11-2'.

Step 3.

To a solution of iodide 11-2 (6.5 g, 16.2 mmol) and tri-n-butyl(1-ethoxyvinyl)stannane (6.02 mL, 17.8 mmol) in dioxane (70 mL) was added $Pd(PPh_3)_2Cl_2$ (0.57 g, 0.81 mmol). The resulting solution was bubbled with $N_2$ for 15 min and heated at 80° C. for 17 hrs. The reaction mixture was treated with $H_2O$ (24 mL) and cooled to 0° C. To the solution was added NBS (3.17 g, 17.8 mmol) in portions over 15 min. After about 30 min stirring, the volatiles were removed in vacuo and the residue was partitioned between DCM and water. The aqueous layer was back extracted with DCM. The combined organic phase was dried over anhydrous $Na_2SO_4$, filtered and concentrated. The crude mixture was purified by flash column chromatography (Hexanes/AcOEt=5/1 (v/v) to 1/1 (v/v) and DCM/MeOH=10/1(v/v)) to afford 11-3 (4.6 g pure). $^1$H NMR (300 MHz, $CDCl_3$): δ 8.90 (s, 1H), 8.41 (dd, 1H), 8.22 (d, 1H), 7.76 (s, 1H), 7.59 (m, 2H), 4.58 (s, 0.5H), 4.44 (s, 1.5H) ppm.

Step 4.

A solution of 11-3 (3.3 g, 8.33 mmol) in $CH_3CN$ (15 mL) was added drop-wisely over 5 minutes to a solution of N-Cbz-L-proline (2.26 g, 9.16 mmol) and triethylamine (1.74 mL, 12.5 mmol) in $CH_3CN$ (30 mL). The resulting mixture was stirred for 90 min. The volatiles were removed in vacuo and the residue was partitioned between water and DCM. The aqueous layer was extracted with DCM. The combined organic phase was dried over anhydrous $Na_2SO_4$, filtered and concentrated. The crude mixture was purified by flash column chromatography (DCM to DCM/MeOH=10/1(v/v)) to afford the ketoester intermediate (3.4 g). LC-MS (ESI): m/z 564 [M+H]+.

The solution of ketoester from above (3.4 g, 6.03 mmol), ammonium acetate (6.97 g, 90.5 mmol) and triethylamine (12.6 mL, 90.5 mml) in xylene (70 mL) was placed in a sealed tube and heated at 140° C. with stir for 2 hrs. The solvent was removed in vacuo, and the residue was partitioned between water and AcOEt. The aqueous layer was extracted with AcOEt. The combined organic phase was dried with anhydrous $Na_2SO_4$, filtered and concentrated. The crude mixture was purified by flash column chromatography (DCM/MeOH=10/1 (v/v)) to afford compound 11-4 (2.0 g). LC-MS (ESI): m/z 544 [M+H]+.

Step 5.

To a solution of 11-4 (1.9 g, 3.5 mmol) in dioxane (35 mL) was added bis(pinacolato)diboron (2.22 g, 8.75 mmol), tetrakis(triphenylphosphine)palladium (202 mg, 0.175 mmol) and potassium acetate (1.03 g, 10.5 mmol). The resulting solution was degassed by bubbling with $N_2$ for 15 min, and then heated at 95° C. for 5 hrs. The reaction mixture was filtered through a pad of Celite. The organic solvent was removed in vacuo. The residue was purified by flash column chromatography (DCM/MeOH=10/1 (v/v)) to afford compound 11-5 (1.5 g). LC-MS (ESI): m/z 510 [M+H]+.

Step 6.

To a solution of 11-5 (1.5 g, 2.5 mmol) in THF (30 mL) was added (S)-tert-butyl 2-(5-iodo-1H-imidazol-2-yl)pyrrolidine-1-carboxylate (1.0 g, 2.78 mmol), dichloro[1,1'-bis(diphenylphosphino)ferrocene]palladium(II) (102 mg, 0.125 mmol) and sodium carbonate (2 M, 12 mL). The resulting solution was bubbled with $N_2$ for 15 min, then refluxed overnight. The solvent was removed in vacuo and the residue was partitioned between water and DCM. The aqueous layer was extracted with DCM. The combined organic phase was dried over anhydrous $Na_2SO_4$, filtered and concentrated. The crude mixture was purified by flash column chromatography (DCM/MeOH=9/1(v/v)) to afford compound 11-6 (1.3 g). LC-MS (ESI): m/z 351 $[M+2H]^{2+}$.

Step 7.

By treating a sample of compound 11-6 under the conditions of General Procedure B, compound 11-8 was synthesized. LC-MS (ESI): m/z 758.3 $[M+H]^+$.

Example 23

Preparation of 11-10

Step 1.

Compound 11-8 was treated with $H_2$ in the presence of Pd/C for the removal of Cbz protecting group to give 11-9. LC-MS (ESI): m/z 624.3 $[M+H]^+$.

Step 2.

Following conditions in General Procedure B, 11-9 was converted to compound 11-10. $^1H$ NMR (300 MHz, $CDCl_3$): δ 8.28 (bs, 2H), 8.20 (s, 1H), 8.05 (d, 1H), 7.82 (m, 2H), 7.42-7.32 (m, 5H), 7.20 (m, 2H), 6.36 (bs, 1H), 5.60 (d, 1H), 5.52 (m, 1H), 5.32 (m, 2H), 4.40 (t, 1H), 4.03-3.85 (m, 3H), 3.68 (s, 3H), 3.62 (s, 3H), 3.32 (m, 1H), 2.60 (m, 1H), 2.42-2.08 (m, 7H), 1.92 (m, 1H), 1.09-0.90 (m, 6H) ppm; LC-MS (ESI): m/z 815.8 $[M+H]^+$.

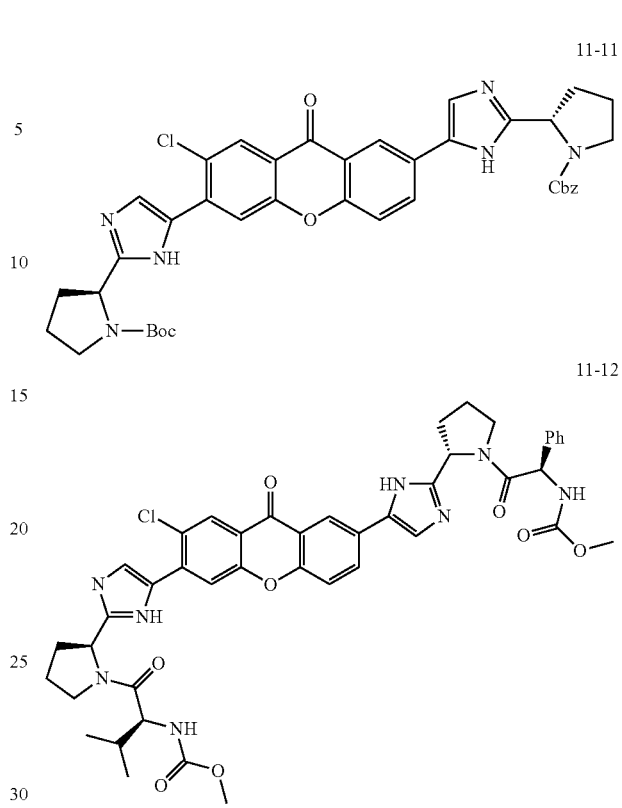

Example 24

Preparation of 11-12

Following the procedures described in Scheme 11 and substituting 4-bromo-2,5-dichloro-5-nitrobenzoic acid for 4-bromo-2-chloro-5-nitrobenzoic acid in Step 1. Compounds 11-11 and 11-12 were obtained. LC-MS (ESI): m/z 735.3 $[M+H]^+$ for 11-11 and LC-MS (ESI): m/z 850.3 $[M+H]^+$ for 11-12.

Scheme 11a

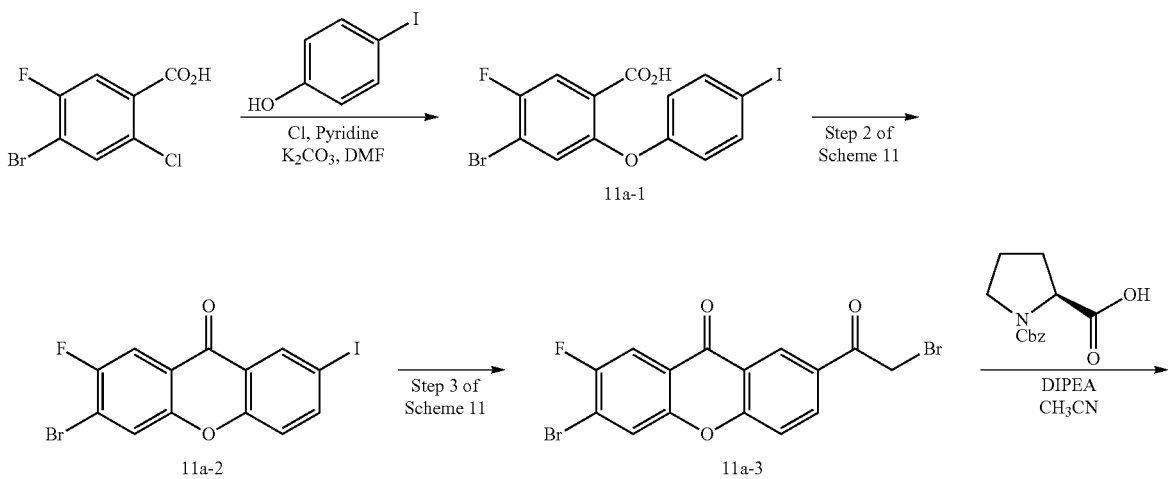

-continued
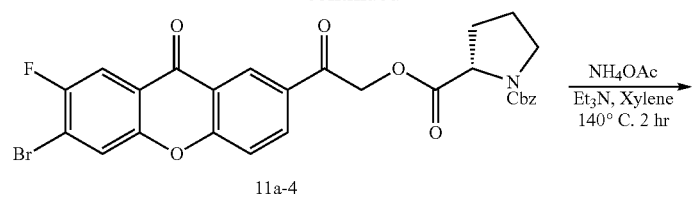
11a-4
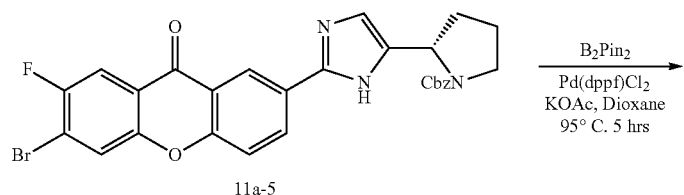
11a-5
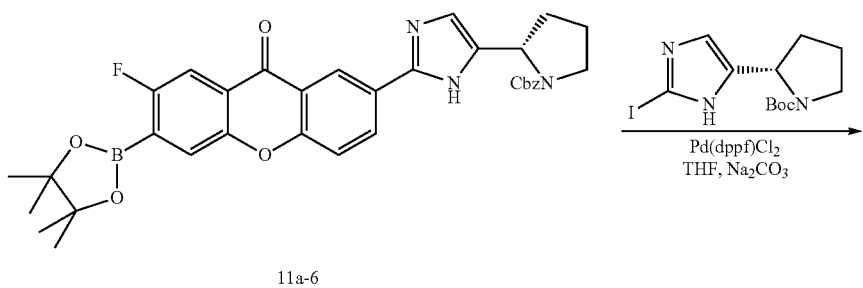
11a-6
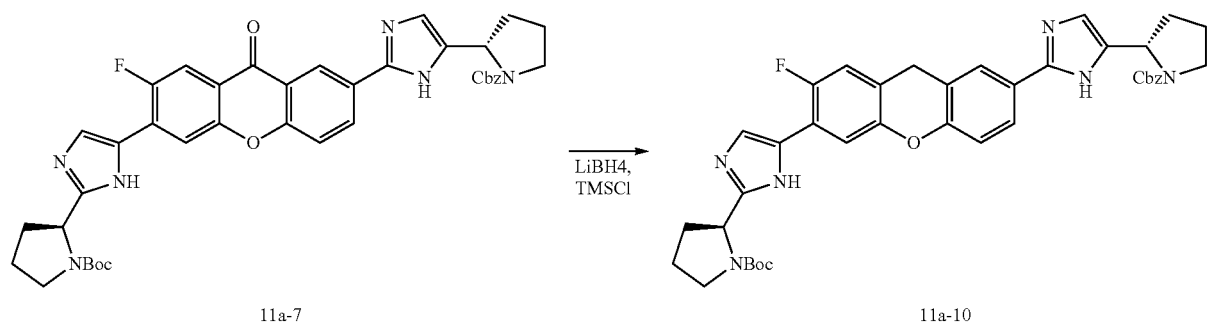
11a-7          11a-10
1) TFA, DCM
2) L-Moc-Val-OH, HATU
1) TFA, DCM
2) L-Moc-Val-OH, HATU
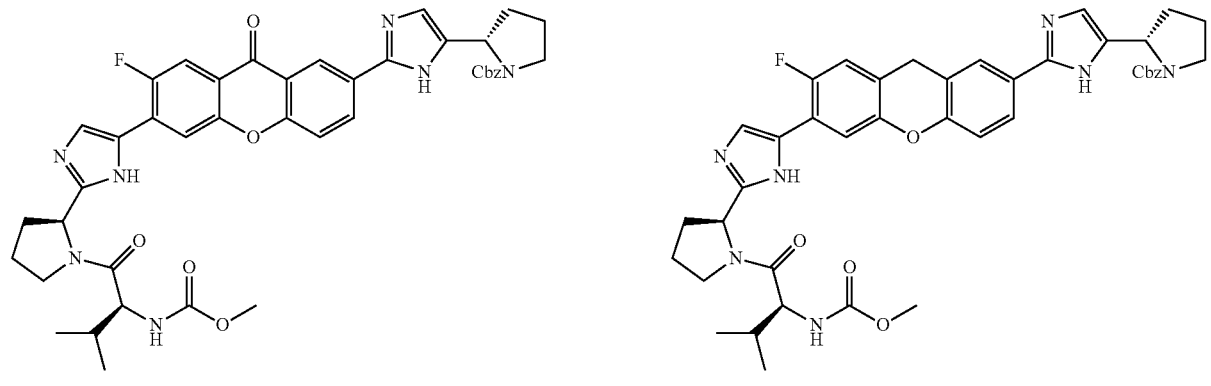
11a-8          11a-11
1. Pd, H₂, MeOH, Na₂CO₃
2. HATU, L-N-Moc-THP-Gly-OH
1. Pd, H₂, MeOH, Na₂CO₃
2. HATU, L-N-Moc-OMe-Thr-OH

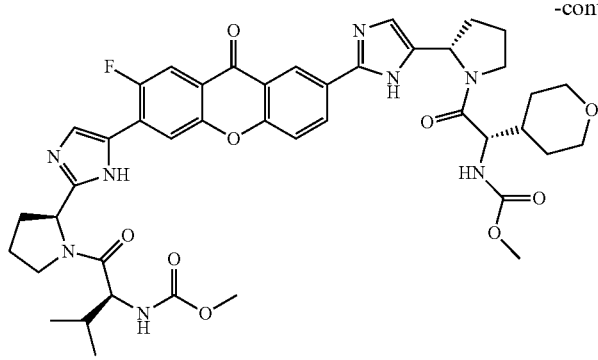

11a-9

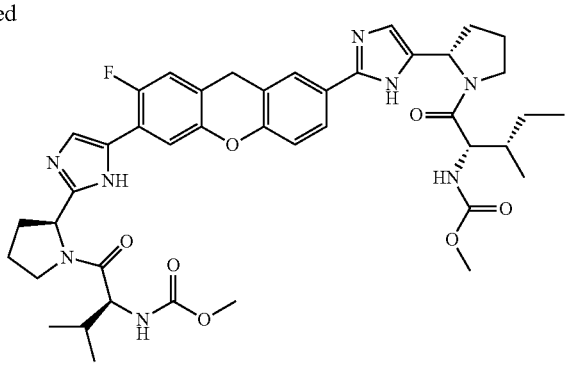

11a-12

Step 1.

Referring to Scheme 11a, copper (0.20 g, 3.15 mmol), copper(I) iodide (0.20 g, 1.05 mmol), pyridine (1.6 mL, 19.7 mmol) and potassium carbonate (4.54 g, 32.9 mmol) were added to a solution of 4-bromo-2-chloro-5-fluorobenzoic acid (5 g, 19.7 mmol) and 4-iodophenol (9.1 g, 41.4 mmol) in DMF (40 mL). The resulting solution was heated at 100° C. with a condenser for 7 hrs. The reaction mixture was cooled to rt and diluted with saturated sodium carbonate (100 mL). The mixture was washed with diethyl ether (3×100 mL). The aqueous suspension was acidified by concentrated HCl to pH 1 and extracted with ethyl acetate (3×200 mL). The combined organic layers were washed with brine, 1M sodium bisulfite, water and dried over sodium sulfate and concentrated to afford the aryl ether product, which was used without further purification.

Step 2.

The product from above was treated with concentrated sulfuric acid (30 mL). The solution was heated at 110° C. for 1 hr. After cooled to rt, the reaction mixture was poured into an ice-water slurry. The suspension was diluted with dichloromethane (1 L), washed with water, brine, 1N NaOH, 1N NaHSO$_3$, water. The organic solution was dried over anhydrous Na$_2$SO$_4$ and concentrated to 3-bromo-2-fluoro-7-iodo-9H-xanthen-9-one (11a-2, 1.80 g, 21% yield). LC-MS (ESI): m/z 420 [M+H]$^+$.

Step 3.

Pd (PPh$_3$)$_2$Cl$_2$ (0.13 g, 0.19 mmol) was added to a solution of 11a-2 (1.8 g, 4.30 mmol) and tri-n-butyl(1-ethoxyvinyl)stannane (1.60 mL, 4.73 mmol) in dioxane (50 mL). The resulting solution was bubbled with N$_2$ for 15 min, then heated to 80° C. for 17 hrs. The reaction mixture was treated with H$_2$O (80 mL), cooled to 0° C., and then NBS (0.80 g, 4.5 mmol) was added in portions over 15 min. After about 30 min, the volatile component was removed in vacuo, and the residue was partitioned between DCM (200 mL) and water. The aqueous layer was extracted with DCM (3×50 mL). The combined organic phases were washed by brine, water, dried over anhydrous Na$_2$SO$_4$. After concentration to remove all solvents, the crude residue was triturated with DCM (3×15 mL) to remove most of stannane impurities to afford 11a-3 (1.8 g, 95% yield). LC-MS (ESI): m/z 415 [M+H]$^+$.

Step 4.

(S)-Cbz-proline (1.19 g, 4.79 mmol) and N,N-diisopropylethylamine (0.87 mL, 5.0 mmol) was added to a solution of 11a-3 (1.8 g, 4.35 mmol) in CH$_3$CN (50 mL). The mixture was stirred rt overnight. The volatile components were removed in vacuo, and the residue was partitioned between water and DCM. The aqueous layer was extracted with DCM. The combined organic phase was washed by brine, saturated sodium carbonate, water, dried over anhydrous Na$_2$SO$_4$. After concentration, 11a-4 was obtained and used in the next step without further purification.

Step 5.

The mixture of 11a-4 (~2 g from above), ammonium acetate (3.35 g, 43.5 mmol), N,N-diisopropylethylamine (2.0 mL, 4.35 mmol), and xylene (20 mL) was heated in a sealed tube at 140° C. for 4 hrs. LC-MS showed the reaction was completed. The solvent was removed in vacuo, and the residue was partitioned between water and DCM. The aqueous layer was extracted with DCM. The combined organic phases were washed by brine, water, and dried over Na$_2$SO$_4$. After removing the solvents, the crude mixture was purified by flash column chromatography (DCM/MeOH=10/1 (v/v)) to afford compound 11a-5 (1.6 g, 65% yield for 2 steps). LC-MS (ESI): m/z 563 [M+H]$^+$ Step 6.

To a solution of 11a-5 (1.5 g, 2.67 mmol) in dioxane (30 mL) was added bis(pinacolato)diboron (0.67 g, 3.20 mmol), [1,1'-bis(diphenylphosphino)ferrocene]dichloropalladium (II), complex with dichloromethane (71 mg, 0.087 mmol) and potassium acetate (830 mg, 8.52 mmol). The resulting solution was bubbled N$_2$ for 15 min, and then heated at 85° C. overnight. After removal of the volatile solvents in vacuo, the residue was partitioned between water and DCM. The aqueous layer was extracted with DCM. The combined organic phase was washed by brine, water, and dried over Na$_2$SO$_4$. Removed the solvents by vacuo to afford crude 11a-6 (1.3 g, 75% yield). LC-MS (ESI): m/z 610 [M+H]$^+$.

Step 7.

(S)-tert-butyl 2-(2-iodo-1H-imidazol-5-yl)pyrrolidine-1-carboxylate (0.72 g, 1.97 mmol), dichloro[1,1'-bis(diphenylphosphino) ferrocene]palladium(II) (75 mg, 0.1 mmol) and 2 M aq. sodium carbonate (10 mL) were added to a solution of the crude 11a-6 (1.2 g, 1.97 mmol) in THF (20 mL). The resulting solution was bubbled with N$_2$ for 15 min, and then heated at 85° C. overnight. The residue was partitioned between water and DCM. The aqueous layer was extracted with DCM. The combined organic phase was dried (Na$_2$SO$_4$), filtered, and concentrated. The crude mixture was purified by flash column chromatography (ethyl acetate/methanol=100/1 (v/v)) to afford compound 1a-7 (0.95 g, 45% yield). LC-MS (ESI): m/z 389 [M+2H]$^{2+}$ Step 8.

Compound 11a-8 was obtained following conditions described in General Procedure B.

Step 9.

10% Pd/C (0.38 g) and concentrated HCl (3 drops) were added to a solution of 11a-8 (0.54 g, 0.70 mmol) in methanol (12 mL). The reaction was charged by hydrogen in a Parr shaker apparatus at 60 psi overnight at rt. The reaction mixture was filtered through celite. The organic solvent was removed in vacuo to afford the Cbz-deprotected compound (0.36 g, 81% yield), which was acylated with L-N-Moc-tetrhydropyranylglycine under the conditions described in General Procedure B to give compound 11a-9. LC-MS (ESI): m/z 421 $[M+2H]^{2+}$ Step 10.

Lithium borohydride (0.25 g) was added to a sample of 11a-7 (0.25 g, 0.35 mmol) in anhydrous THF (10 mL). The resulting solution was warmed up to 60° C. After stirring for 3 hrs, the reaction was cooled to r.t. and slowly transferred to another bottle, which was charged with chlorotrimethylsilane (0.3 mL, 2.36 mmol) in THF (10 mL). The mixture was stirred for additional 20 min at rt and quenched by methanol. After removal of all the solvents, 11a-10 was obtained (0.23 g, 92% yield) LC-MS (ESI): m/z 353 $[M+2H]^{2+}$.

Step 11.

Compound 11a-11 (0.25 g, 63% yield for 2 steps) was obtained following General Procedure B. LC-MS (ESI): m/z 381.5 $[M+2H]^{2+}$ Step 12.

10% Pd/C (0.16 g) and concentrated HCl (3 drops) were added to a solution of 11a-11 (0.23 g, 0.302 mmol) in methanol (5 mL). The reaction was charged by hydrogen in a Parr shaker apparatus at 60 psi overnight at rt. The reaction mixture was filtered through celite. The organic solvent was removed in vacuo to afford the Cbz-deprotected compound (0.16 g, 82% yield), which was acylated with L-N-Moc-O-methylthreonine under the conditions described in General Procedure B to give compound 11a-12. LC-MS (ESI): m/z 401 $[M+2H]^{2+}$.

Scheme 11b

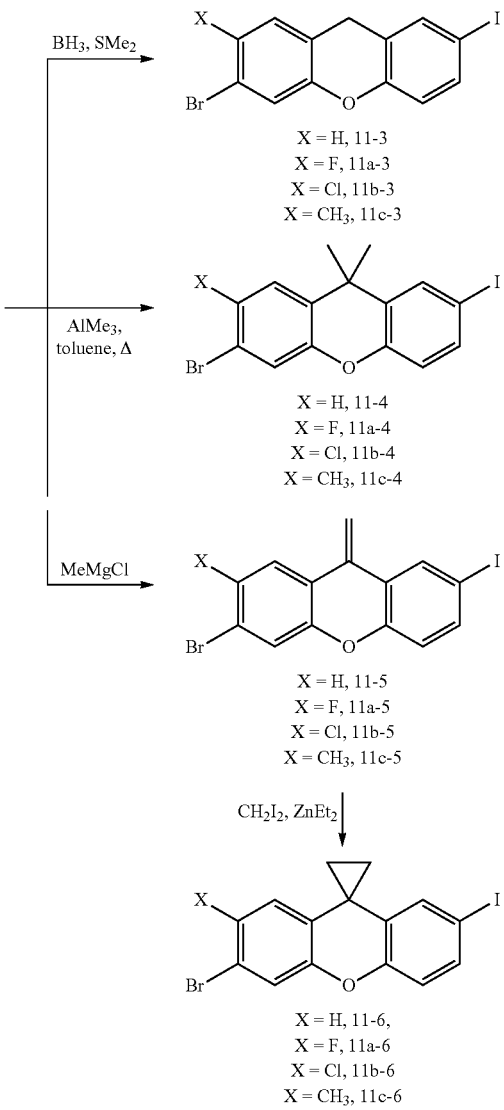

The syntheses of compounds 11-2 and 11a-2 were described in Example 11-8 and Example 11a-9. Following the same procedures and substituting 4-bromo-2-chlorobenzoic acid with the corresponding 5-substituted benzoic acids, the respective tricyclic xanthenone compounds 11b-2 and 11c-2 were obtained. Xanthones bearing other substituents and substitution patterns may be prepared similarly.

The xanthene compounds (11-3, 11a-3, 11b-3, 11c-3) were made from the reduction of corresponding xanthones (11-2, 11a-2, 11b-2, 11c-2) with $BH_3.SMe_2$. (Reference: *Org. Lett.* 2002, 4, 3139-3142).

Compounds (11-4, 11a-4, 11b-4, 11c-4) were made by alkylating the responding xanthones (11-2, 11a-2, 11b-2, 11c-2) with $AlMe_3$ with toluene as solvent. (Reference: *J. Am. Chem. Soc.*, 1990, 112, 8902-8906).

Compounds (11-5, 11a-5, 11b-5, 11c-5) were made by treating xanthones (11-2, 11a-2, 11b-2, 11c-2) with MeMgCl.

Compounds (11-6, 11a-6, 11b-6, 11c-6) were made by treating 6-bromo-2-iodo-9-methylene-9H-xanthene (11-2, 11a-2, 11b-2, 11c-2) with cyclopropanation reagents such as $CH_2I_2$ and $ZnEt_2$. (Reference: *Org. Lett.* 2007, 9, 3499-2502).

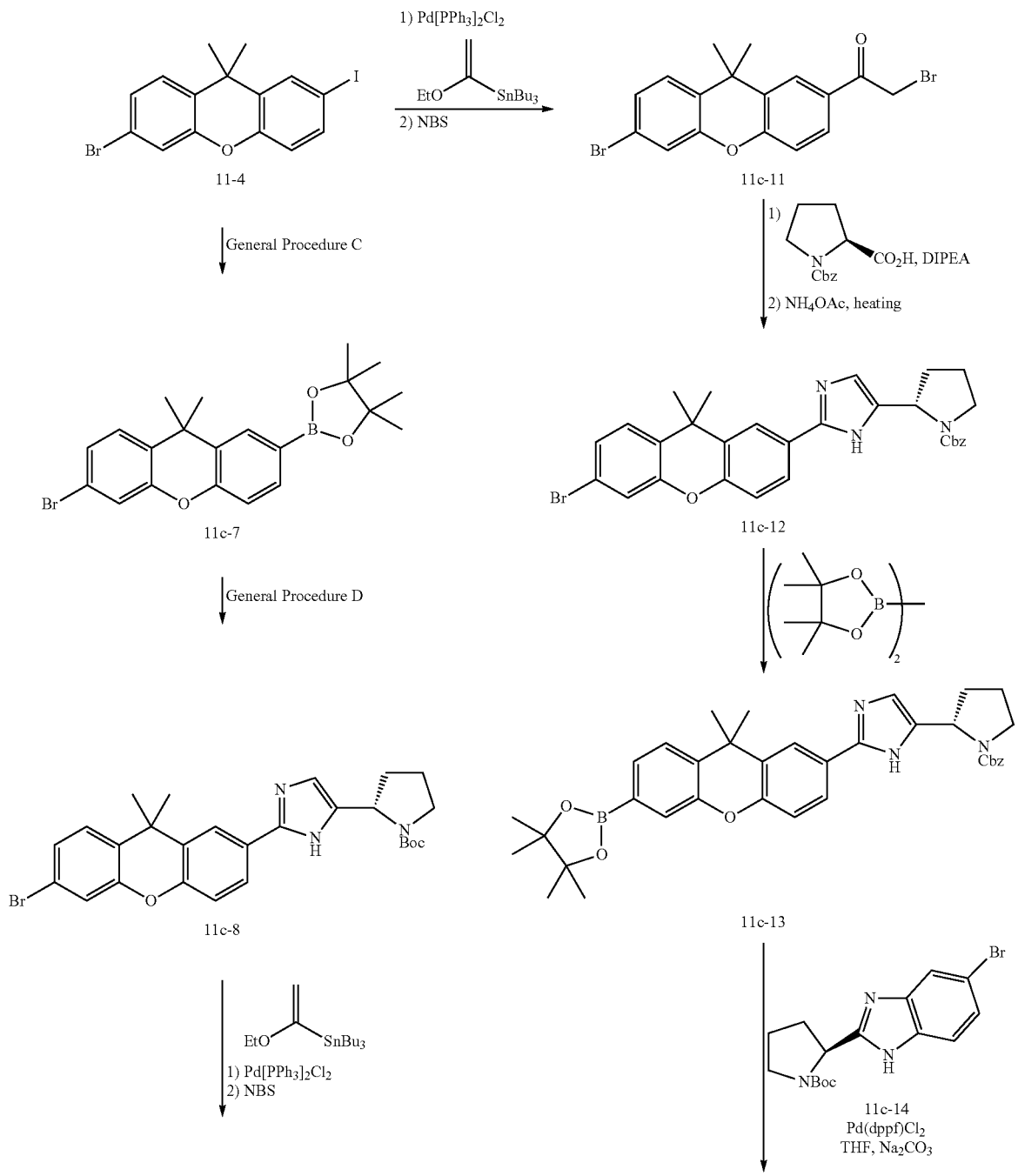

Scheme 11c

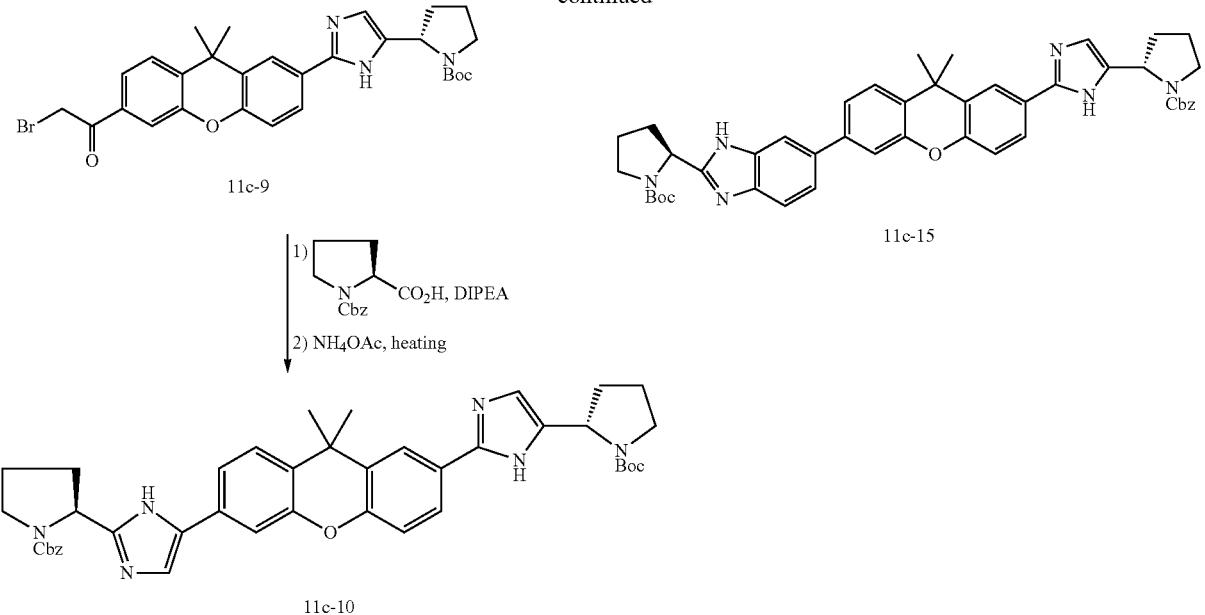

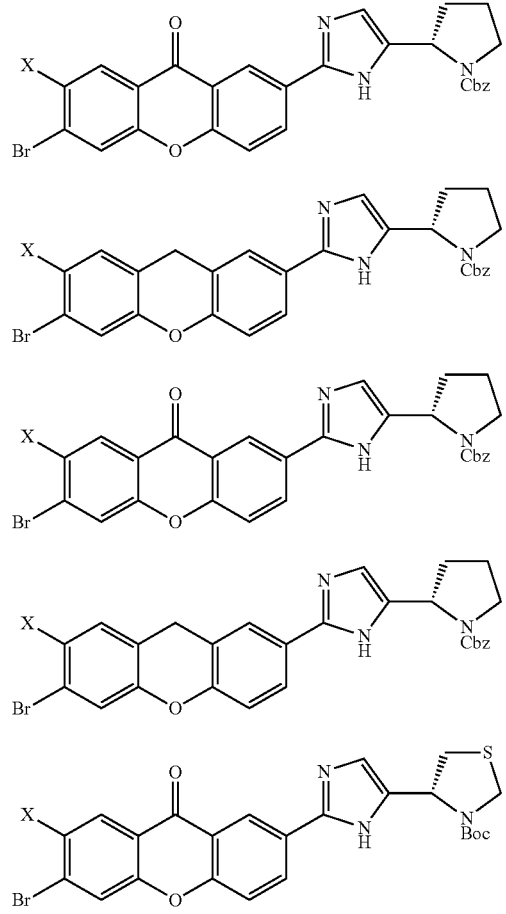

Using compound 11-4 as an example, Scheme 11c demonstrated the routes that were used for functionalizing the two sides of the molecule differentially.

Example 11c-10

Step 1. Referring to Scheme 1c, Compound 11-4 was treated with 1 equivalent of 4,4,4',4',5,5,5',5'-octamethyl-2,2'-bi(1,3,2-dioxaborolane) in the presence of Pd(dppf)Cl$_2$ under the conditions described in General Procedure C (Step 1 of Example 13). Compound 11c-7 was obtained in 25% yield. LC-MS (ESI): m/z 416 [M+H]$^+$.

Compound 11c-7 was converted to 11c-8 under the conditions described in General Procedure D (Step 2 of Example 13) in 61% yield. LC-MS (ESI): m/z 524 [M+H]$^+$.

Compound 11c-9 was produced by treating Compound 11c-8 under the conditions described in General Procedure E (Step 3 of Example 22). LC-MS (ESI): m/z 567 [M+H]$^+$.

Compound 11c-10 was obtained by reacting Compound 11c-9 and L-(S)-1-(benzyloxycarbonyl)piperidine-2-carboxylic acid under the conditions of General Procedure A (Step 2 of Example 1). LC-MS (ESI): m/z 715 [M+H]$^+$.

Again referring to Scheme 11c, Compound 11c-11 was obtained by following conditions described in General Procedure E (Steps 1a and 2a of Example 18) and substituting 6-bromo-2-iodo-9,9-dimethyl-9H-xanthene for 3-bromo-2-fluoro-7-iodo-9H-xanthen-9-one. LC-MS (ESI): m/z 411 [M+H]$^+$.

Compound 11c-11 was converted to compound 11c-12 following conditions described in General Procedure A (Step 2 of Example 1). LC-MS (ESI): m/z 559 [M+H]$^+$.

Compound 11c-12 was converted to compound 11c-13 following conditions described in General Procedure A. LC-MS (ESI): m/z 559 [M+H]$^+$.

Compound 11c-15 was obtained by following conditions described in General Procedure D (Step 2 of Example 13) and substituting (S)-tert-butyl 2-(5-bromo-1H-benzo[d]imidazol-2-yl)pyrrolidine-1-carboxylate (11c-14) for (S)-tert-butyl 2-(4-iodo-1H-imidazol-2-yl)pyrrolidine-1-carboxylate. 34% yield, LC-MS (ESI): m/z 766 [M+H]$^+$.

TABLE A

Monoimidazole intermediates prepared using chemistry described in Scheme 11b.

TABLE A-continued
Monoimidazole intermediates prepared using chemistry described in Scheme 11b.
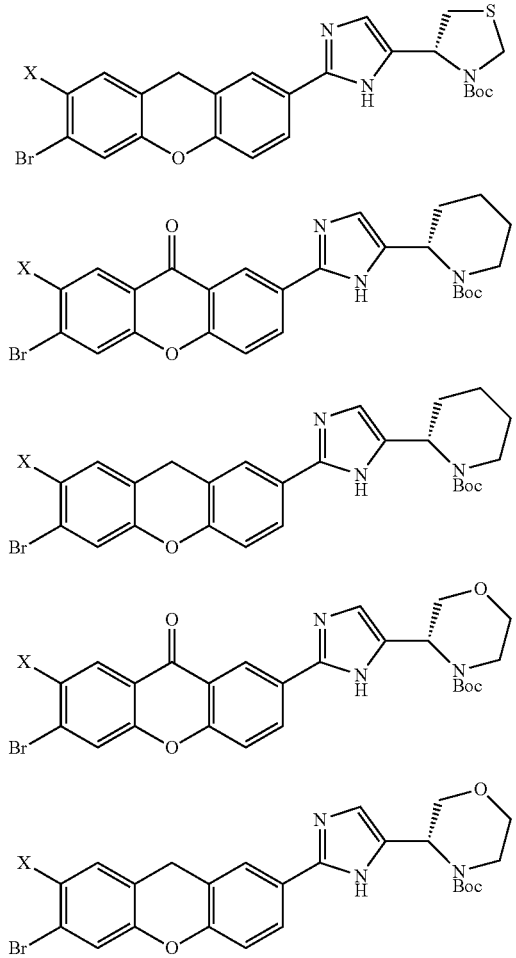
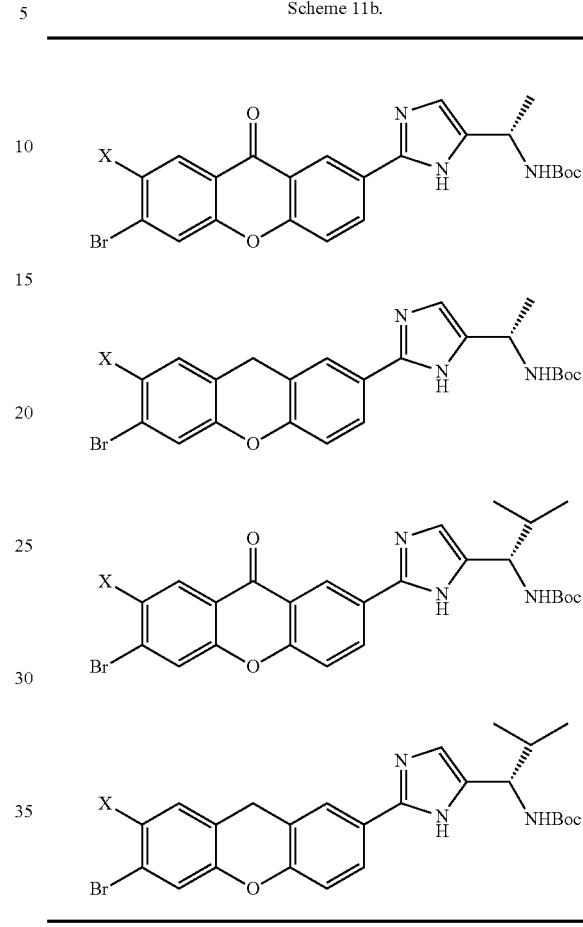
X = H, F, Cl, CH₃, CN
TABLE B
Scaffolds bearing two imidazoles or one imidazole and one benzimidazole, in which,
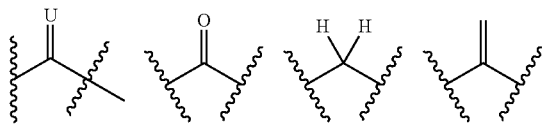
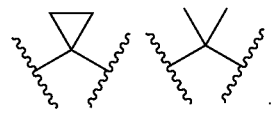
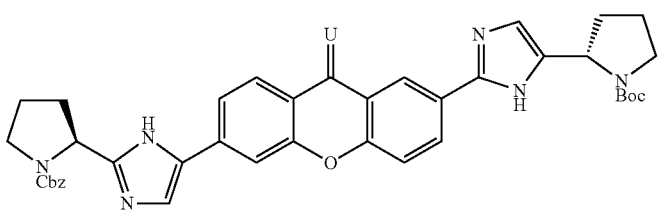

TABLE B-continued
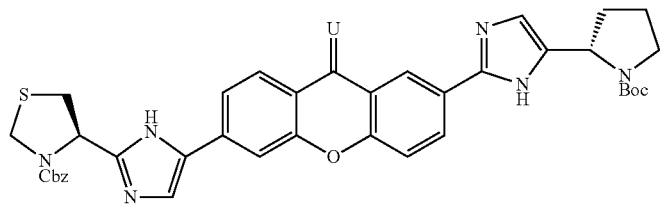
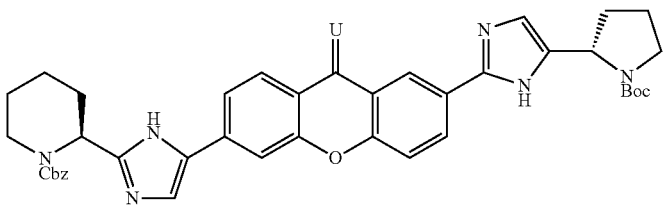
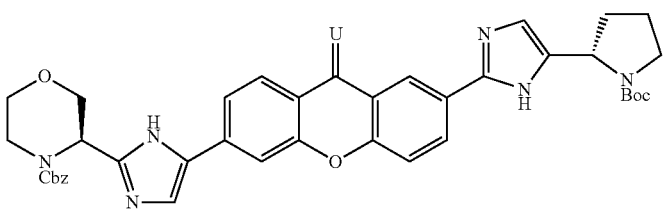
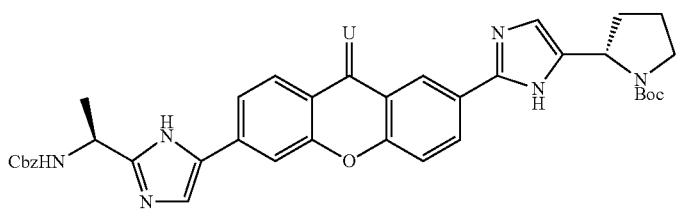
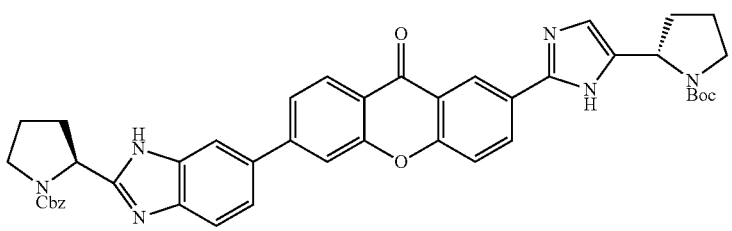 [SMILES: CC(C)(C)OC(=O)N1CCC[C@H]1c1cnc(-c2ccc3oc4cc(-c5ccc6nc([C@@H]7CCCN7C(=O)OCc7ccccc7)[nH]c6c5)ccc4c(=O)c3c2)[nH]1]
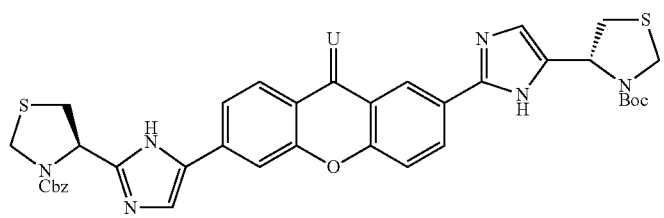
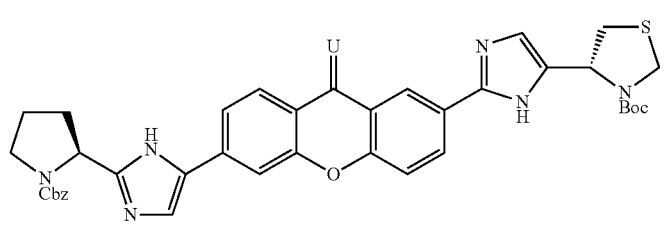

TABLE B-continued
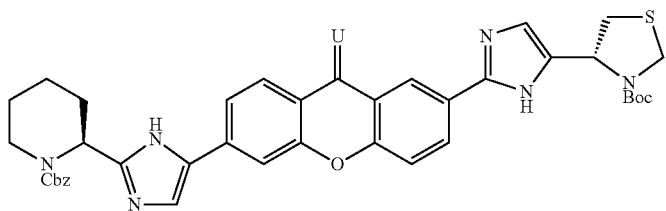
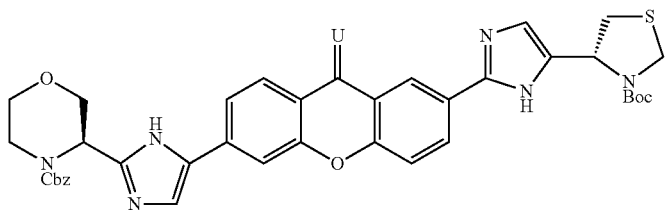
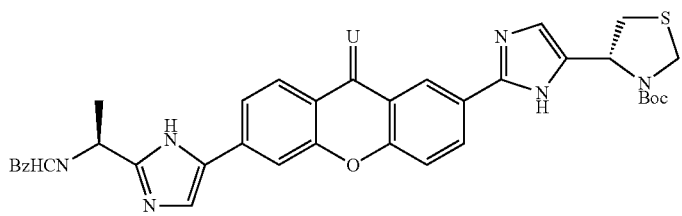
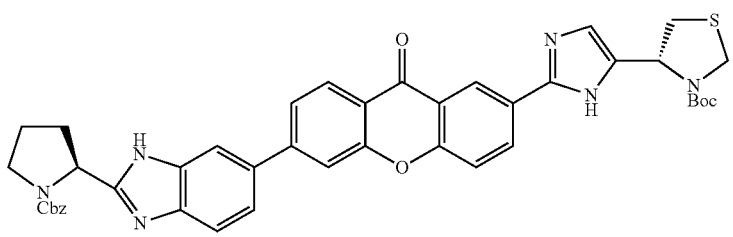 [SMILES: CC(C)(C)OC(=O)N1CSC[C@H]1c1cnc(-c2ccc3oc4cc(-c5ccc6nc([C@@H]7CCCN7C(=O)OCc7ccccc7)[nH]c6c5)ccc4c(=O)c3c2)[nH]1]
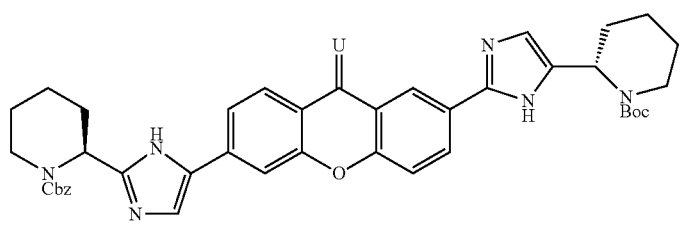
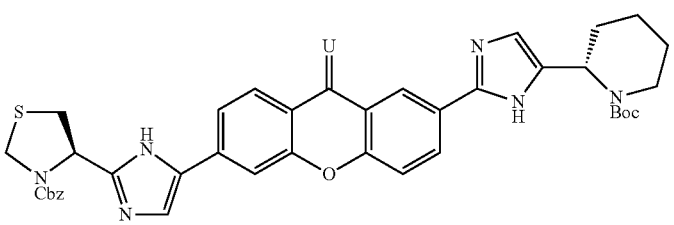
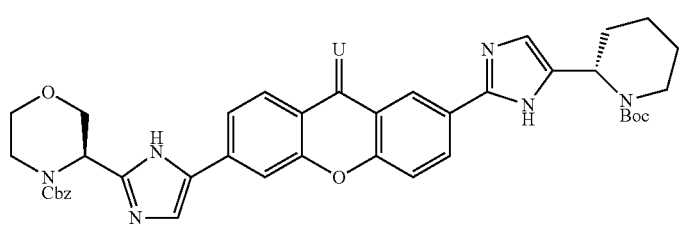

TABLE B-continued
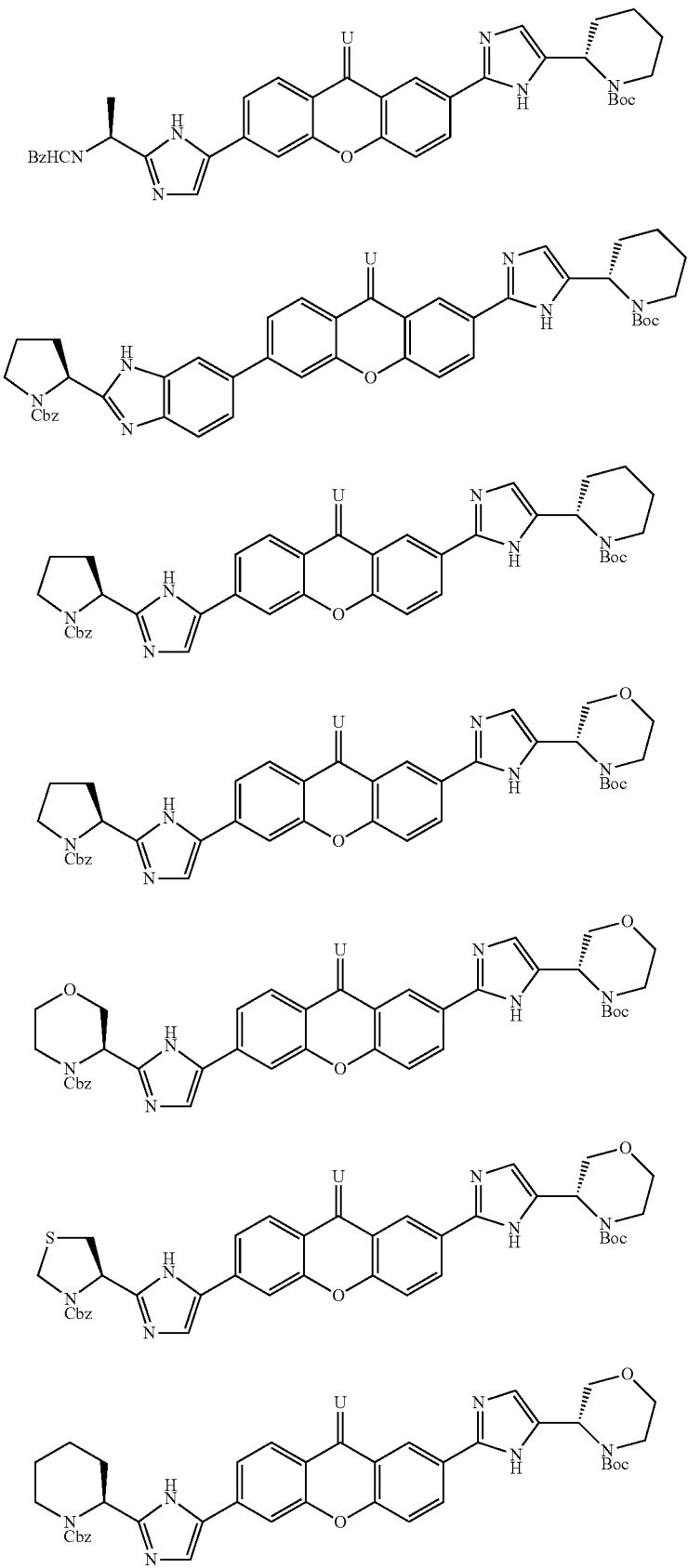

TABLE B-continued
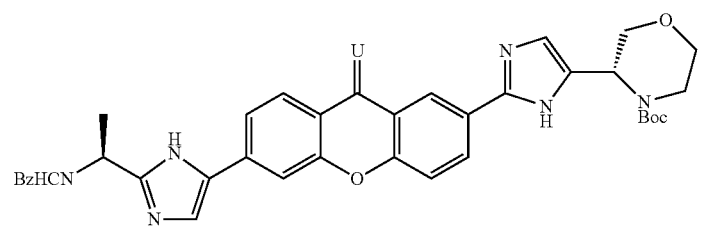
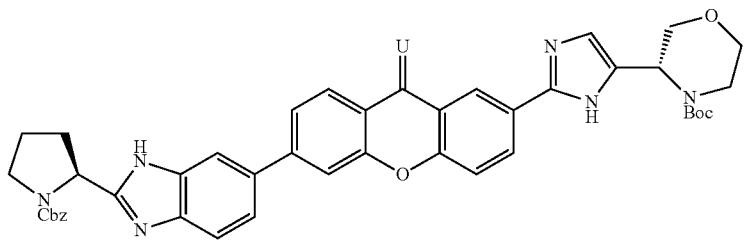
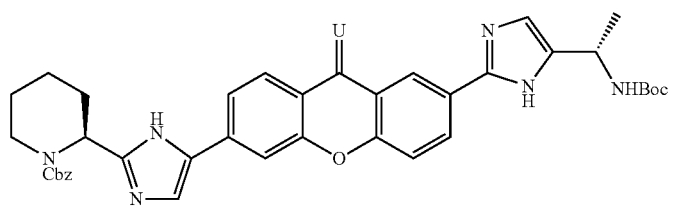
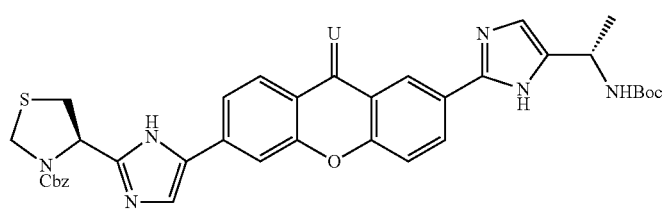
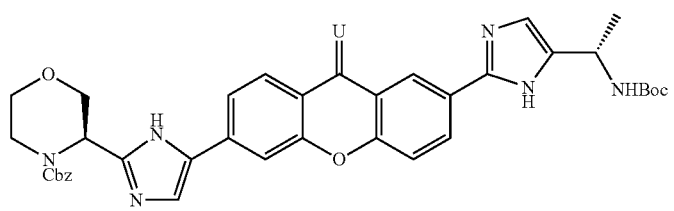
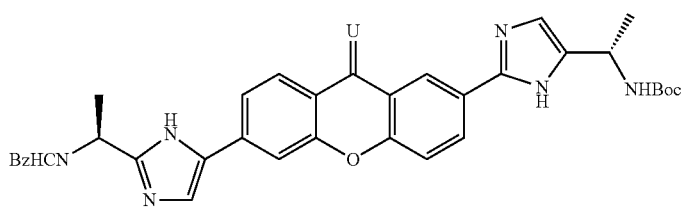
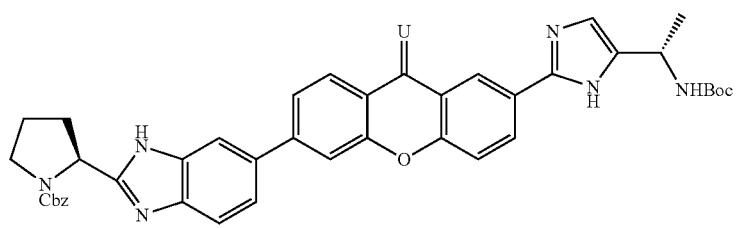

TABLE B-continued

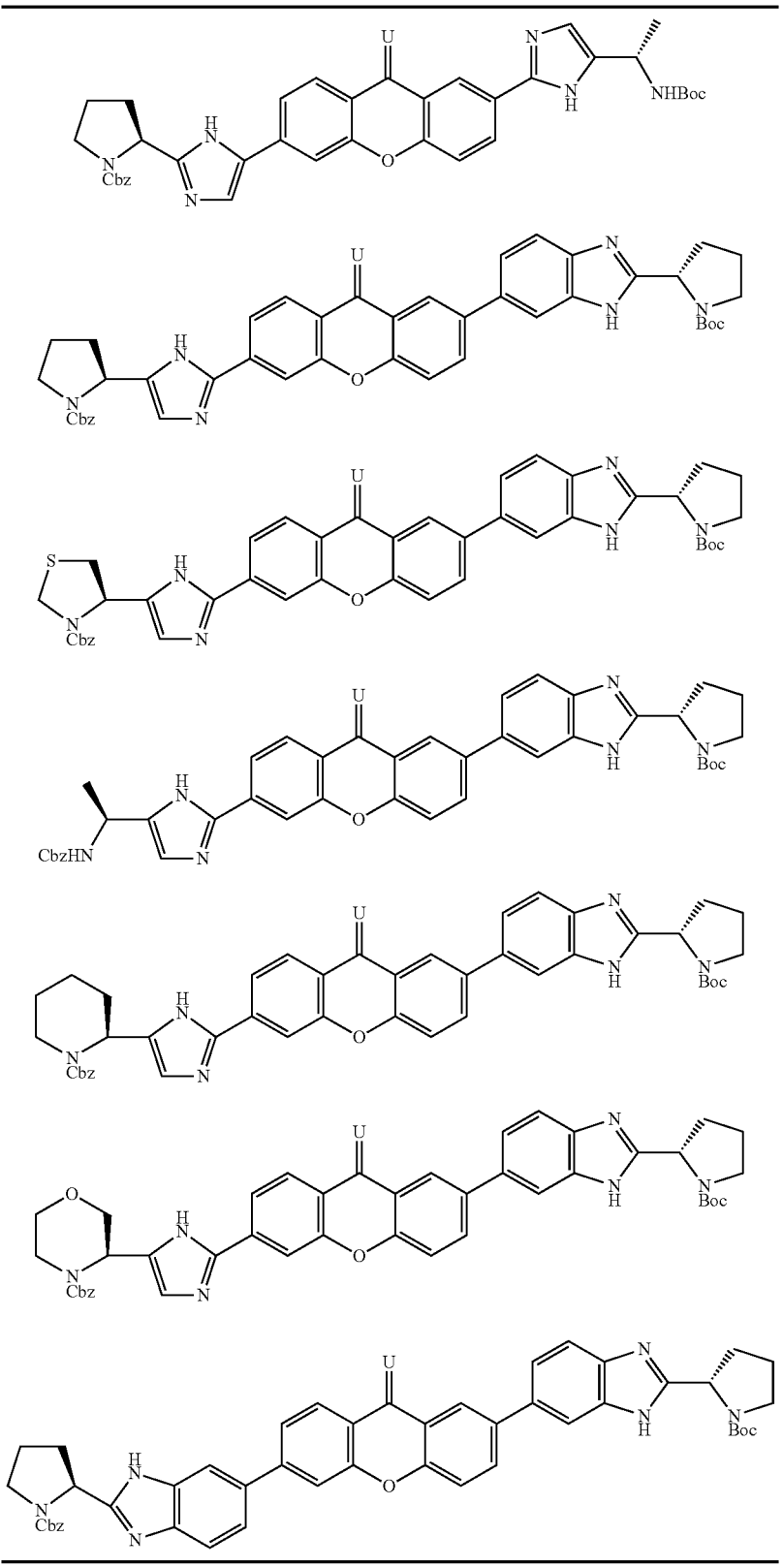

The nitrogen protecting group, Boc or Cbz, on one of the scaffolds of Table 2 can be selectively removed to release the amine for further derivatization, typically an acylation with a proper amino acid. When done, the other remaining protecting group can be unmasked for functionalization of the amine with a different acylating group or the same as the first one.

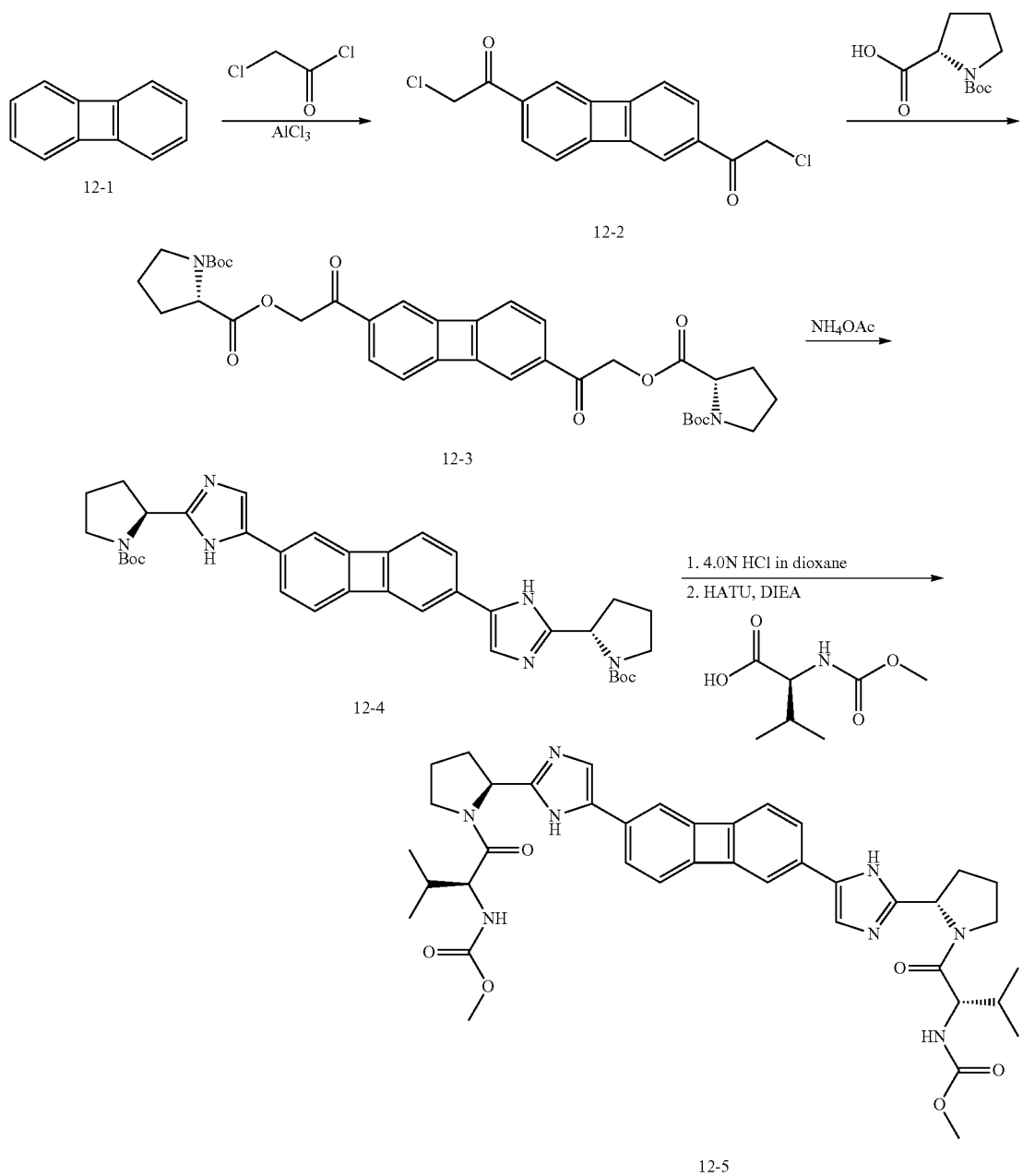

Example 25

Preparation of 12-5

Step 1.

Referring to Scheme 12, to a solution of 12-1 (200 mg, 1.31 mmol) in CS₂ (20 mL), AlCl₃ (876 mg, 6.57 mmol) and 2-chloroacetyl chloride (964 mg, 8.54 mmol) were added at 0° C. After stirring at 0° C. for 1 h, the reaction mixture was added to H₂O (50 mL). The mixture was extracted with EtOAc for several times (3×50 mL) and the extracts were combined and dried with anhydrous Na₂SO₄. The solvent was removed and the residue was purified by silica gel column chromatography (Petroleum ether/EtOAc=10/1 (v/v)) to give 12-2 (140 mg, 35% yield). LC-MS (ESI): m/z 305 $[M+H]^+$.

Step 2.

To a solution of 12-2 (140 mg, 0.459 mmol) in DCM (10 mL), (S)—N-Boc-Pro-OH (197 g, 0.917 mmol) and Et₃N (0.26 mL, 1.84 mmol) were added at rt. After stirring at rt overnight, the reaction mixture was concentrated and the residue was dried in vacuo to give crude 12-3 (100 mg), which was used for the next step without further purification. LC-MS (ESI): m/z 663 $[M+H]^+$.

Step 3.

To a solution of crude 12-3 (100 mg, 0.124 mmol) in toluene (20 mL) was added NH₄OAc (95.0 mg, 1.24 mmol).

After refluxing overnight, the reaction mixture was concentrated and the residue was purified by silica gel column chromatography (Petroleum Ether/EtOAc=3/1 (v/v)) to give 12-4 (34 mg, 45% yield) as a yellow solid. LC-MS (ESI): m/z 623 [M+H]⁺.

Step 4.

To a stirred solution of compound 12-4 (33 mg, 0.050 mmol) in dioxane (1 mL) was added 4 N HCl in dioxane (2 mL). After stirring at rt for 2 h, the reaction mixture was concentrated and the residue was dried in vacuo to give an HCl salt, which was used for the next step without further purification.

To a mixture of the HCl salt in DMF (2 mL) was added DIPEA (0.1 mL, 0.5 mmol), followed by N-Moc-L-Val-OH (22 mg, 0.13 mmol) and HATU (50 mg, 0.13 mmol). After stirred at rt for 30 min, the reaction mixture was poured into water. The solid was filtrated and purified by preparative HPLC to give 12-5 (10 mg, 27%) as an off-white solid. $^1$H NMR (500 MHz, CD$_3$OD): δ 7.92 (s, 2H), 7.25 (d, J=7.0, 2H), 7.16 (s, 2H), 6.91 (d, J=6.5, 2H), 5.21 (s, 2H), 4.22 (d, J=6.5, 2H), 4.09 (s, 2H), 3.91 (s, 2H), 3.65 (s, 6H), 2.55 (s, 2H), 2.28 (s, 2H), 2.17 (s, 2H), 2.07 (d, J=6.0, 2H), 1.00-0.88 (m, 12H) ppm; LC-MS (ESI): m/z 737 [M+H]⁺.

Scheme 13

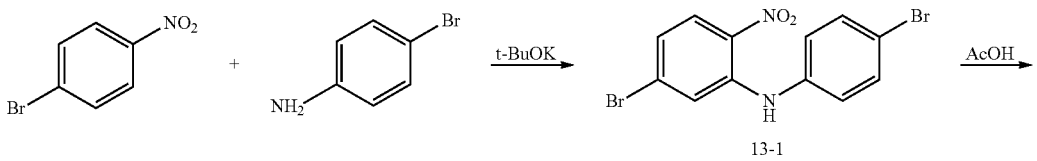

13-1

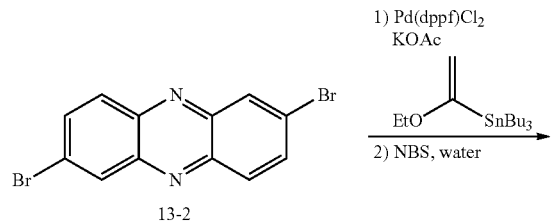

13-2

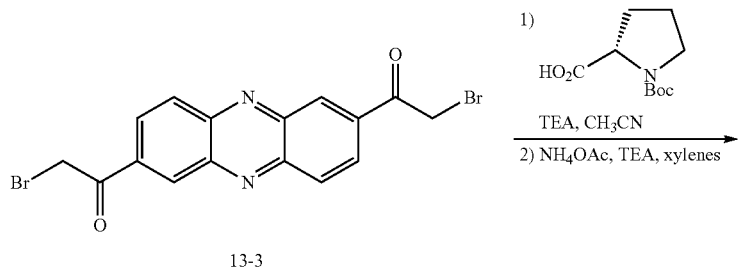

13-3

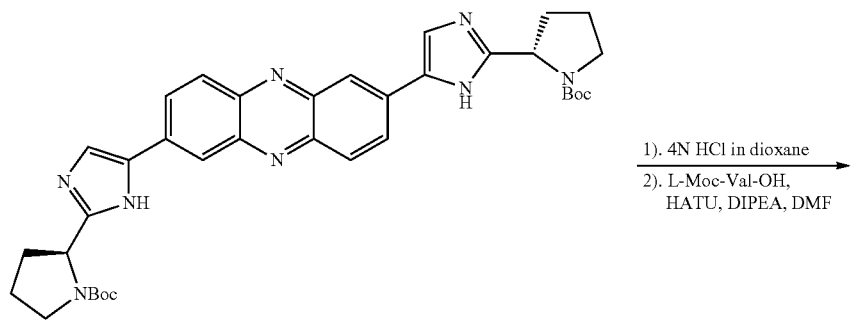

13-4

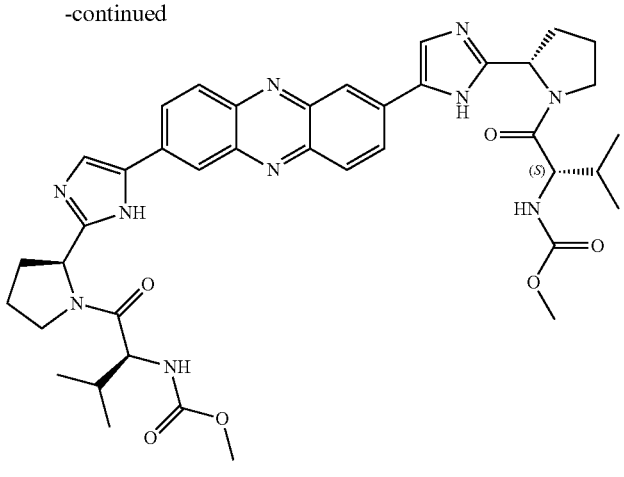

13-5

Example 26

Preparation of 13-5

Step 1.

Referring to Scheme 13, a solution of 4-bromoaniline (10 g, 58.1 mmol) in DMF (30 mL) was added dropwise to a solution of potassium t-butoxide (19.57 g, 174 mmol) in DMF (60 mL) at −60° C., followed immediately by a solution of 1-bromo-4-nitrobenzene (11.74 g, 58.1 mmol) in DMF (45 mL). The mixture was stirred for 5 min, and then a cooled mixture of AcOH (45 mL) and DMF (45 mL) was added in one portion. The mixture was allowed to warm to room temperature, and poured into water (500 mL) and extracted with EtOAc (3×300 mL), the organics were combined and washed with water (3×500 mL), brine (500 mL) and the organic layer was dried over anhydrous $MgSO_4$, filtered and concentrated in vacuo to afford a crude brown solid. The product was purified by silica gel chromatography ($SiO_2$, 0-10% (v/v) of EtOAc/isohexane) to afford 13-1 as brown solid (10 g, 48.3% yield).

Step 2.

5-bromo-N-(4-bromophenyl)-2-nitrosoaniline (13-1) (10 g, 28.1 mmol) in AcOH (300 mL) was heated under reflux for 1.5 hrs. Water (400 mL) was then added and the brown precipitate formed was collected by filtration after washing with water (2×200 mL). The product was purified by silica gel chromatography ($SiO_2$, hexanes/DCM=1/1(v/v)) to afford a brown solid, 2,7-dibromophenazine 13-2 (1.52 g, 16% yield). $^1$H NMR ($CDCl_3$): δ 8.43 (2H, dd, J 2.2, 0.4 Hz), 8.10 (2H, dd, J 9.2, 0.4 Hz), 7.91 (2H, dd, J 9.2, 2.2 Hz) ppm. LC-MS (ESI): m/z 338.6 [M+H]$^+$.

Step 3.

To a solution of 2,7-dibromophenazine (13-2) (1.52 g, 4.50 mmol) in dry dioxane (75 mL) under $N_2$ was added tributyl (1-ethoxyvinyl)stannane (3.34 ml, 9.89 mmol) and Pd(dppf)$Cl_2$ (0.316 g, 0.450 mmol). The resultant mixture was heated at 100° C. for 4 hrs in a sealed tube. The crude reaction mixture was filtered through CELITE™ 545, and the volatiles were removed in vacuo. The crude brown solid was triturated with isohexanes and filtered to give 2,7-bis(1-ethoxyvinyl)phenazine as a brown solid (1.27 g, 88% yield). $^1$H NMR ($CDCl_3$): δ 8.55-8.53 (2H, m), 8.19-8.15 (2H, m), 8.11-8.07 (2H, m), 4.98 (2H, d, J=3 Hz), 4.49 (2H, d, J=3 Hz), 4.03 (4H, q, J=7 Hz), 1.50 (6H, t, J=7 Hz) ppm. LC-MS (ESI): m/z 322.1 [M+H]$^+$.

N-Bromosuccinimide (1.411 g, 7.93 mmol) was added to a stirred solution of 2,7-bis(1-ethoxyvinyl)phenazine (1.27 g, 3.96 mmol) in THF (95 mL) and water (20 mL) and left to stir at rt for 1 hr. The reaction mixture was filtered and the yellow solid collected was washed with water and dried under vacuum to afford 1,1'-(phenazine-2,7-diyl)bis(2-bromoethanone) (13-3) (991 mg, 59.2% yield) as a yellow solid.

$^1$H NMR ($CDCl_3$): δ 8.93-8.91 (2H, m), 8.47-8.46 (2H, m), 8.41-8.37 (2H, m), 4.66 (4H, s) ppm. LC-MS (ESI): m/z 423.8 [M+H]$^+$.

Step 4.

The bisimidazole compound 13-4, (2S,2'S)-tert-butyl 2,2'-(5,5'-(phenazine-2,7-diyl)bis(1H-imidazole-5,2-diyl))dipyrrolidine-1-carboxylate was prepared under the conditions of general procedure A. LC-MS (ESI): m/z 651.1 [M+H]$^+$.

Step 5.

Compound 13-5, Dimethyl (2S,2'S)-1,1'-((2S,2'S)-2,2'-(5,5'-(phenazine-2,7-diyl)bis(1H-imidazole-5,2-diyl))bis(pyrrolidine-2,1-diyl))bis(3-methyl-1-oxobutane-2,1-diyl)dicarbamate. This product was prepared using general procedure B to give an orange solid (57 mg, 88% yield). LC-MS (ESI): m/z 765.2 (M+H)$^+$; 763.1 [M−H]$^−$.

Scheme 14

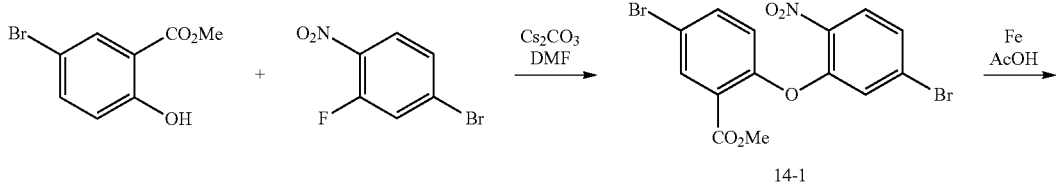

14-1

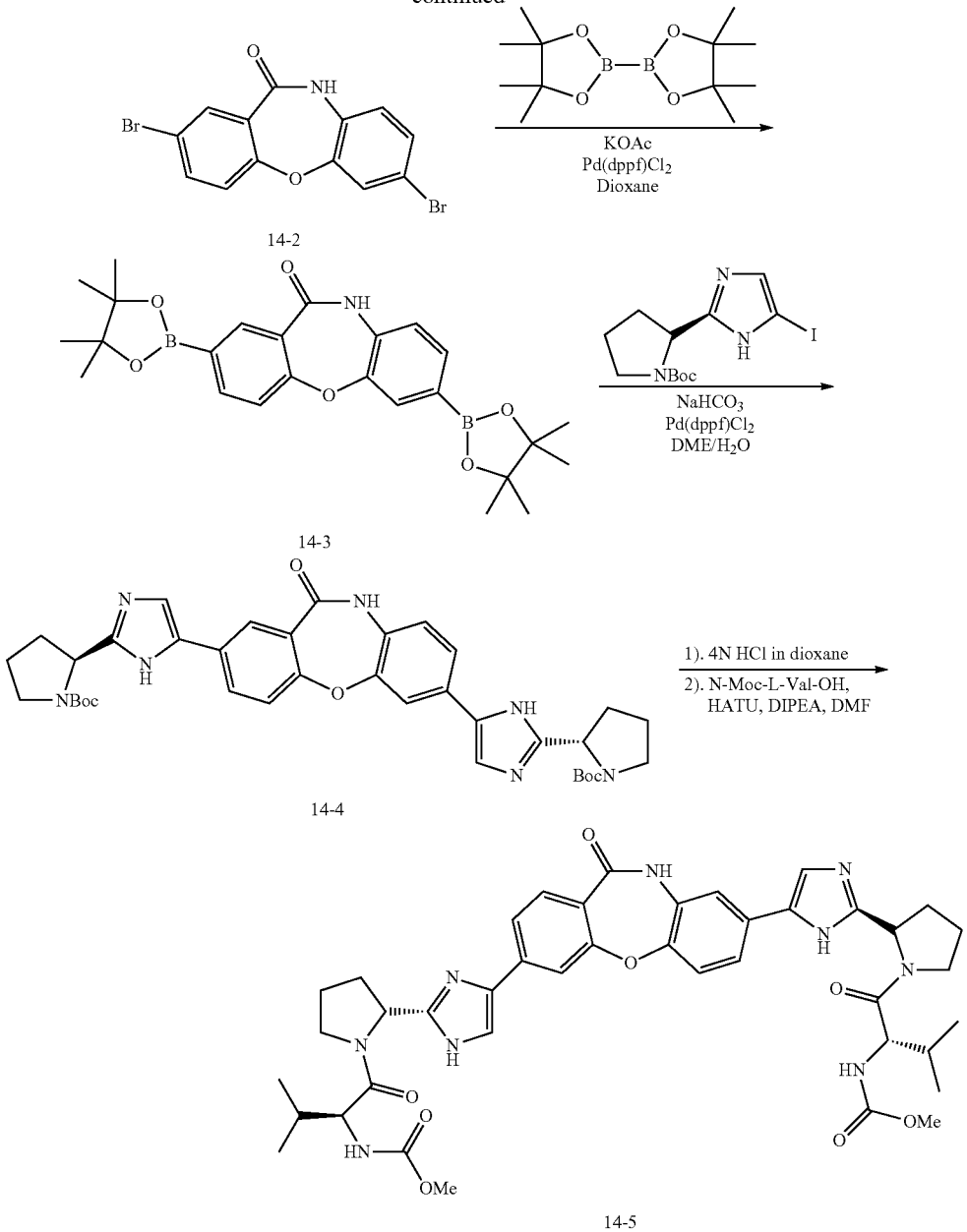

Example 27

Preparation of 14-5

Step 1.

Referring to Scheme 14, cesium carbonate (6.20 g, 19.0 mmol) was added to a solution of methyl 5-bromo-2-hydroxybenzoate (4.0 g, 17.3 mmol) in DMF (20 mL) and the mixture was stirred for 30 min. 4-bromo-2-fluoro-1-nitrobenzene (3.81 g, 17.3 mmol) was then added and the mixture was heated at 60° C. for 3 hrs. After cooling at the completion of the reaction, the mixture was poured into water (500 mL) and extracted with ether (2×250 mL). The combined organic layers were washed with brine, dried over anhydrous $Na_2SO_4$, filtered and concentrated to give crude 14-1 as brown oil (5.85 g, 78% yield).

Step 2.

The crude product from above was dissolved in AcOH (12 mL) and treated with iron powder (320 mesh, 4.55 g, 81 mmol) at 115° C. for 40 mins. The reaction mixture was cooled to rt, poured into water (300 mL) and extracted with EtOAc (2×200 mL). The combined organic extracts were sequentially washed with water (300 mL), aq. $NaHCO_3$ (300 mL) and brine (200 mL) and concentrated in vacuo. The residue was taken up in minimal amount of $Et_2O$ and precipitated with addition of hexanes. Precipitate was collected by filtration to give 14-2 as a white solid in 72% yield. LC-MS (ESI): m/z 368.2 [M−H]⁻.

Step 3.

Compound 14-3 was prepared in 69% by treating 14-2 under General Procedure C.

Step 4.
Compound 14-4 was obtained in 64% yield by treating 14-3 under General Procedure D. LC-MS (ESI): m/z 682.8 [M+H]+.
Step 5.
Compound 14-5 was obtained in 45% yield by treating 14-4 under General Procedure B. LC-MS (ESI): m/z 796 [M+H]+.
Scheme 15
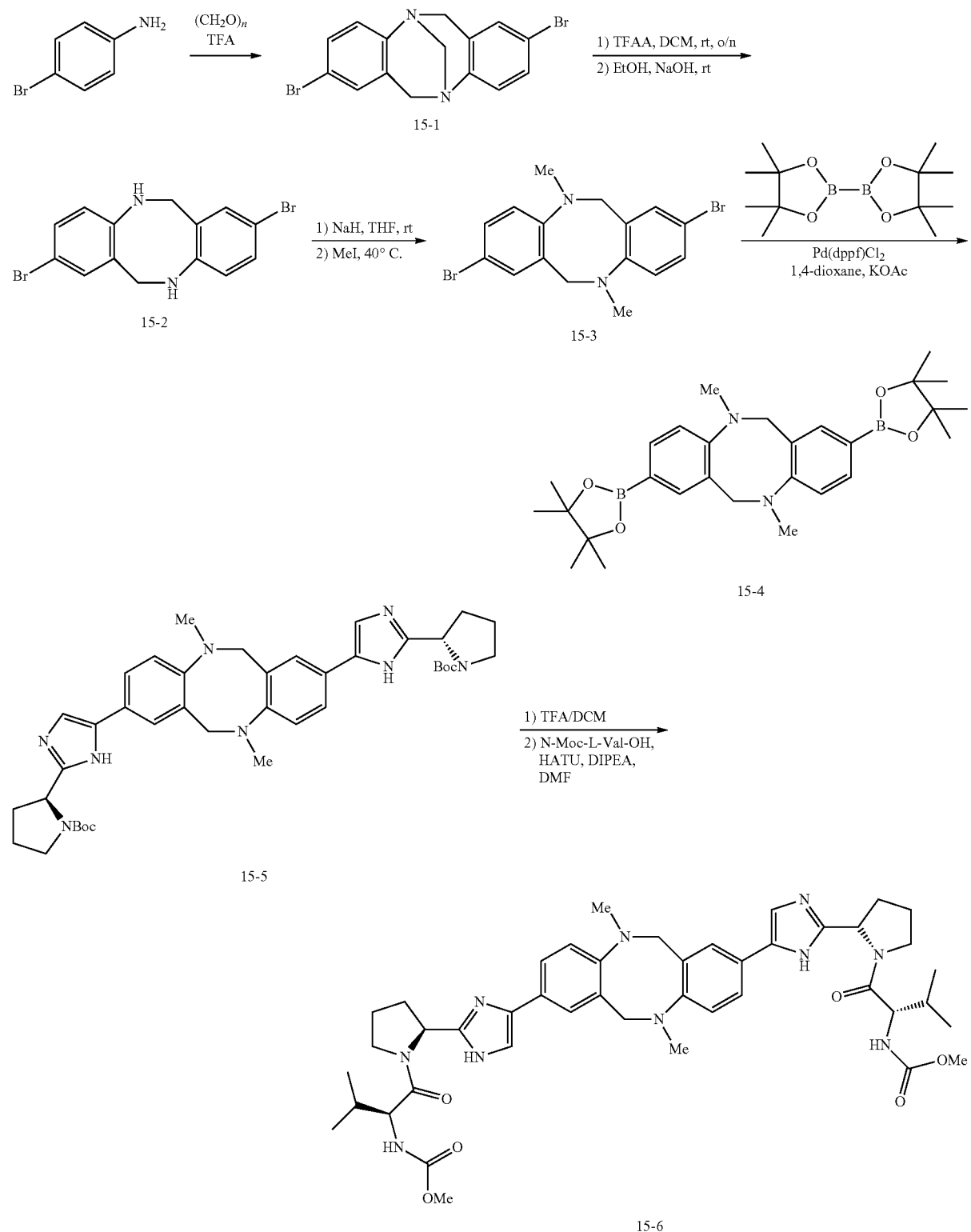

Example 28

Preparation of 15-6

Step 1.

Referring to Scheme 15, 4-Bromoaniline and paraformaldehyde were added to TFA (23 mL) at −15° C. After stirred at rt for 24 hrs, the reaction mixture was slowly added to a stirred mixture of ice and 30% aqueous $NH_3$ (40 mL). The entire mixture (solid and solution) was extracted with DCM (3×10 mL), the extracts were dried over $MgSO_4$, filtered and concentrated in vacuo to afford 15-1 (2.35 g, 57%, yellow solid).

Step 2.

Compound 15-1 was suspended in a mixture of TFAA (4 mL) and DCM (8 mL) and stirred at rt in a sealed vessel overnight. LC-MS indicated the presence of trifluoroacetylated product and the absence of starting 15-1. The reaction was then quenched with $H_2O$ and basified with aqueous $NaHCO_3$. The mixture was extracted with DCM (3×100 mL). The combined organic layers were dried over $MgSO_4$, filtered and concentrated in vacuo. The residue was dissolved in EtOH (40 mL) with sodium hydroxide (800 mg) and stirred at rt for 2 hrs. The reaction was concentrated under reduced pressure and the residue dissolved in a mixture of water and DCM. The organic layer was dried over $MgSO_4$, filtered and concentrated in vacuo to give product 15-2 in 57% yield.

Step 3.

NaH (60% mineral oil dispersion, 0.103 g, 4.29 mmol) was added to a solution of 15-2 (0.75 g, 2.04 mmol) in THF (10 mL) at 0° C. The reaction mixture was stirred for 45 mins at rt. MeI (0.638 g, 4.50 mmol) was added at 0° C., and the reaction mixture stirred at rt overnight. The reaction was cooled down to rt and quenched with water. The aqueous layer was extracted with DCM (3×50 mL) and $Et_2O$ (2×50 mL), respectively. The combined organic layers were dried over $MgSO_4$, filtered and concentrated in vacuo. The crude product was purified by silica gel chromatography eluted with mixed solvents of hexanes and DCM in 9:1 (v/v) ratio to give 15-3 (0.634 g, 78% yield). LC-MS (ESI): m/z 397.1 $[M+H]^+$.

Step 4.

Compound 15-4 was prepared in 66% by treating 15-3 under general procedure C.

Step 5.

Compound 15-5 was obtained in 54% yield by treating 15-4 under general procedure D. LC-MS (ESI): m/z 709.6 $[M+H]^+$.

Step 6.

Compound 15-6 was obtained in 32% yield by treating 15-5 under general procedure B. LC-MS (ESI): m/z 823.5 $[M+H]^+$.

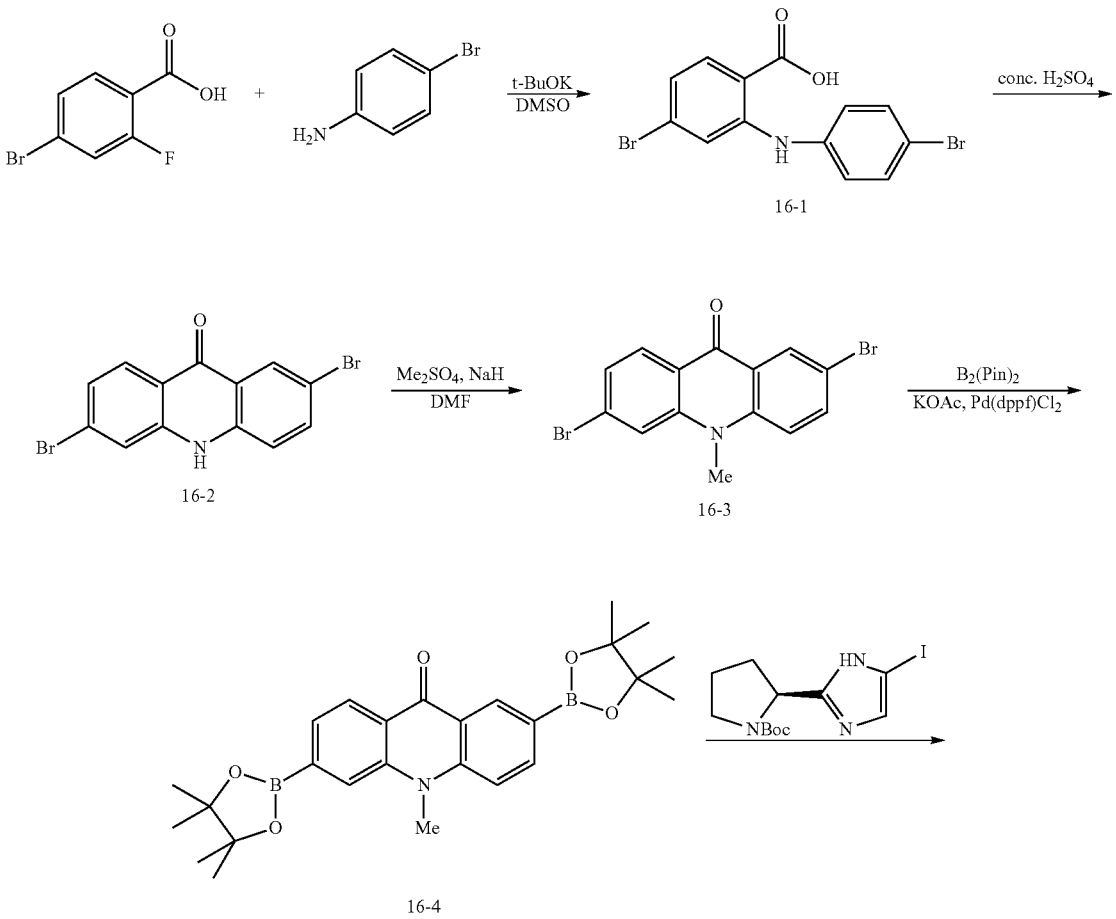

Scheme 16

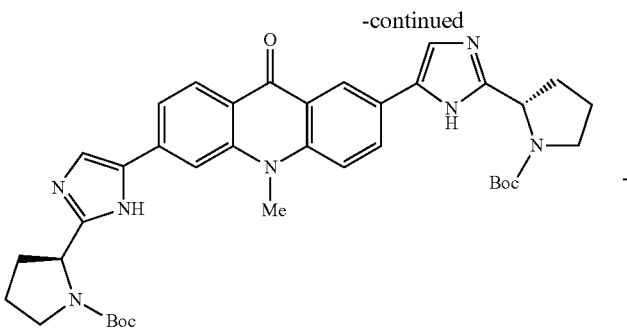

16-5

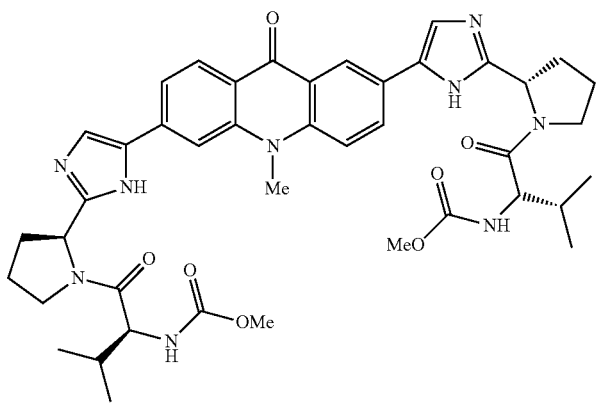

16-6

Example 29

Preparation of 16-6

Step 1.

Referring to Scheme 16, to a solution of acid 4-bromo-4-fluorobenzoic acid (6 g) and 4-bromoaniline (7 g) in DMSO (75 mL) was added potassium tert-butoxide (1.3 g) at rt. After stirring for three days, the reaction was diluted with water (300 mL) and extracted with diethyl ether (3×100 mL). The aqueous layer was acidified by 2 M HCl to pH 1, extracted by ethyl acetate (with 10% MeOH). The combined organic layers were dried over anhydrous $Na_2SO_4$, filtered and concentrated to provide the crude product, which was recrystallized in MeOH to provide 16-1 (1.2 g, red solid, 12% yield). LC-MS (ESI): m/z 372 [M+H]$^+$.

Step 2.

Compound 16-1 (1.2 g) was dissolved in conc. $H_2SO_4$ (6 mL) and the solution was warmed up to 110° C. After stirring for 1 hr, the reaction was cooled to rt and slowly transferred to ice-water (100 mL). The yellow precipitation from ice-water solution was filtered to afford 16-2 (900 mg), which was used without further purification. LC-MS (ESI): m/z 352 [M+H]$^+$.

Step 3.

To a solution of 16-2 (900 mg) in dry DMF (20 mL) was added sodium hydride (60% dispersion, 355 mg) at rt. The reaction was stirred for 1 h and dimethyl sulfate (482 mg) was added. After stirring overnight, the reaction was quenched with ice-water. The yellow precipitation from ice-water solution was filtered to afford 16-3 (900 mg) without further purification. LC-MS (ESI): m/z 366 [M+H]$^+$.

Step 4.

To a solution of 16-3 (100 mg, 0.272 mmol) in 24 mL of dioxane was added bis(pinacolato)diboron (166 mg, 0.653 mmol), dichloro[1,1'-bis(diphenylphosphino) ferrocene]palladium(II) (11 mg, 0.014 mmol) and potassium acetate (160 mg, 1.63 mmol) under $N_2$ atmosphere. The reaction mixture was stirred at 80° C. overnight, and then cooled to rt and diluted with dichloromethane (150 mL) and then aq. phase was extracted with dichloromethane. The organic phase was washed with water, dried over sodium sulfate and concentrated in vacuo to give crude 16-4 (140 mg). LC-MS (ESI): m/z 462 [M+H]$^+$.

Step 5.

To a solution of 16-4 (140 mg, 0.272 mmol) in 3.2 mL of THF and 2M $Na_2CO_3$ (3/1(v/v) was added (S)-tert-butyl 2-(5-iodo-1H-imidazol-2-yl)pyrrolidine-1-carboxylate (300 mg, 0.598 mmol), dichloro[1,1'-bis(diphenylphosphino)ferrocene]palladium (II) (11 mg, 0.014 mmol) and sodium bicarbonate (2.7 g, 32 mmol) under $N_2$ atmosphere. The reaction mixture was stirred at 80° C. overnight and diluted with dichloromethane (120 mL). The organic phase was washed with water, dried over anhydrous $Na_2SO_4$ and concentrated in vacuo. The residue was further purified by silica gel column chromatography (Hexane/acetone=1/1 (v/v)) to give 16-5 (110 mg, 43%) as a yellow solid. LC-MS (ESI): m/z 680 [M+H]$^+$.

Step 6.

To a stirred solution of 16-5 (55 mg) in dichloromethane (10 mL) was added trifluoroacetic acid (1 mL). After 3 hrs, the reaction was concentrated to dryness to provide de-Boc-16-5. de-Boc-16-5 was dissolved in DMF (2 mL) and DIPEA (100 μL), N-Moc-L-Val-OH (18 mg) and DMTMM (20 mg) were added subsequently. After one h stirring, the reaction was diluted with water. The reaction was extracted with dichloromethane. The combined extracts were washed with brine and water, dried over $Na_2SO_4$, filtered and concentrated. The crude product was purified by prep-HPLC (Phenomenex, C18-Luna column, H$_2$O-MeCN, 0.1% HCO$_2$H) to provide 16-6 (6.0 mg, 6.5% yield). $^1$H NMR (300 MHz, CD$_3$OD): δ8.77-8.69 (m, 1H), 8.56-8.45 (m, 1H), 8.31-8.18 (m, 3H), 8.06-8.01 (m, 1H), 7.96 (s, 1H), 7.74-7.71 (m, 1H), 5.33-5.26 (m, 2H), 4.27-4.24 (m, 2H), 4.17-4.04 (m, 3H), 3.99-3.80 (m, 2H), 3.70-3.60 (m, 6H), 2.62-2.55 (m, 2H), 2.38-2.05 (m, 8H), 1.03-0.86 (m, 12H) ppm; LC-MS (ESI): m/z 794 [M+H]$^+$.

Biological Activity

Biological activity of the compounds of the invention was determined using an HCV replicon assay. The HCV 1b_Huh-Luc/Neo-ET cell line persistently expressing a bicistronic genotype 1b replicon in Huh 7 cells was obtained from ReBLikon GMBH. This cell line was used to test compound inhibition using luciferase enzyme activity readout as a measurement of compound inhibition of replicon levels.

On Day 1 (the day after plating cells), each compound is added in triplicate to the cells. Plates are incubated for 72 h prior to determining luciferase levels. Enzyme activity was measured using a Bright-Glo Kit (cat. number E2620) manufactured by Promega Corporation. The following equation was used to generate a percent control value for each compound.

% Control=(Compound Luciferase Level/Control Luciferase Level)*100

The EC$_{50}$ value was determined using GraphPad Prism and the following equation:

Y=Bottom asymptote+(Top asymptote-Bottom asymptote)/(1+10^((Log EC$_{50}$-X)*HillSlope))

EC$_{50}$ values of compounds are determined several times in the replicon assay to generate average EC$_{50}$ values.

Example compounds of the disclosed invention are illustrated in Table 1. The table shows inhibitory activity of many of the example compounds with respect to HCV 1b. The biological activity is indicated as being *, , * or ****, which corresponds to EC$_{50}$ ranges of >1000 nM, 999 nM to 10 nM, 9.9 nM to 1 nM, or <1 nM respectively. The table further provides mass spectrometry results for the synthesized example compounds. Additional compounds of the disclosed invention are illustrated in Table 2.

Pharmaceutical Compositions

A twelfth aspect of the invention provides a pharmaceutical composition comprising the compounds of the invention. In a first embodiment, the pharmaceutical composition further comprises one or more pharmaceutically acceptable excipients or vehicles, and optionally other therapeutic and/or prophylactic ingredients. Such excipients are known to those of skill in the art. The compounds of the present invention include, without limitation, basic compounds such as free bases and pharmaceutically acceptable salts of these compounds. A thorough discussion of pharmaceutically acceptable excipients and salts is available in Remington's Pharmaceutical Sciences, 18th Edition (Easton, Pa.: Mack Publishing Company, 1990).

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like.

For oral administration, the composition will generally take the form of a tablet, capsule, a softgel capsule nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents and the like.

A thirteenth aspect of the invention provides use of the compounds of the invention in the manufacture of a medicament.

In a first embodiment of the thirteenth aspect the medicament is for the treatment of hepatitis C.

A fourteenth aspect of the invention provides a method of treating hepatitis C comprising administering to a subject in need thereof, a therapeutically effective amount of a compound of the invention, optionally in a pharmaceutical composition. A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. The subject may be administered as many doses as is required to reduce and/or alleviate the signs, symptoms or causes of the disorder in question, or bring about any other desired alteration of a biological system. One of ordinary skill in the art of treating such diseases will be able, without undue experimentation and in reliance upon personal knowledge and the disclosure of this application, to ascertain a therapeutically effective amount of the compounds of this invention for a given disease.

Combination Therapy

The compounds of the present invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention may include, without limitation, all classes of HCV antivirals. For combination therapies, mechanistic classes of agents that may be useful when combined with the compounds of the present invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-900518), ITMN-191 (R-7227), TMC-435350 (a.k.a. TMC-435), MK-7009, MK-5172, BI-201335, BI-2061 (ciluprevir), BMS-650032, ACH-1625, ACH-1095 (HCV NS4A protease co-factor inhibitor), VX-500, VX-813, PHX-1766, PHX2054, IDX-136, IDX-316, ABT-450 EP-013420 (and congeners) and VBY-376; the Nucleosidic HCV polymerase (replicase) inhibitors useful in the invention include, but are not limited to, R7128, PSI-7851, PSI-7977, IDX-184, IDX-102, R1479, UNX-08189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nuclosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, NS5A inhibitors of the present invention may be used in combination with cyclophyllin and immunophyllin antagonists (eg, without limitation, DEBIO compounds, NM-811 as well as cyclosporine and its derivatives), kinase inhibitors, inhibitors of heat shock proteins (e.g., HSP90 and HSP70), other immunomodulatory agents that may include, without limitation, interferons (-alpha, -beta, -omega, -gamma, -lambda or synthetic) such as Intron A™, Roferon-A™, Canferon-A300™, Advaferon™, Infergen™, Humoferon™, Sumiferon MP™, Alfaferone™, IFN-β™, Feron™ and the like; polyethylene glycol derivatized (pegylated) interferon compounds, such as PEG interferon-α-2a (Pegasys™), PEG interferon-α-2b (PEGIntron™), pegylated IFN-α-con1 and the like; long acting formulations and derivatizations of interferon compounds such as the albumin-fused interferon, Albuferon™, Locteron™ and the like; interferons with various types of controlled delivery systems (e.g. ITCA-638, omega-interferon delivered by the DUROS™subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL™, REMICADE™ and HUMIRA™.

In addition, NS5A inhibitors of the present invention may be used in combination with antiprotozoans and other antivirals thought to be effective in the treatment of HCV infection, such as, without limitation, the prodrug nitazoxanide. Nitazoxanide can be used as an agent in combination the compounds disclosed in this invention as well as in combination with other agents useful in treating HCV infection such as peginterferon alfa-2a and ribavarin (see, for example, Rossignol, J F and Keeffe, E B, Future Microbiol. 3:539-545, 2008).

NS5A inhibitors of the present invention may also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. No. 5,807,876; U.S. Pat. No. 6,498,178; U.S. Pat. No. 6,344,465; U.S. Pat. No. 6,054,472; WO97/40028; WO98/40381; WO00/56331, WO 02/04425; WO 03/007945; WO 03/010141; WO 03/000254; WO 01/32153; WO 00/06529; WO 00/18231; WO 00/10573; WO 00/13708; WO 01/85172; WO 03/037893; WO 03/037894; WO 03/037895; WO 02/100851; WO 02/100846; EP 1256628; WO 99/01582; WO 00/09543; WO02/18369; WO98/17679, WO00/056331; WO 98/22496; WO 99/07734; WO 05/073216, WO 05/073195 and WO 08/021,927.

Additionally, combinations of, for example, ribavirin and interferon, may be administered as multiple combination therapy with at least one of the compounds of the present invention. The present invention is not limited to the aforementioned classes or compounds and contemplates known and new compounds and combinations of biologically active agents (see, Strader, D. B., Wright, T., Thomas, D. L. and Seeff, L. B., *AASLD Practice Guidelines*. 1-22, 2009 and Manns, M. P., Foster, G. R., Rockstroh, J. K., Zeuzem, S., Zoulim, F. and Houghton, M., *Nature Reviews Drug Discovery*. 6:991-1000, 2007, Pawlotsky, J-M., Chevaliez, S, and McHutchinson, J. G., *Gastroenterology*. 132:179-1998, 2007, Lindenbach, B. D. and Rice, C. M., *Nature* 436:933-938, 2005, Klebl, B. M., Kurtenbach, A., Salassidis, K., Daub, H. and Herget, T., *Antiviral Chemistry & Chemotherapy*. 16:69-90, 2005, Beaulieu, P. L., *Current Opinion in Investigational Drugs*. 8:614-634, 2007, Kim, S-J., Kim, J-H., Kim, Y-G., Lim, H-S, and Oh, W-J., *The Journal of Biological Chemistry*. 48:50031-50041, 2004. Okamoto, T., Nishimura, Y., Ichimura, T., Suzuki, K., Miyamura, T., Suzuki, T., Moriishi, K. and Matsuura, Y., *The EMBO Journal*. 1-11, 2006, Soriano, V., Peters, M. G. and Zeuzem, S. *Clinical Infectious Diseases*. 48:313-320, 2009, Huang, Z., Murray, M. G. and Secrist, J. A., *Antiviral Research*. 71:351-362, 2006 and Neyts, J., *Antiviral Research*. 71:363-371, 2006, each of which is incorporated by reference in their entirety herein). It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the professional judgment of the person administering or supervising the administration of the combination therapy.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

TABLE 1

Example Compounds and Assay Data

| Compound # | Structure | Inhibition of HCV genotype 1b | MS [M + H]$^+$ |
|---|---|---|---|
| 1 | 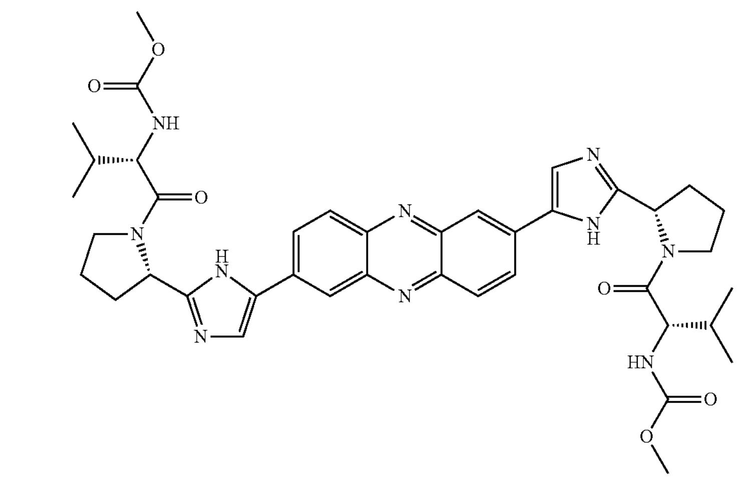 [SMILES: COC(=O)N[C@H](C(=O)N1CCC[C@H]1c1ncc(-c2ccc3nc4cc(-c5cnc([C@@H]6CCCN6C(=O)[C@@H](NC(=O)OC)C(C)C)[nH]5)ccc4nc3c2)[nH]1)C(C)C] | **** | 765.4 |
| 2 | 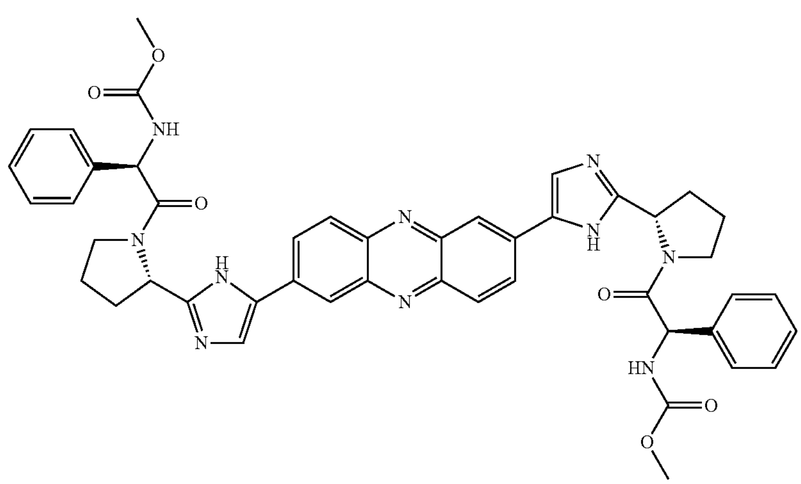 [SMILES: COC(=O)N[C@@H](C(=O)N1CCC[C@H]1c1ncc(-c2ccc3nc4cc(-c5cnc([C@@H]6CCCN6C(=O)[C@H](NC(=O)OC)c6ccccc6)[nH]5)ccc4nc3c2)[nH]1)c1ccccc1] | **** | 833.3 |

TABLE 1-continued

Example Compounds and Assay Data

| Compound # | Structure | Inhibition of HCV genotype 1b | MS [M + H]+ |
|---|---|---|---|
| 3 | 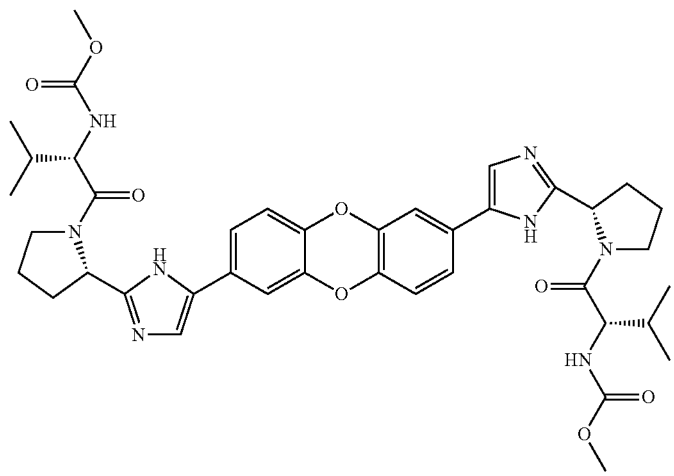 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C(C)C)[nH]4)cc2O3)[nH]1)C(C)C] | **** | 769.4 |
| 4 | 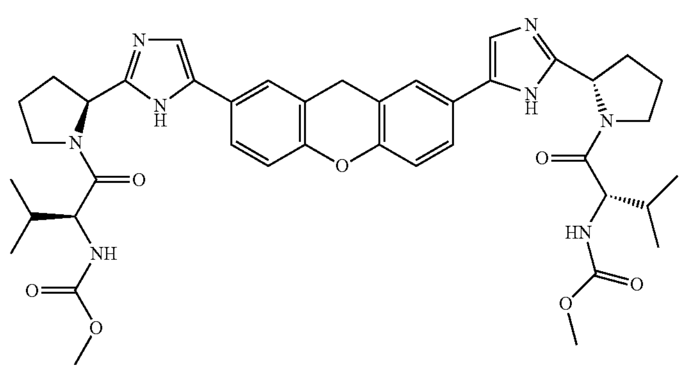 [SMILES: COC(=O)N[C@H](C(=O)N1CCC[C@H]1c1ncc(-c2ccc3c(c2)Cc2cc(-c4cnc([C@@H]5CCCN5C(=O)[C@@H](NC(=O)OC)C(C)C)[nH]4)ccc2O3)[nH]1)C(C)C] | ** | 767.4 |
| 5 | 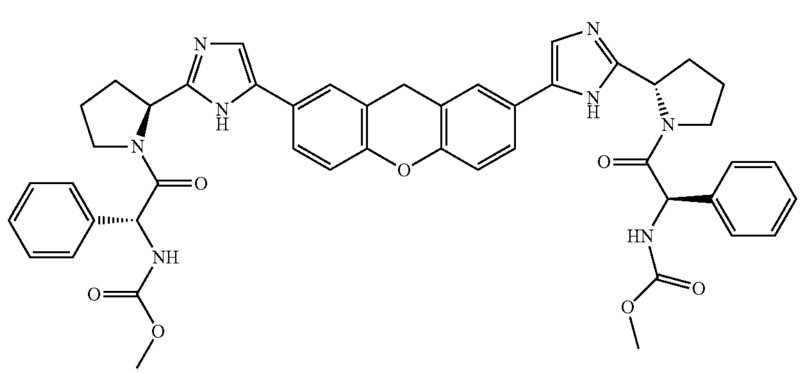 [SMILES: COC(=O)N[C@@H](C(=O)N1CCC[C@H]1c1ncc(-c2ccc3c(c2)Cc2cc(-c4cnc([C@@H]5CCCN5C(=O)[C@H](NC(=O)OC)c5ccccc5)[nH]4)ccc2O3)[nH]1)c1ccccc1] | **** | 835.3 |

TABLE 1-continued

Example Compounds and Assay Data

| Compound # | Structure | Inhibition of HCV genotype 1b | MS [M + H]+ |
|---|---|---|---|
| 6 | 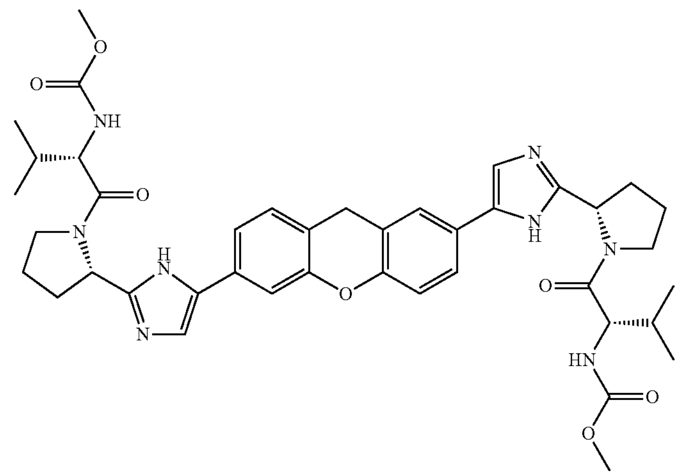 | **** | 767.4 |
| 7 | 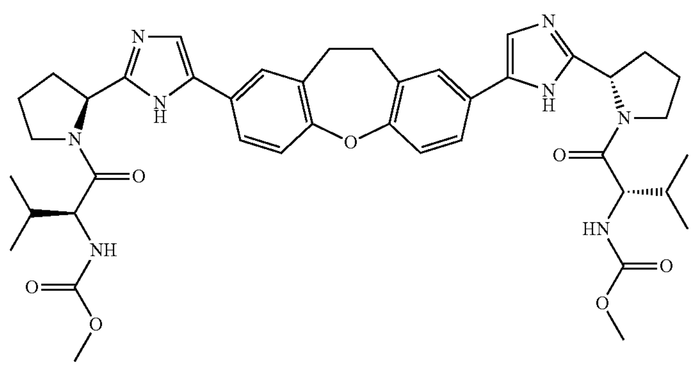 [SMILES: COC(=O)N[C@H](C(=O)N1CCC[C@H]1c1ncc(-c2ccc3c(c2)CCc2cc(-c4cnc([C@@H]5CCCN5C(=O)[C@@H](NC(=O)OC)C(C)C)[nH]4)ccc2O3)[nH]1)C(C)C] | **** | 781.4 |
| 8 | 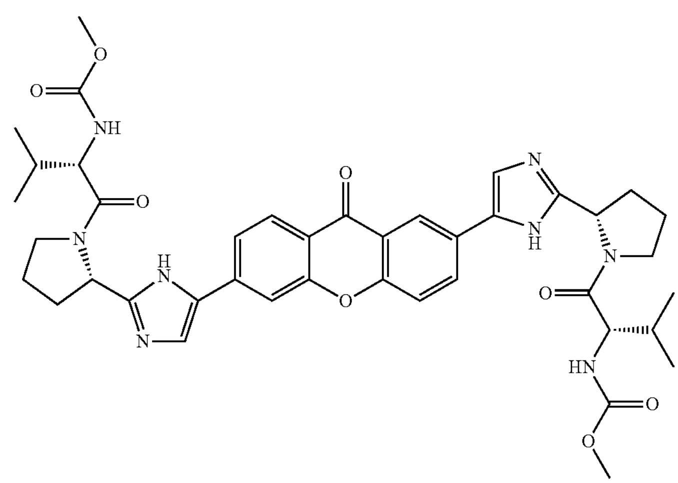 [SMILES: COC(=O)N[C@H](C(=O)N1CCC[C@H]1c1ncc(-c2ccc3c(=O)c4cc(-c5cnc([C@@H]6CCCN6C(=O)[C@@H](NC(=O)OC)C(C)C)[nH]5)ccc4oc3c2)[nH]1)C(C)C] | **** | 781.4 |
| 9 | 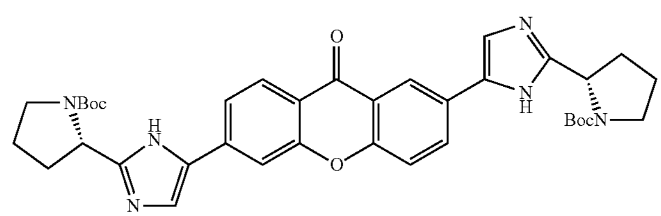 [SMILES: CC(C)(C)OC(=O)N1CCC[C@H]1c1ncc(-c2ccc3c(=O)c4cc(-c5cnc([C@@H]6CCCN6C(=O)OC(C)(C)C)[nH]5)ccc4oc3c2)[nH]1] | ** | 667.3 |

TABLE 1-continued

Example Compounds and Assay Data

| Compound # | Structure | Inhibition of HCV genotype 1b | MS [M + H]+ |
|---|---|---|---|
| 10 | 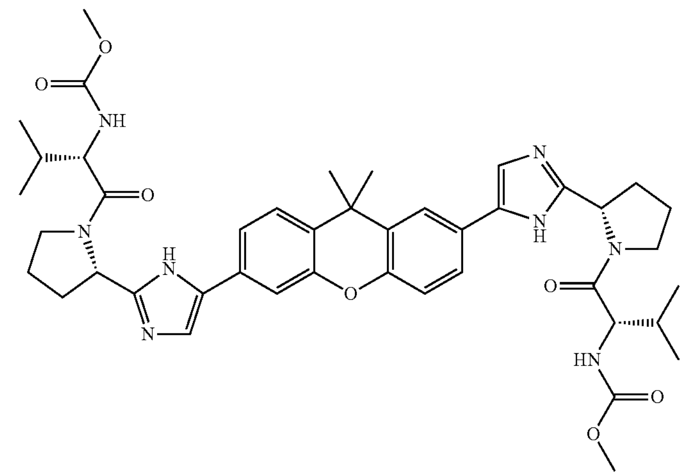 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C(C)C)[nH]4)cc2C3(C)C)[nH]1)C(C)C] | **** | 795.4 |
| 11 | 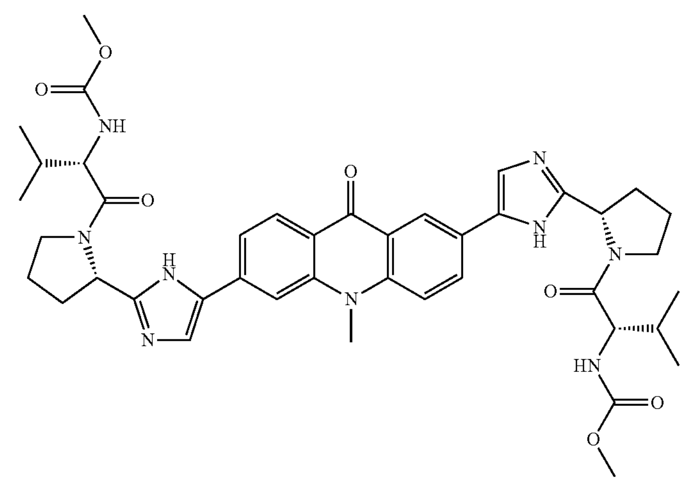 [SMILES: COC(=O)N[C@H](C(=O)N1CCC[C@H]1c1ncc(-c2ccc3c(c2)c(=O)c2ccc(-c4cnc([C@@H]5CCCN5C(=O)[C@@H](NC(=O)OC)C(C)C)[nH]4)cc2n3C)[nH]1)C(C)C] | **** | 794.4 |
| 12 | 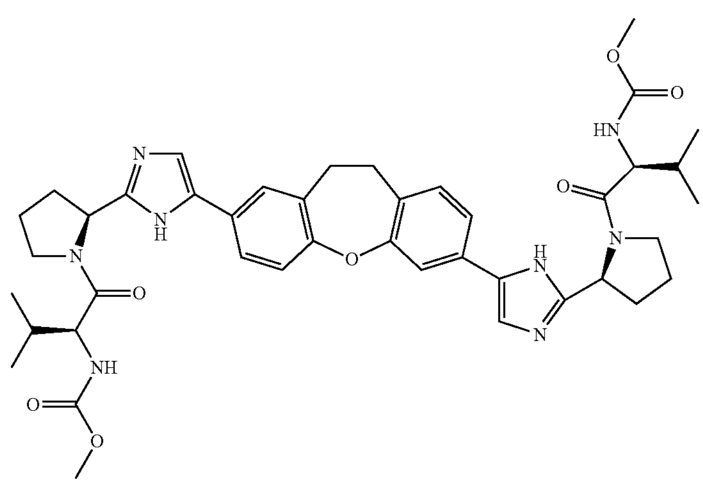 [SMILES: COC(=O)N[C@H](C(=O)N1CCC[C@H]1c1ncc(-c2ccc3c(c2)CCc2ccc(-c4cnc([C@@H]5CCCN5C(=O)[C@@H](NC(=O)OC)C(C)C)[nH]4)cc2O3)[nH]1)C(C)C] | **** | 781.4 |

TABLE 1-continued
Example Compounds and Assay Data
| Compound # | Structure | Inhibition of HCV genotype 1b | MS [M + H]+ |
|---|---|---|---|
| 13 | 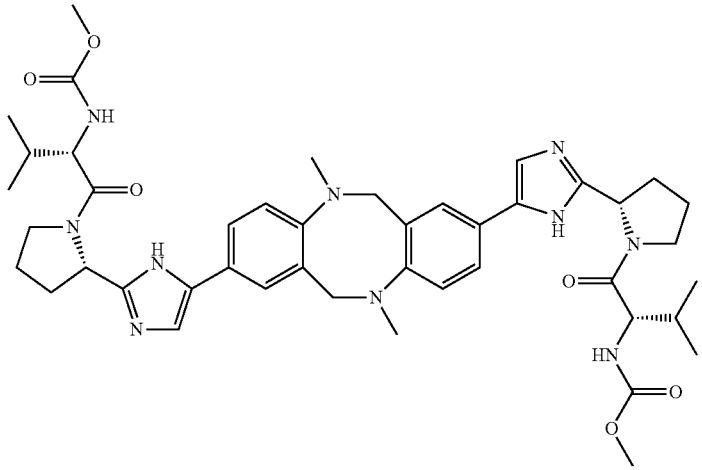 [SMILES: COC(=O)N[C@H](C(=O)N1CCC[C@H]1c1ncc(-c2ccc3c(c2)CN(C)c2ccc(-c4cnc([C@@H]5CCCN5C(=O)[C@@H](NC(=O)OC)C(C)C)[nH]4)cc2CN3C)[nH]1)C(C)C] | **** | 823.5 |
| 14 | 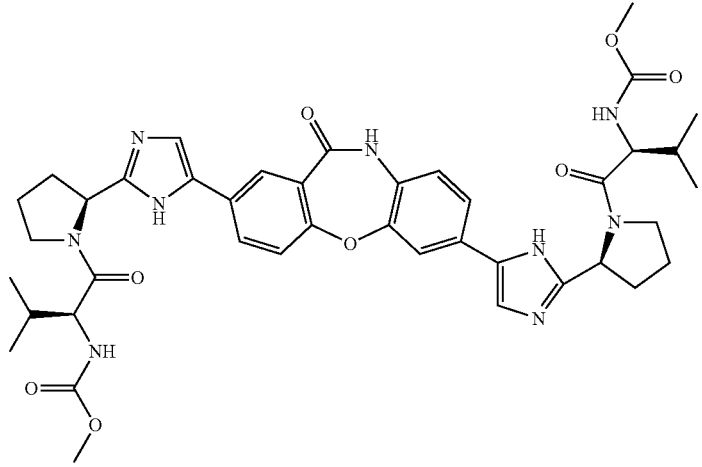 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C(C)C)[nH]4)cc2C(=O)N3)[nH]1)C(C)C] | ** | 796.4 |
| 15 | 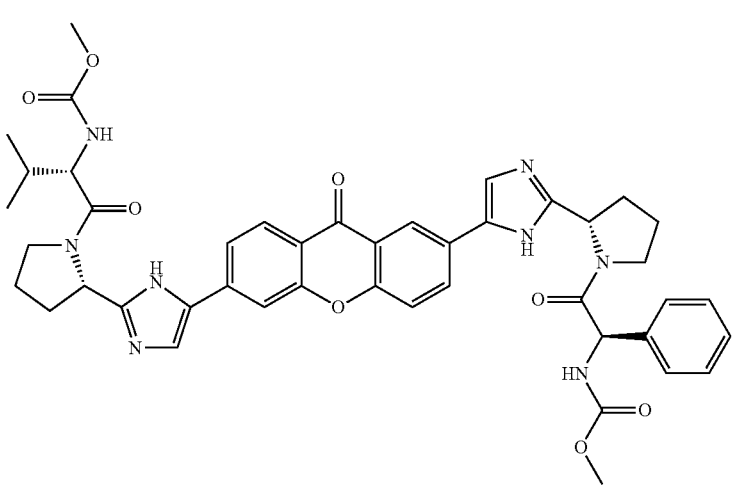 [SMILES: COC(=O)N[C@H](C(=O)N1CCC[C@H]1c1ncc(-c2ccc3c(=O)c4cc(-c5cnc([C@@H]6CCCN6C(=O)[C@H](NC(=O)OC)c6ccccc6)[nH]5)ccc4oc3c2)[nH]1)C(C)C] | **** | 815.3 |

TABLE 1-continued

Example Compounds and Assay Data

| Compound # | Structure | Inhibition of HCV genotype 1b | MS [M + H]+ |
|---|---|---|---|
| 16 | 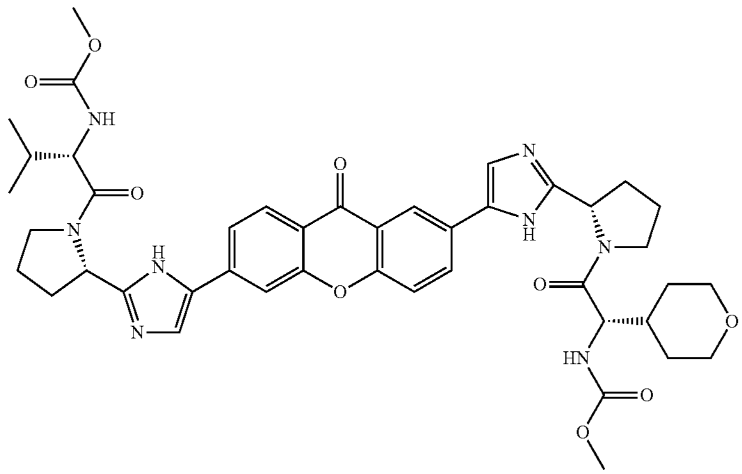 [SMILES: COC(=O)N[C@H](C(=O)N1CCC[C@H]1c1ncc(-c2ccc3c(=O)c4cc(-c5cnc([C@@H]6CCCN6C(=O)[C@@H](NC(=O)OC)C6CCOCC6)[nH]5)ccc4oc3c2)[nH]1)C(C)C] | **** | 823.4 |
| 17 | 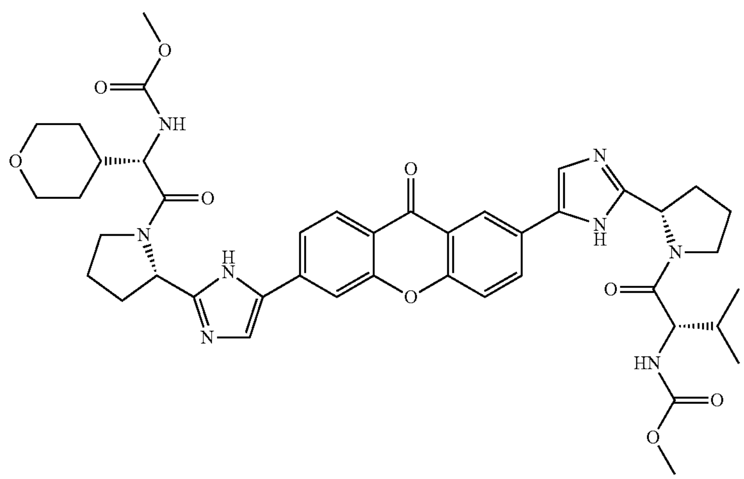 [SMILES: COC(=O)N[C@H](C(=O)N1CCC[C@H]1c1ncc(-c2ccc3oc4cc(-c5cnc([C@@H]6CCCN6C(=O)[C@@H](NC(=O)OC)C6CCOCC6)[nH]5)ccc4c(=O)c3c2)[nH]1)C(C)C] | **** | 823.4 |
| 18 | 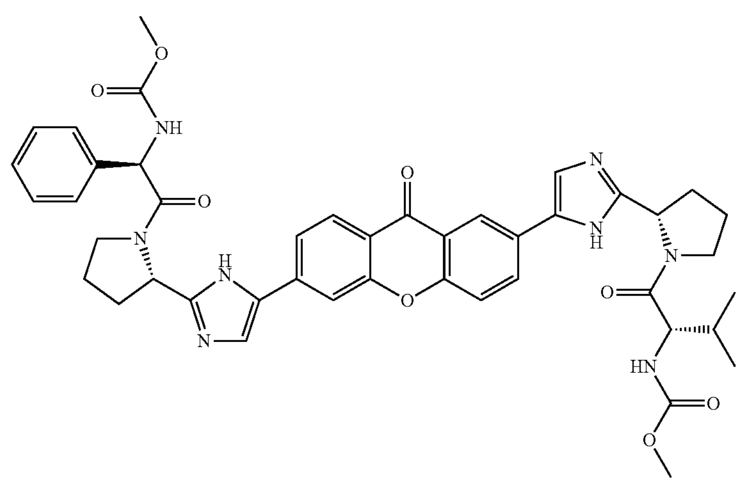 [SMILES: COC(=O)N[C@H](C(=O)N1CCC[C@H]1c1ncc(-c2ccc3oc4cc(-c5cnc([C@@H]6CCCN6C(=O)[C@H](NC(=O)OC)c6ccccc6)[nH]5)ccc4c(=O)c3c2)[nH]1)C(C)C] | **** | 815.3 |

TABLE 1-continued

Example Compounds and Assay Data

| Compound # | Structure | Inhibition of HCV genotype 1b | MS [M + H]+ |
|---|---|---|---|
| 19 | 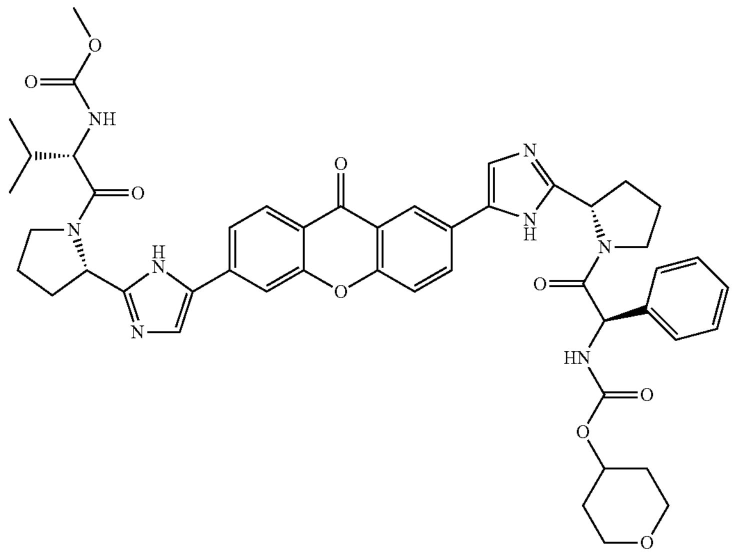 [SMILES: COC(=O)N[C@H](C(=O)N1CCC[C@H]1c1ncc(-c2ccc3c(=O)c4cc(-c5cnc([C@@H]6CCCN6C(=O)[C@H](NC(=O)OC6CCOCC6)c6ccccc6)[nH]5)ccc4oc3c2)[nH]1)C(C)C] | **** | 885.4 |
| 20 | 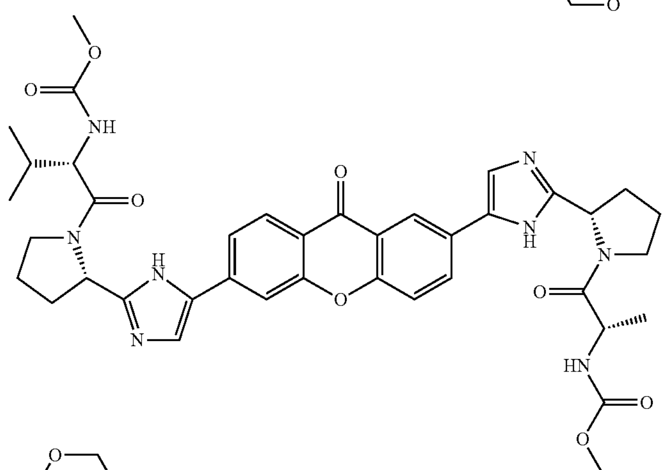 | **** | 753.3 |
| 21 | 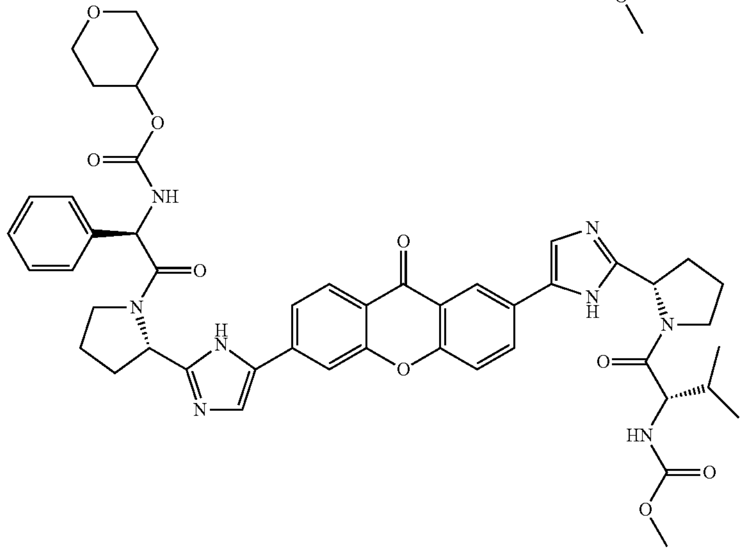 [SMILES: COC(=O)N[C@H](C(=O)N1CCC[C@H]1c1ncc(-c2ccc3oc4cc(-c5cnc([C@@H]6CCCN6C(=O)[C@H](NC(=O)OC6CCOCC6)c6ccccc6)[nH]5)ccc4c(=O)c3c2)[nH]1)C(C)C] | **** | 885.4 |

TABLE 1-continued

Example Compounds and Assay Data

| Compound # | Structure | Inhibition of HCV genotype 1b | MS [M + H]+ |
|---|---|---|---|
| 22 | 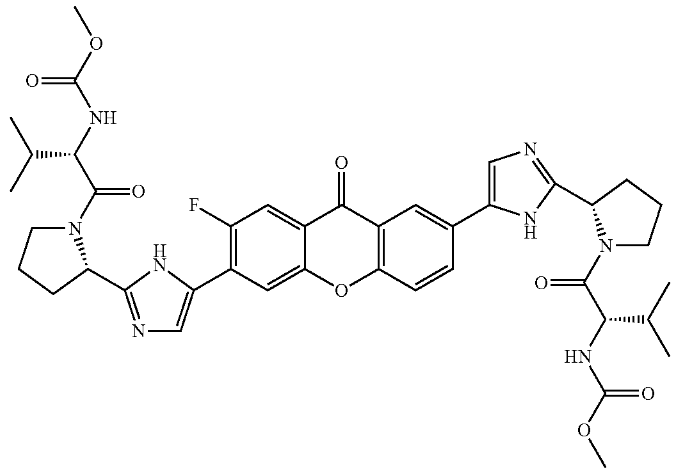 [SMILES: COC(=O)N[C@H](C(=O)N1CCC[C@H]1c1ncc(-c2ccc3oc4cc(-c5cnc([C@@H]6CCCN6C(=O)[C@@H](NC(=O)OC)C(C)C)[nH]5)c(F)cc4c(=O)c3c2)[nH]1)C(C)C] | **** | 799.4 |
| 23 | 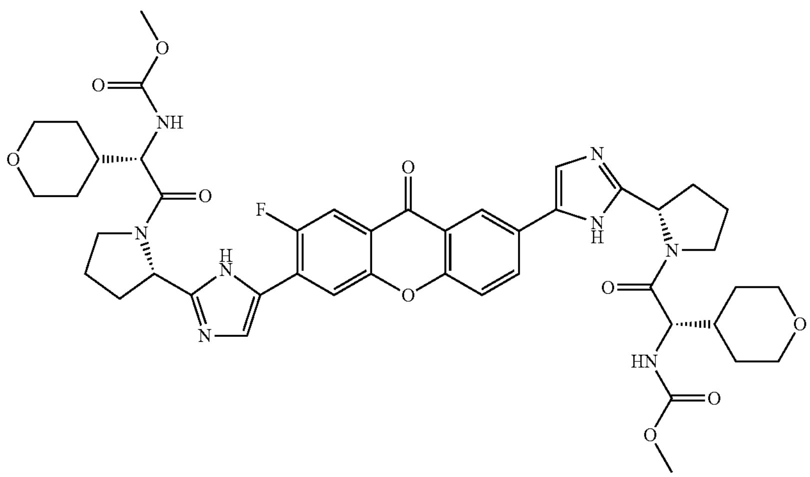 [SMILES: COC(=O)N[C@H](C(=O)N1CCC[C@H]1c1ncc(-c2ccc3oc4cc(-c5cnc([C@@H]6CCCN6C(=O)[C@@H](NC(=O)OC)C6CCOCC6)[nH]5)c(F)cc4c(=O)c3c2)[nH]1)C1CCOCC1] | **** | 883.4 |
| 24 | 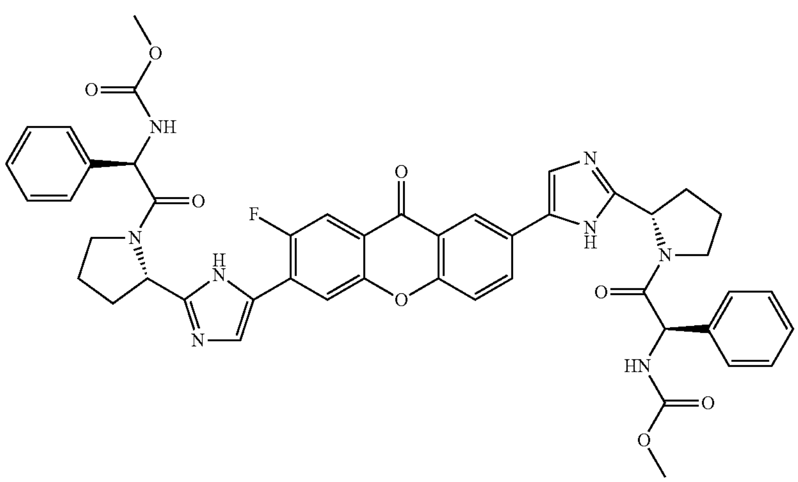 [SMILES: COC(=O)N[C@@H](C(=O)N1CCC[C@H]1c1ncc(-c2ccc3oc4cc(-c5cnc([C@@H]6CCCN6C(=O)[C@H](NC(=O)OC)c6ccccc6)[nH]5)c(F)cc4c(=O)c3c2)[nH]1)c1ccccc1] | **** | 867.3 |

TABLE 1-continued

Example Compounds and Assay Data

| Compound # | Structure | Inhibition of HCV genotype 1b | MS [M + H]+ |
|---|---|---|---|
| 25 | 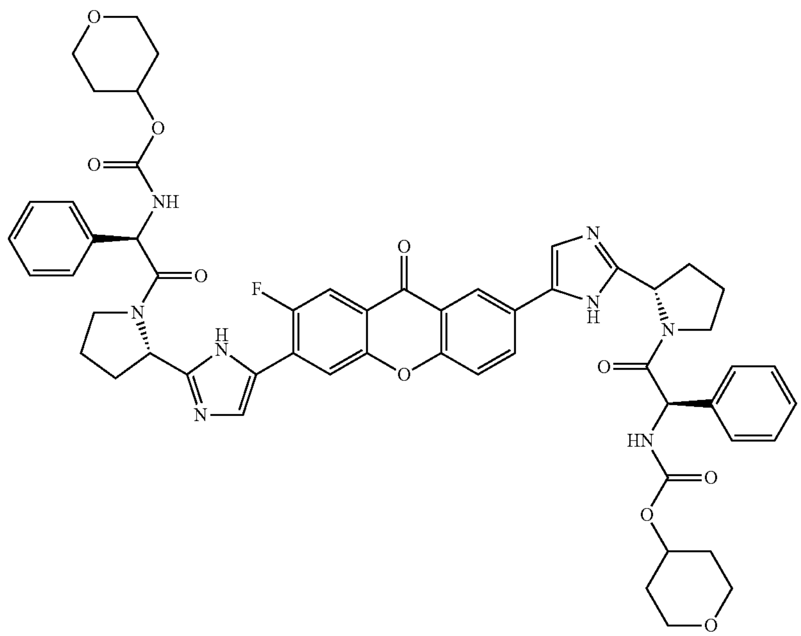 [SMILES: O=C(N[C@@H](C(=O)N1CCC[C@H]1c1ncc(-c2ccc3oc4cc(-c5cnc([C@@H]6CCCN6C(=O)[C@H](NC(=O)OC6CCOCC6)c6ccccc6)[nH]5)c(F)cc4c(=O)c3c2)[nH]1)c1ccccc1)OC1CCOCC1] | **** | 1007.4 |
| 26 | 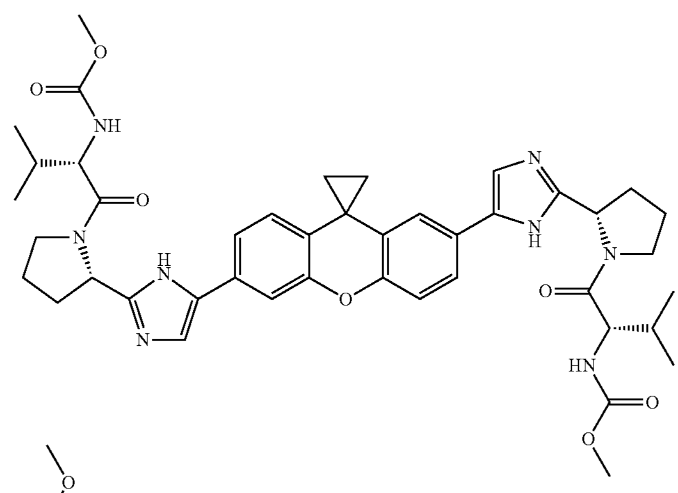 | **** | 793.4 |
| 27 | 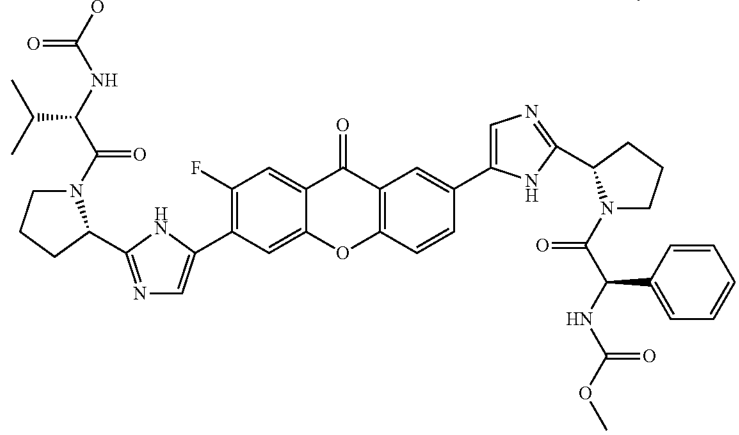 | **** | 833.3 |

TABLE 1-continued

Example Compounds and Assay Data

| Compound # | Structure | Inhibition of HCV genotype 1b | MS [M + H]+ |
|---|---|---|---|
| 28 | 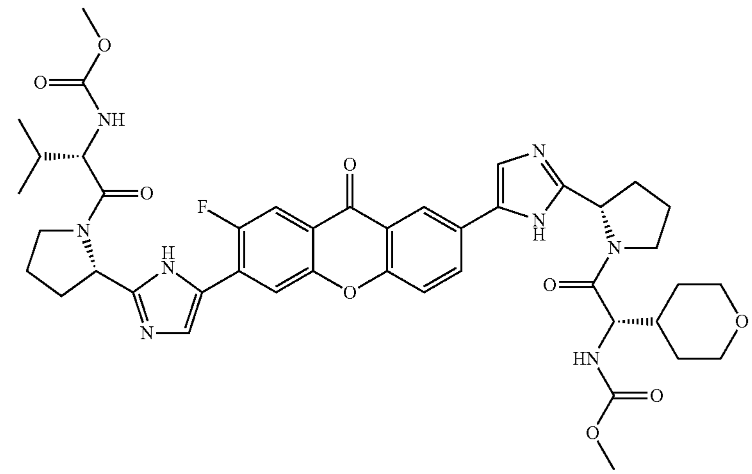 [SMILES: COC(=O)N[C@H](C(=O)N1CCC[C@H]1c1ncc(-c2cc3oc4ccc(-c5cnc([C@@H]6CCCN6C(=O)[C@@H](NC(=O)OC)C6CCOCC6)[nH]5)cc4c(=O)c3cc2F)[nH]1)C(C)C] | **** | 841.4 |
| 29 | 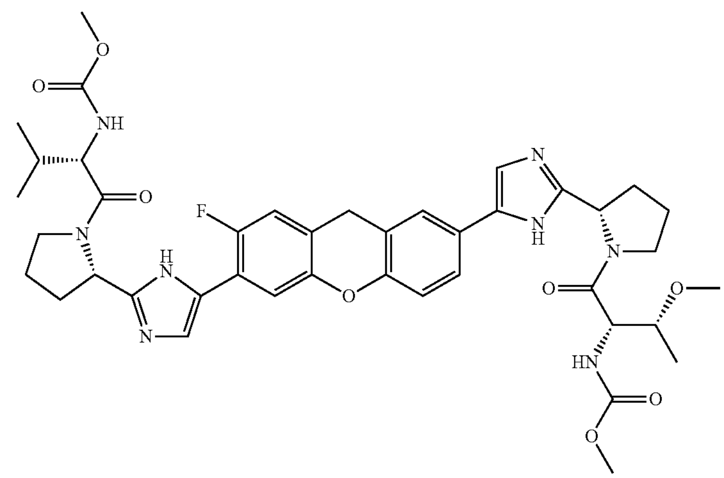 [SMILES: COC(=O)N[C@H](C(=O)N1CCC[C@H]1c1ncc(-c2cc3c(cc2F)Cc2cc(-c4cnc([C@@H]5CCCN5C(=O)[C@@H](NC(=O)OC)[C@@H](C)OC)[nH]4)ccc2O3)[nH]1)C(C)C] | **** | 801.4 |
| 30 | 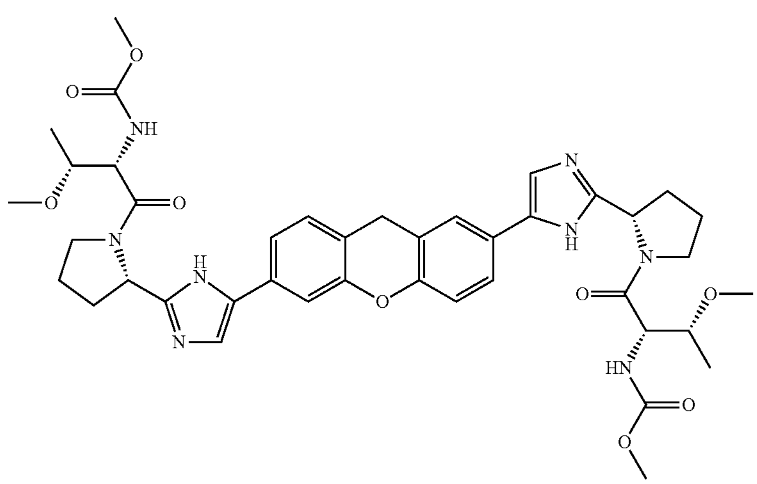 | **** | 799.4 |

TABLE 1-continued

Example Compounds and Assay Data

| Compound # | Structure | Inhibition of HCV genotype 1b | MS [M + H]+ |
|---|---|---|---|
| 31 | 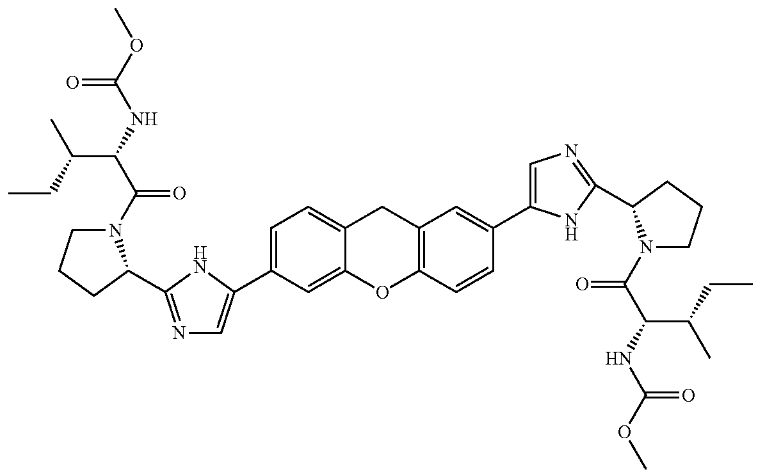 [SMILES: CC[C@H](C)[C@H](NC(=O)OC)C(=O)N1CCC[C@H]1c1ncc(-c2ccc3c(c2)Cc2ccc(-c4cnc([C@@H]5CCCN5C(=O)[C@@H](NC(=O)OC)[C@@H](C)CC)[nH]4)cc2O3)[nH]1] | **** | 795.4 |
| 32 | 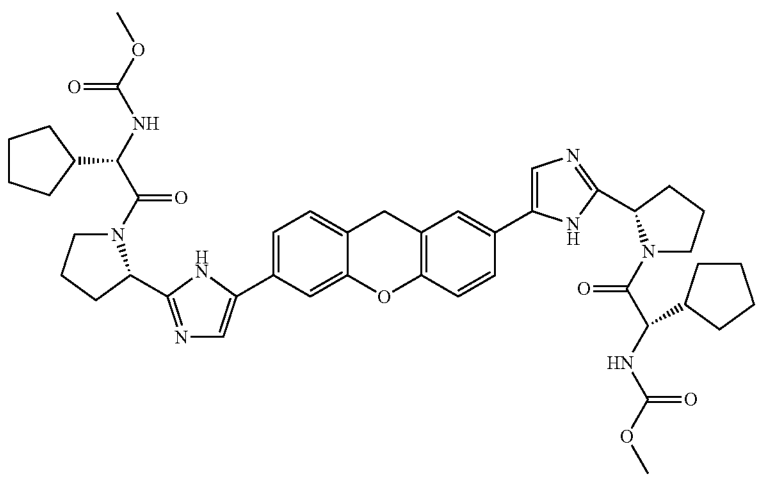 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C5CCCC5)[nH]4)cc2O3)[nH]1)C1CCCC1] | **** | 819.4 |
| 33 | 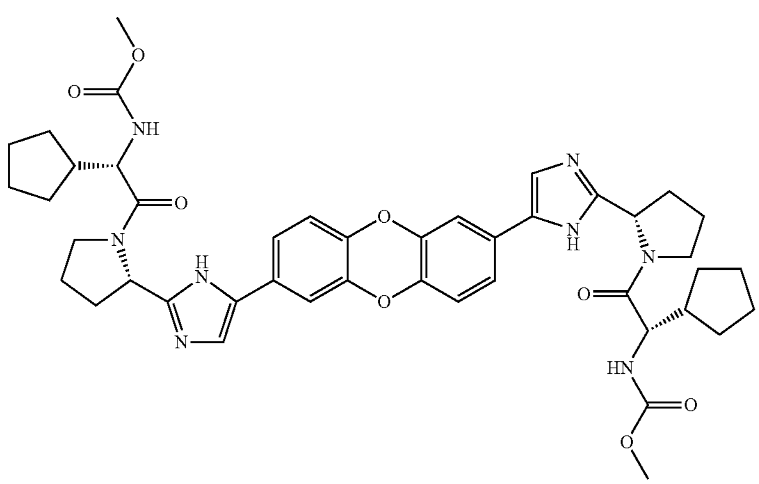 | **** | 821.4 |

TABLE 1-continued

Example Compounds and Assay Data

| Compound # | Structure | Inhibition of HCV genotype 1b | MS [M + H]+ |
|---|---|---|---|
| 34 | 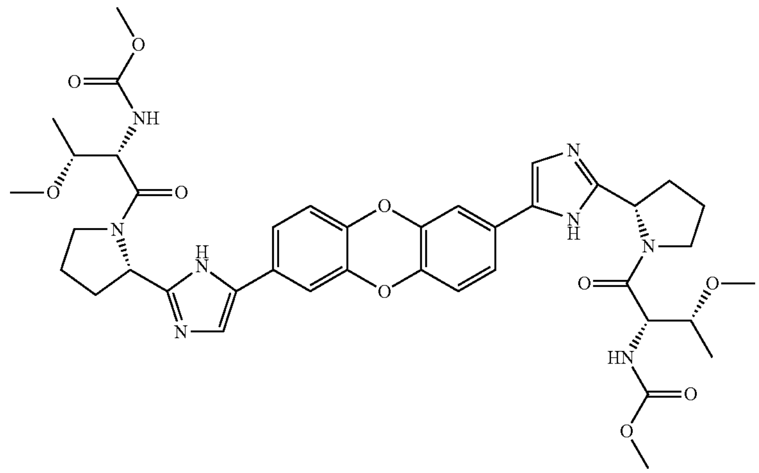 | **** | 801.3 |
| 35 | 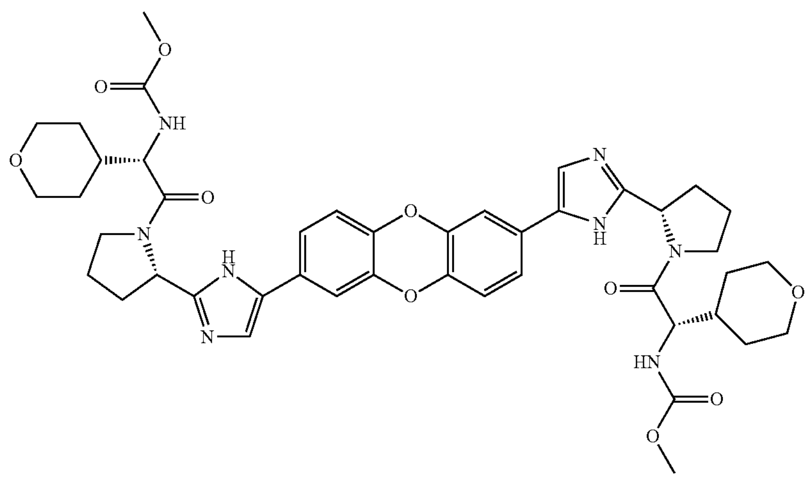 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C5CCOCC5)[nH]4)cc2O3)[nH]1)C1CCOCC1] | **** | 853.4 |
| 36 | 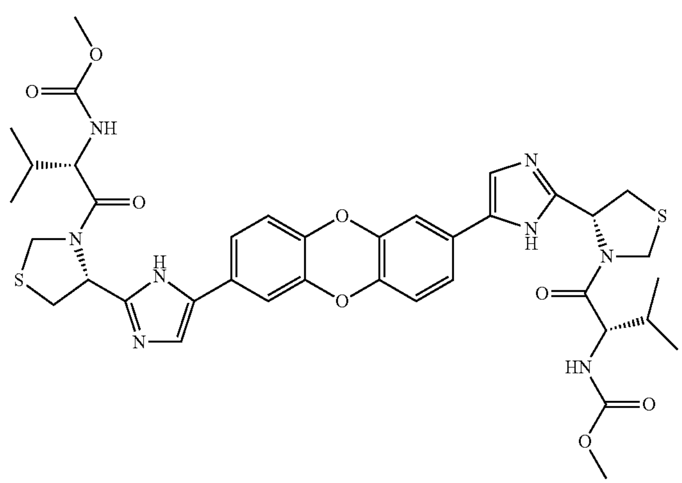 | **** | 805.3 |

TABLE 1-continued

Example Compounds and Assay Data

| Compound # | Structure | Inhibition of HCV genotype 1b | MS [M + H]+ |
|---|---|---|---|
| 37 | 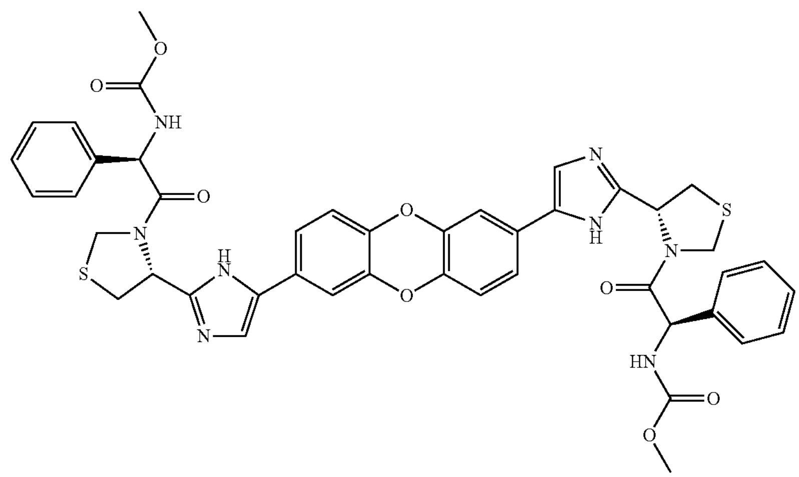 [SMILES: COC(=O)N[C@@H](C(=O)N1CSC[C@H]1c1ncc(-c2ccc3c(c2)Oc2ccc(-c4cnc([C@@H]5CSCN5C(=O)[C@H](NC(=O)OC)c5ccccc5)[nH]4)cc2O3)[nH]1)c1ccccc1] | **** | 873.2 |
| 38 | 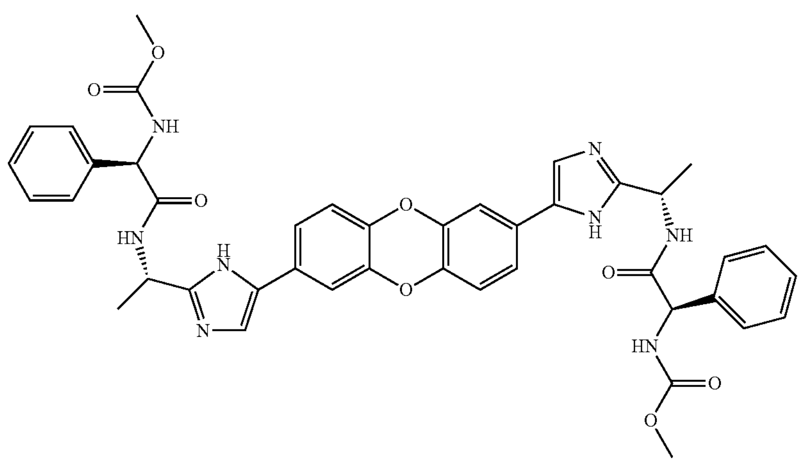 [SMILES: COC(=O)N[C@@H](C(=O)N[C@@H](C)c1ncc(-c2ccc3c(c2)Oc2ccc(-c4cnc([C@H](C)NC(=O)[C@H](NC(=O)OC)c5ccccc5)[nH]4)cc2O3)[nH]1)c1ccccc1] | **** | 785.3 |
| 39 | 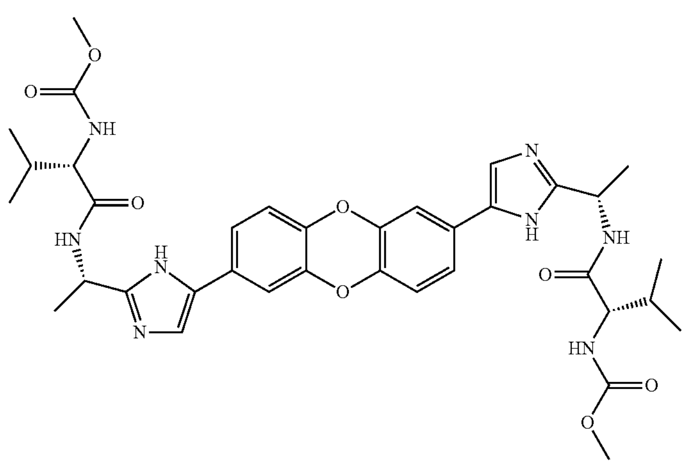 [SMILES: COC(=O)N[C@H](C(=O)N[C@@H](C)c1ncc(-c2ccc3c(c2)Oc2ccc(-c4cnc([C@H](C)NC(=O)[C@@H](NC(=O)OC)C(C)C)[nH]4)cc2O3)[nH]1)C(C)C] | **** | 717.3 |

TABLE 1-continued

Example Compounds and Assay Data

| Compound # | Structure | Inhibition of HCV genotype 1b | MS [M + H]+ |
|---|---|---|---|
| 40 | 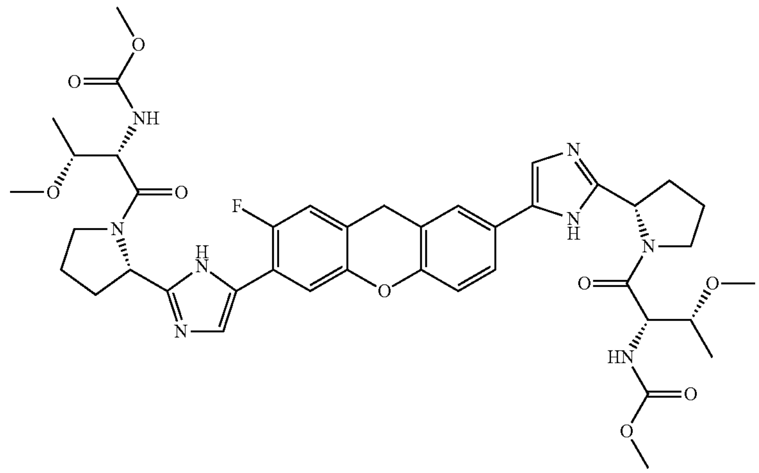 | **** | 817.4 |
| 41 | 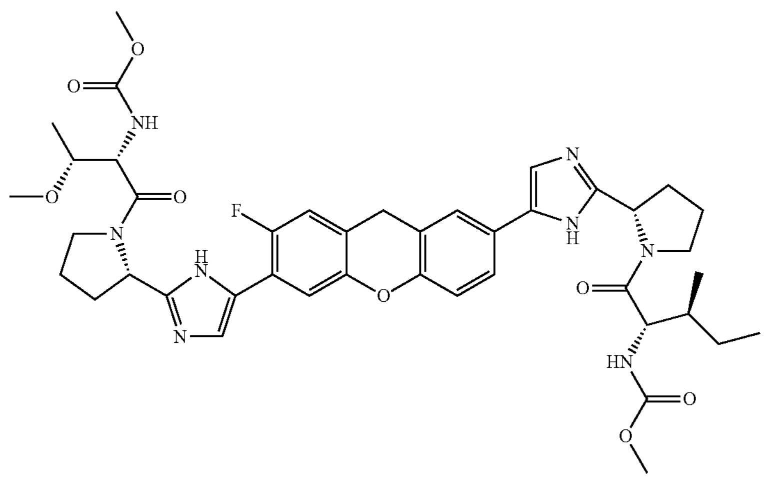 [SMILES: CC[C@H](C)[C@H](NC(=O)OC)C(=O)N1CCC[C@H]1c1ncc(-c2ccc3c(c2)Cc2cc(F)c(-c4cnc([C@@H]5CCCN5C(=O)[C@@H](NC(=O)OC)[C@@H](C)OC)[nH]4)cc2O3)[nH]1] | **** | 815.4 |
| 42 | 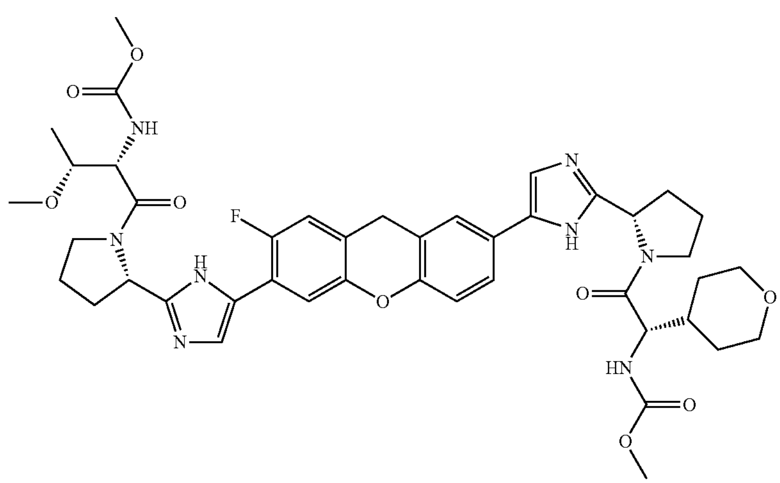 [SMILES: COC(=O)N[C@H](C(=O)N1CCC[C@H]1c1ncc(-c2ccc3c(c2)Cc2cc(F)c(-c4cnc([C@@H]5CCCN5C(=O)[C@@H](NC(=O)OC)[C@@H](C)OC)[nH]4)cc2O3)[nH]1)C1CCOCC1] | **** | 843.4 |

TABLE 1-continued

Example Compounds and Assay Data

| Compound # | Structure | Inhibition of HCV genotype 1b | MS [M + H]+ |
|---|---|---|---|
| 43 | 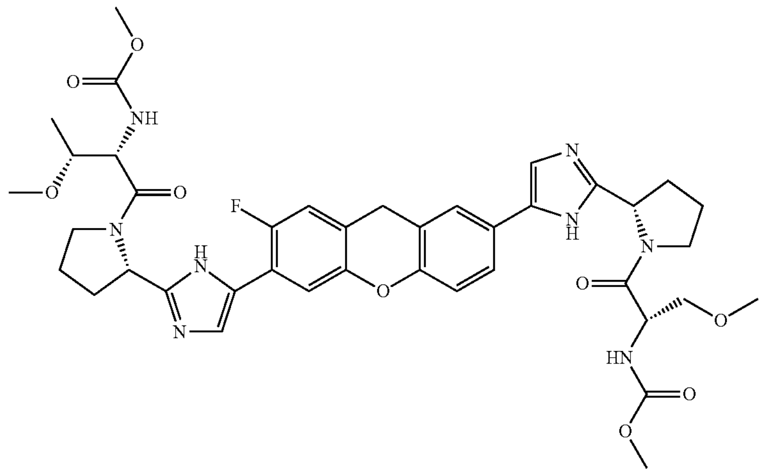 | **** | 803.3 |
| 44 | 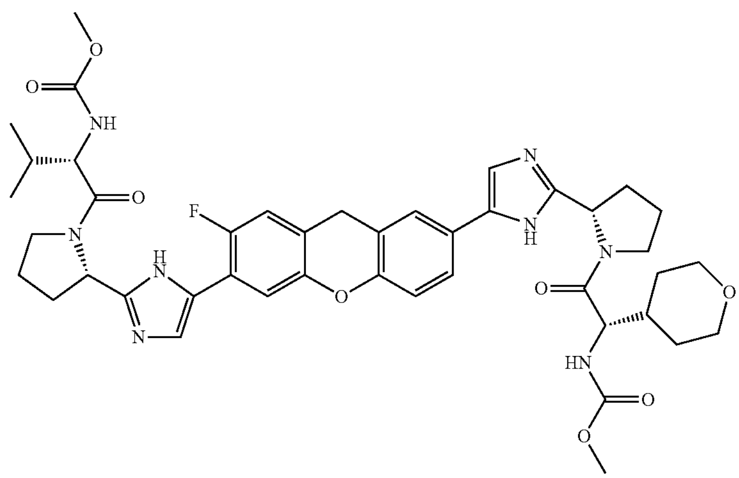 [SMILES: COC(=O)N[C@H](C(=O)N1CCC[C@H]1c1ncc(-c2cc3c(cc2F)Cc2cc(-c4cnc([C@@H]5CCCN5C(=O)[C@@H](NC(=O)OC)C5CCOCC5)[nH]4)ccc2O3)[nH]1)C(C)C] | **** | 827.4 |
| 45 | 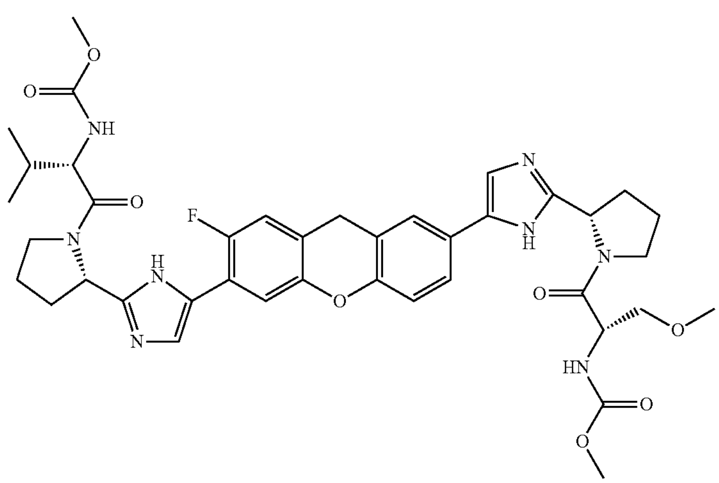 [SMILES: COC[C@H](NC(=O)OC)C(=O)N1CCC[C@H]1c1ncc(-c2ccc3c(c2)Cc2cc(F)c(-c4cnc([C@@H]5CCCN5C(=O)[C@@H](NC(=O)OC)C(C)C)[nH]4)cc2O3)[nH]1] | **** | 787.4 |

TABLE 1-continued

Example Compounds and Assay Data

| Compound # | Structure | Inhibition of HCV genotype 1b | MS [M + H]+ |
|---|---|---|---|
| 46 | 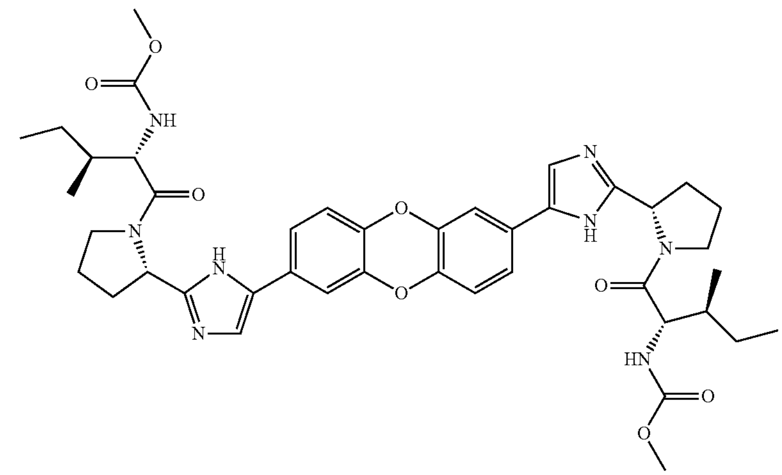 [SMILES: CC[C@H](C)[C@H](NC(=O)OC)C(=O)N1CCC[C@H]1c1ncc(-c2ccc3c(c2)Oc2ccc(-c4cnc([C@@H]5CCCN5C(=O)[C@@H](NC(=O)OC)[C@@H](C)CC)[nH]4)cc2O3)[nH]1] | **** | 797.4 |
| 47 | 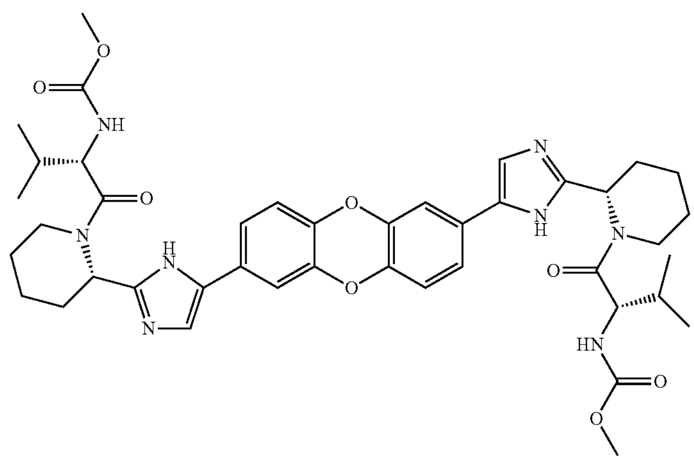 [SMILES: COC(=O)N[C@H](C(=O)N1CCCC[C@H]1c1ncc(-c2ccc3c(c2)Oc2ccc(-c4cnc([C@@H]5CCCCN5C(=O)[C@@H](NC(=O)OC)C(C)C)[nH]4)cc2O3)[nH]1)C(C)C] | **** | 797.4 |
| 48 | 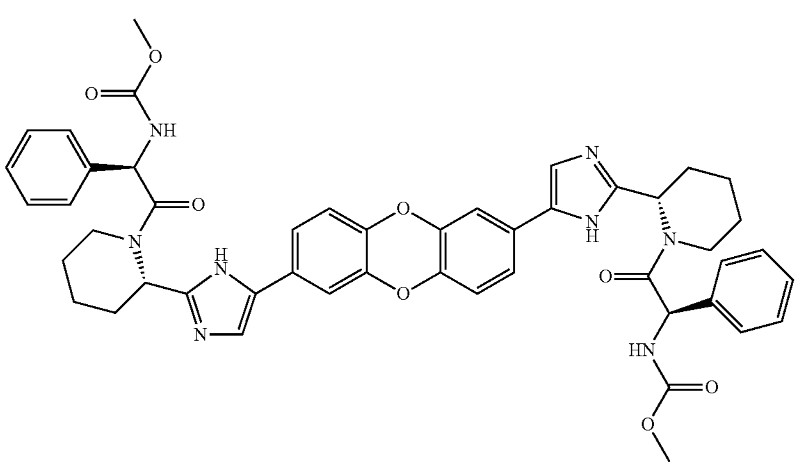 | **** | 865.4 |

TABLE 1-continued

Example Compounds and Assay Data

| Compound # | Structure | Inhibition of HCV genotype 1b | MS [M + H]+ |
|---|---|---|---|
| 49 | 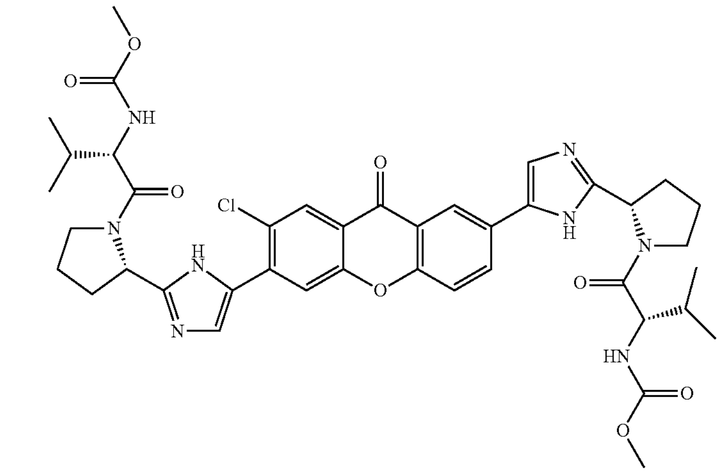 [SMILES: COC(=O)N[C@H](C(=O)N1CCC[C@H]1c1ncc(-c2ccc3oc4cc(-c5cnc([C@@H]6CCCN6C(=O)[C@@H](NC(=O)OC)C(C)C)[nH]5)c(Cl)cc4c(=O)c3c2)[nH]1)C(C)C] | **** | 815.3 |
| 50 | 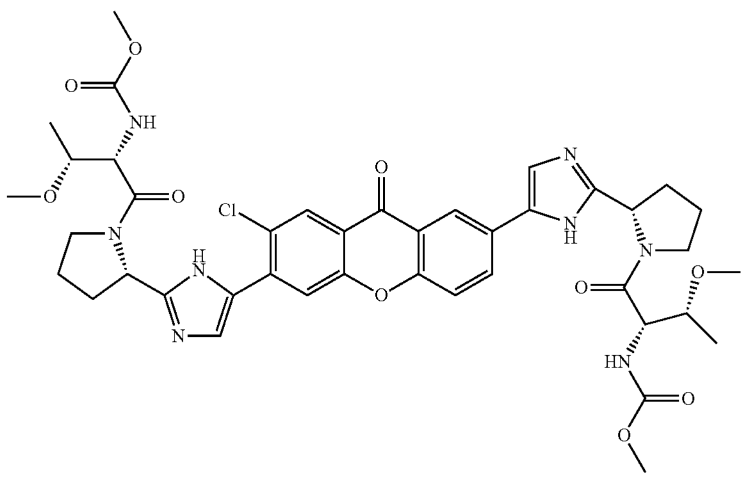 | **** | 847.3 |
| 51 | 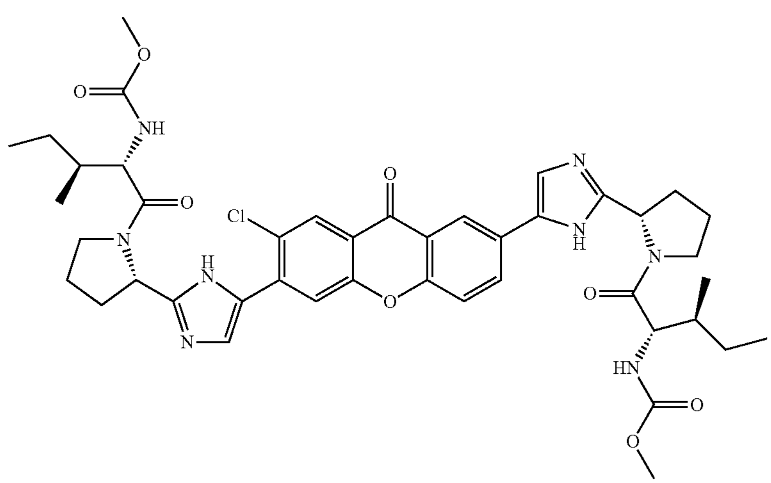 [SMILES: CC[C@H](C)[C@H](NC(=O)OC)C(=O)N1CCC[C@H]1c1ncc(-c2ccc3oc4cc(-c5cnc([C@@H]6CCCN6C(=O)[C@@H](NC(=O)OC)[C@@H](C)CC)[nH]5)c(Cl)cc4c(=O)c3c2)[nH]1] | **** | 843.4 |

TABLE 1-continued
Example Compounds and Assay Data
| Compound # | Structure | Inhibition of HCV genotype 1b | MS [M + H]+ |
|---|---|---|---|
| 52 | 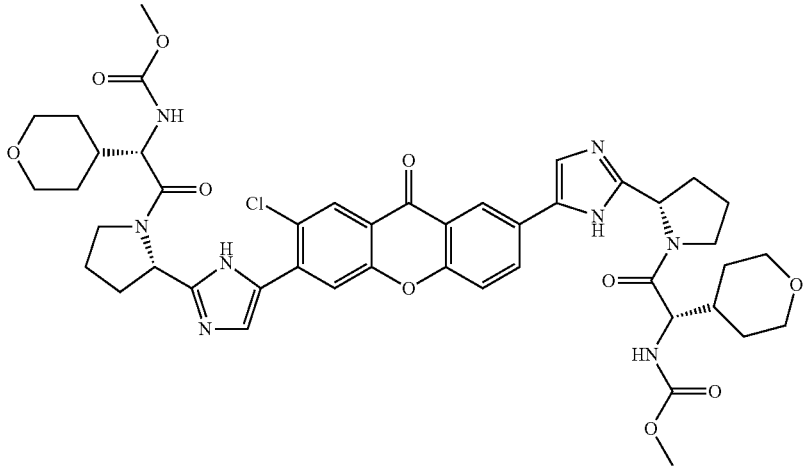 [SMILES: COC(=O)N[C@H](C(=O)N1CCC[C@H]1c1ncc(-c2ccc3oc4cc(-c5cnc([C@@H]6CCCN6C(=O)[C@@H](NC(=O)OC)C6CCOCC6)[nH]5)c(Cl)cc4c(=O)c3c2)[nH]1)C1CCOCC1] | **** | 899.3 |
| 53 | 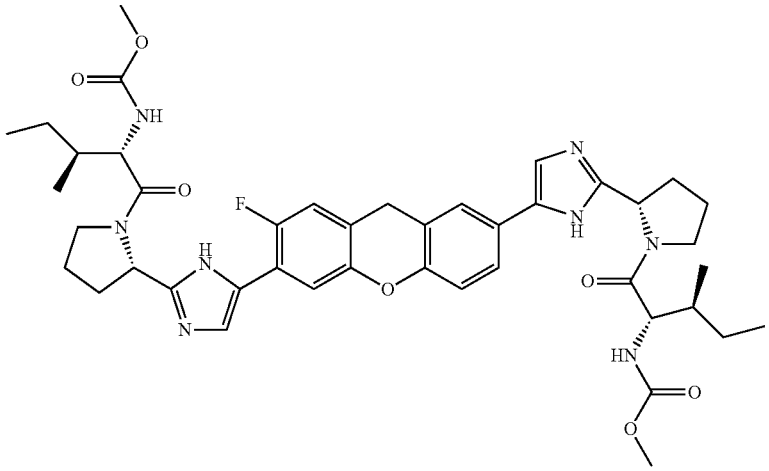 | **** | 813.4 |
| 54 | 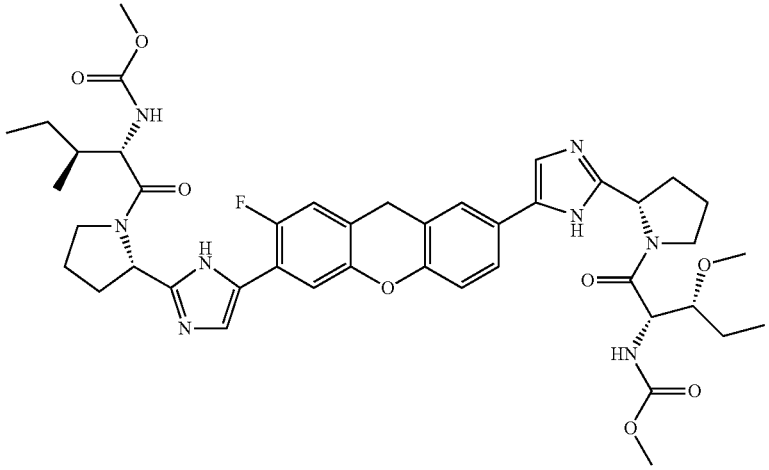 [SMILES: CC[C@H](C)[C@H](NC(=O)OC)C(=O)N1CCC[C@H]1c1ncc(-c2cc3c(cc2F)Cc2cc(-c4cnc([C@@H]5CCCN5C(=O)[C@@H](NC(=O)OC)[C@@H](CC)OC)[nH]4)ccc2O3)[nH]1] | **** | 815.4 |

TABLE 1-continued

Example Compounds and Assay Data

| Compound # | Structure | Inhibition of HCV genotype 1b | MS [M + H]+ |
|---|---|---|---|
| 55 | 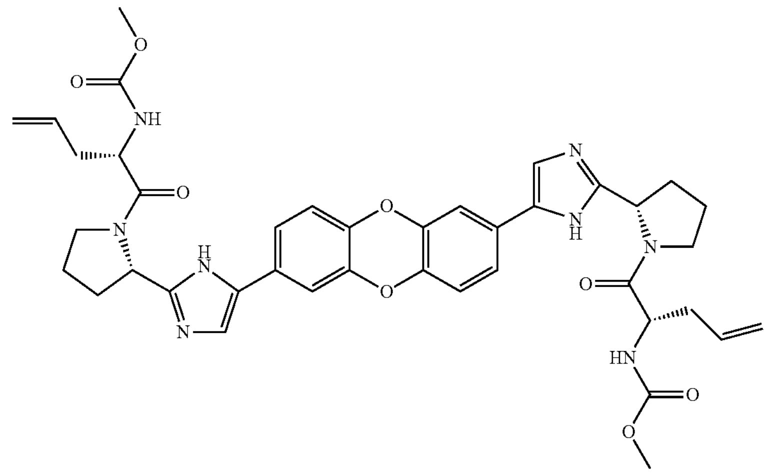 [SMILES: C=CC[C@H](NC(=O)OC)C(=O)N1CCC[C@H]1c1ncc(-c2ccc3c(c2)Oc2ccc(-c4cnc([C@@H]5CCCN5C(=O)[C@H](CC=C)NC(=O)OC)[nH]4)cc2O3)[nH]1] | **** | 765.3 |
| 56 | 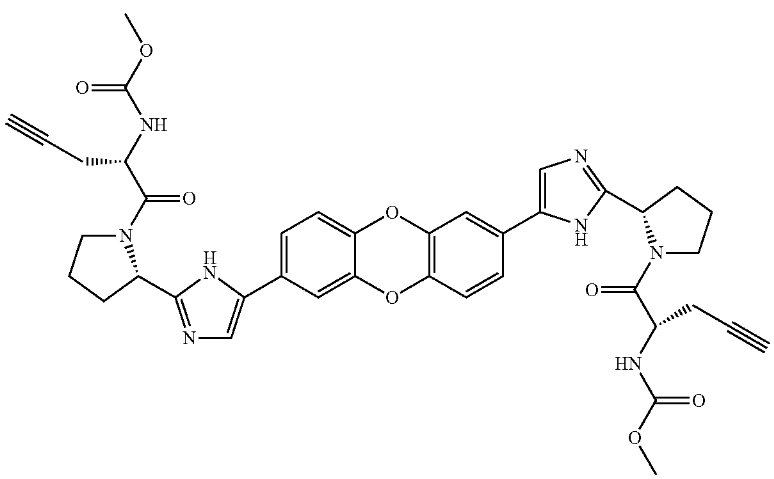 [SMILES: C#CC[C@H](NC(=O)OC)C(=O)N1CCC[C@H]1c1ncc(-c2ccc3c(c2)Oc2ccc(-c4cnc([C@@H]5CCCN5C(=O)[C@H](CC#C)NC(=O)OC)[nH]4)cc2O3)[nH]1] | **** | 761.3 |
| 57 | 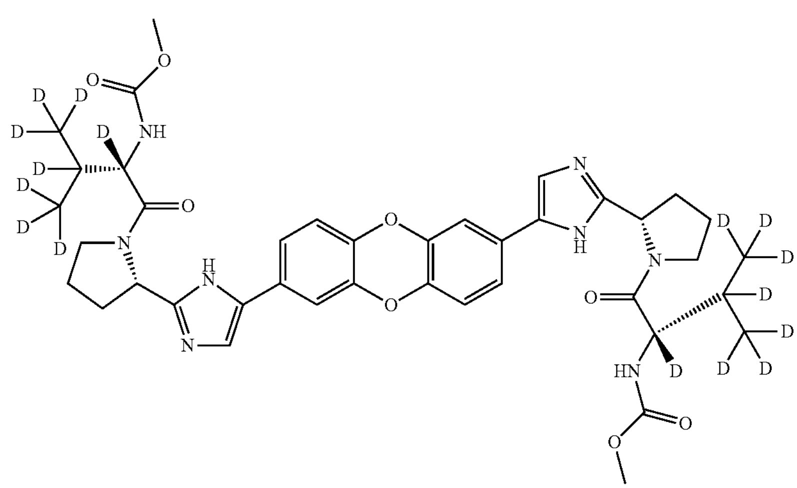 [SMILES: [2H]C([2H])([2H])C([2H])(C([2H])([2H])[2H])[C@]([2H])(NC(=O)OC)C(=O)N1CCC[C@H]1c1ncc(-c2ccc3c(c2)Oc2ccc(-c4cnc([C@@H]5CCCN5C(=O)[C@@]([2H])(NC(=O)OC)C([2H])(C([2H])([2H])[2H])C([2H])([2H])[2H])[nH]4)cc2O3)[nH]1] | **** | 785.5 |

TABLE 1-continued

Example Compounds and Assay Data

| Compound # | Structure | Inhibition of HCV genotype 1b | MS [M + H]+ |
|---|---|---|---|
| 58 | 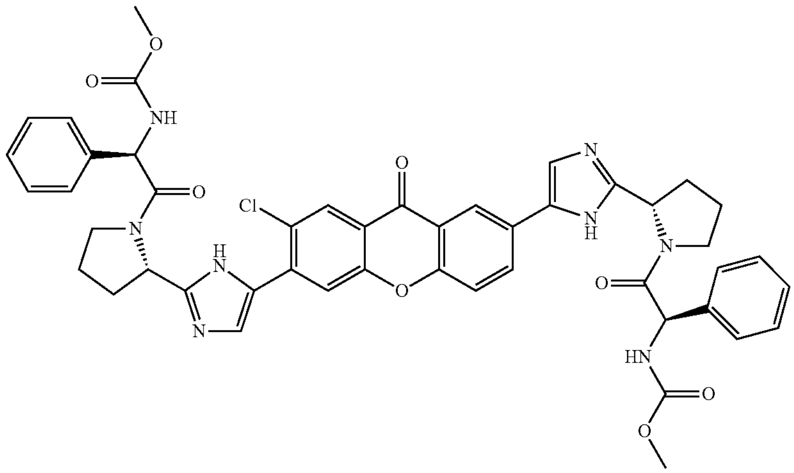 [SMILES: COC(=O)N[C@@H](C(=O)N1CCC[C@H]1c1ncc(-c2ccc3oc4cc(-c5cnc([C@@H]6CCCN6C(=O)[C@H](NC(=O)OC)c6ccccc6)[nH]5)c(Cl)cc4c(=O)c3c2)[nH]1)c1ccccc1] | **** | 883.3 |
| 59 | 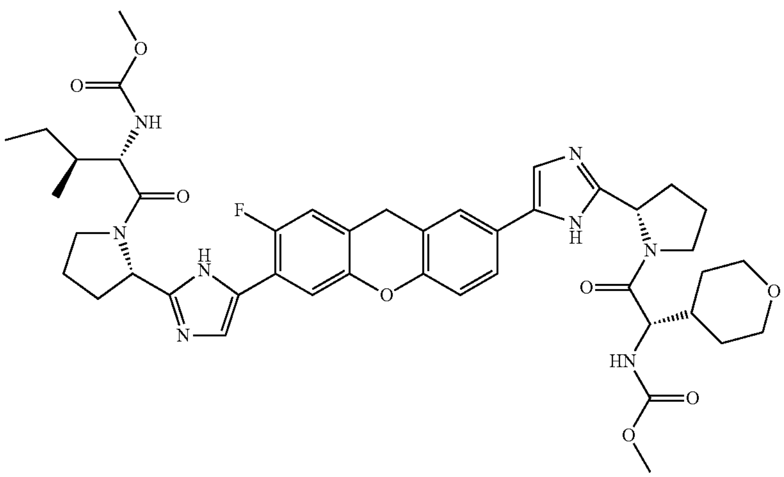 [SMILES: CC[C@H](C)[C@H](NC(=O)OC)C(=O)N1CCC[C@H]1c1ncc(-c2cc3c(cc2F)Cc2cc(-c4cnc([C@@H]5CCCN5C(=O)[C@@H](NC(=O)OC)C5CCOCC5)[nH]4)ccc2O3)[nH]1] | **** | 841.4 |
| 60 | 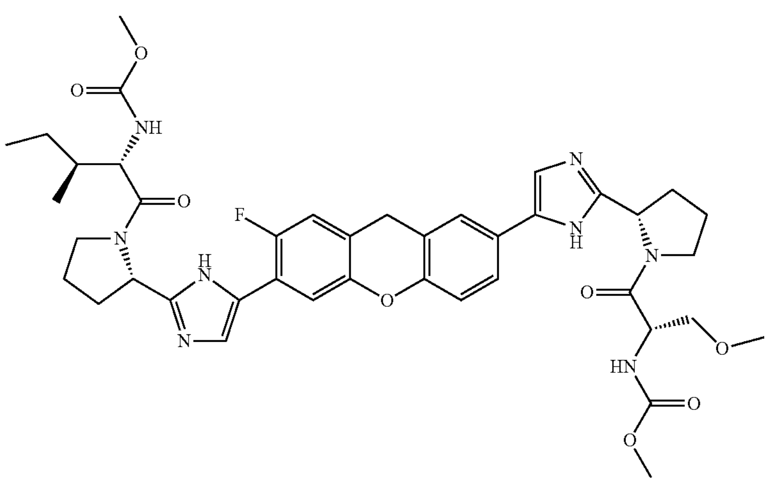 [SMILES: CC[C@H](C)[C@H](NC(=O)OC)C(=O)N1CCC[C@H]1c1ncc(-c2cc3c(cc2F)Cc2cc(-c4cnc([C@@H]5CCCN5C(=O)[C@H](COC)NC(=O)OC)[nH]4)ccc2O3)[nH]1] | **** | 801.4 |

TABLE 1-continued

Example Compounds and Assay Data

| Compound # | Structure | Inhibition of HCV genotype 1b | MS [M + H]+ |
|---|---|---|---|
| 61 | 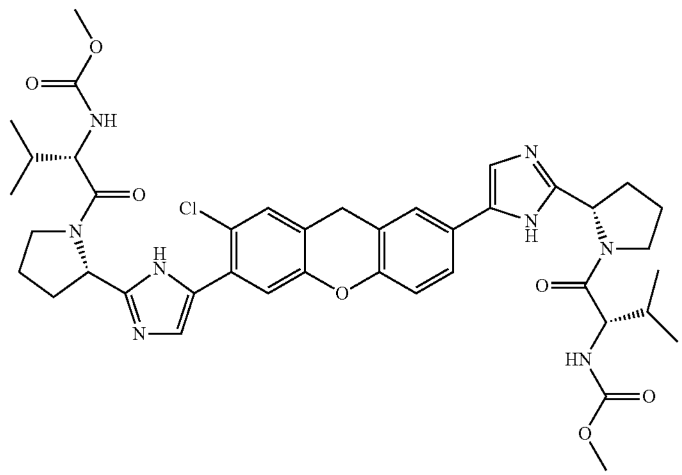 [SMILES: COC(=O)N[C@H](C(=O)N1CCC[C@H]1c1ncc(-c2ccc3c(c2)Cc2cc(Cl)c(-c4cnc([C@@H]5CCCN5C(=O)[C@@H](NC(=O)OC)C(C)C)[nH]4)cc2O3)[nH]1)C(C)C] | **** | 801.3 |
| 62 | 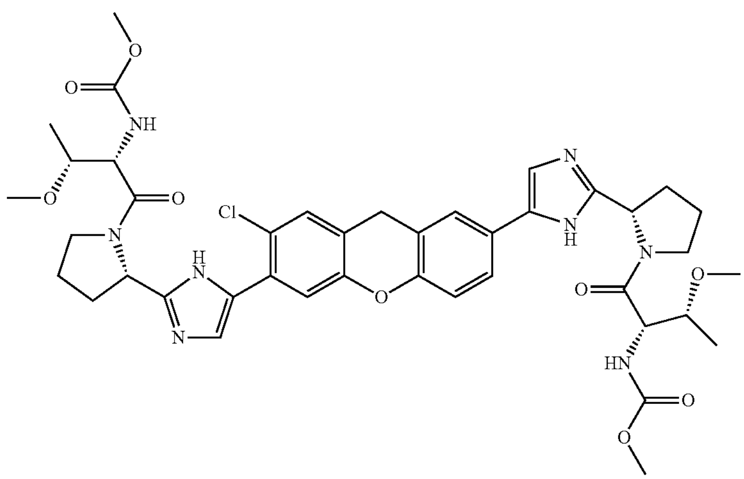 | **** | 833.3 |
| 63 | 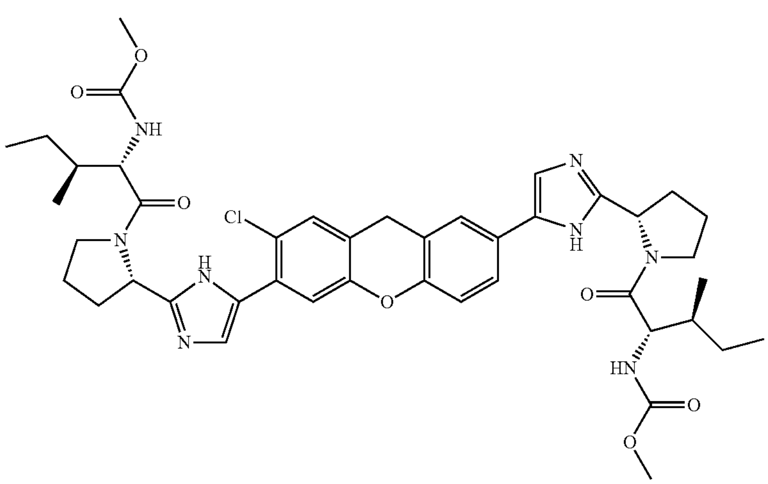 [SMILES: CC[C@H](C)[C@H](NC(=O)OC)C(=O)N1CCC[C@H]1c1ncc(-c2ccc3c(c2)Cc2cc(Cl)c(-c4cnc([C@@H]5CCCN5C(=O)[C@@H](NC(=O)OC)[C@@H](C)CC)[nH]4)cc2O3)[nH]1] | **** | 829.4 |

TABLE 1-continued

Example Compounds and Assay Data

| Compound # | Structure | Inhibition of HCV genotype 1b | MS [M + H]+ |
|---|---|---|---|
| 64 | 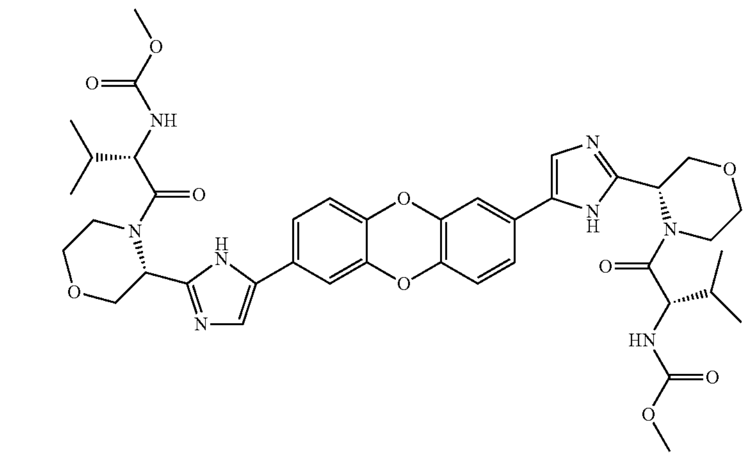 [SMILES: COC(=O)N[C@H](C(=O)N1CCOC[C@H]1c1ncc(-c2ccc3c(c2)Oc2ccc(-c4cnc([C@@H]5COCCN5C(=O)[C@@H](NC(=O)OC)C(C)C)[nH]4)cc2O3)[nH]1)C(C)C] | **** | 801.3 |
| 65 | 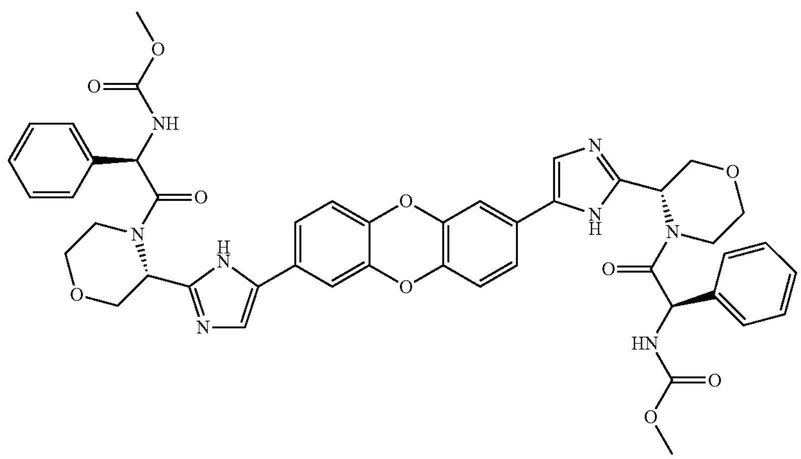 [SMILES: COC(=O)N[C@@H](C(=O)N1CCOC[C@H]1c1ncc(-c2ccc3c(c2)Oc2ccc(-c4cnc([C@@H]5COCCN5C(=O)[C@H](NC(=O)OC)c5ccccc5)[nH]4)cc2O3)[nH]1)c1ccccc1] | **** | 869.3 |
| 66 | 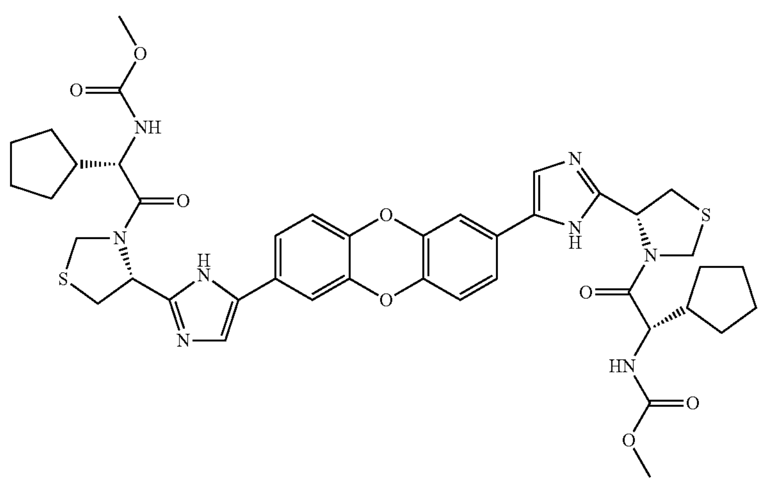 [SMILES: COC(=O)N[C@H](C(=O)N1CSC[C@H]1c1ncc(-c2ccc3c(c2)Oc2ccc(-c4cnc([C@@H]5CSCN5C(=O)[C@@H](NC(=O)OC)C5CCCC5)[nH]4)cc2O3)[nH]1)C1CCCC1] | **** | 857.3 |

TABLE 1-continued

Example Compounds and Assay Data

| Compound # | Structure | Inhibition of HCV genotype 1b | MS [M + H]+ |
|---|---|---|---|
| 67 | 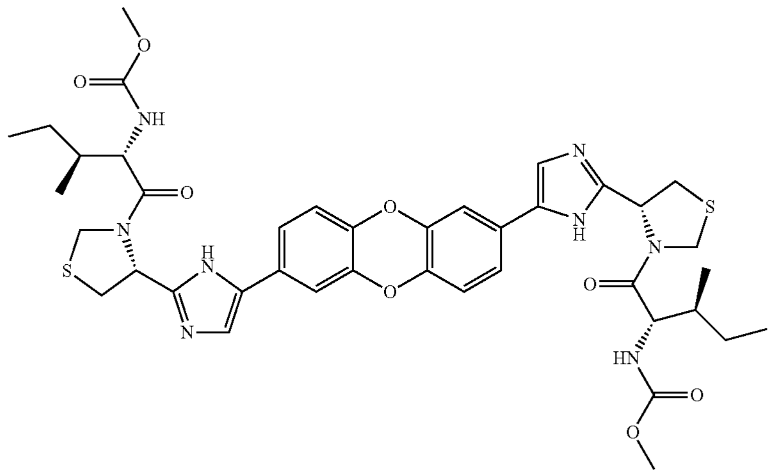 | **** | 833.3 |
| 120 | 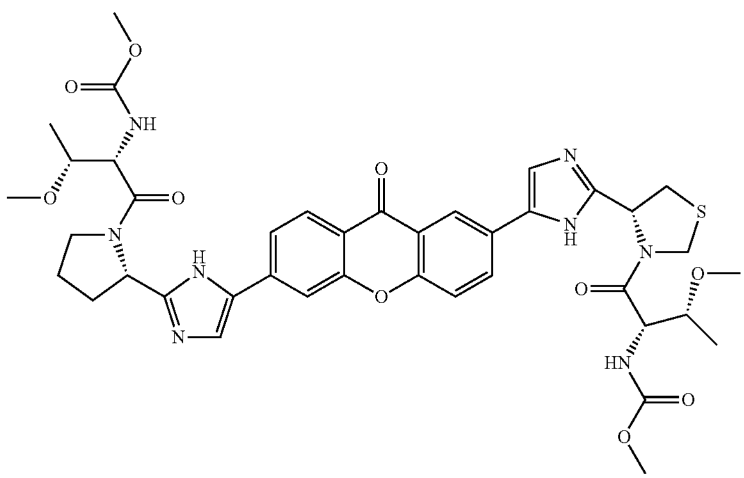 | **** | 831.3 |
| 121 | 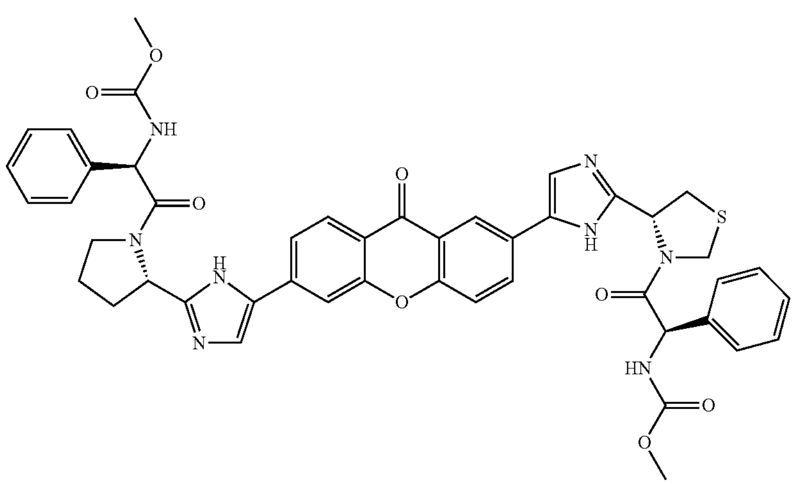 [SMILES: COC(=O)N[C@@H](C(=O)N1CCC[C@H]1c1ncc(-c2ccc3c(=O)c4cc(-c5cnc([C@@H]6CSCN6C(=O)[C@H](NC(=O)OC)c6ccccc6)[nH]5)ccc4oc3c2)[nH]1)c1ccccc1] | **** | 867.3 |

TABLE 1-continued

Example Compounds and Assay Data

| Compound # | Structure | Inhibition of HCV genotype 1b | MS [M + H]+ |
|---|---|---|---|
| 122 | 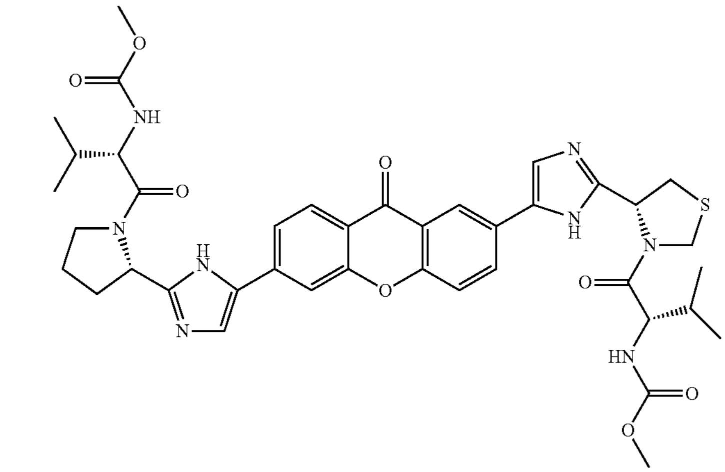 | **** | 799.3 |
| 123 | 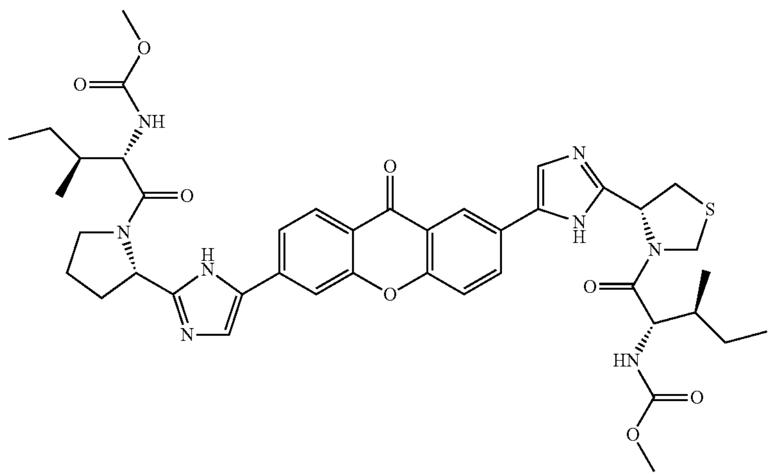 [SMILES: CC[C@H](C)[C@H](NC(=O)OC)C(=O)N1CCC[C@H]1c1ncc(-c2ccc3c(=O)c4cc(-c5cnc([C@@H]6CSCN6C(=O)[C@@H](NC(=O)OC)[C@@H](C)CC)[nH]5)ccc4oc3c2)[nH]1] | **** | 827.3 |
| 124 | 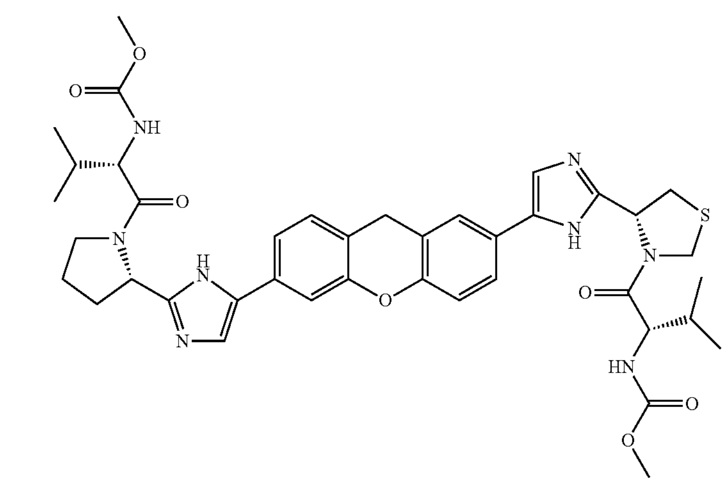 [SMILES: COC(=O)N[C@H](C(=O)N1CCC[C@H]1c1ncc(-c2ccc3c(c2)Oc2ccc(-c4cnc([C@@H]5CSCN5C(=O)[C@@H](NC(=O)OC)C(C)C)[nH]4)cc2C3)[nH]1)C(C)C] | **** | 785.3 |

TABLE 1-continued

Example Compounds and Assay Data

| Compound # | Structure | Inhibition of HCV genotype 1b | MS [M + H]+ |
|---|---|---|---|
| 125 | 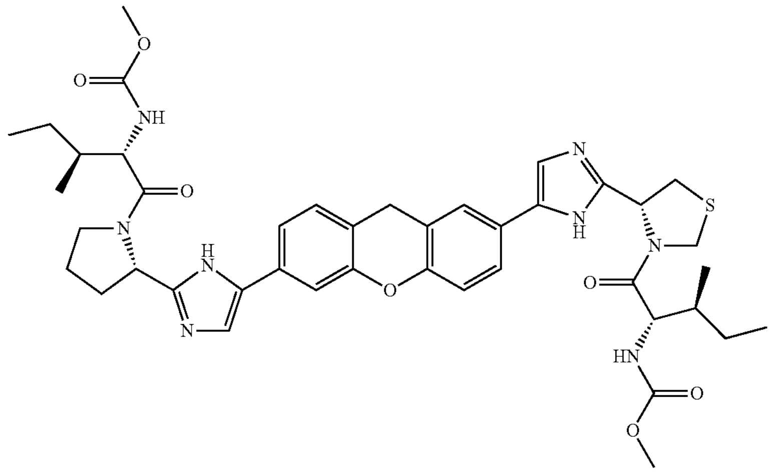 [SMILES: CC[C@H](C)[C@H](NC(=O)OC)C(=O)N1CCC[C@H]1c1ncc(-c2ccc3c(c2)Oc2ccc(-c4cnc([C@@H]5CSCN5C(=O)[C@@H](NC(=O)OC)[C@@H](C)CC)[nH]4)cc2C3)[nH]1] | **** | 813.4 |
| 126 | 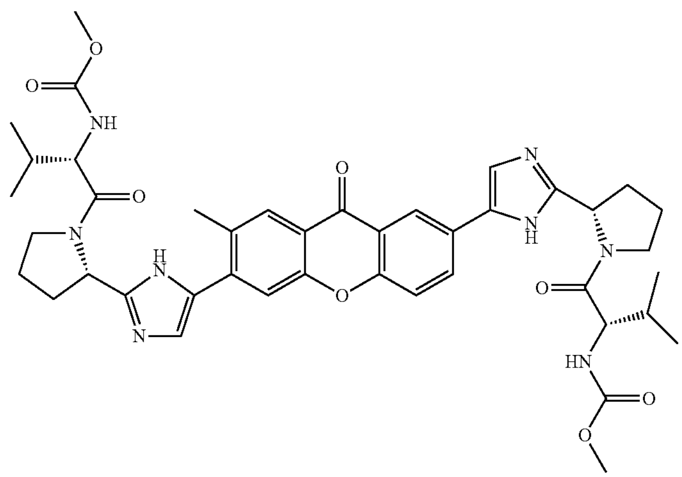 [SMILES: COC(=O)N[C@H](C(=O)N1CCC[C@H]1c1ncc(-c2ccc3oc4cc(-c5cnc([C@@H]6CCCN6C(=O)[C@@H](NC(=O)OC)C(C)C)[nH]5)c(C)cc4c(=O)c3c2)[nH]1)C(C)C] | **** | 795.4 |
| 127 | 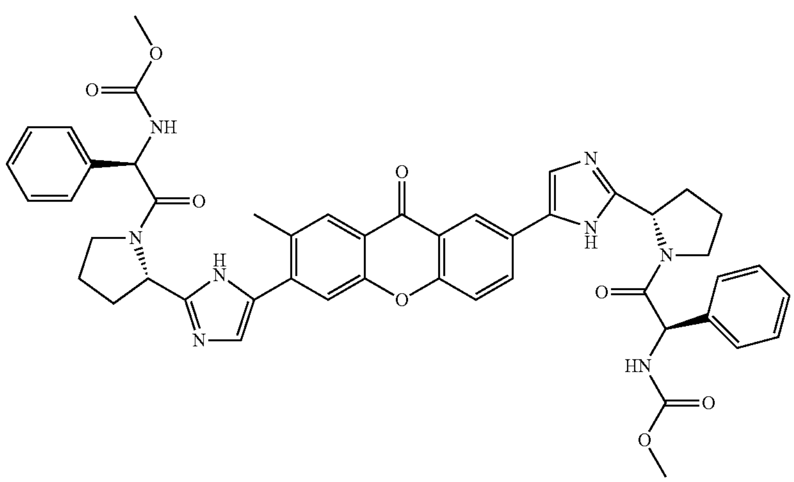 [SMILES: COC(=O)N[C@@H](C(=O)N1CCC[C@H]1c1ncc(-c2ccc3oc4cc(-c5cnc([C@@H]6CCCN6C(=O)[C@H](NC(=O)OC)c6ccccc6)[nH]5)c(C)cc4c(=O)c3c2)[nH]1)c1ccccc1] | **** | 863.3 |

TABLE 1-continued

Example Compounds and Assay Data

| Compound # | Structure | Inhibition of HCV genotype 1b | MS [M + H]+ |
|---|---|---|---|
| 128 | 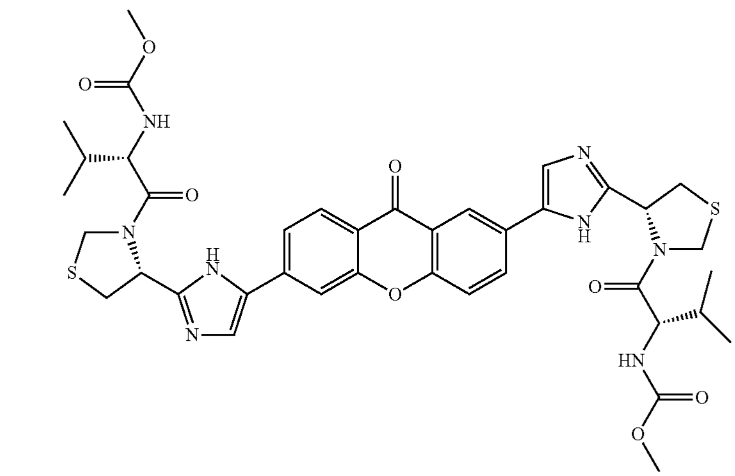 | **** | 817.3 |
| 129 | 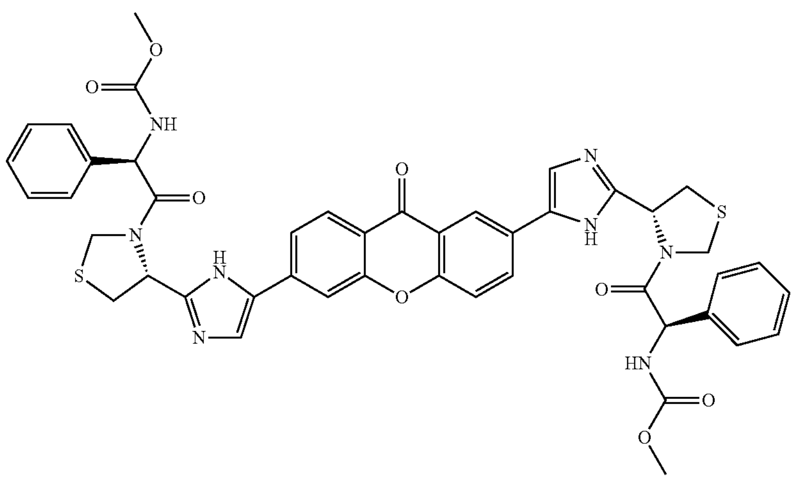 | **** | 885.2 |
| 130 | 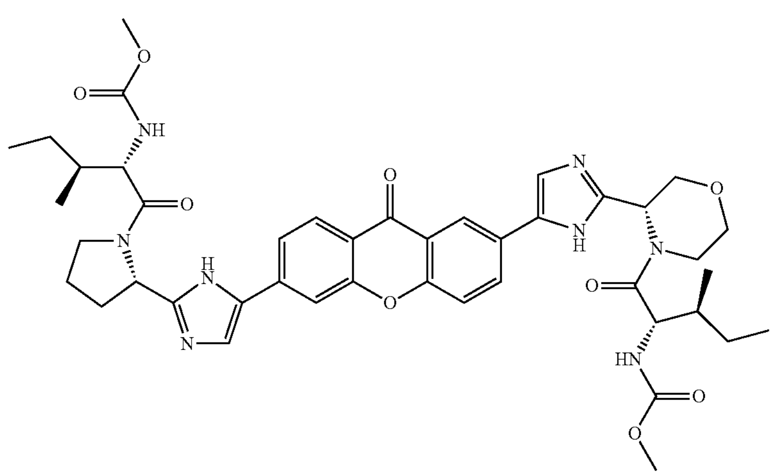 [SMILES: CC[C@H](C)[C@H](NC(=O)OC)C(=O)N1CCC[C@H]1c1ncc(-c2ccc3c(=O)c4cc(-c5cnc([C@@H]6COCCN6C(=O)[C@@H](NC(=O)OC)[C@@H](C)CC)[nH]5)ccc4oc3c2)[nH]1] | **** | 825.5 |

TABLE 1-continued

Example Compounds and Assay Data

| Compound # | Structure | Inhibition of HCV genotype 1b | MS [M + H]+ |
|---|---|---|---|
| 131 | 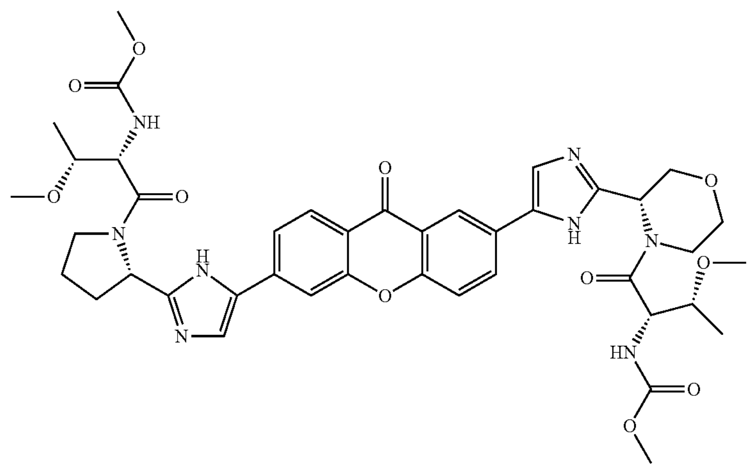 | **** | 829.3 |
| 132 | 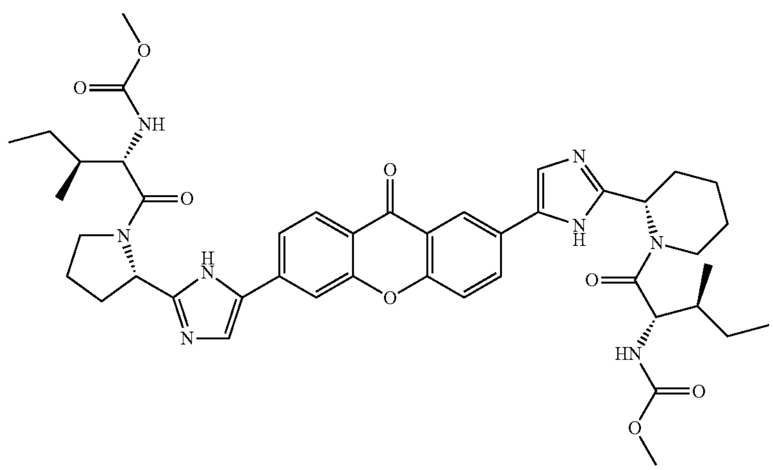 | **** | 823.4 |
| 133 | 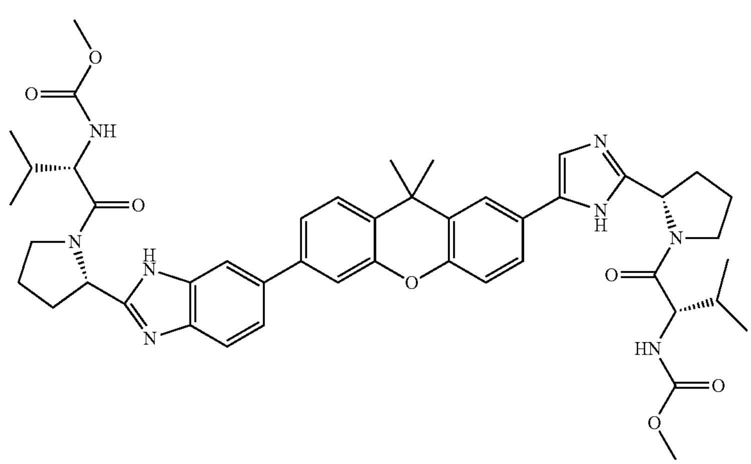 [SMILES: COC(=O)N[C@H](C(=O)N1CCC[C@H]1c1ncc(-c2ccc3c(c2)C(C)(C)c2ccc(-c4ccc5nc([C@@H]6CCCN6C(=O)[C@@H](NC(=O)OC)C(C)C)[nH]c5c4)cc2O3)[nH]1)C(C)C] | **** | 845.4 |

TABLE 1-continued

Example Compounds and Assay Data

| Compound # | Structure | Inhibition of HCV genotype 1b | MS [M + H]+ |
|---|---|---|---|
| 134 | 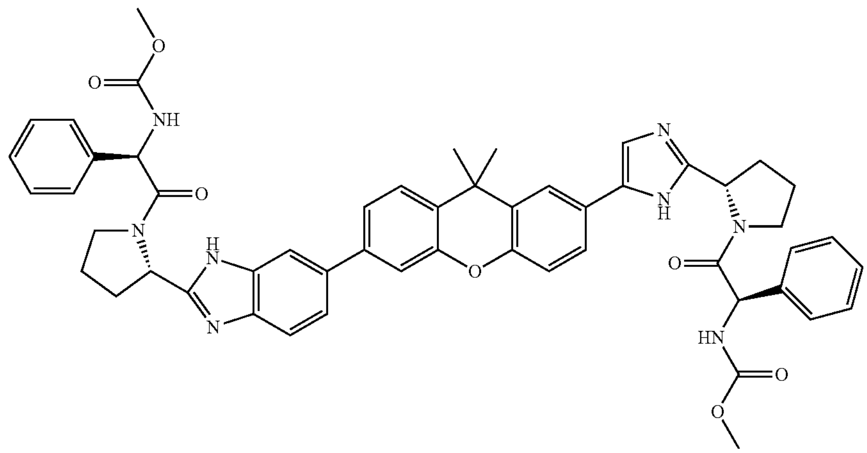 [SMILES: COC(=O)N[C@@H](C(=O)N1CCC[C@H]1c1ncc(-c2ccc3c(c2)C(C)(C)c2ccc(-c4ccc5nc([C@@H]6CCCN6C(=O)[C@H](NC(=O)OC)c6ccccc6)[nH]c5c4)cc2O3)[nH]1)c1ccccc1] | **** | 913.4 |
| 71 | 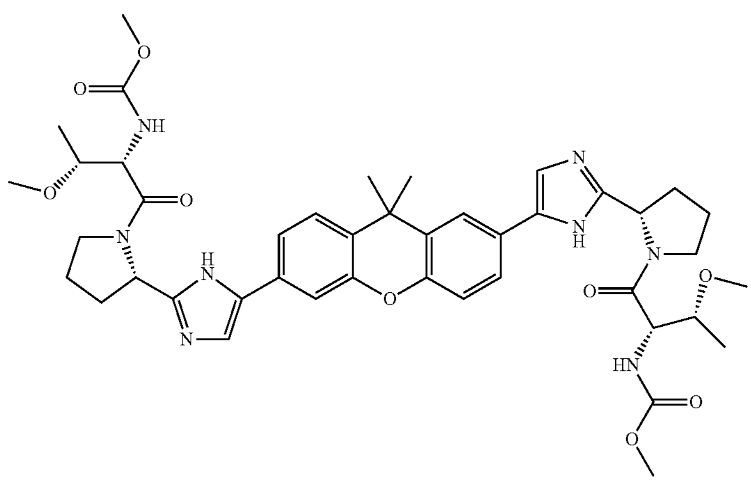 | **** | 827.4 |
| 75 | 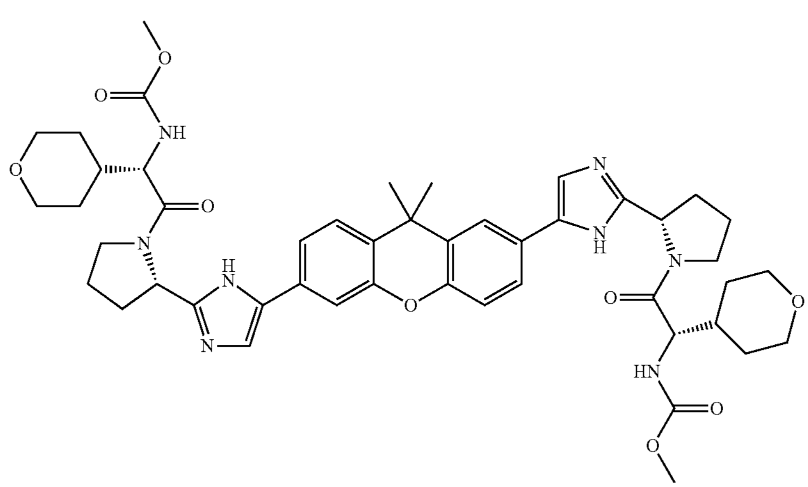 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C5CCOCC5)[nH]4)cc2C3(C)C)[nH]1)C1CCOCC1] | **** | 879.4 |

TABLE 1-continued

Example Compounds and Assay Data

| Compound # | Structure | Inhibition of HCV genotype 1b | MS [M + H]+ |
|---|---|---|---|
| 135 | 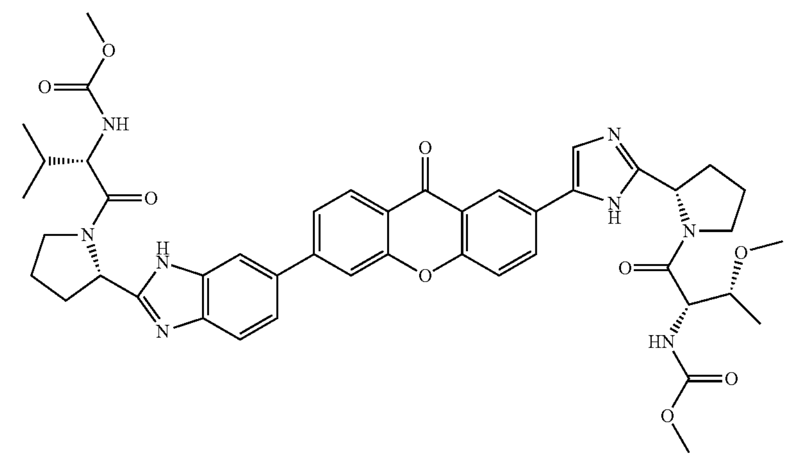 [SMILES: COC(=O)N[C@H](C(=O)N1CCC[C@H]1c1nc2ccc(-c3ccc4c(=O)c5cc(-c6cnc([C@@H]7CCCN7C(=O)[C@@H](NC(=O)OC)[C@@H](C)OC)[nH]6)ccc5oc4c3)cc2[nH]1)C(C)C] | **** | 847.4 |
| 136 | 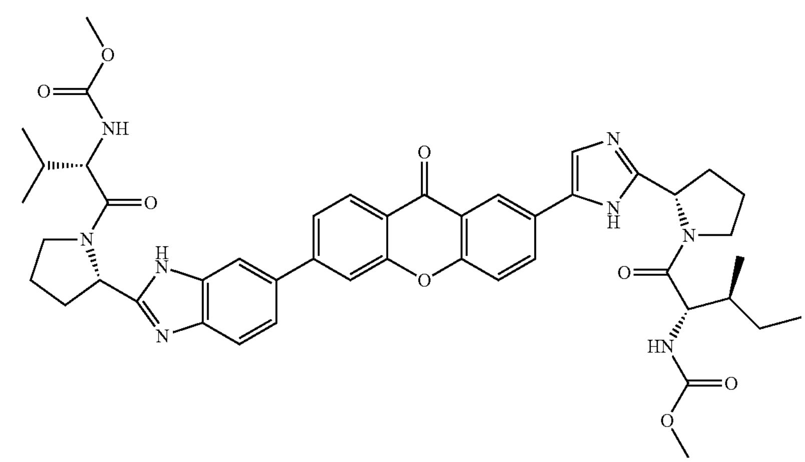 [SMILES: CC[C@H](C)[C@H](NC(=O)OC)C(=O)N1CCC[C@H]1c1ncc(-c2ccc3oc4cc(-c5ccc6nc([C@@H]7CCCN7C(=O)[C@@H](NC(=O)OC)C(C)C)[nH]c6c5)ccc4c(=O)c3c2)[nH]1] | **** | 845.4 |
| 137 | 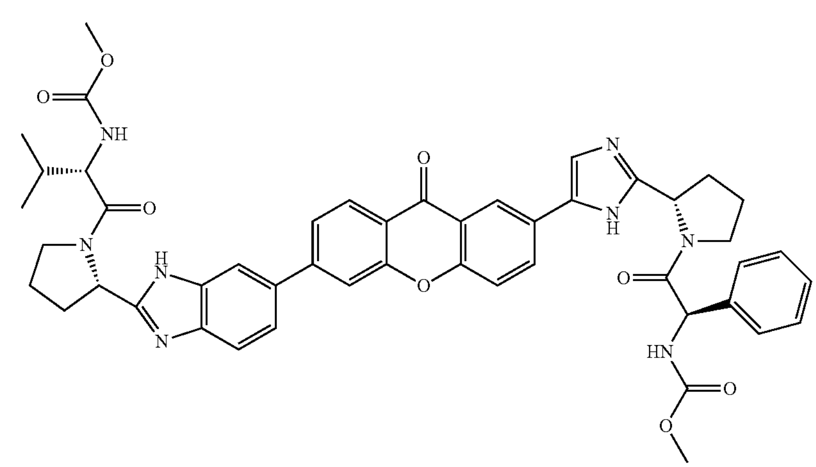 [SMILES: COC(=O)N[C@H](C(=O)N1CCC[C@H]1c1nc2ccc(-c3ccc4c(=O)c5cc(-c6cnc([C@@H]7CCCN7C(=O)[C@H](NC(=O)OC)c7ccccc7)[nH]6)ccc5oc4c3)cc2[nH]1)C(C)C] | **** | 865.4 |

TABLE 1-continued

Example Compounds and Assay Data

| Compound # | Structure | Inhibition of HCV genotype 1b | MS [M + H]+ |
|---|---|---|---|
| 79 | 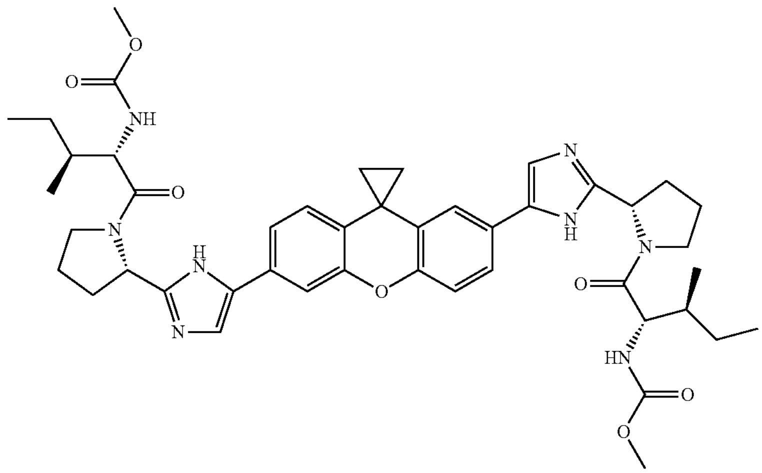 [SMILES: CC[C@H](C)[C@H](NC(=O)OC)C(=O)N1CCC[C@H]1c1ncc(-c2ccc3c(c2)Oc2ccc(-c4cnc([C@@H]5CCCN5C(=O)[C@@H](NC(=O)OC)[C@@H](C)CC)[nH]4)cc2C32CC2)[nH]1] | **** | 821.4 |
| 138 | 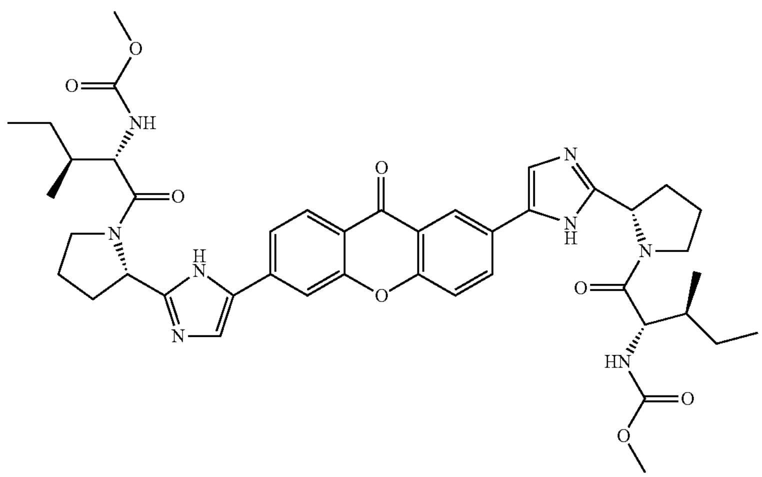 [SMILES: CC[C@H](C)[C@H](NC(=O)OC)C(=O)N1CCC[C@H]1c1ncc(-c2ccc3c(=O)c4cc(-c5cnc([C@@H]6CCCN6C(=O)[C@@H](NC(=O)OC)[C@@H](C)CC)[nH]5)ccc4oc3c2)[nH]1] | **** | 809.4 |
| 139 | 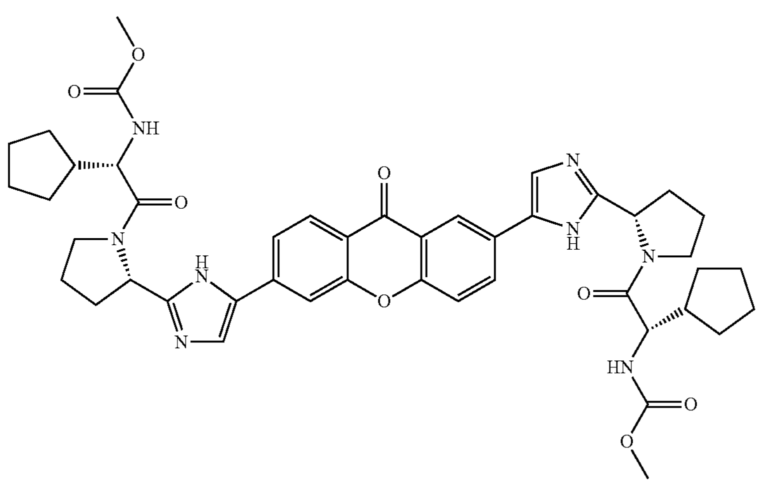 [SMILES: COC(=O)N[C@H](C(=O)N1CCC[C@H]1c1ncc(-c2ccc3c(=O)c4cc(-c5cnc([C@@H]6CCCN6C(=O)[C@@H](NC(=O)OC)C6CCCC6)[nH]5)ccc4oc3c2)[nH]1)C1CCCC1] | **** | 833.4 |

TABLE 1-continued

Example Compounds and Assay Data

| Compound # | Structure | Inhibition of HCV genotype 1b | MS [M + H]+ |
|---|---|---|---|
| 140 | 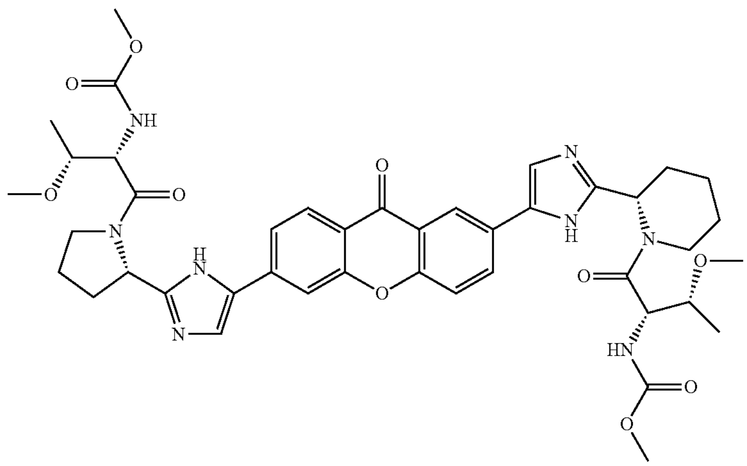 | **** | 827.4 |
| 70 | 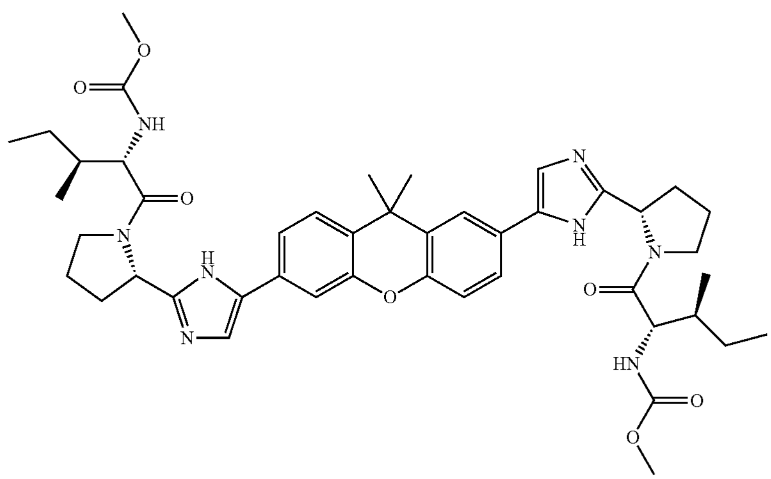 [SMILES: CC[C@H](C)[C@H](NC(=O)OC)C(=O)N1CCC[C@H]1c1ncc(-c2ccc3c(c2)Oc2ccc(-c4cnc([C@@H]5CCCN5C(=O)[C@@H](NC(=O)OC)[C@@H](C)CC)[nH]4)cc2C3(C)C)[nH]1] | **** | 823.4 |
| 141 | 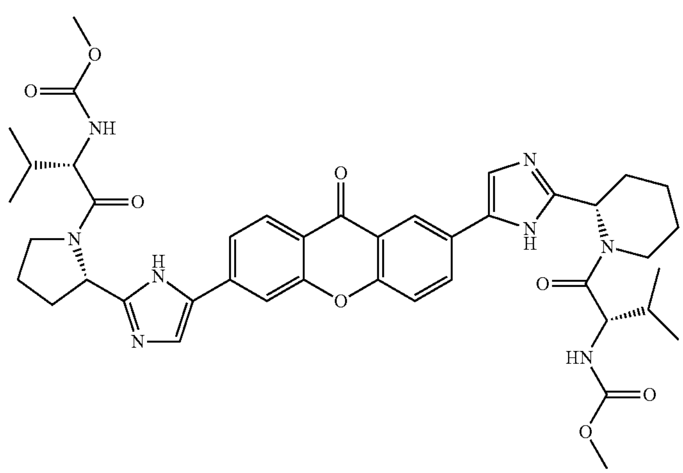 [SMILES: COC(=O)N[C@H](C(=O)N1CCCC[C@H]1c1ncc(-c2ccc3oc4cc(-c5cnc([C@@H]6CCCN6C(=O)[C@@H](NC(=O)OC)C(C)C)[nH]5)ccc4c(=O)c3c2)[nH]1)C(C)C] | **** | 795.4 |

TABLE 1-continued
Example Compounds and Assay Data
| Compound # | Structure | Inhibition of HCV genotype 1b | MS [M + H]+ |
|---|---|---|---|
| 142 | 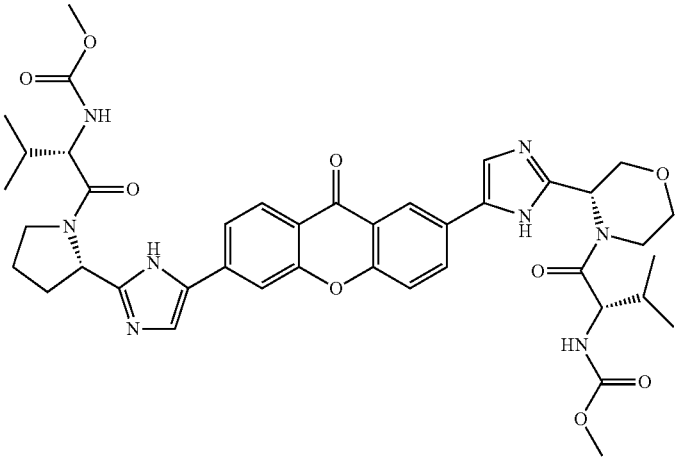 | **** | 797.4 |
| 143 | 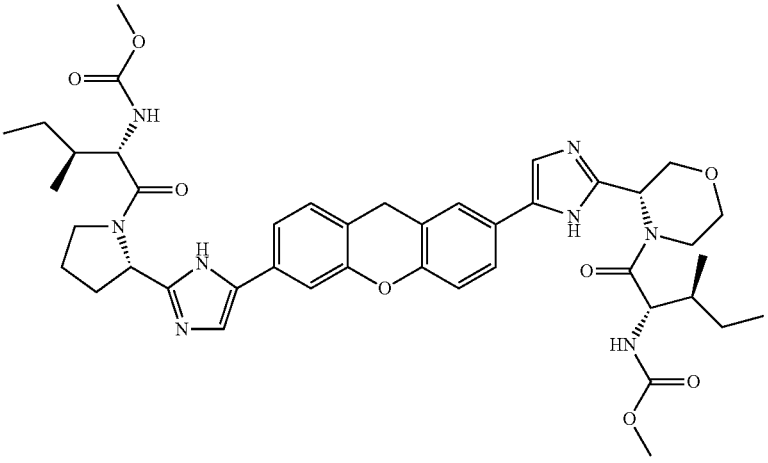 [SMILES: CC[C@H](C)[C@H](NC(=O)OC)C(=O)N1CCC[C@H]1c1ncc(-c2ccc3c(c2)Oc2ccc(-c4cnc([C@@H]5COCCN5C(=O)[C@@H](NC(=O)OC)[C@@H](C)CC)[nH]4)cc2C3)[nH]1] | **** | 811.4 |
| 144 | 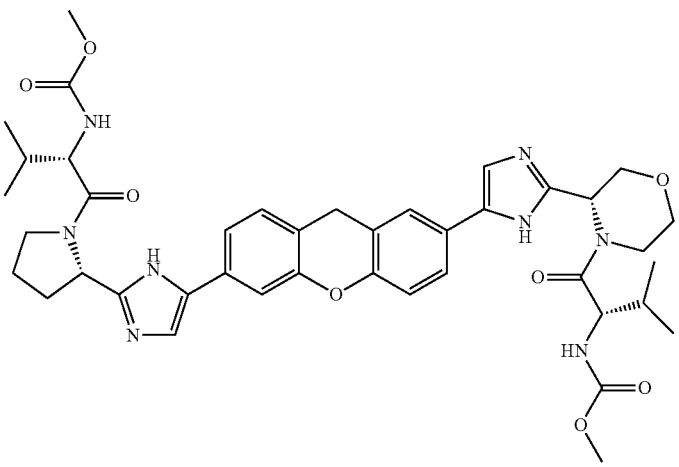 [SMILES: COC(=O)N[C@H](C(=O)N1CCC[C@H]1c1ncc(-c2ccc3c(c2)Oc2ccc(-c4cnc([C@@H]5COCCN5C(=O)[C@@H](NC(=O)OC)C(C)C)[nH]4)cc2C3)[nH]1)C(C)C] | **** | 783.4 |

TABLE 1-continued

Example Compounds and Assay Data

| Compound # | Structure | Inhibition of HCV genotype 1b | MS [M + H]+ |
|---|---|---|---|
| 145 | 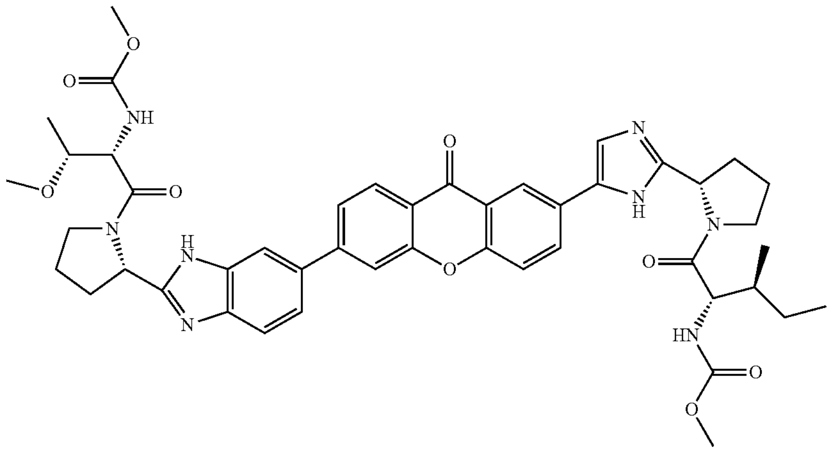 [SMILES: CC[C@H](C)[C@H](NC(=O)OC)C(=O)N1CCC[C@H]1c1ncc(-c2ccc3oc4cc(-c5ccc6nc([C@@H]7CCCN7C(=O)[C@@H](NC(=O)OC)[C@@H](C)OC)[nH]c6c5)ccc4c(=O)c3c2)[nH]1] | **** | 861.4 |
| 146 | 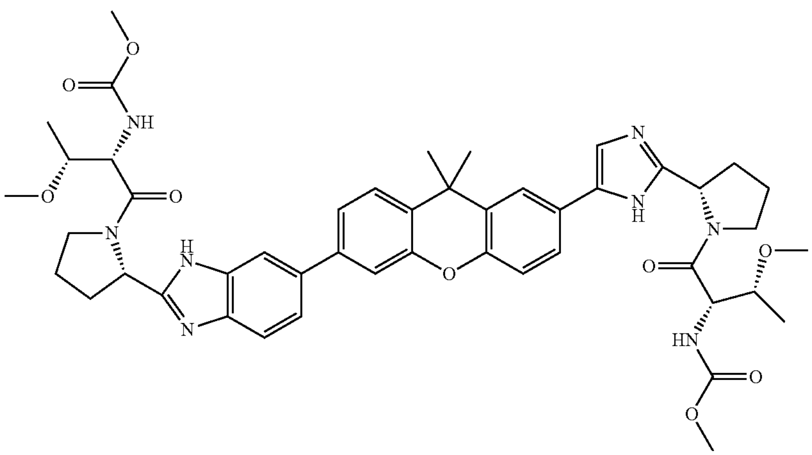 | **** | 877.4 |
| 147 | 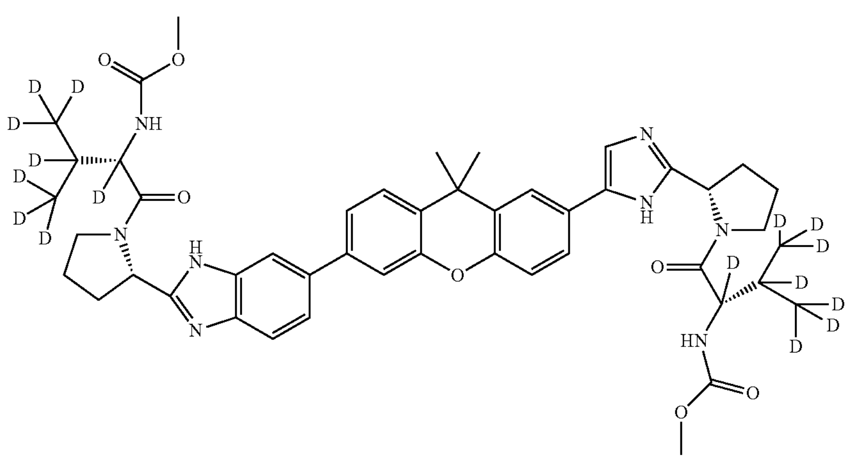 [SMILES: [2H]C([2H])([2H])C([2H])(C([2H])([2H])[2H])[C@]([2H])(NC(=O)OC)C(=O)N1CCC[C@H]1c1ncc(-c2ccc3c(c2)C(C)(C)c2ccc(-c4ccc5nc([C@@H]6CCCN6C(=O)[C@@]([2H])(NC(=O)OC)C([2H])(C([2H])([2H])[2H])C([2H])([2H])[2H])[nH]c5c4)cc2O3)[nH]1] | **** | 861.5 |

TABLE 1-continued

Example Compounds and Assay Data

| Compound # | Structure | Inhibition of HCV genotype 1b | MS [M + H]+ |
|---|---|---|---|
| 148 | 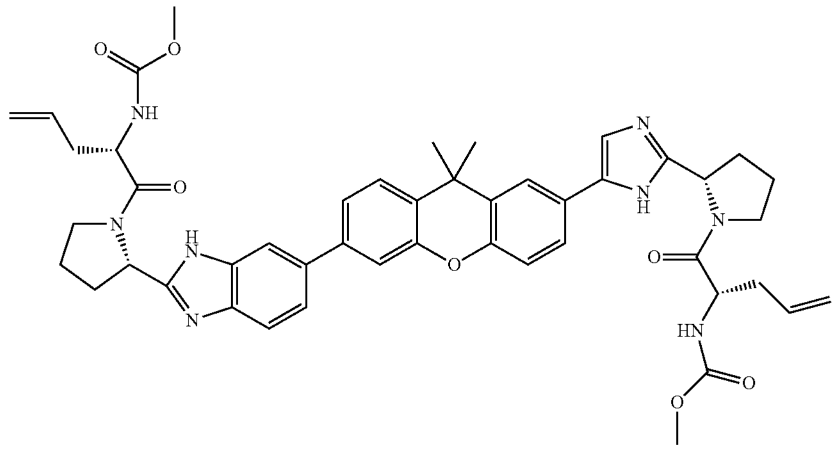 [SMILES: C=CC[C@H](NC(=O)OC)C(=O)N1CCC[C@H]1c1ncc(-c2ccc3c(c2)C(C)(C)c2ccc(-c4ccc5nc([C@@H]6CCCN6C(=O)[C@H](CC=C)NC(=O)OC)[nH]c5c4)cc2O3)[nH]1] | **** | 841.4 |
| 149 | 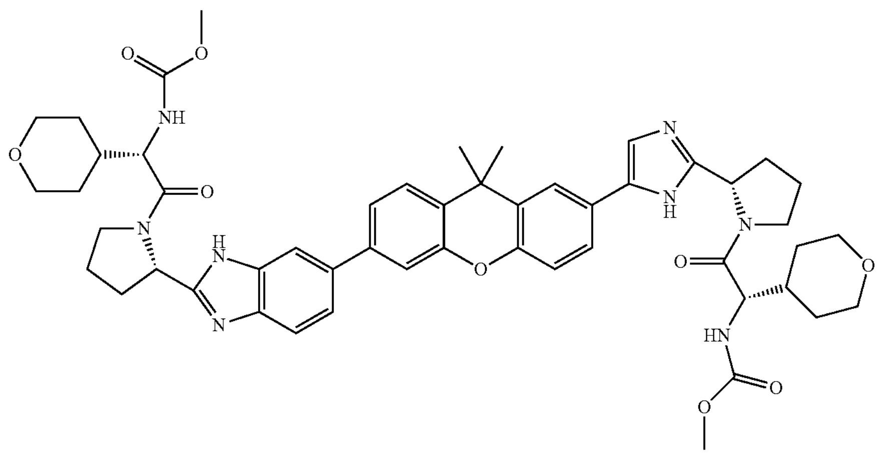 [SMILES: COC(=O)N[C@H](C(=O)N1CCC[C@H]1c1ncc(-c2ccc3c(c2)C(C)(C)c2ccc(-c4ccc5nc([C@@H]6CCCN6C(=O)[C@@H](NC(=O)OC)C6CCOCC6)[nH]c5c4)cc2O3)[nH]1)C1CCOCC1] | **** | 929.4 |
| 150 | 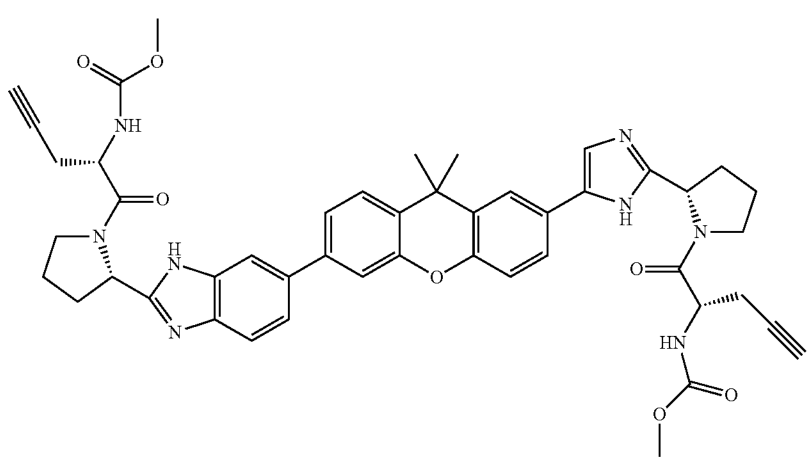 [SMILES: C#CC[C@H](NC(=O)OC)C(=O)N1CCC[C@H]1c1ncc(-c2ccc3c(c2)C(C)(C)c2ccc(-c4ccc5nc([C@@H]6CCCN6C(=O)[C@H](CC#C)NC(=O)OC)[nH]c5c4)cc2O3)[nH]1] | **** | 837.4 |

TABLE 1-continued
Example Compounds and Assay Data
| Compound # | Structure | Inhibition of HCV genotype 1b | MS [M + H]+ |
|---|---|---|---|
| 151 | 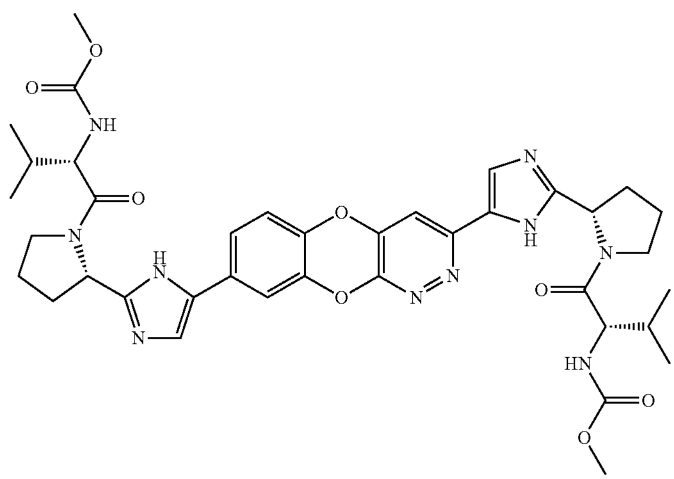 [SMILES: COC(=O)N[C@H](C(=O)N1CCC[C@H]1c1ncc(-c2ccc3c(c2)Oc2nnc(-c4cnc([C@@H]5CCCN5C(=O)[C@@H](NC(=O)OC)C(C)C)[nH]4)cc2O3)[nH]1)C(C)C] | *** | 771.4 |
TABLE 2
Additional Example Compounds
| Compound # | Structure |
|---|---|
| 72 | 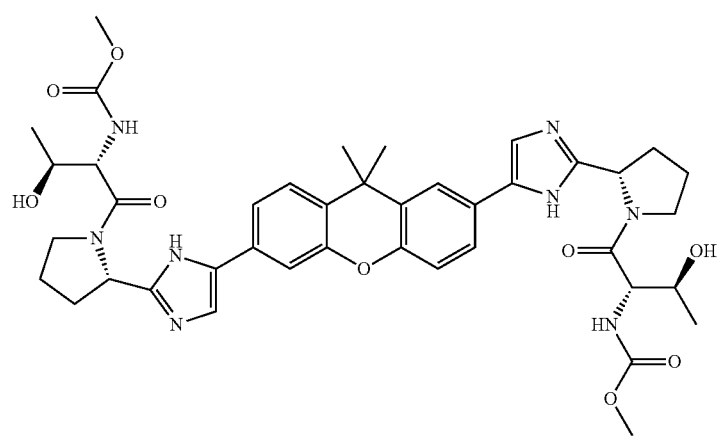 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)[C@H](C)O)[nH]4)cc2C3(C)C)[nH]1)[C@H](C)O] |

TABLE 2-continued
Additional Example Compounds
| Compound # | Structure |
|---|---|
| 73 | 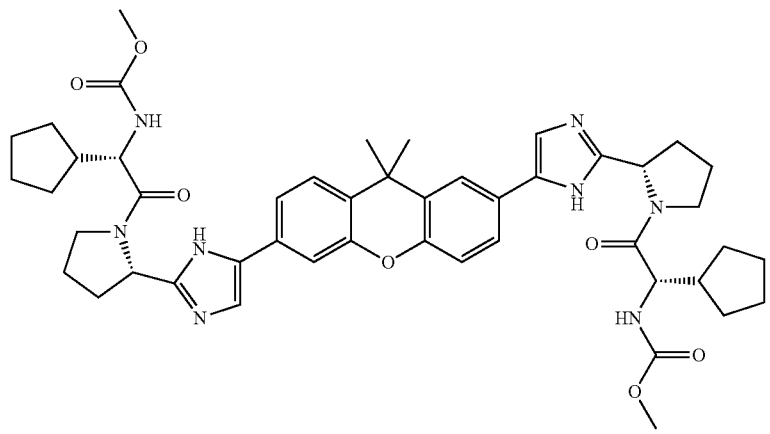 |
| 74 | 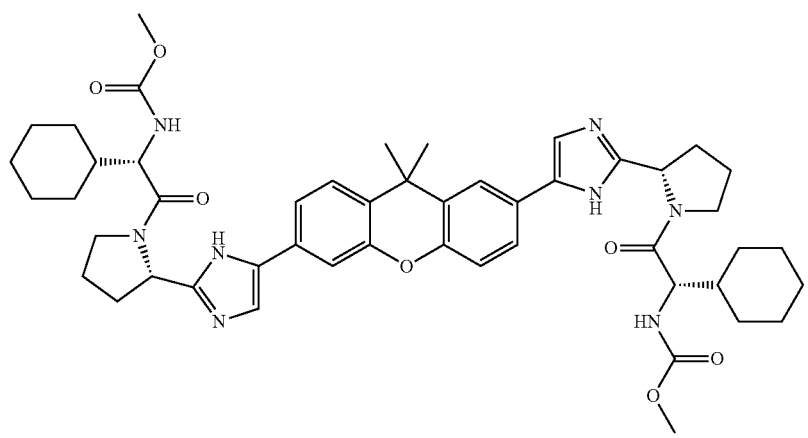 |
| 76 | 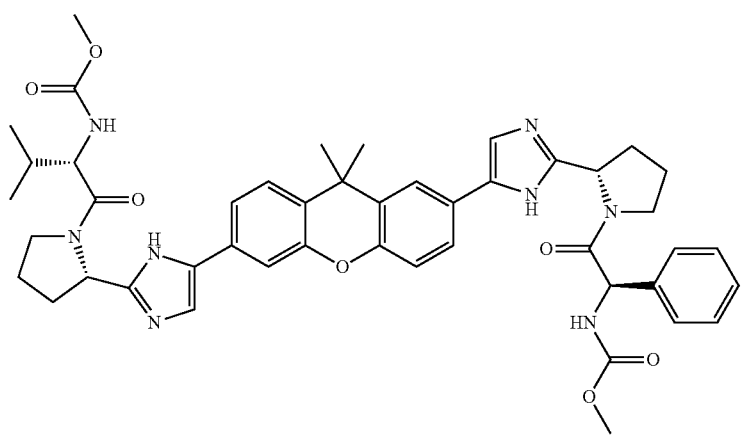 [SMILES: COC(=O)N[C@H](C(=O)N1CCC[C@H]1c1ncc(-c2ccc3c(c2)Oc2ccc(-c4cnc([C@@H]5CCCN5C(=O)[C@H](NC(=O)OC)c5ccccc5)[nH]4)cc2C3(C)C)[nH]1)C(C)C] |

TABLE 2-continued
Additional Example Compounds
| Compound # | Structure |
|---|---|
| 77 | 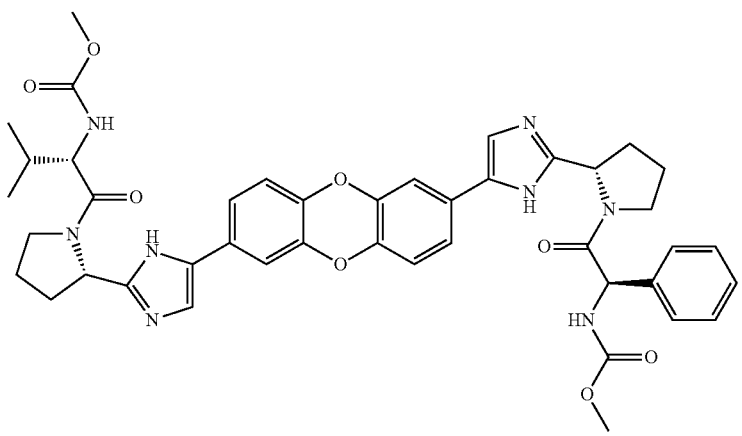 [SMILES: COC(=O)N[C@H](C(=O)N1CCC[C@H]1c1ncc(-c2ccc3c(c2)Oc2ccc(-c4cnc([C@@H]5CCCN5C(=O)[C@H](NC(=O)OC)c5ccccc5)[nH]4)cc2O3)[nH]1)C(C)C] |
| 78 | 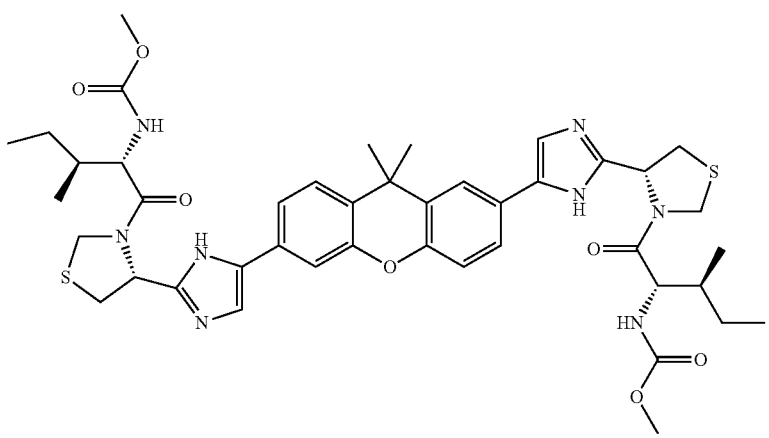 [SMILES: CC[C@H](C)[C@H](NC(=O)OC)C(=O)N1CSC[C@H]1c1ncc(-c2ccc3c(c2)Oc2ccc(-c4cnc([C@@H]5CSCN5C(=O)[C@@H](NC(=O)OC)[C@@H](C)CC)[nH]4)cc2C3(C)C)[nH]1] |
| 80 | 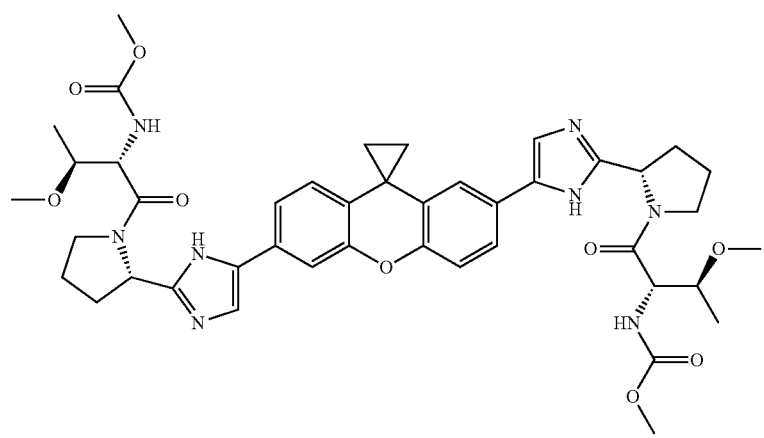 |

TABLE 2-continued
Additional Example Compounds
| Compound # | Structure |
|---|---|
| 81 | 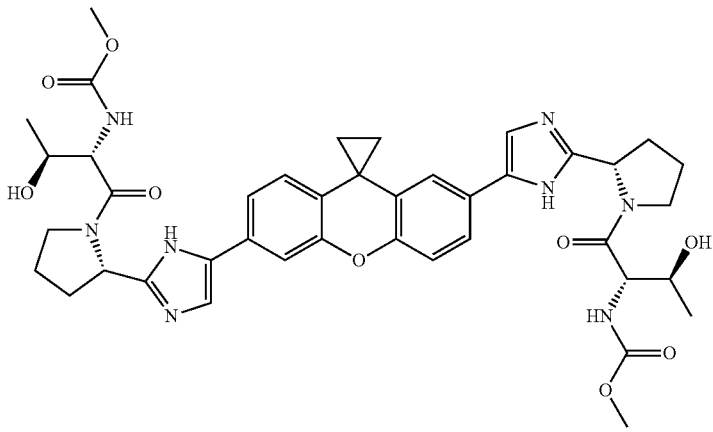 |
| 82 | 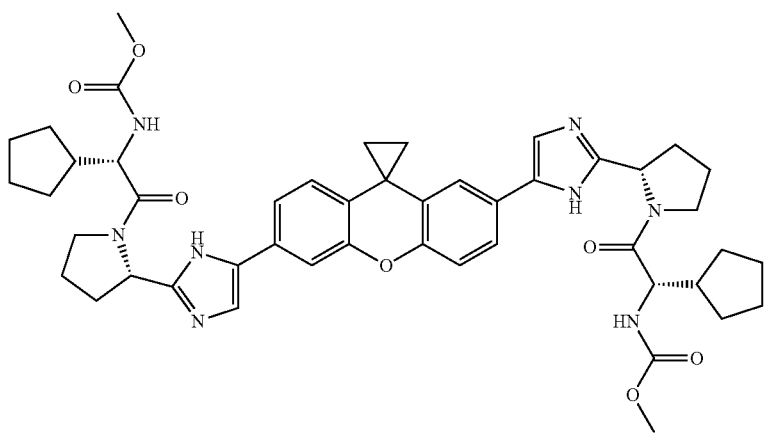 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C5CCCC5)[nH]4)cc2C32CC2)[nH]1)C1CCCC1] |
| 83 | 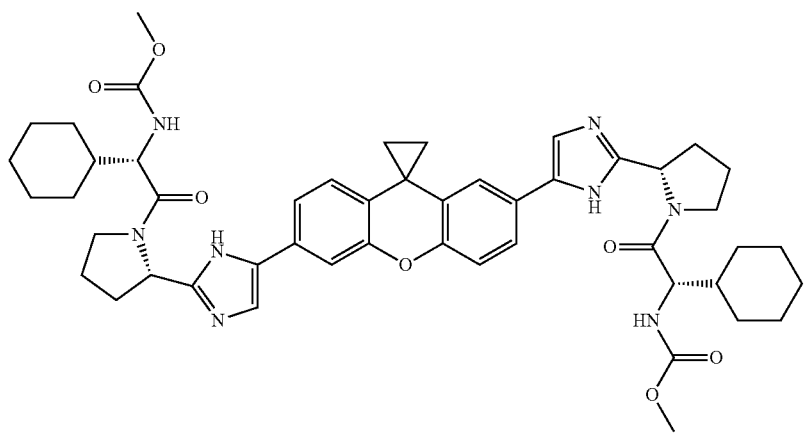 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C5CCCCC5)[nH]4)cc2C32CC2)[nH]1)C1CCCCC1] |

TABLE 2-continued
Additional Example Compounds
| Compound # | Structure |
|---|---|
| 84 | 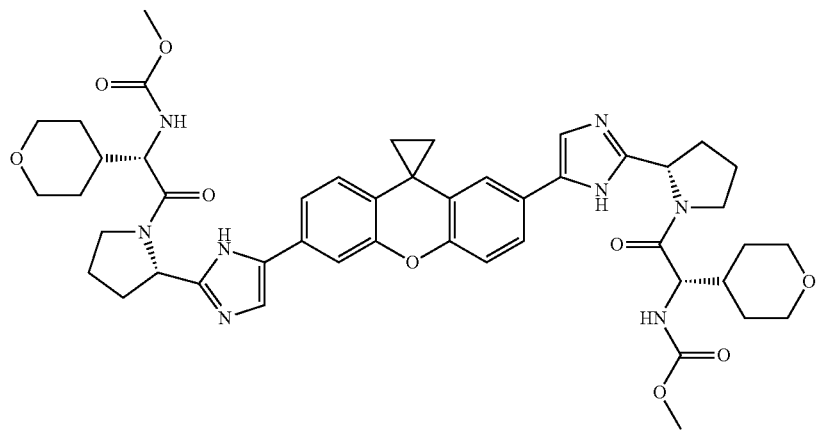 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C5CCOCC5)[nH]4)cc2C32CC2)[nH]1)C1CCOCC1] |
| 85 | 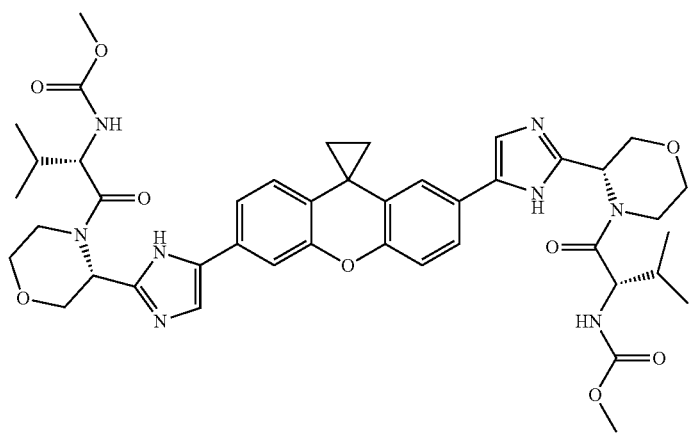 [SMILES: COC(=O)N[C@H](C(=O)N1CCOC[C@H]1c1ncc(-c2ccc3c(c2)Oc2ccc(-c4cnc([C@@H]5COCCN5C(=O)[C@@H](NC(=O)OC)C(C)C)[nH]4)cc2C32CC2)[nH]1)C(C)C] |
| 86 | 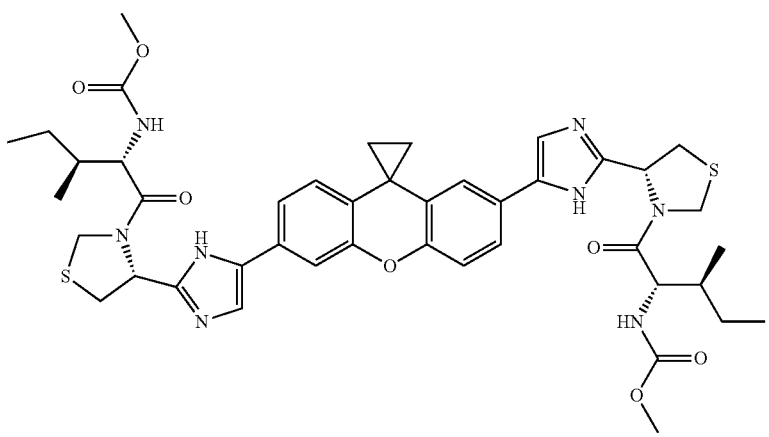 |

TABLE 2-continued
Additional Example Compounds
| Compound # | Structure |
|---|---|
| 87 | 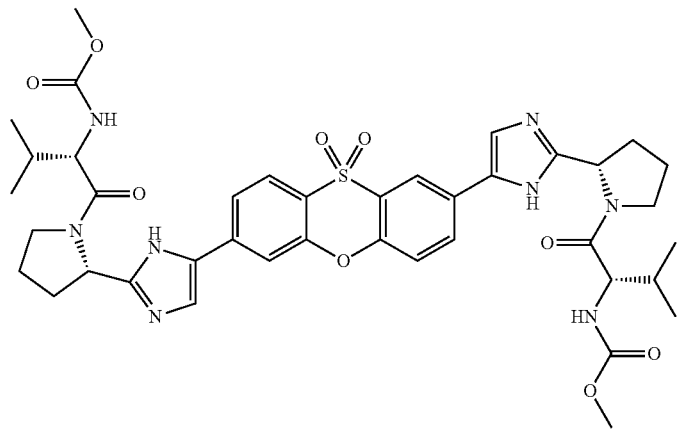 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C(C)C)[nH]4)cc2S3(=O)=O)[nH]1)C(C)C] |
| 88 | 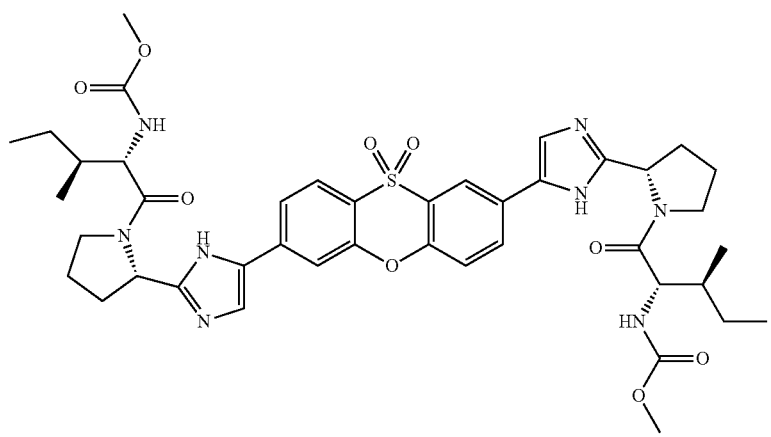 [SMILES: CC[C@H](C)[C@H](NC(=O)OC)C(=O)N1CCC[C@H]1c1ncc(-c2ccc3c(c2)Oc2ccc(-c4cnc([C@@H]5CCCN5C(=O)[C@@H](NC(=O)OC)[C@@H](C)CC)[nH]4)cc2S3(=O)=O)[nH]1] |
| 89 | 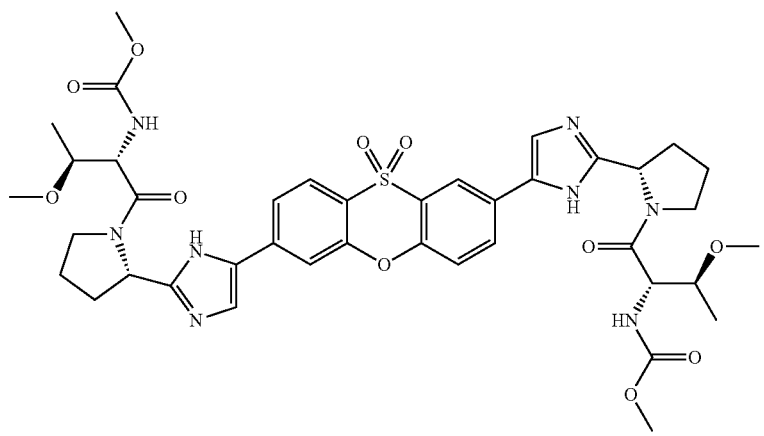 |

TABLE 2-continued
Additional Example Compounds
| Compound # | Structure |
|---|---|
| 90 | 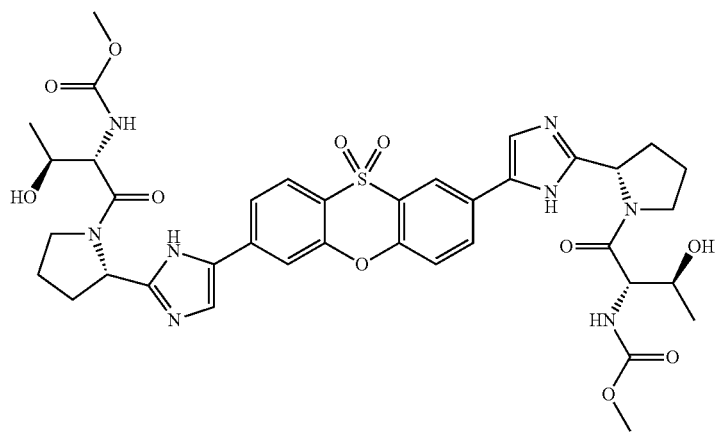 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)[C@H](C)O)[nH]4)cc2S3(=O)=O)[nH]1)[C@H](C)O] |
| 91 | 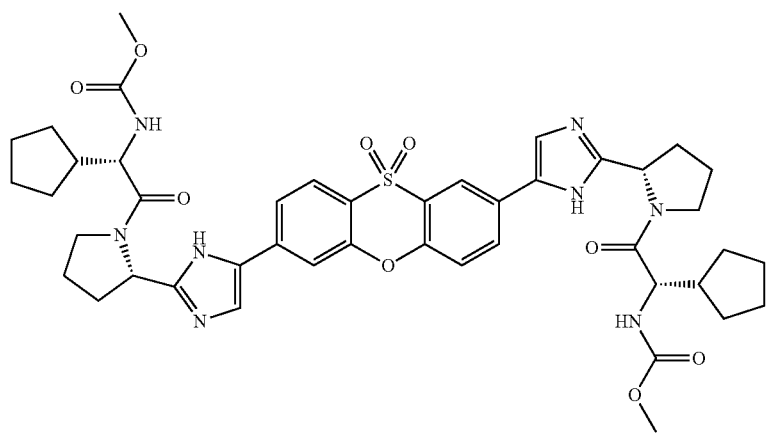 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C5CCCC5)[nH]4)cc2S3(=O)=O)[nH]1)C1CCCC1] |
| 92 | 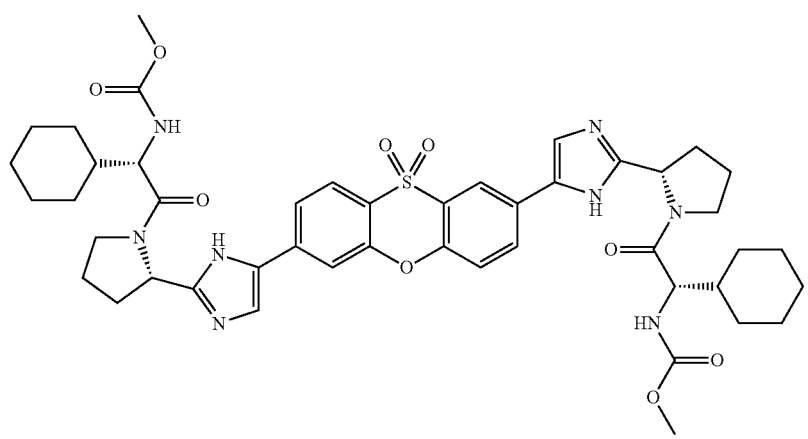 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C5CCCCC5)[nH]4)cc2S3(=O)=O)[nH]1)C1CCCCC1] |

TABLE 2-continued
Additional Example Compounds
| Compound # | Structure |
|---|---|
| 93 | 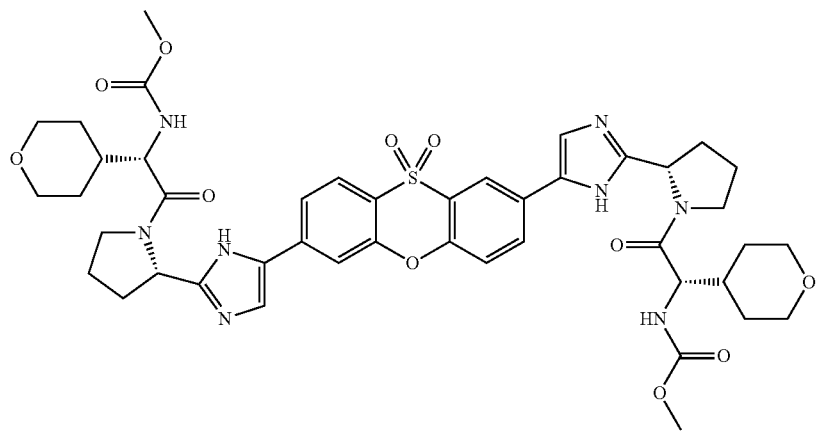 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C5CCOCC5)[nH]4)cc2S3(=O)=O)[nH]1)C1CCOCC1] |
| 94 | 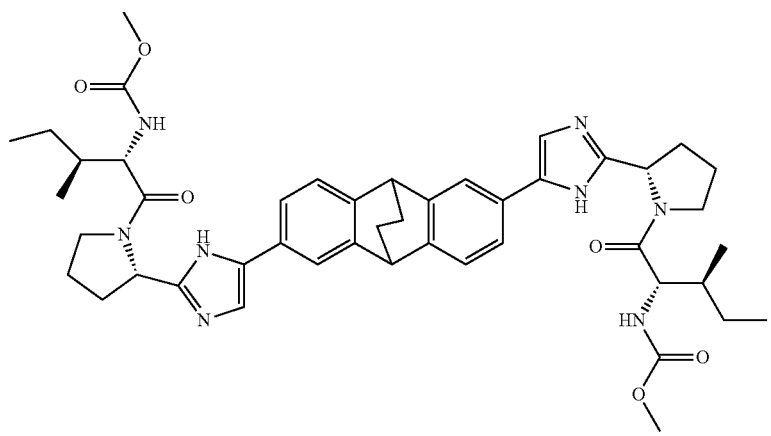 [SMILES: CC[C@H](C)[C@H](NC(=O)OC)C(=O)N1CCC[C@H]1c1ncc(-c2ccc3c(c2)C2CCC3c3cc(-c4cnc([C@@H]5CCCN5C(=O)[C@@H](NC(=O)OC)[C@@H](C)CC)[nH]4)ccc32)[nH]1] |
| 95 | 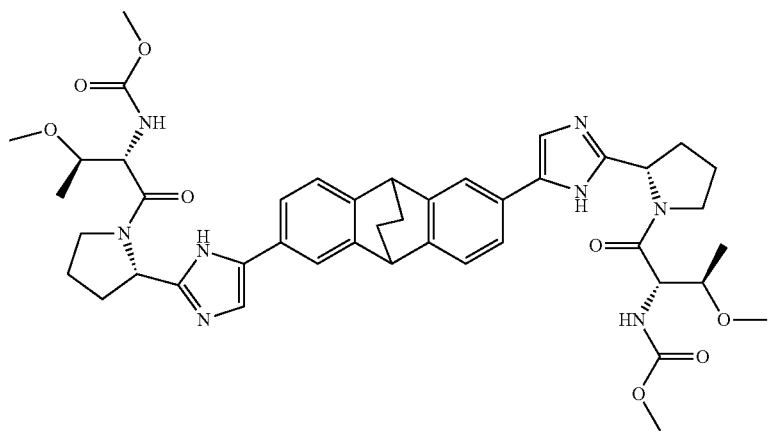 |

TABLE 2-continued

Additional Example Compounds

| Compound # | Structure |
|---|---|
| 96 | 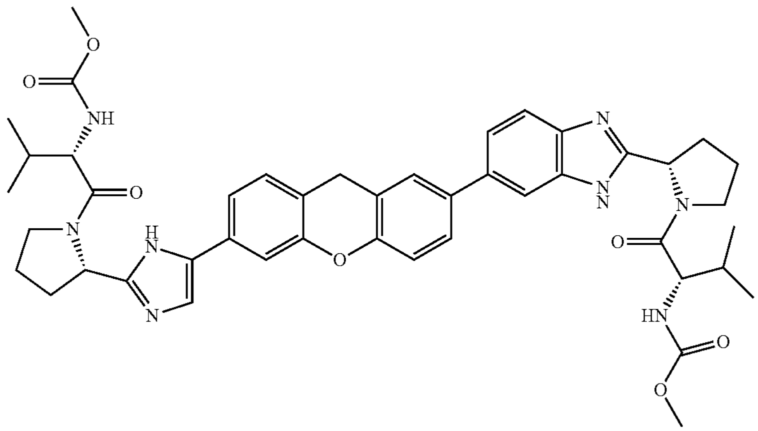 |
| 97 | 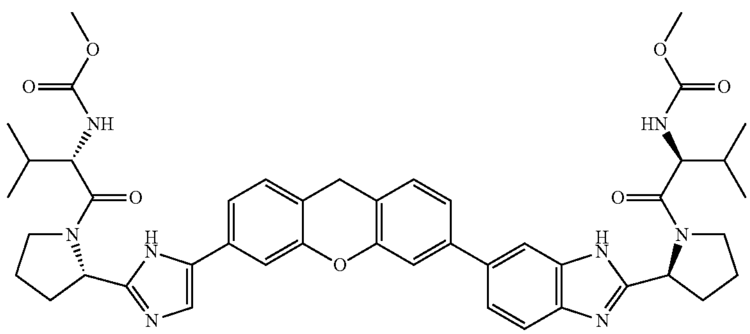 |
| 98 | 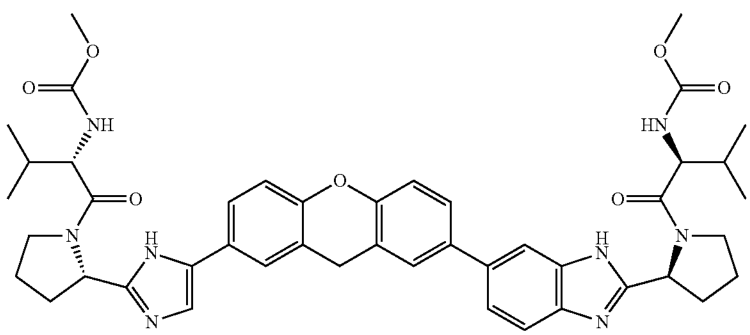 |
| 99 | 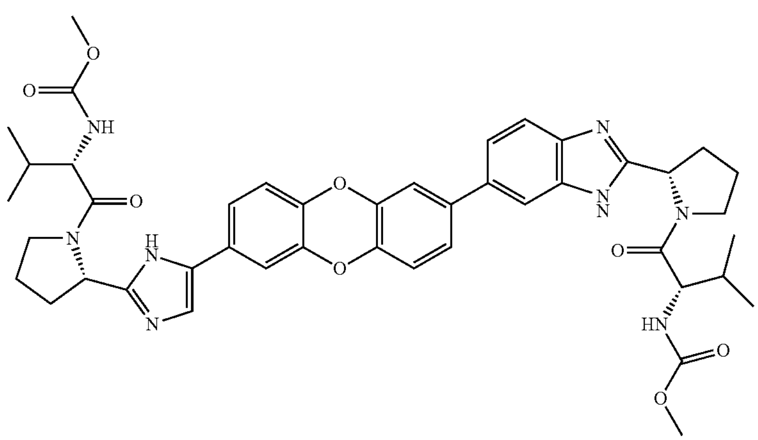 |

TABLE 2-continued

Additional Example Compounds

| Compound # | Structure |
|---|---|
| 100 | 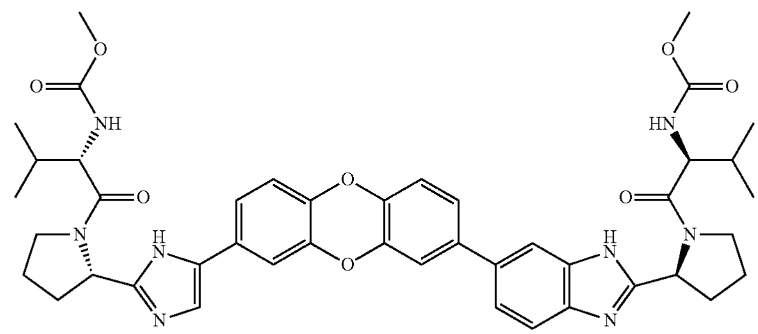 [SMILES: COC(=O)N[C@H](C(=O)N1CCC[C@H]1c1ncc(-c2ccc3c(c2)Cc2cc(-c4ccc5nc([C@@H]6CCCN6C(=O)[C@@H](NC(=O)OC)C(C)C)[nH]c5c4)ccc2O3)[nH]1)C(C)C] |
| 101 | 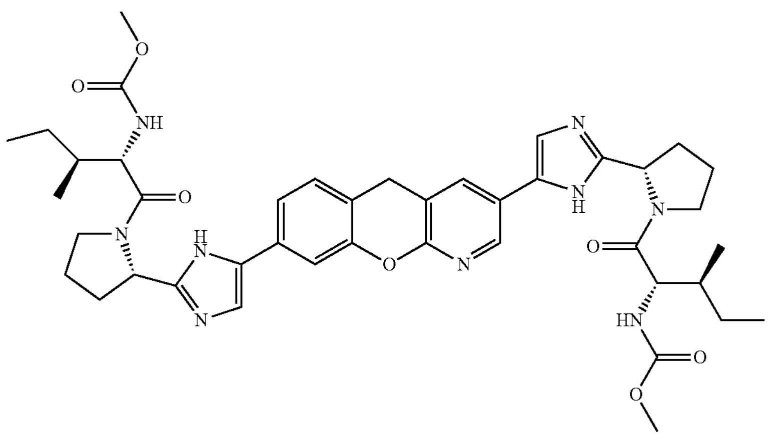 [SMILES: CC[C@H](C)[C@H](NC(=O)OC)C(=O)N1CCC[C@H]1c1ncc(-c2cnc3c(c2)Cc2ccc(-c4cnc([C@@H]5CCCN5C(=O)[C@@H](NC(=O)OC)[C@@H](C)CC)[nH]4)cc2O3)[nH]1] |
| 102 | 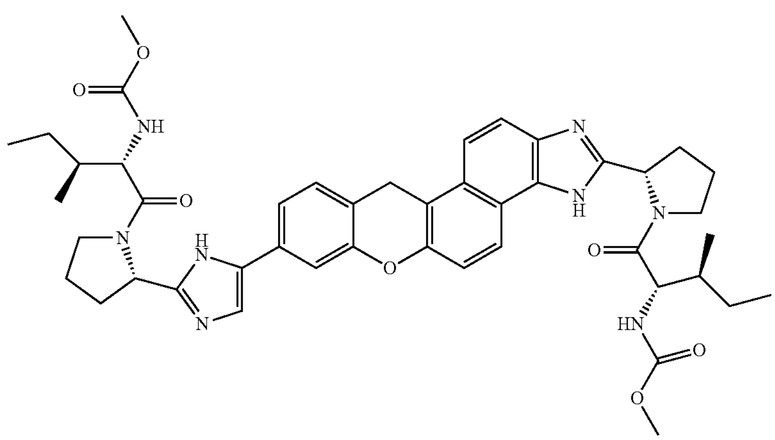 [SMILES: CC[C@H](C)[C@H](NC(=O)OC)C(=O)N1CCC[C@H]1c1ncc(-c2ccc3c(c2)Oc2ccc4c(ccc5nc([C@@H]6CCCN6C(=O)[C@@H](NC(=O)OC)[C@@H](C)CC)[nH]c54)c2C3)[nH]1] |
| 103 | 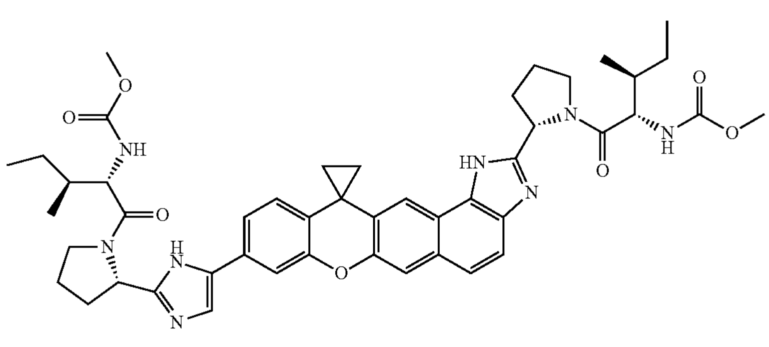 [SMILES: CC[C@H](C)[C@H](NC(=O)OC)C(=O)N1CCC[C@H]1c1ncc(-c2ccc3c(c2)Oc2cc4ccc5nc([C@@H]6CCCN6C(=O)[C@@H](NC(=O)OC)[C@@H](C)CC)[nH]c5c4cc2C32CC2)[nH]1] |

TABLE 2-continued

Additional Example Compounds

| Compound # | Structure |
|---|---|
| 104 | 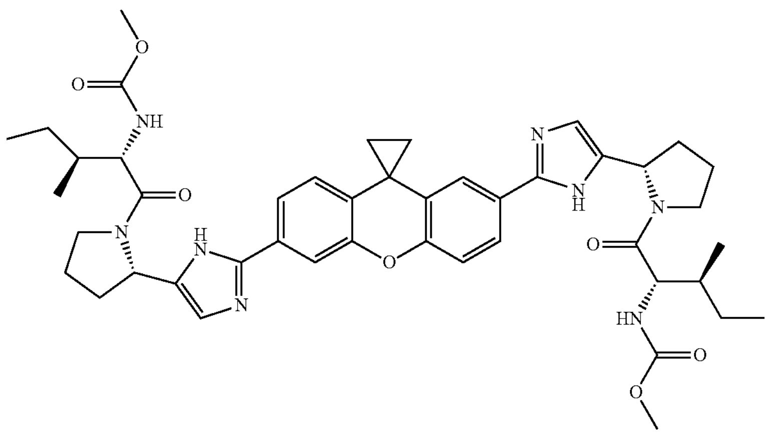 [SMILES: CC[C@H](C)[C@H](NC(=O)OC)C(=O)N1CCC[C@H]1c1cnc(-c2ccc3c(c2)Oc2ccc(-c4ncc([C@@H]5CCCN5C(=O)[C@@H](NC(=O)OC)[C@@H](C)CC)[nH]4)cc2C32CC2)[nH]1] |
| 105 | 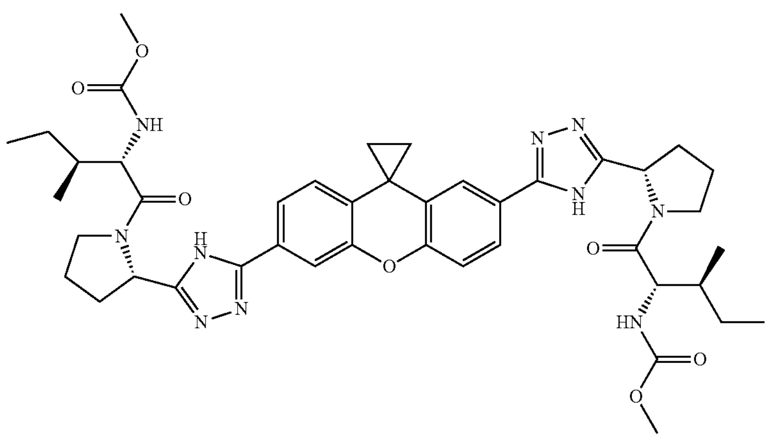 [SMILES: CC[C@H](C)[C@H](NC(=O)OC)C(=O)N1CCC[C@H]1c1nnc(-c2ccc3c(c2)Oc2ccc(-c4nnc([C@@H]5CCCN5C(=O)[C@@H](NC(=O)OC)[C@@H](C)CC)[nH]4)cc2C32CC2)[nH]1] |
| 106 | 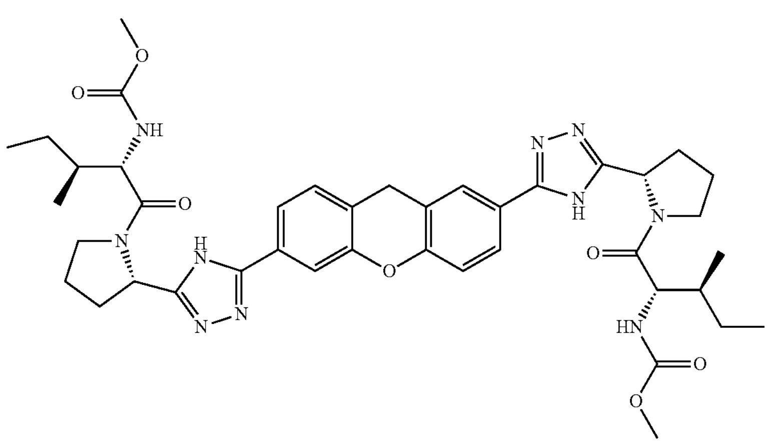 |

TABLE 2-continued

Additional Example Compounds

| Compound # | Structure |
|---|---|
| 107 | 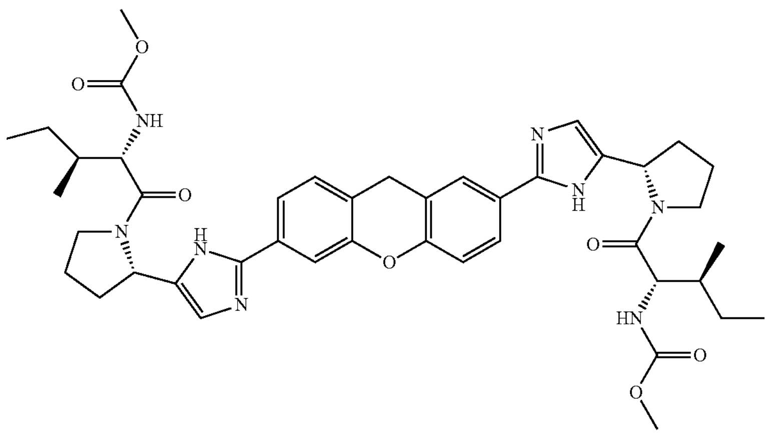 [SMILES: CC[C@H](C)[C@H](NC(=O)OC)C(=O)N1CCC[C@H]1c1cnc(-c2ccc3c(c2)Cc2ccc(-c4ncc([C@@H]5CCCN5C(=O)[C@@H](NC(=O)OC)[C@@H](C)CC)[nH]4)cc2O3)[nH]1] |
| 108 | 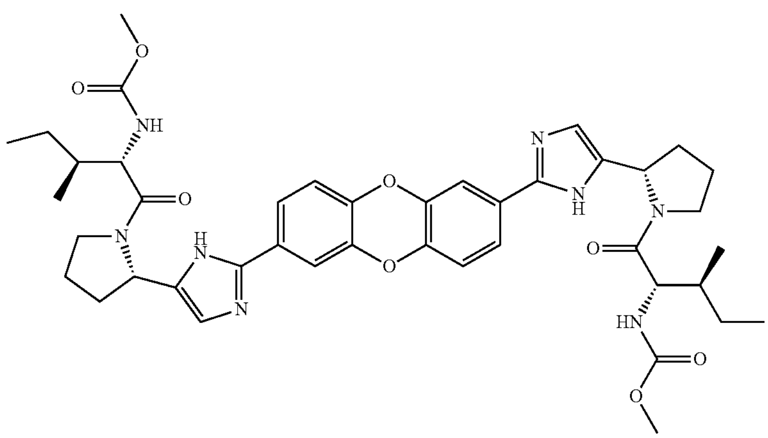 |
| 109 | 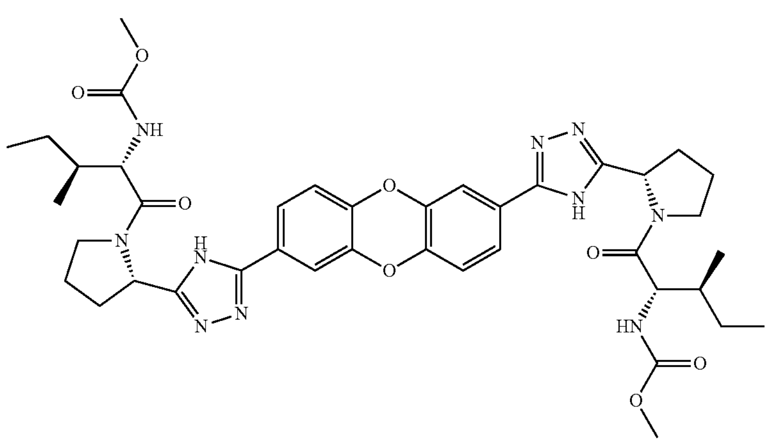 [SMILES: CC[C@H](C)[C@H](NC(=O)OC)C(=O)N1CCC[C@H]1c1nnc(-c2ccc3c(c2)Oc2ccc(-c4nnc([C@@H]5CCCN5C(=O)[C@@H](NC(=O)OC)[C@@H](C)CC)[nH]4)cc2O3)[nH]1] |

TABLE 2-continued

Additional Example Compounds

| Compound # | Structure |
|---|---|
| 110 | 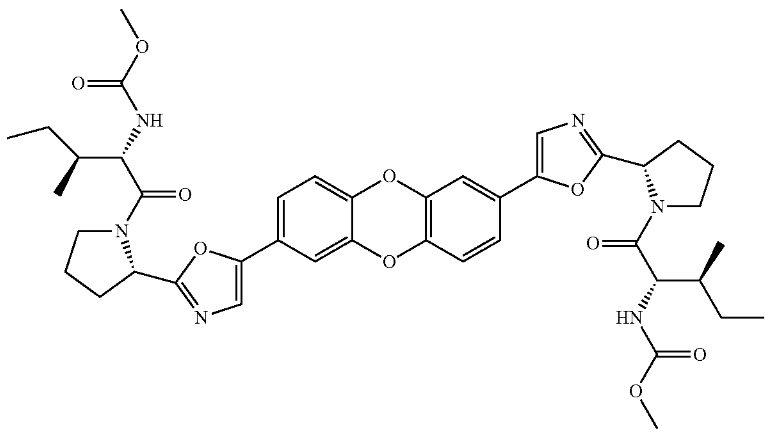 [SMILES: CC[C@H](C)[C@H](NC(=O)OC)C(=O)N1CCC[C@H]1c1ncc(-c2ccc3c(c2)Oc2ccc(-c4cnc([C@@H]5CCCN5C(=O)[C@@H](NC(=O)OC)[C@@H](C)CC)o4)cc2O3)o1] |
| 111 | 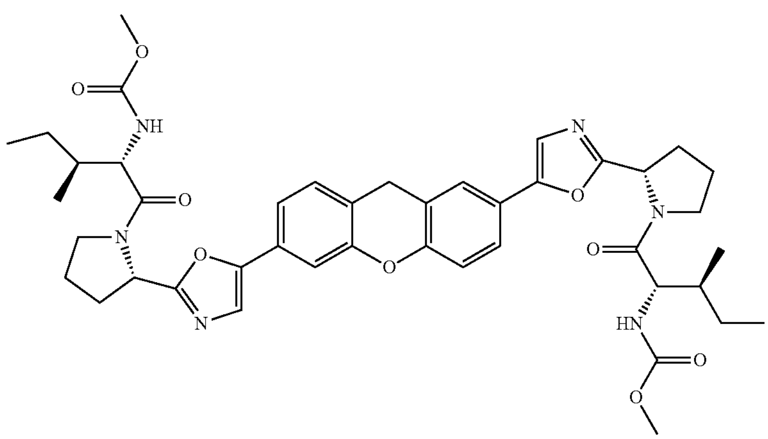 |
| 112 | 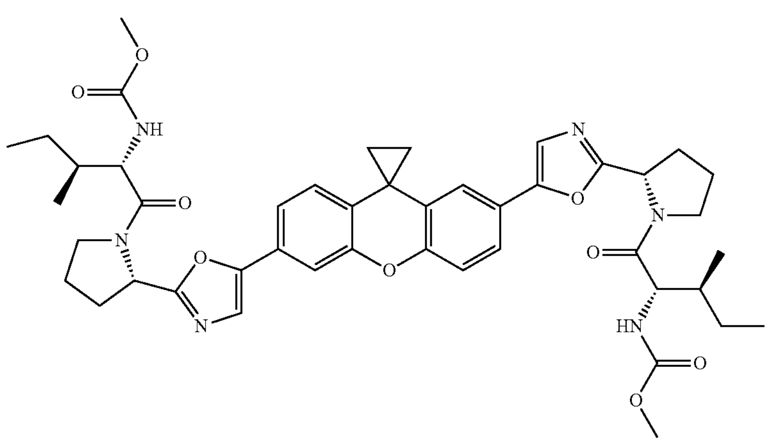 [SMILES: CC[C@H](C)[C@H](NC(=O)OC)C(=O)N1CCC[C@H]1c1ncc(-c2ccc3c(c2)Oc2ccc(-c4cnc([C@@H]5CCCN5C(=O)[C@@H](NC(=O)OC)[C@@H](C)CC)o4)cc2C32CC2)o1] |

TABLE 2-continued
Additional Example Compounds
| Compound # | Structure |
|---|---|
| 113 | 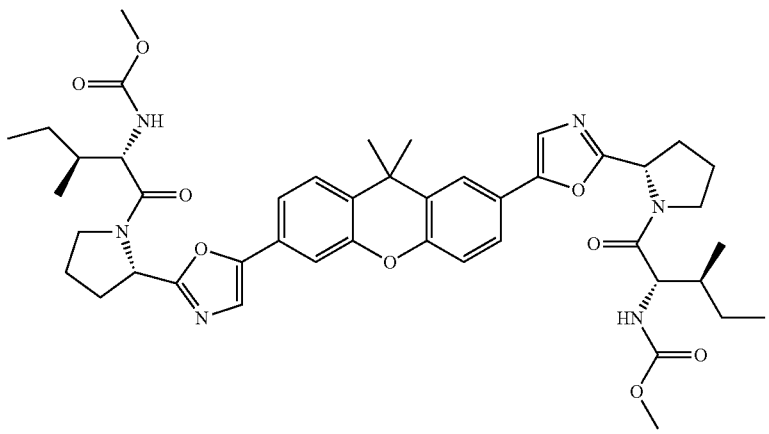 |
| 114 | 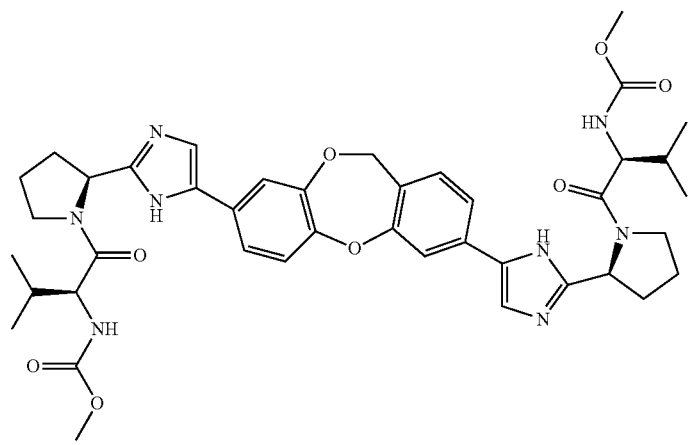 [SMILES: COC(=O)N[C@H](C(=O)N1CCC[C@H]1c1ncc(-c2ccc3c(c2)Oc2ccc(-c4cnc([C@@H]5CCCN5C(=O)[C@@H](NC(=O)OC)C(C)C)[nH]4)cc2OC3)[nH]1)C(C)C] |
| 115 | 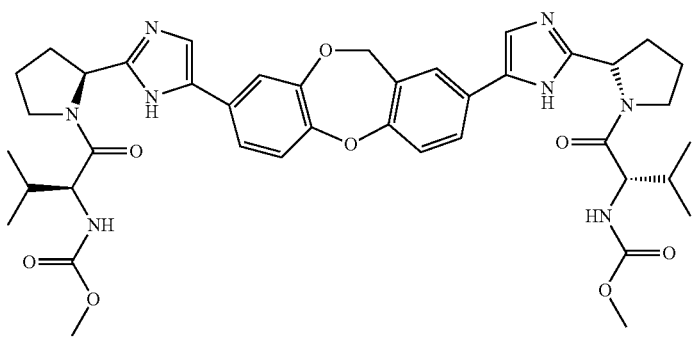 |

TABLE 2-continued
Additional Example Compounds
| Compound # | Structure |
|---|---|
| 155 | 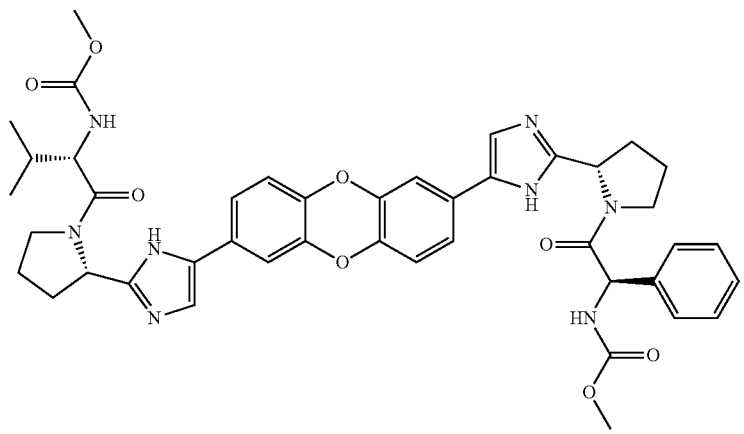 [SMILES: COC(=O)N[C@H](C(=O)N1CCC[C@H]1c1ncc(-c2ccc3c(c2)Oc2ccc(-c4cnc([C@@H]5CCCN5C(=O)[C@H](NC(=O)OC)c5ccccc5)[nH]4)cc2O3)[nH]1)C(C)C] |
| 156 | 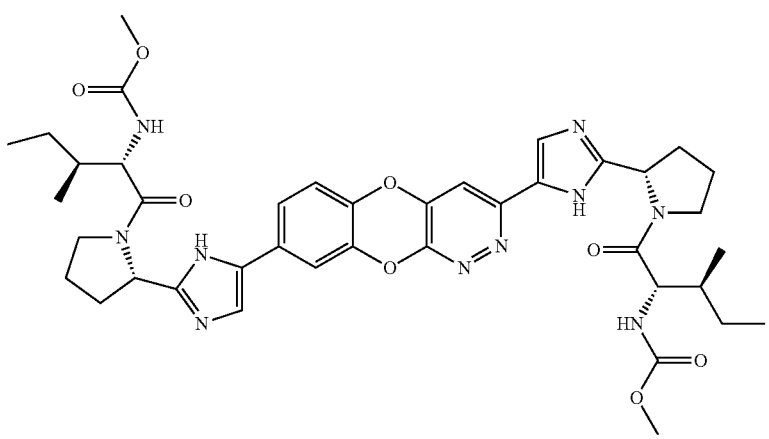 |
| 157 | 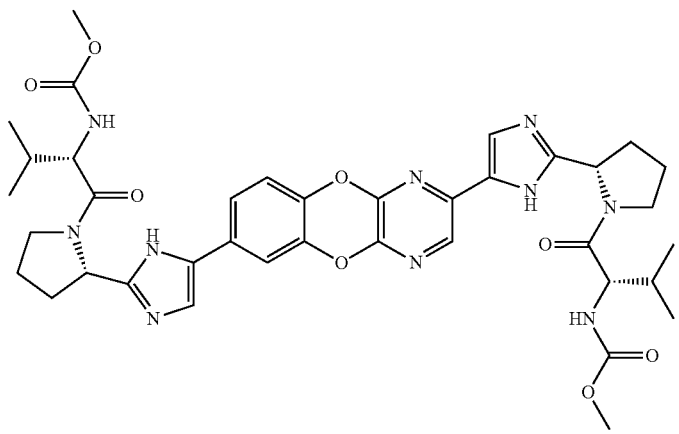 [SMILES: COC(=O)N[C@H](C(=O)N1CCC[C@H]1c1ncc(-c2ccc3c(c2)Oc2ncc(-c4cnc([C@@H]5CCCN5C(=O)[C@@H](NC(=O)OC)C(C)C)[nH]4)nc2O3)[nH]1)C(C)C] |

TABLE 2-continued

Additional Example Compounds

| Compound # | Structure |
|---|---|
| 158 | 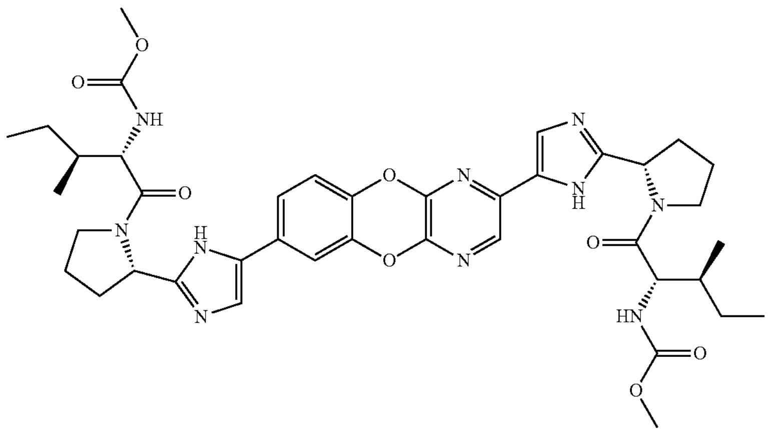 [SMILES: CC[C@H](C)[C@H](NC(=O)OC)C(=O)N1CCC[C@H]1c1ncc(-c2ccc3c(c2)Oc2ncc(-c4cnc([C@@H]5CCCN5C(=O)[C@@H](NC(=O)OC)[C@@H](C)CC)[nH]4)nc2O3)[nH]1] |

We claim:
1. A compound having a formula selected from:

261
-continued
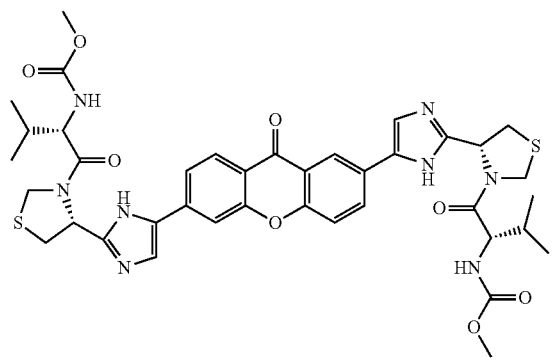 [SMILES: COC(=O)N[C@H](C(=O)N1CSC[C@H]1c1ncc(-c2ccc3c(=O)c4cc(-c5cnc([C@@H]6CSCN6C(=O)[C@@H](NC(=O)OC)C(C)C)[nH]5)ccc4oc3c2)[nH]1)C(C)C]
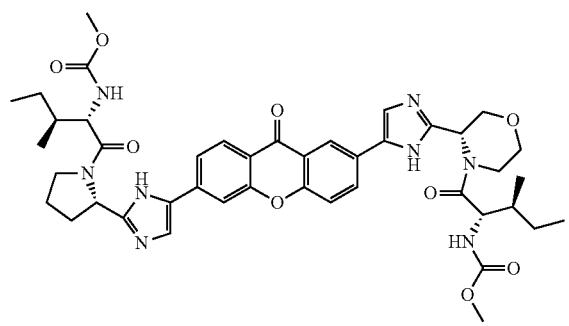
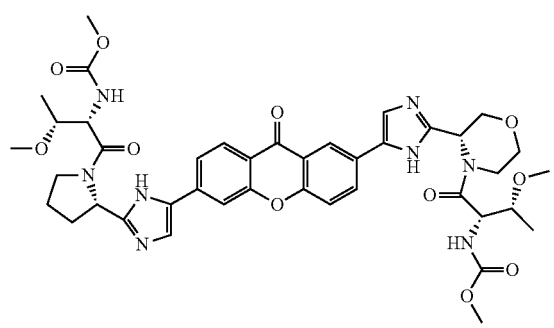
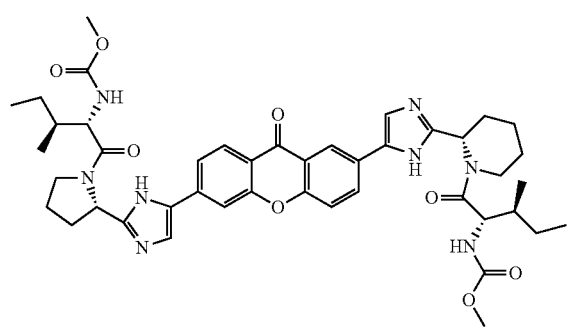 [SMILES: CC[C@H](C)[C@H](NC(=O)OC)C(=O)N1CCCC[C@H]1c1ncc(-c2ccc3oc4cc(-c5cnc([C@@H]6CCCN6C(=O)[C@@H](NC(=O)OC)[C@@H](C)CC)[nH]5)ccc4c(=O)c3c2)[nH]1]
262
-continued
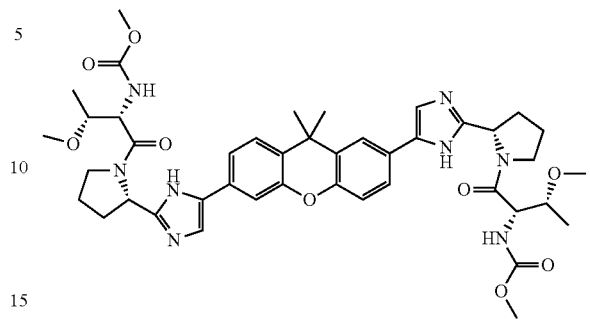
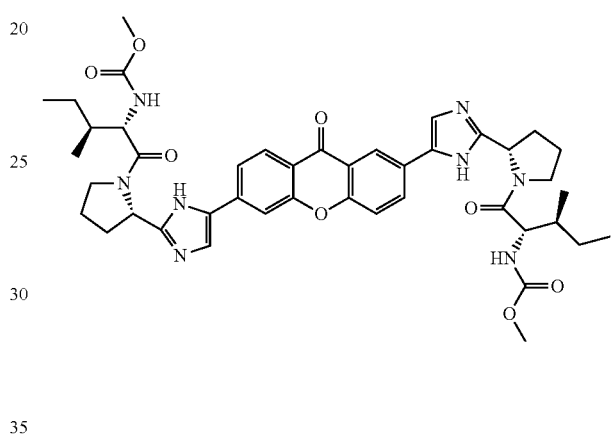
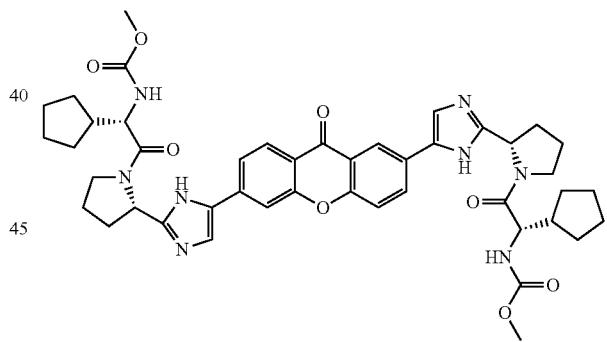
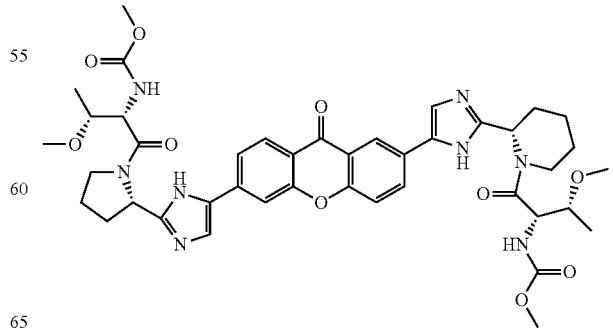

263
-continued
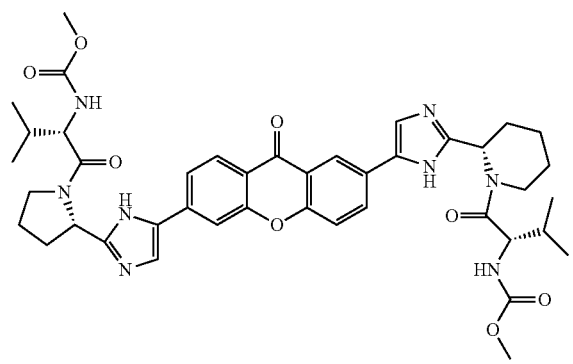 [SMILES: COC(=O)N[C@H](C(=O)N1CCCC[C@H]1c1ncc(-c2ccc3oc4cc(-c5cnc([C@@H]6CCCN6C(=O)[C@@H](NC(=O)OC)C(C)C)[nH]5)ccc4c(=O)c3c2)[nH]1)C(C)C]
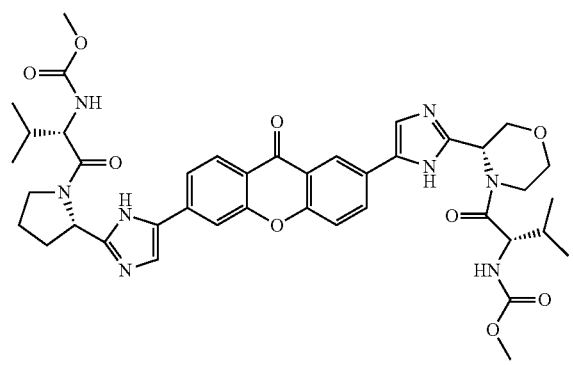 [SMILES: COC(=O)N[C@H](C(=O)N1CCC[C@H]1c1ncc(-c2ccc3c(=O)c4cc(-c5cnc([C@@H]6COCCN6C(=O)[C@@H](NC(=O)OC)C(C)C)[nH]5)ccc4oc3c2)[nH]1)C(C)C]
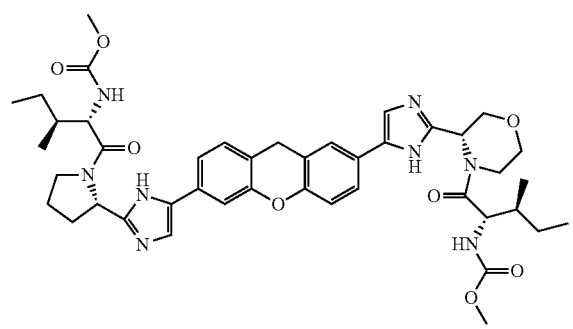 [SMILES: CC[C@H](C)[C@H](NC(=O)OC)C(=O)N1CCC[C@H]1c1ncc(-c2ccc3c(c2)Oc2ccc(-c4cnc([C@@H]5COCCN5C(=O)[C@@H](NC(=O)OC)[C@@H](C)CC)[nH]4)cc2C3)[nH]1]
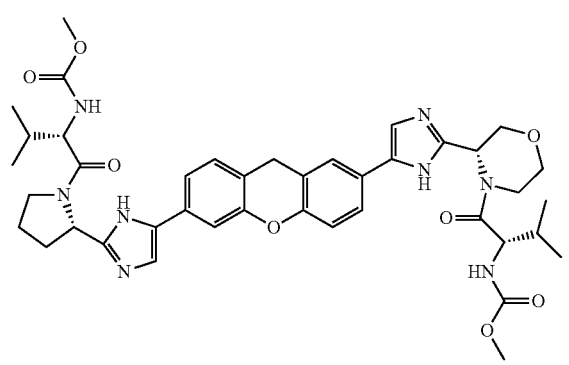 [SMILES: COC(=O)N[C@H](C(=O)N1CCC[C@H]1c1ncc(-c2ccc3c(c2)Oc2ccc(-c4cnc([C@@H]5COCCN5C(=O)[C@@H](NC(=O)OC)C(C)C)[nH]4)cc2C3)[nH]1)C(C)C]
264
-continued
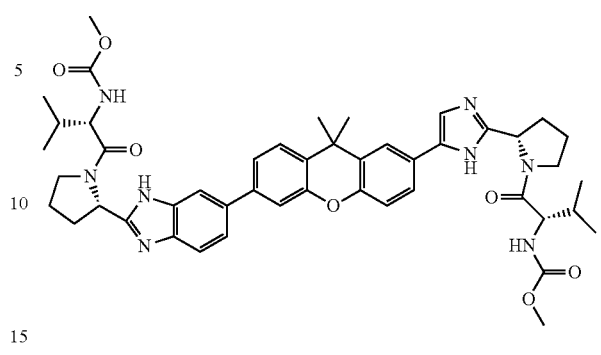
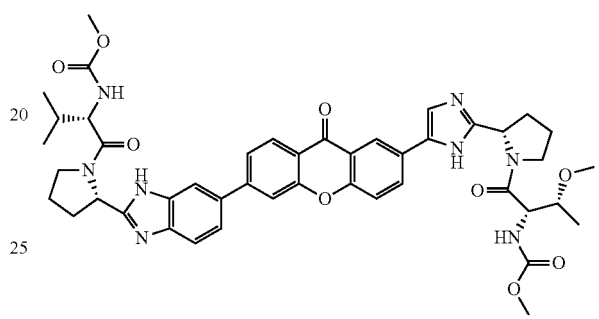
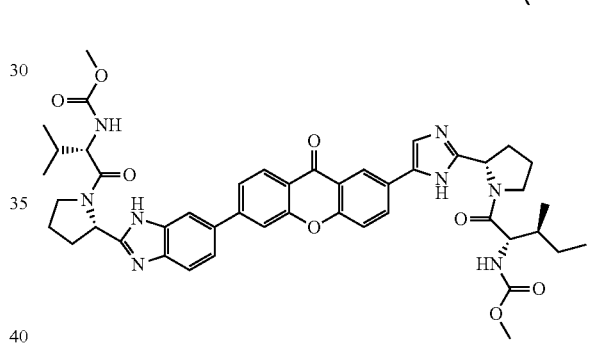
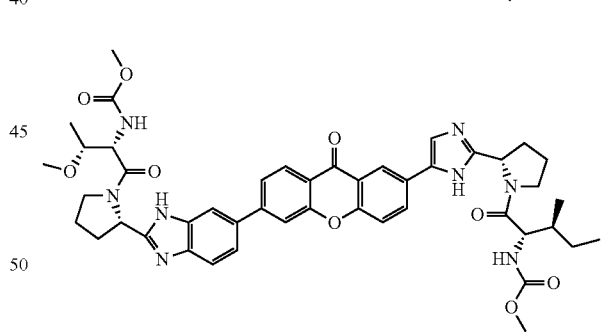

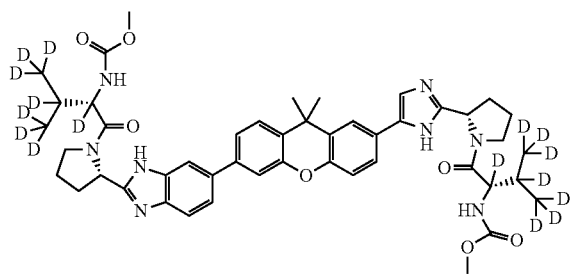 [SMILES: [2H]C([2H])([2H])C([2H])(C([2H])([2H])[2H])[C@]([2H])(NC(=O)OC)C(=O)N1CCC[C@H]1c1ncc(-c2ccc3c(c2)C(C)(C)c2ccc(-c4ccc5nc([C@@H]6CCCN6C(=O)[C@@]([2H])(NC(=O)OC)C([2H])(C([2H])([2H])[2H])C([2H])([2H])[2H])[nH]c5c4)cc2O3)[nH]1]
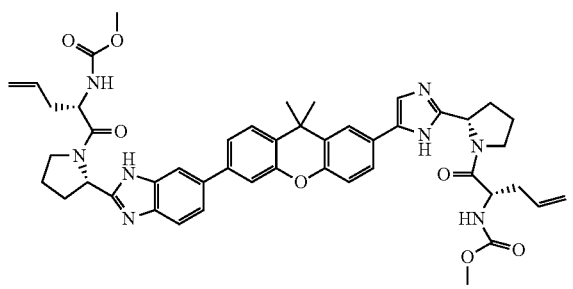 [SMILES: C=CC[C@H](NC(=O)OC)C(=O)N1CCC[C@H]1c1ncc(-c2ccc3c(c2)C(C)(C)c2ccc(-c4ccc5nc([C@@H]6CCCN6C(=O)[C@H](CC=C)NC(=O)OC)[nH]c5c4)cc2O3)[nH]1]
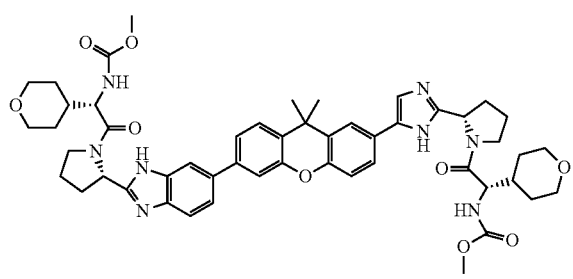 [SMILES: COC(=O)N[C@H](C(=O)N1CCC[C@H]1c1ncc(-c2ccc3c(c2)C(C)(C)c2ccc(-c4ccc5nc([C@@H]6CCCN6C(=O)[C@@H](NC(=O)OC)C6CCOCC6)[nH]c5c4)cc2O3)[nH]1)C1CCOCC1]
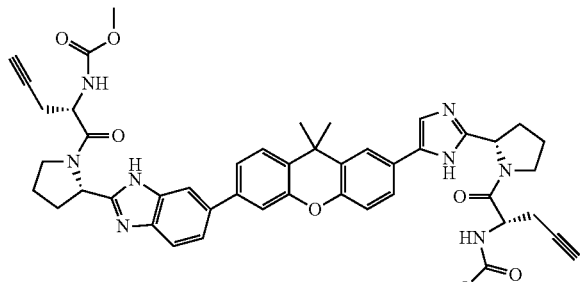
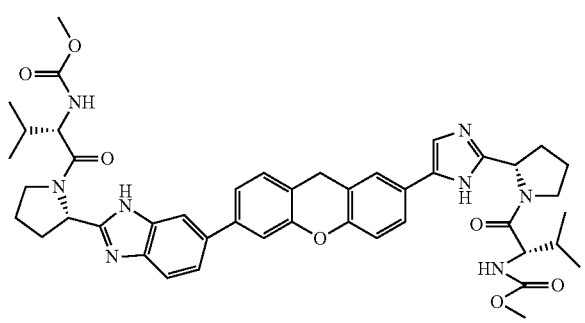 [SMILES: COC(=O)N[C@H](C(=O)N1CCC[C@H]1c1ncc(-c2ccc3c(c2)Cc2ccc(-c4ccc5nc([C@@H]6CCCN6C(=O)[C@@H](NC(=O)OC)C(C)C)[nH]c5c4)cc2O3)[nH]1)C(C)C]
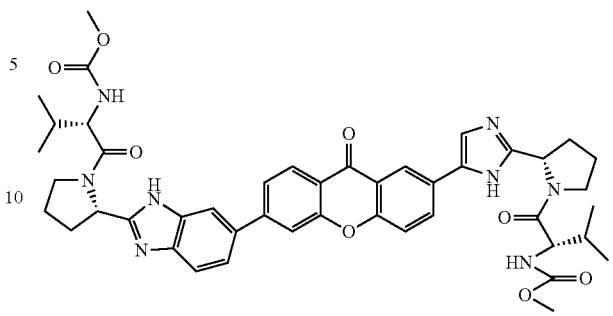 [SMILES: COC(=O)N[C@H](C(=O)N1CCC[C@H]1c1ncc(-c2ccc3oc4cc(-c5ccc6nc([C@@H]7CCCN7C(=O)[C@@H](NC(=O)OC)[C@@H](C)OC)[nH]c6c5)ccc4c(=O)c3c2)[nH]1)C(C)C]
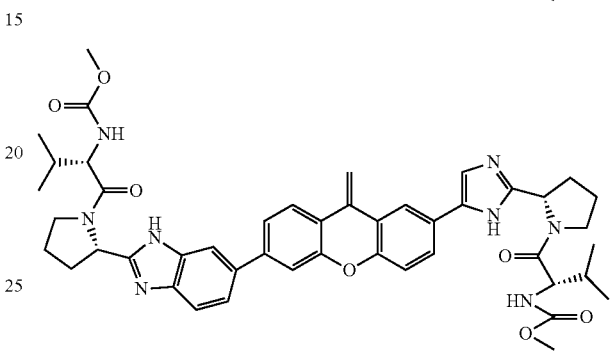
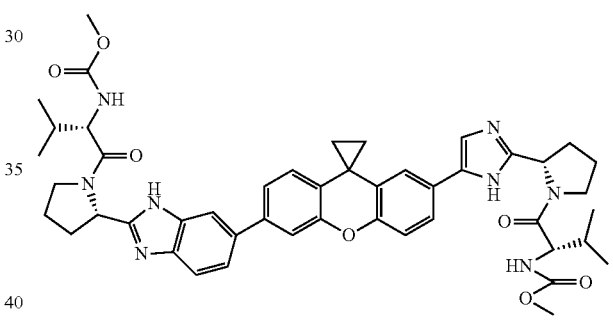
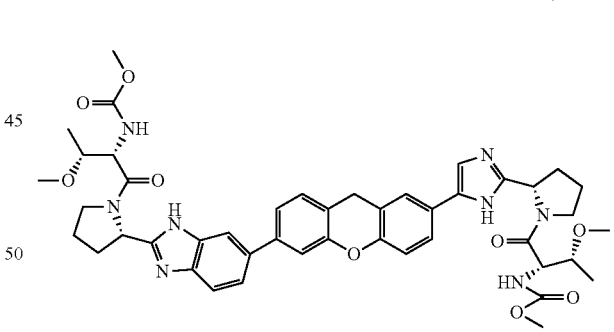
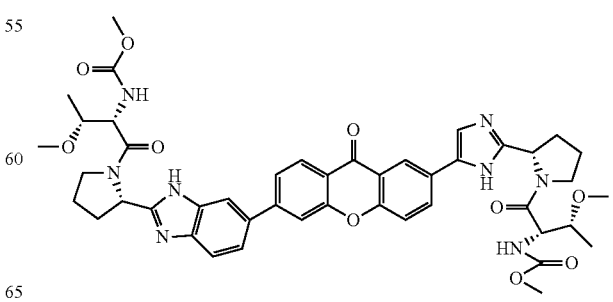

267
-continued
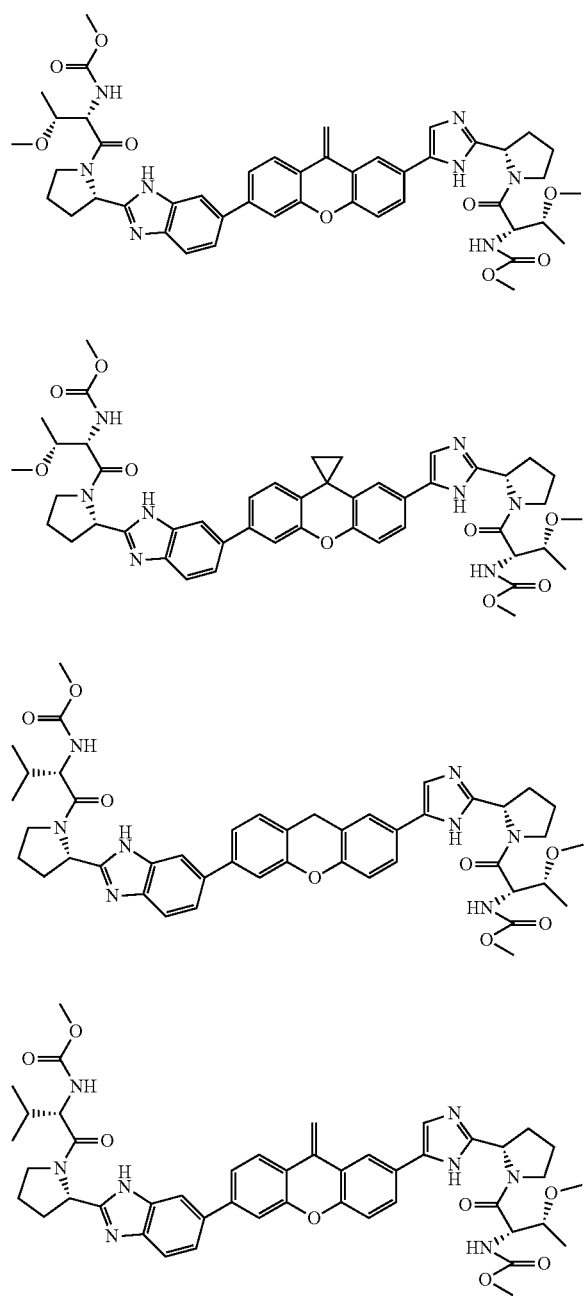
268
-continued
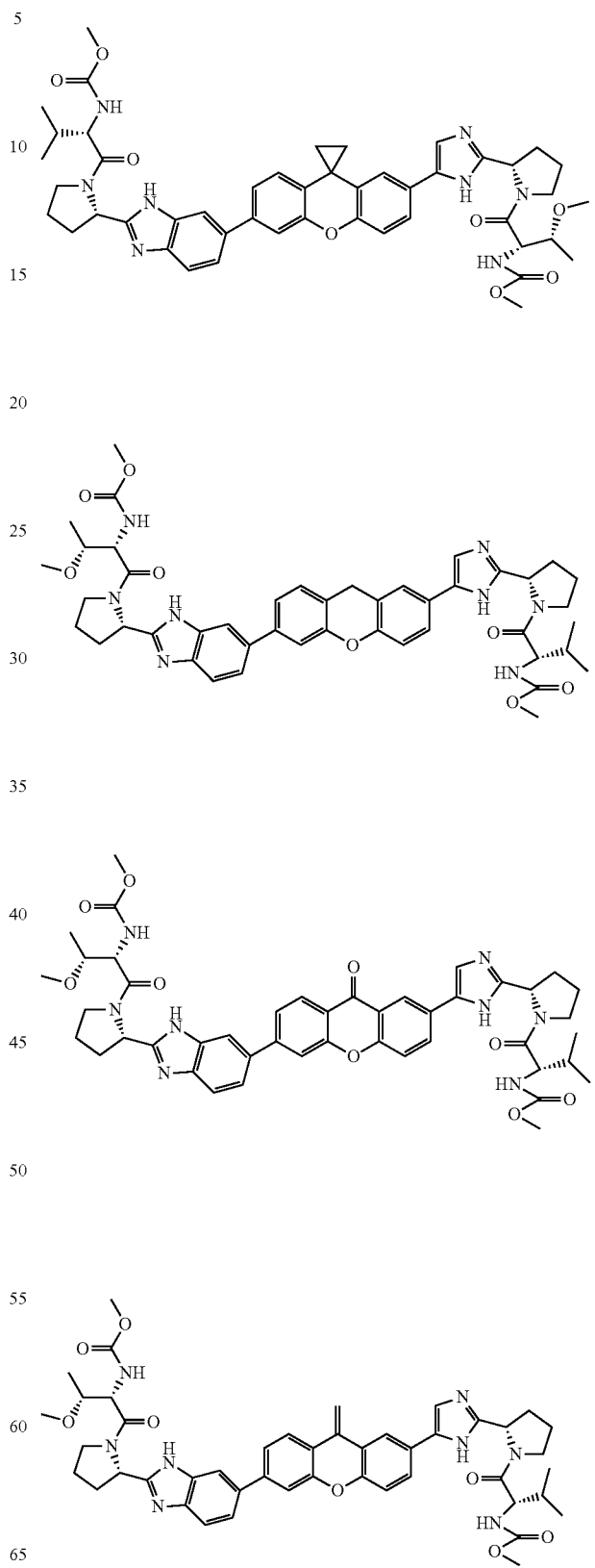

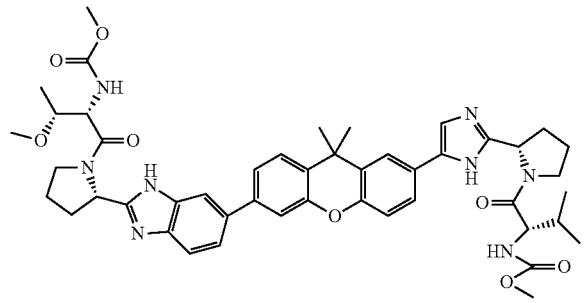 [SMILES: COC(=O)N[C@H](C(=O)N1CCC[C@H]1c1ncc(-c2ccc3c(c2)C(C)(C)c2ccc(-c4ccc5nc([C@@H]6CCCN6C(=O)[C@@H](NC(=O)OC)[C@@H](C)OC)[nH]c5c4)cc2O3)[nH]1)C(C)C]
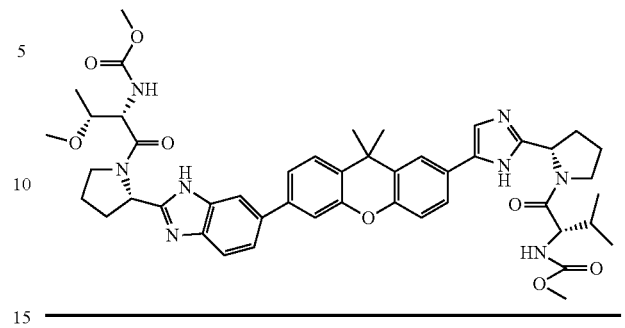
or a pharmaceutically acceptable salt thereof.
2. A pharmaceutical composition comprising the compound of claim 1.
3. A compound having a formula selected from:
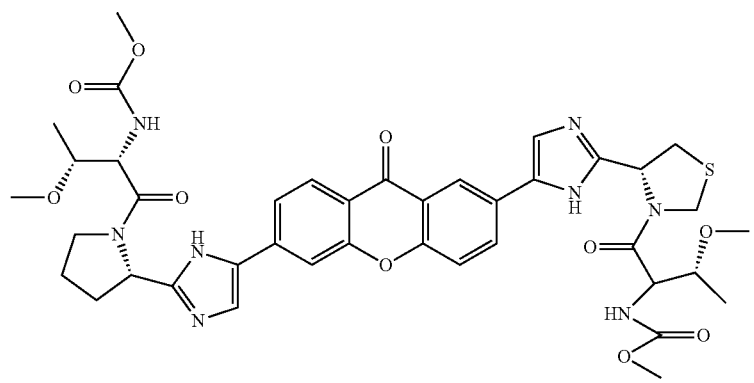
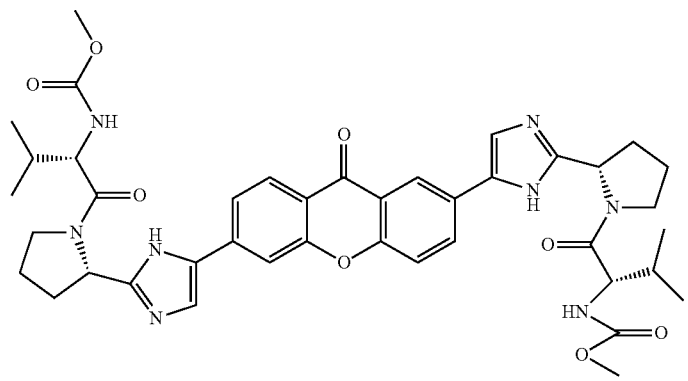 [SMILES: COC(=O)N[C@H](C(=O)N1CCC[C@H]1c1ncc(-c2ccc3c(=O)c4cc(-c5cnc([C@@H]6CCCN6C(=O)[C@@H](NC(=O)OC)C(C)C)[nH]5)ccc4oc3c2)[nH]1)C(C)C]
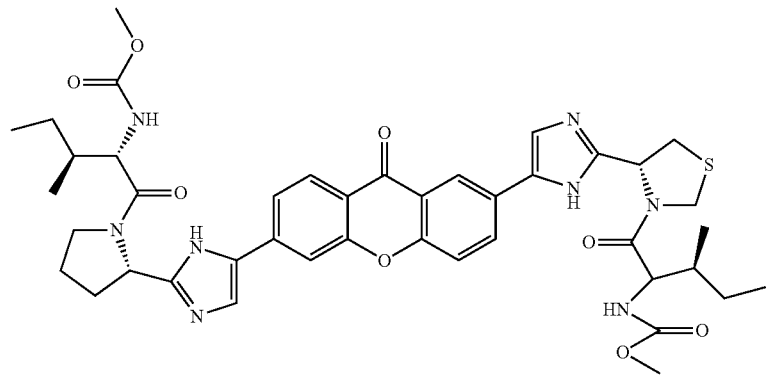 [SMILES: CC[C@H](C)C(NC(=O)OC)C(=O)N1CSC[C@H]1c1ncc(-c2ccc3oc4cc(-c5cnc([C@@H]6CCCN6C(=O)[C@@H](NC(=O)OC)[C@@H](C)CC)[nH]5)ccc4c(=O)c3c2)[nH]1]

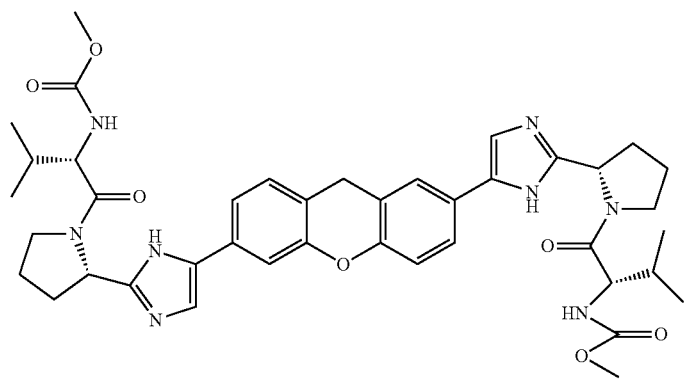 [SMILES: COC(=O)N[C@H](C(=O)N1CCC[C@H]1c1ncc(-c2ccc3c(c2)Cc2ccc(-c4cnc([C@@H]5CCCN5C(=O)[C@@H](NC(=O)OC)C(C)C)[nH]4)cc2O3)[nH]1)C(C)C]
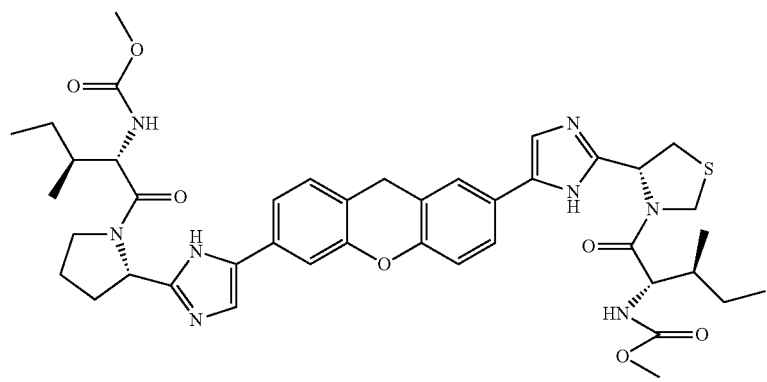 [SMILES: CC[C@H](C)[C@H](NC(=O)OC)C(=O)N1CCC[C@H]1c1ncc(-c2ccc3c(c2)Oc2ccc(-c4cnc([C@@H]5CSCN5C(=O)[C@@H](NC(=O)OC)[C@@H](C)CC)[nH]4)cc2C3)[nH]1]
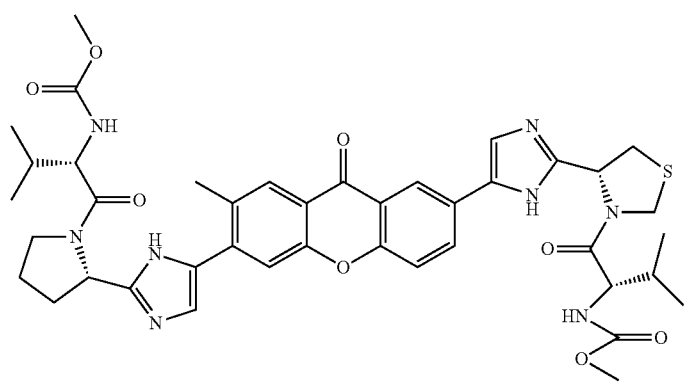 [SMILES: COC(=O)N[C@H](C(=O)N1CSC[C@H]1c1ncc(-c2ccc3oc4cc(-c5cnc([C@@H]6CCCN6C(=O)[C@@H](NC(=O)OC)C(C)C)[nH]5)c(C)cc4c(=O)c3c2)[nH]1)C(C)C]
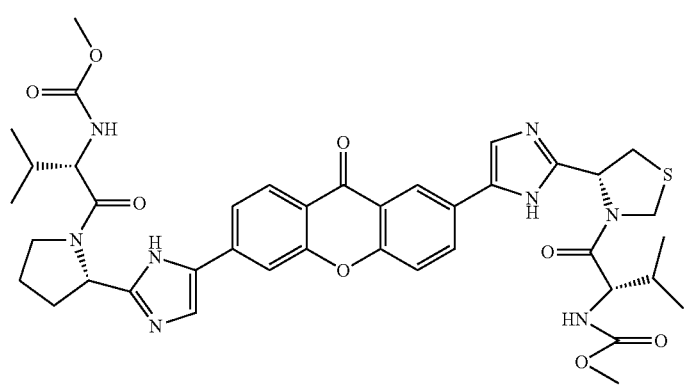

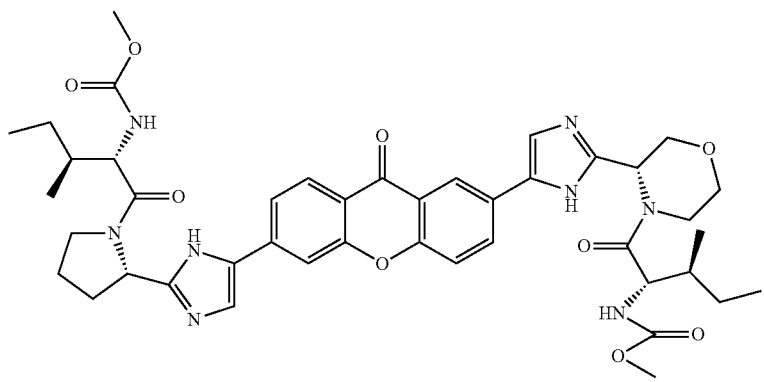 [SMILES: CC[C@H](C)[C@H](NC(=O)OC)C(=O)N1CCC[C@H]1c1ncc(-c2ccc3c(=O)c4cc(-c5cnc([C@@H]6COCCN6C(=O)[C@@H](NC(=O)OC)[C@@H](C)CC)[nH]5)ccc4oc3c2)[nH]1]
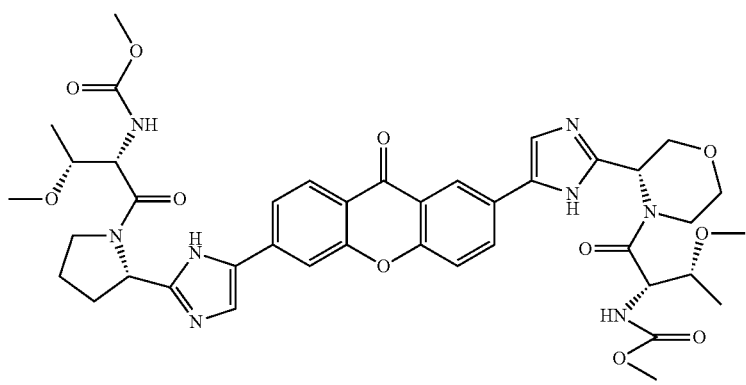
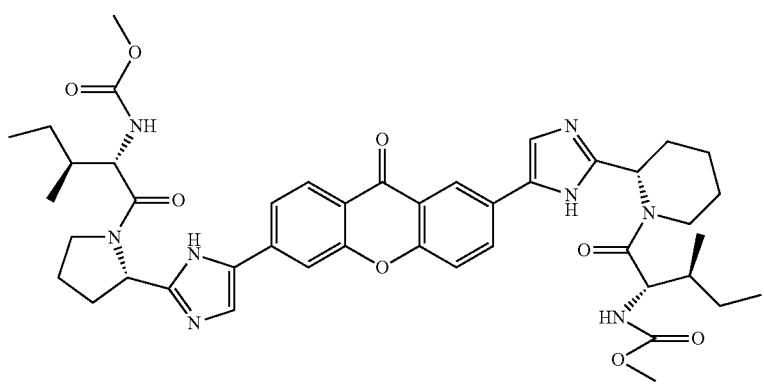 [SMILES: CC[C@H](C)[C@H](NC(=O)OC)C(=O)N1CCCC[C@H]1c1ncc(-c2ccc3oc4cc(-c5cnc([C@@H]6CCCN6C(=O)[C@@H](NC(=O)OC)[C@@H](C)CC)[nH]5)ccc4c(=O)c3c2)[nH]1]
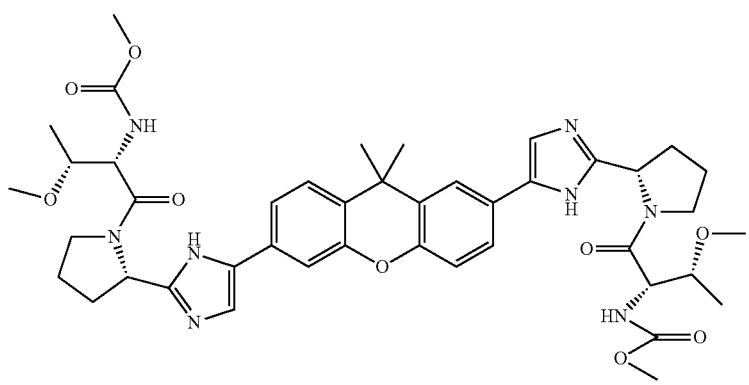

-continued
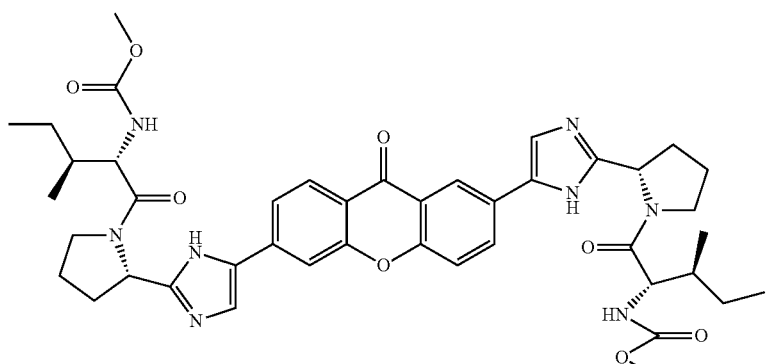
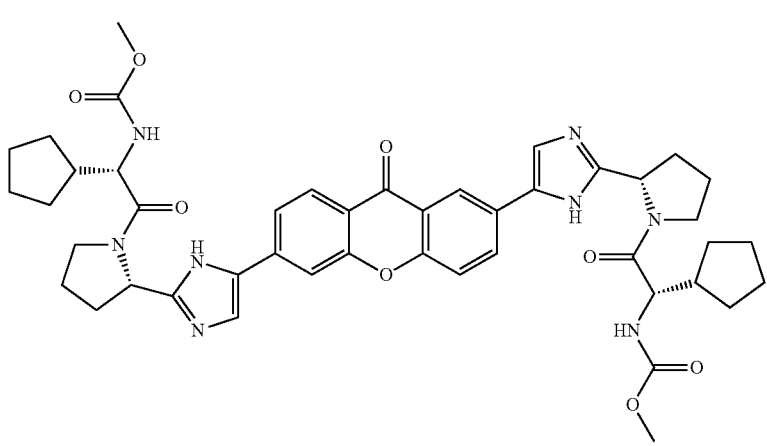 [SMILES: COC(=O)N[C@H](C(=O)N1CCC[C@H]1c1ncc(-c2ccc3c(=O)c4cc(-c5cnc([C@@H]6CCCN6C(=O)[C@@H](NC(=O)OC)C6CCCC6)[nH]5)ccc4oc3c2)[nH]1)C1CCCC1]
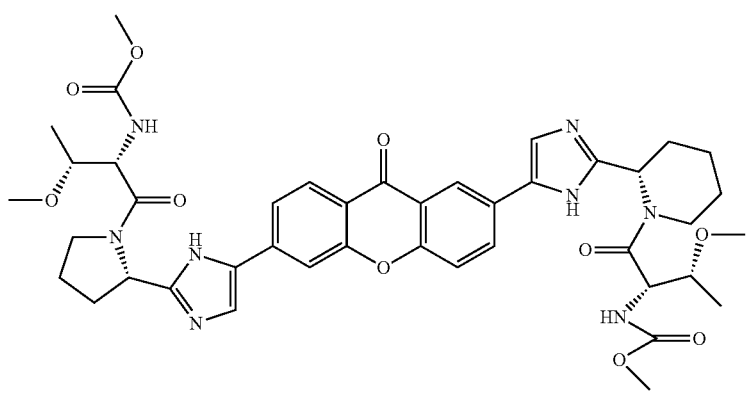
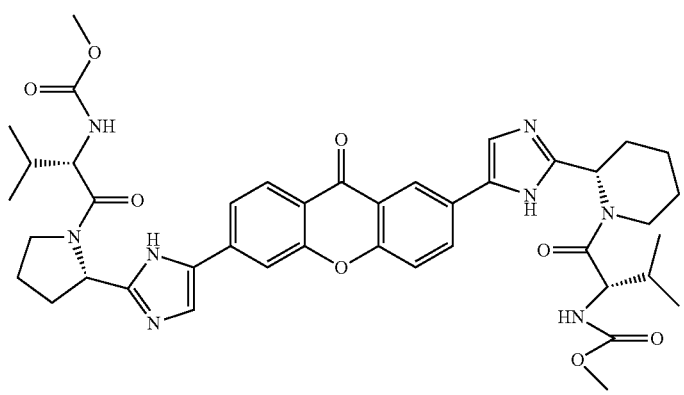 [SMILES: COC(=O)N[C@H](C(=O)N1CCCC[C@H]1c1ncc(-c2ccc3oc4cc(-c5cnc([C@@H]6CCCN6C(=O)[C@@H](NC(=O)OC)C(C)C)[nH]5)ccc4c(=O)c3c2)[nH]1)C(C)C]

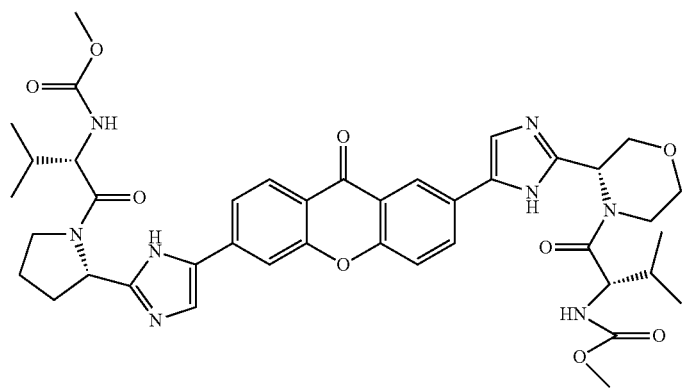
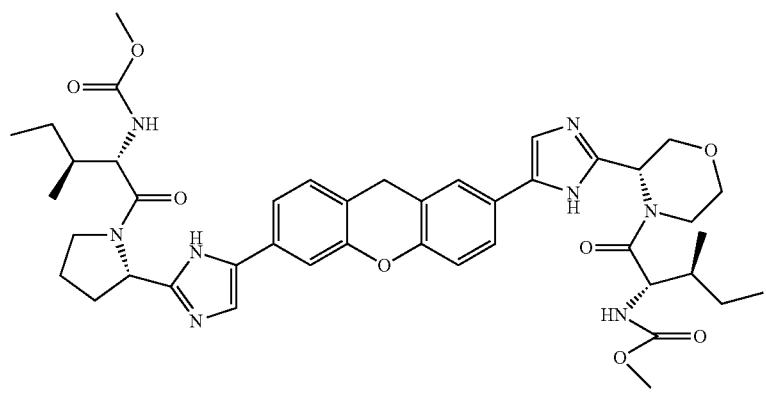 [SMILES: CC[C@H](C)[C@H](NC(=O)OC)C(=O)N1CCC[C@H]1c1ncc(-c2ccc3c(c2)Oc2ccc(-c4cnc([C@@H]5COCCN5C(=O)[C@@H](NC(=O)OC)[C@@H](C)CC)[nH]4)cc2C3)[nH]1]
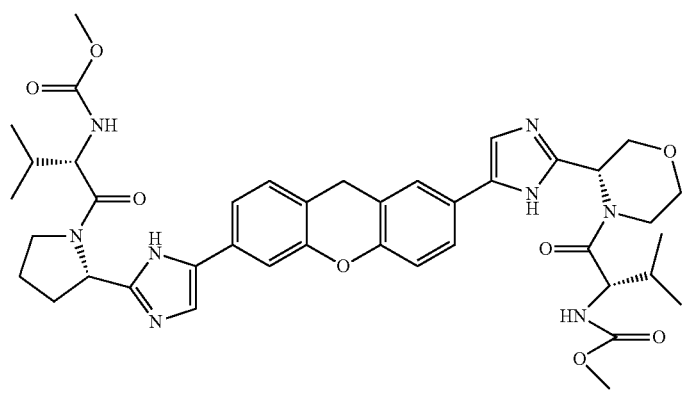 [SMILES: COC(=O)N[C@H](C(=O)N1CCC[C@H]1c1ncc(-c2ccc3c(c2)Oc2ccc(-c4cnc([C@@H]5COCCN5C(=O)[C@@H](NC(=O)OC)C(C)C)[nH]4)cc2C3)[nH]1)C(C)C]
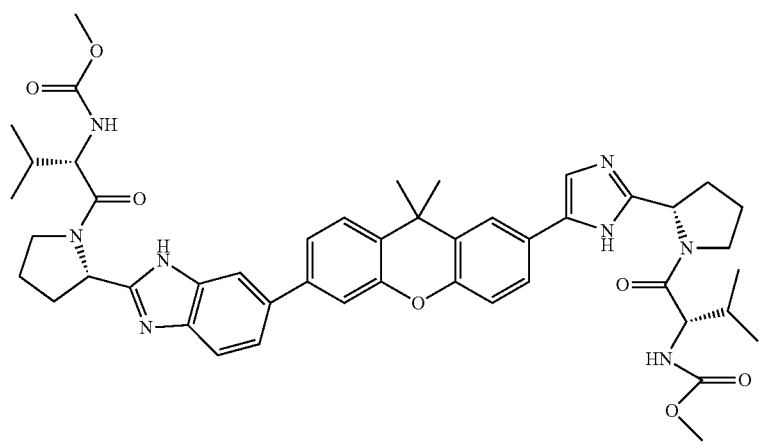 [SMILES: COC(=O)N[C@H](C(=O)N1CCC[C@H]1c1ncc(-c2ccc3c(c2)C(C)(C)c2ccc(-c4ccc5nc([C@@H]6CCCN6C(=O)[C@@H](NC(=O)OC)C(C)C)[nH]c5c4)cc2O3)[nH]1)C(C)C]

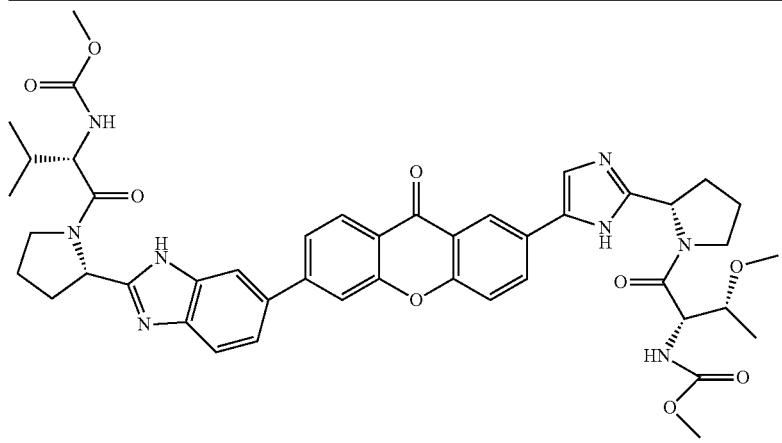
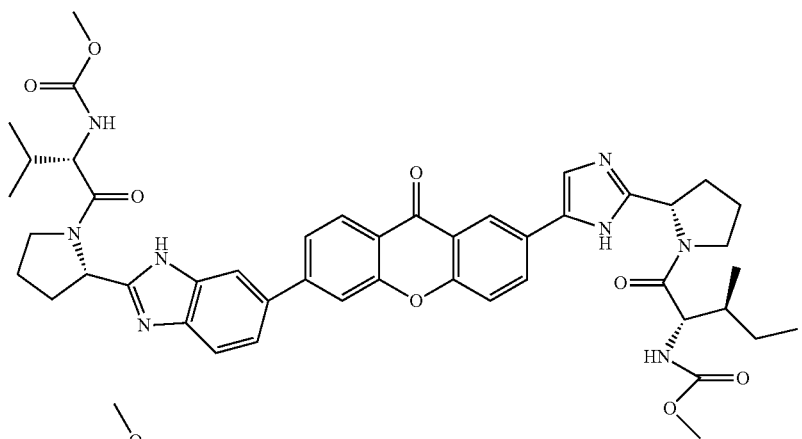 [SMILES: CC[C@H](C)[C@H](NC(=O)OC)C(=O)N1CCC[C@H]1c1ncc(-c2ccc3oc4cc(-c5ccc6nc([C@@H]7CCCN7C(=O)[C@@H](NC(=O)OC)C(C)C)[nH]c6c5)ccc4c(=O)c3c2)[nH]1]
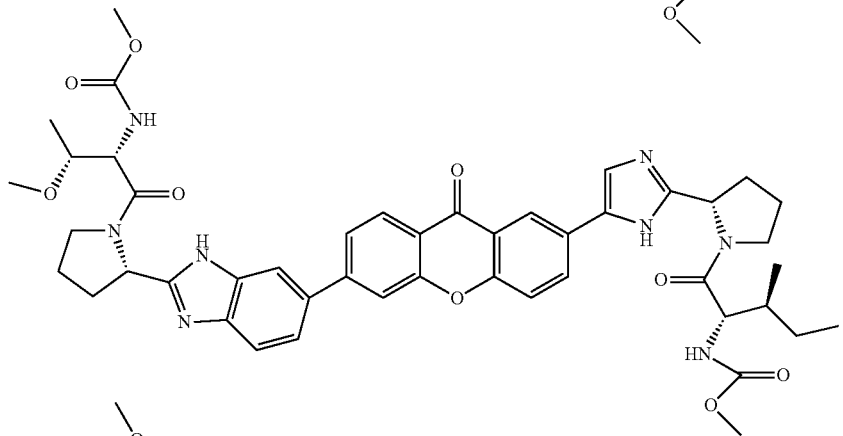
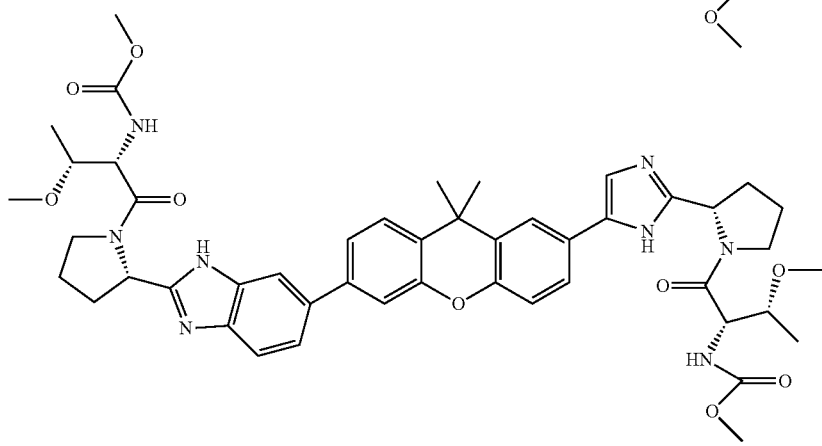

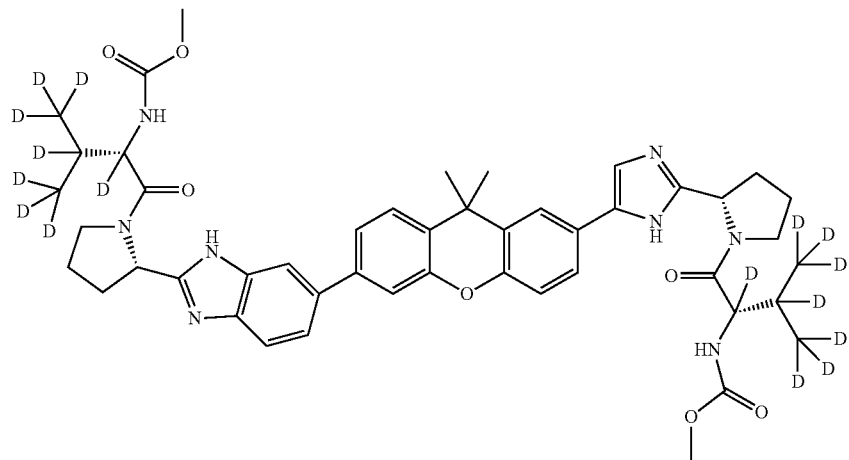 [SMILES: [2H]C([2H])([2H])C([2H])(C([2H])([2H])[2H])[C@]([2H])(NC(=O)OC)C(=O)N1CCC[C@H]1c1ncc(-c2ccc3c(c2)C(C)(C)c2ccc(-c4ccc5nc([C@@H]6CCCN6C(=O)[C@@]([2H])(NC(=O)OC)C([2H])(C([2H])([2H])[2H])C([2H])([2H])[2H])[nH]c5c4)cc2O3)[nH]1]
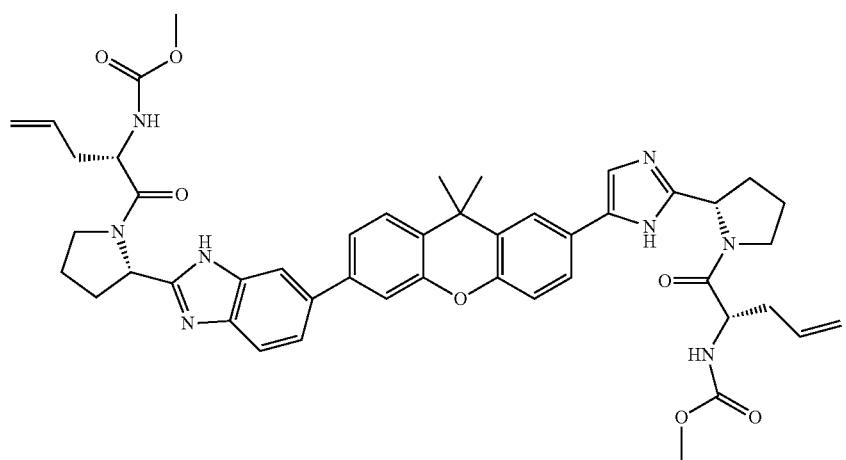 [SMILES: C=CC[C@H](NC(=O)OC)C(=O)N1CCC[C@H]1c1ncc(-c2ccc3c(c2)C(C)(C)c2ccc(-c4ccc5nc([C@@H]6CCCN6C(=O)[C@H](CC=C)NC(=O)OC)[nH]c5c4)cc2O3)[nH]1]
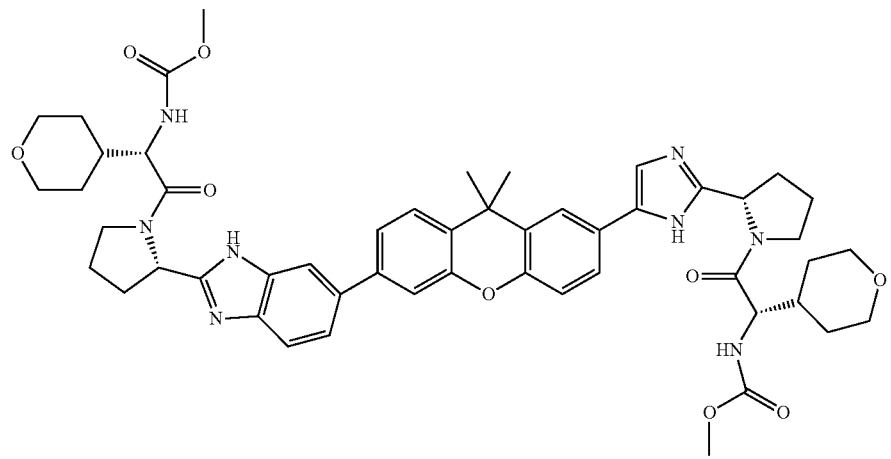 [SMILES: COC(=O)N[C@H](C(=O)N1CCC[C@H]1c1ncc(-c2ccc3c(c2)C(C)(C)c2ccc(-c4ccc5nc([C@@H]6CCCN6C(=O)[C@@H](NC(=O)OC)C6CCOCC6)[nH]c5c4)cc2O3)[nH]1)C1CCOCC1]

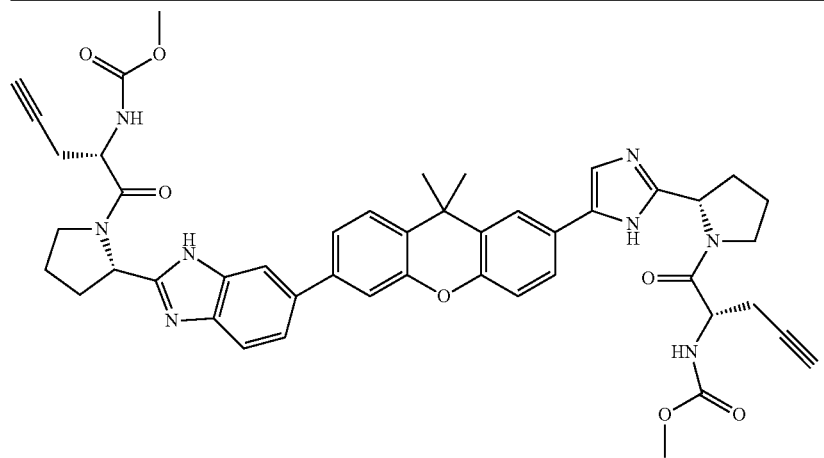
or a pharmaceutically acceptable salt thereof.
4. A pharmaceutical composition comprising the compound of claim 3.
* * * * *